(12) United States Patent
He et al.

(10) Patent No.: US 9,534,059 B2
(45) Date of Patent: Jan. 3, 2017

(54) TIKI INHIBITORS

(71) Applicant: Children's Medical Center Corporation, Boston, MA (US)

(72) Inventors: Xi He, Jamaica Plain, MA (US); Xinjun Zhang, Brookline, MA (US); Bryan MacDonald, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/391,971

(22) PCT Filed: Apr. 12, 2013

(86) PCT No.: PCT/US2013/036422
§ 371 (c)(1),
(2) Date: Oct. 10, 2014

(87) PCT Pub. No.: WO2013/155447
PCT Pub. Date: Oct. 17, 2013

(65) Prior Publication Data
US 2015/0166671 A1 Jun. 18, 2015

Related U.S. Application Data

(60) Provisional application No. 61/623,744, filed on Apr. 13, 2012, provisional application No. 61/654,299, filed on Jun. 1, 2012.

(51) Int. Cl.

| | |
|---|---|
| *C07K 16/40* | (2006.01) |
| *A61K 39/395* | (2006.01) |
| *A61K 31/713* | (2006.01) |
| *C12N 15/113* | (2010.01) |
| *C12N 9/64* | (2006.01) |
| *A61K 31/7088* | (2006.01) |

(52) U.S. Cl.
CPC .......... *C07K 16/40* (2013.01); *A61K 31/7088* (2013.01); *A61K 31/713* (2013.01); *A61K 39/3955* (2013.01); *C12N 9/6489* (2013.01); *C12N 15/1137* (2013.01); *C07K 2317/76* (2013.01); *C12N 2310/11* (2013.01); *C12N 2310/3233* (2013.01)

(58) Field of Classification Search
CPC .. C07K 16/40; C07K 2317/76; A61K 39/3955
See application file for complete search history.

(56) References Cited

U.S. PATENT DOCUMENTS

| | | | |
|---|---|---|---|
| 2004/0198651 A1 | 10/2004 | Klammer et al. | |
| 2007/0077244 A1 | 4/2007 | Niehrs et al. | |
| 2011/0231942 A1 | 9/2011 | He et al. | |
| 2011/0300160 A1 | 12/2011 | Rabbani et al. | |
| 2012/0045437 A1 | 2/2012 | Ma et al. | |
| 2013/0101582 A1 | 4/2013 | He et al. | |

FOREIGN PATENT DOCUMENTS

| | | |
|---|---|---|
| WO | WO 2008/012505 | 1/2008 |
| WO | WO 2011/088127 | 7/2011 |

OTHER PUBLICATIONS

Bazan et al., Dev. Cell, vol. 25, Issue 3, May 13, 2013, pp. 225-227.*
International Preliminary Report on Patentability issued in International Application No. PCT/US2013/036422, issued Oct. 14, 2014, 9 pages.
International Search Report and Written Opinion issued in International Application No. PCT/US2013/036422, mailed Jul. 29, 2013, 14 pages.
Non-final Office Action issued in U.S. Appl. No. 13/715,443, dated Dec. 5, 2014, 16 pages.
Non-final Office Action issued in U.S. Appl. No. 13/049,436, dated Sep. 26, 2012, 10 pages.
Bachmann et al., "Importance of P-cadherin, beta-catenin, and Wnt5a/frizzled for progression of melanocytic tumors and prognosis in cutaneous melanoma," 2005, Clin Cancer Res, 11:8606-8614.
Bafico et al., "Novel mechanism of Wnt signalling inhibition mediated by Dickkopf-1 interaction with LRP6/Arrow," 2001, Nat Cell Biol, 3:683-686.
Banziger et al., "Wntless, a conserved membrane protein dedicated to the secretion of Wnt proteins from signaling cells," 2006, Cell 125:509-522.
Becker et al., "Xanthan gum biosynthesis and application: a biochemical/genetic perspective," 1998, Applied microbiology and biotechnology, 50:145-152.
Brannon et al., "A beta-catenin/XTcf-3 complex binds to the siamois promoter to regulate 20 dorsal axis specification in Xenopus." 1997, Genes & development 11:2359-2370.
Chan-on et al., "Robust fluorescent detection of protein fatty-acylation with chemical reporters," 2009, JACS, 131:4967.
Chien et al., "Activated Wnt/beta-catenin signaling in melanoma is associated with decreased proliferation in patient tumors and a murine melanoma model," 2009, PNAS, 106:1193-1198.
Cho et al., "Molecular nature of Spemann's organizer: the role of the Xenopus homeobox gene Goosecoid," 1991, Cell, 67:1111-1120.
Christian and Moon, "Interactions between Xwnt-8 and Spemann organizer signaling pathways generate dorsoventral pattern in the embryonic mesoderm of Xenopus," 1993, Genes & development, 7:13-28.
Clevers, "Wnt/beta-catenin signaling in development and disease," 2006, Cell, 127:469-480.
Cong et al., "Wnt signals across the plasma membrane to activate the beta-catenin pathway by forming oligomers containing its receptors, Frizzled and LRP," 2004, Development (Cambridge, England) 131: 5103-5115.
Coombs et al., "WLS-dependent secretion of WNT3A requires Ser209 acylation and vacuolar acidification," 2010, Journal of cell science, 123:3357-3367.
De Robertis and Kuroda, "Dorsal-ventral patterning and neural induction in Xenopus embryos," 2004, Annual review of cell and developmental biology, 20:285-308.

(Continued)

*Primary Examiner* — Daniel C Gamett
(74) *Attorney, Agent, or Firm* — Fish & Richardson P.C.

(57) ABSTRACT

Modulators of Wnt activity, e.g., Wnt inhibitors, that act on TIKI proteins and inhibit TIKI-mediated cleavage of Wnt proteins, as well as methods of identifying such modulators and methods of use thereof.

12 Claims, 57 Drawing Sheets

(56) References Cited

OTHER PUBLICATIONS

Dejmek et al., "Wnt-5a protein expression in primary dukes B colon cancers identifies a subgroup of patients with good prognosis," 2005, Cancer Res, 65:9142-9146.
Drisdel et al., "Labeling and quantifying sites of protein palmitoylation," 2004, Biotechniques, 36:276-285.
Ellison et al., "β-Catenin Status Predicts a Favorable Outcome in Childhood Medulloblastoma: The United Kingdom Children's Cancer Study Group Brain Tumour Committee," 2005, J Clin Oncol, 23:7951-7957.
Ellwanger et al., "Targeted disruption of the Wnt regulator Kremen induces limb defects and high bone density," 2008, Mol. Cell. Biol., 28:4875-4882.
Fattet et al., "Beta-catenin status in paediatric medulloblastomas," 2009, J Pathol, 218:86-94.
Franch-Marro et al., "In vivo role of lipid adducts on Wingless," 2008, Journal of cell science, 121:1587-1592.
Furushima et al., "Mouse homologues of Shisa antagonistic to Wnt and Fgf signaling," 2007, Dev. Biol., 306:480-492.
Glinka et al., "Dickkopf-1 is a member of a new family of secreted proteins and functions in head induction," 1998, Nature, 391:357-362.
Harland et al., "Formation and function of Spemann's organizer," 1997, Annu. Rev. Cell Dev. Biol., 13:611-667.
Hausmann et al., "Helping Wingless take flight: how WNT proteins are secreted," 2007, Nature Reviews, 8:331-336.
He et al., "LDL receptor-related proteins 5 and 6 in Wnt/beta-catenin signaling: arrows point the way," 2004, Development (Cambridge, England) 131:1663-1677.
Kageshita et al., "Loss of beta-catenin expression associated with disease progression in malignant melanoma," 2001, Br J Dermatol, 145:210-216.
Kanis et al., "A reference standard for the description of osteoporosis," 2008, Bone, 42:467-475.
Kansara et al., "Wnt inhibitory factor 1 is epigenetically silenced in human osteosarcoma, and targeted disruption accelerates osteosarcomagenesis in mice," 2009, J. Clin. Invest., 119:837-851.
Kato et al., "A component of the ARC/Mediator complex required for TGF beta/Nodal signaling," 2002, Nature 418, 641-646.
Katzen et al., "New mobilizable vectors suitable for gene replacement in gram-negative bacteria and their use in mapping of the 3' end of the Xanthomonas campestris pv. campestris gum operon," 1999, Applied and environmental microbiology, 65:278-282.
Kiecker and Niehrs, "A morphogen gradient of Wnt/beta-catenin signalling regulates anteroposterior neural patterning in Xenopus," 2001, Development, Cambridge, England, 128:4189-4201.
Komekado et al., "Glycosylation and palmitoylation of Wnt-3 a are coupled to produce an active form of Wnt-3a," 2007, Genes Cells, 12:521-534.
Kool et al., "Integrated Genomics Identifies Five Medulloblastoma Subtypes with Distinct Genetic Profiles, Pathway Signatures and Clinicopathological Features," 2008, Plos One, 3:e3088, 14 total pages.
Kurayoshi et al., "Post-translational palmitoylation and glycosylation of Wnt-5a are necessary for its signaling," 2007, Biochem J, 402:515-523.
Larue and Delmas, "The WNT/Beta-catenin pathway in melanoma," 2006, Frontiers in Bioscience, 11:733-742.
Lattin et al., "Expression analysis of G Protein-Coupled Receptors in mouse macrophages," 2008, Immunome Res., 4:5.
Li et al., "Sclerostin antibody treatment increases bone formation, bone mass, and bone strength in a rat model of postmenopausal osteoporosis," 2009, J. Bone Miner Res., 24:578-588.
Logan et al., "The Wnt signaling pathway in development and disease," Annu. Rev. Cell. Dev. Biol., 2004, 20:781-810.
Lu et al., "Acquisition and evolution of plant pathogenesis-associated gene clusters and candidate determinants of tissue-specificity in xanthomonas," 2008, PloS one, 3:e3828, 13 total pages.

MacDonald et al., "Wnt signal amplification via activity, cooperativity, and regulation of multiple intracellular PPPSP motifs in the Wnt co-receptor LRP6," 2008, The Journal of biological chemistry, 283:16115-16123.
MacDonald et al., "Bone mass is inversely proportional to Dkk1 levels in mice," 2007, Bone, 41:331-339.
MacDonald et al., "Wnt/beta-catenin signaling: components, mechanisms, and diseases," 2009, Dev. Cell, 17:9-26.
Maelandsmo et al., "Reduced beta-catenin expression in the cytoplasm of advanced-stage superficial spreading malignant melanoma," 2003, Clin Cancer Res, 9:3383-3388.
Major et al., "Wilms tumor suppressor WTX negatively regulates WNT/beta-catenin signaling," 2007, Science, 316:1043-1046.
Mao et al., "LDL-receptor-related protein 6 is a receptor for Dickkopf proteins," 2001, Nature, 411:321-325.
Mao et al., "Kremen proteins are Dickkopf receptors that regulate Wnt/beta-catenin signaling," 2002, Nature, 417:664-667.
McGrew et al., "Wnt and FGF pathways cooperatively pattern anteroposterior neural ectoderm in Xenopus," 1997, Mechanisms of development, 69:105-114.
Molenaar et al., "XTcf-3 transcription factor mediates beta-catenin-induced axis formation in Xenopus embryos," 1996, Cell, 86:391-399.
Moon et al., "WNT and beta-catenin signaling: diseases and therapies," 2004, Nat. Rev. Genet., 5:691-701.
Morvan et al., "XTcf-3 transcription factor mediates beta-catenin-induced axis formation in Xenopus embryos," 2006, J. Bone Miner Res., 21:934-945.
Mulligan et al., "Secreted Wingless-interacting molecule (Swim) promotes long-range signaling by maintaining Wingless solubility," 2012, Proceedings of the National Academy of Sciences of the United States of America, 109:370-377.
Niehrs, "Regionally specific induction by the Spemann-Mangold organizer," 2004, Nat Rev Genet, 5:425-434.
Ong et al., "Stable isotope labeling by amino acids in cell culture, SILAC, as a simple and accurate approach to expression proteomics," 2002, Mol Cell Proteomics, 1:376-386.
Pei and Tuschl, "On the art of identifying effective and specific siRNAs," Nature Methods, 2006, 3:670-676.
Petersen and Reddien, "Wnt signaling and the polarity of the primary body axis," 2009, Cell 139:1056-1068.
Polakis, "Wnt signaling and cancer," 2000, Genes Dev., 14:1837-1851.
Resh, "Trafficking and signaling by fatty-acylated and prenylated Proteins," 2006, Nature chemical biology 2:584-590.
Roth et al., "Global analysis of protein palmitoylation in yeast," 2006, Cell, 125:1003-1013.
Satoh et al., "Sfrpl, Sfrp2, and Sfrp5 regulate the Wnt/beta-catenin and the planar cell polarity pathways during early trunk formation in mouse," 2008, Genesis, 46:92-103.
Semenov et al., "Head inducer Dickkopf-1 is a ligand for Wnt coreceptor LRP6," 2001, Curr Biol. 11:951-961.
Seth et al., "Delivery and biodistribution of siRNA for cancer therapy: challenges and future prospects," Ther. Deliv., 2012, 3(2):245-261.
Singh et al., "FLEXIQuant: a novel tool for the absolute quantification of proteins, and the simultaneous identification and quantification of potentially modified peptides," 2009, J Proteome Res., 8:2201-2210.
Strigini and Cohen, "Wingless gradient formation in the *Drosophila* wing," 2000, Curr Biol, 10:293-300.
Suzuki et al., "PTH/cAMP/PKA signaling facilitates canonical Wnt signaling via inactivation of glycogen synthase kinase-3beta in osteoblastic Saos-2 cells," J. Cell. Biochem., 104:304-317 (2008).
Takada et al., "Monounsaturated fatty acid modification of Wnt protein: its role in Wnt secretion," 2006, Dev. Cell., 11:791-801.
Tamai et al., "A mechanism for Wnt coreceptor activation," 2004, Mol. Cell., 13:149-156.
Tamai et al., "LDL-receptor-related proteins in Wnt signal transduction," 2000, Nature, 407:530-535.
Willert et al., "Wnt proteins are lipid-modified and can act as stem cell growth factors," 2003, Nature, 423:448-452.

(56) References Cited

OTHER PUBLICATIONS

Yamamoto et al., "Shisa promotes head formation through the inhibition of receptor protein maturation for the caudalizing factors, Wnt and FGF," Jan. 2005, Cell, 120(2): 223-235.
Ysebaert et al., "Expression of β-catenin by acute myeloid leukemia cells predicts enhanced clonogenic capacities and poor prognosis," Leukemia, 2006, 20(7):1211-6.
Zecca et al., "Direct and long-range action of a wingless morphogen gradient," 1996, Cell, 87:833-844.
Zhai et al., "*Drosophila* wnt-1 undergoes a hydrophobic modification and is targeted to lipid rafts, a process that requires porcupine," The Journal of biological chemistry, 2004, 279:33220-33227.
Zhang et al., "A Simple Statistical Parameter for Use in Evaluation and Validation of High Throughput Screening Assays," J. Biol. Screen, 4:67-73 (1999).
Zhang et al., "Tiki1 is required for head formation via Wnt cleavage-oxidation and inactivation," Jun. 2012, Cell, 149(7):1565-1577.
Supplemental European Search Report; EP 13 77 5801; Dec. 1, 2015; 11 pp.

\* cited by examiner

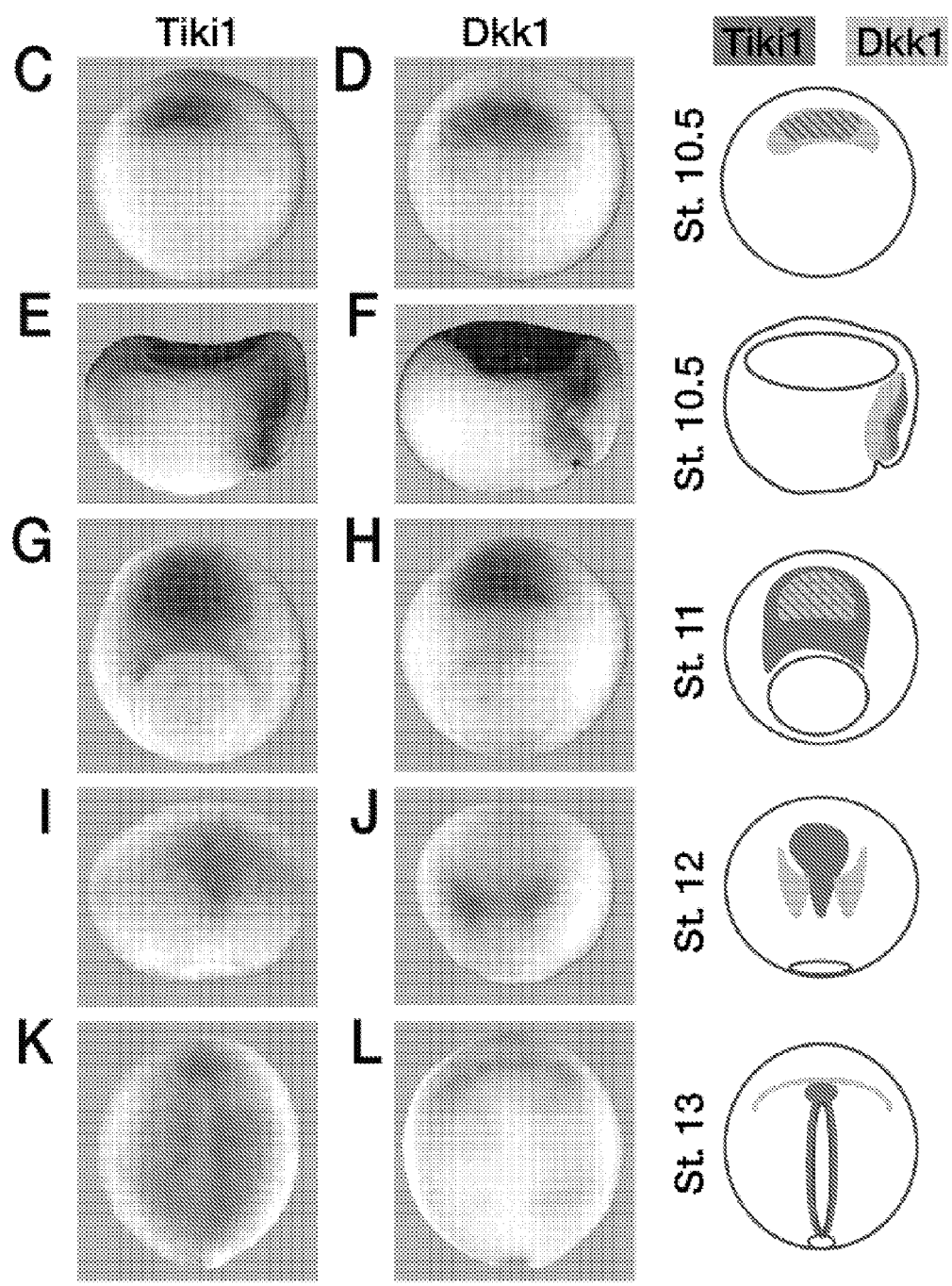
FIGs. 2C-L

% Anterior Deficiency

| Con MO | Dkk1 mRNA | Tiki1 MO | Tiki1 MO+ Dkk1 mRNA |
|---|---|---|---|
| 0% (n=25) | 0%* (n=31) | 45% (n=34) | 0%** (n=28) |
| | * enlarged head | | ** some with enlarged head |

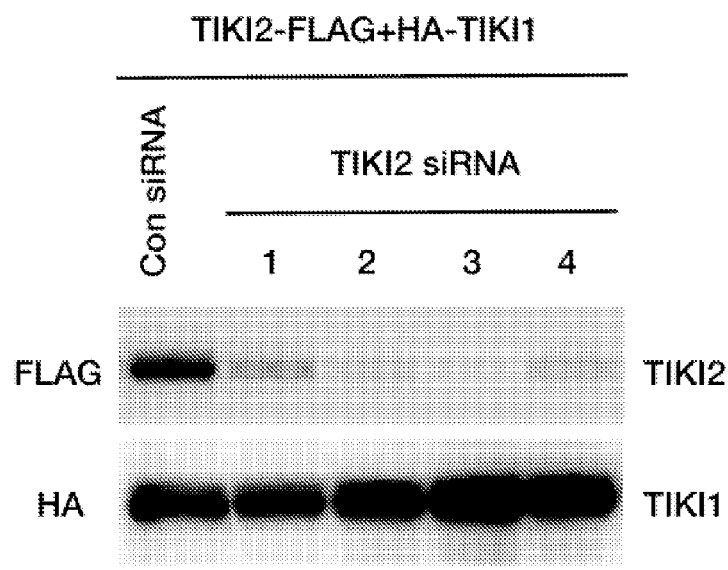
FIG. 4K
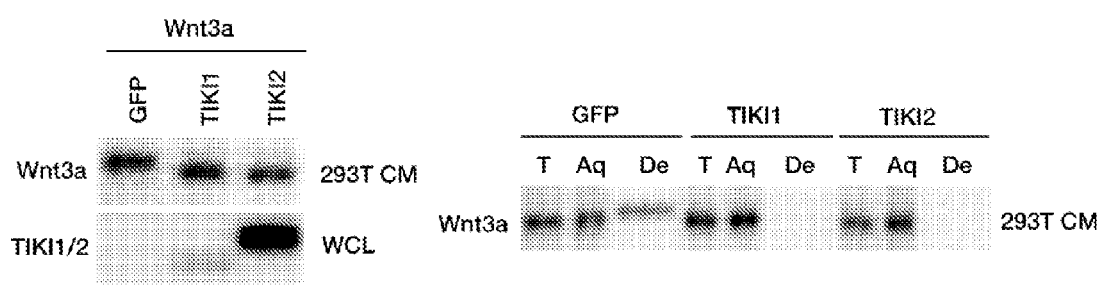
FIG. 4L
FIG. 4M

Wnt3a (Con)      SYPIWWSLAVGPQYSSLSTQPILCASIPGLVPKQL......

Wnt3a (TIKI2)    AVGPQYSSLSTQPILCASIPGLVPKQL......
(Wnt3aΔN)

Xwnt8            AWSVNNFLMTGPKAYLTYSASVAVGAQNGIEECK......

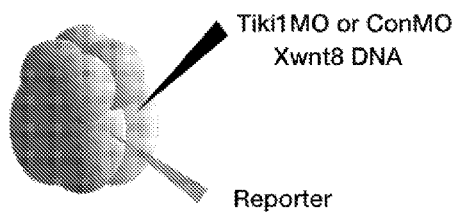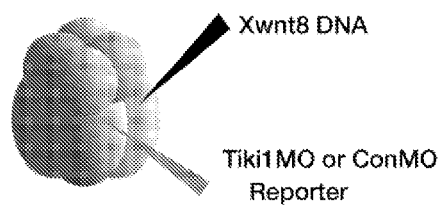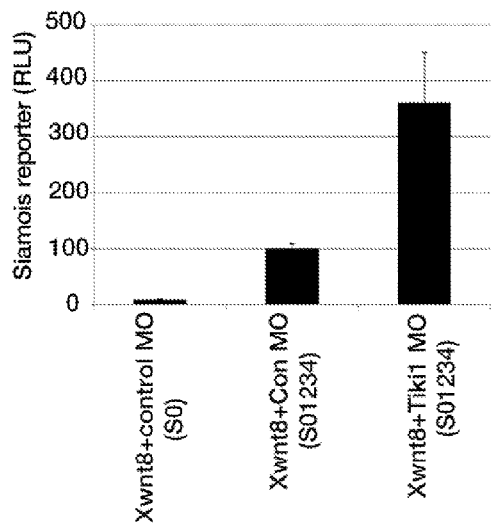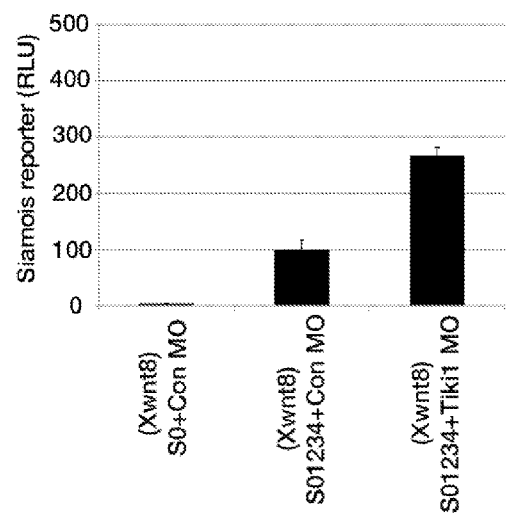
FIG. 7C  FIG. 7D
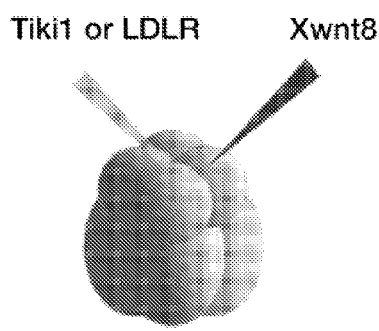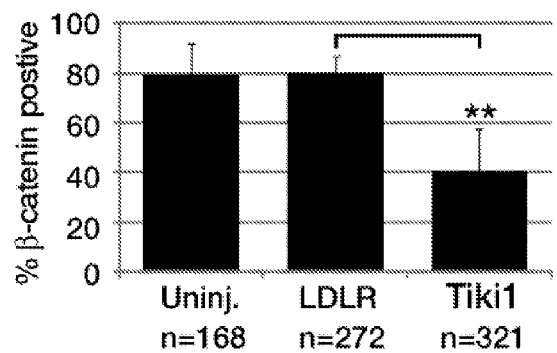
FIG. 7E  FIG. 7F

```
Wnt3A
LOCUS       AAI03924                 385 aa            linear   PRI 04-OCT-2006
DEFINITION  WNT3A protein [Homo sapiens].
ACCESSION   AAI03924
VERSION     AAI03924.1  GI:74355147
DBSOURCE    accession BC103923.1
TITLE       Generation and initial analysis of more than 15,000 full-length
            human and mouse cDNA sequences
JOURNAL     Proc. Natl. Acad. Sci. U.S.A. 99 (26), 16899-16903 (2002)
PUBMED      12477932
REFERENCE   2  (residues 1 to 385)

1 maplgyflll cslkqalgsy piwwslavgp qysslgsqpi lcasipglvp kqlrfcrnyv
 61 eimpsvaegi kigiqecqhq frgrrwnctt vhdslaifgp vldkatresa fvhaiasagv
121 afavtrscae gtaaicgcss rhqgspgkgw kwggcsedie fggmvsrefa darenrpdar
181 samnrhnnea grqaiashmh lkckchglsg scevktcwws qpdfraigdf lkdkydsase
241 mvvekhresr gwvetlrpry tyfkvpterd lvyyeaspnf cepnpetgsf gtrdrtcnvs
301 shgidgcdll ccgrghnara errekcrcv fhwccyvscq ectrvydvht cknpgsragn
361 sahqpphpqp pvrfhpplrr agkvp
```

FIG. 9B

```
LOCUS       BAB61052                 352 aa            linear   PRI 23-JUN-2001
DEFINITION  WNT3A [Homo sapiens].
ACCESSION   BAB61052
VERSION     BAB61052.1  GI:14530679
DBSOURCE    accession AB060284.1
AUTHORS     Saitoh,T., Hirai,M. and Katoh,M.
TITLE       Molecular cloning and characterization of WNT3A and WNT14 clustered
            in human chromosome 1q42 region
JOURNAL     Biochem. Biophys. Res. Commun. 284 (5), 1168-1175 (2001)
PUBMED      11414706

1 maplgyflll cslkqalgsy piwwslavgp qysslgsqpi lcasipglvp kqlrfcrnyv
 61 eimpsvaegi kigiqecqhq frgrrwnctt vhdslaifgp vldkatresa fvhaiasagv
121 afavtrscae gtaaicgcss rhqgspqkgw kwggcsedie fggmvsrefa darenrpdar
181 samnrhnnea grqaiashmh lkckchglsg scevktcwws qpdfraigdf lkdkydsase
241 mvvekhresr gwvetlrpry tyfkvpterd lvyyeaspnf cepnpetgsf gtrdrtcnvs
301 shgidgcdll ccgrghnara errekcrcv fhwccyvscq ectrvydvht ck L 26              S33/S34
                                   —                 ——
  1 maplgyflll cslkqalgsy piwwslavgp qysslgsqpi lcasipglvp kqlrfcrnyv
 61 eimpsvaegi kigiqecqhq frgrrwnctt vhdslaifgp vldkatresa fvhaiasagv
121 afavtrscae gtaaicgcss rhqgspqkgw kwggcsedie fggmvsrefa darenrpdar
181 samnrhnnea grqaiashmh lkckchglsg scevktcwws qpdfraigdf lkdkydsase
241 mvvekhresr gwvetlrpry tyfkvpterd lvyyeaspnf cepnpetgsf gtrdrtcnvs
301 shgidgcdll ccgrghnara errekcrcv fhwccyvscq ectrvydvht cknpgsragn
361 sahqpphpqp pvrfhpplrr agkvp
```

FIG. 9C

```
LOCUS       AAH74783                 381 aa            linear   PRI 18-AUG-2006
DEFINITION  WNT5A protein, partial [Homo sapiens].
ACCESSION   AAH74783
VERSION     AAH74783.2  GI:50959709
DBSOURCE    accession BC074783.2

1 plqksigils pgvalgmags amsskfflva laiffsfaqv vieanswwsl gmnnpvqmse
  61 vyiigaqplc sqlaglsqgq kklchlyqdh mqyigegakt gikecqyqfr hrrwncstvd
 121 ntsvfgrvmq igsretafty avsaagvvna msracregel stcgcsraar pkdlprdwlw
 181 ggcgdnidyg yrfakefvda rererihakg syesarilmn lhnneagrrt vynladvack
 241 chgvsgscsl ktcwlqladf rkvgdalkek ydsaaamrln srgklvqvns rfnspttqdl
 301 vyidpspdyc vrnestgslg tqgrlcnkts egmdgcelmc cgrgydqfkt vqterchckf
 361 hwccyvkckk cteivdqfvc k
```

FIG. 9D

```
Xwnt8

1 mqnttlfila tllifcpfft asawsvnnfl mtgpkaylty sasvavgaqn gieeckyqfa
  61 werwncpest lqlathnglr satretsfvh aissagvmyt ltrncsmgdf dncgcddsrn
 121 griggrgwvw ggcsdnaefg erisklfvdg letgqdaral mnlhnneagr lavketmkrt
 181 ckchgisgsc siqtcwlqla efrdignhlk ikhdqalkle mdkrkmrsgn sadnrgaiad
 241 afssvagsel ifledspdyc lknisglqg tegreclqsg knlsqwerrs ckrlctdcgl
 301 rveekkteii sscnckfhwc ctvkceqckq vvikhfcarr erdsnmlntk rknrghrr
```

FIG. 9E

MAPLGYLVLCSLKQALGYPYDVPDYASYPIWWSLAVGPQYSSLSTQPILCASIPGLVPKQLRFCRNYVEIMPSVAEGV
KAGIQECQHQFRGRRWNCTTVSNSLAIFGPVLDKATRESAFVHAIASAGVAFAVTRSCAEGSAAICGCSS
RLQGSPGEGWKWGGCSEDIEFGGMVSREFADARENRPDARSAMNRHNNEAGRQAIASHMHLKCKCHGLSG
SCEVKTCWWSQPDFRTIGDFLKDKYDSASEMVVEKHRESRGWVETLRPRYTYFKVPTERDLVYYEASPNF
CEPNPETGSFGTRDRTCNVSSHGIDGCDLLCCGRGHNARTERRREKCHCVFHWCCYVSCQECTRVYDVHT
CK

TIKI INHIBITORS

CLAIM OF PRIORITY

This Application is a National Stage Application under 35 USC §371 of International Application No. PCT/US2013/036422, filed Apr. 12, 2013, which claims the benefit of U.S. Provisional Patent Application Nos. 61/623,744, filed on Apr. 13, 2012, and 61/654,299, filed on Jun. 1, 2012. The entire contents of the foregoing are incorporated by reference herein.

FEDERALLY SPONSORED RESEARCH OR DEVELOPMENT

This invention was made with Government support under Grant Nos. RO1 GM057603; RO1 GM05760351, and RO1 AR60359-01 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Dec. 1, 2014, is named 37314-0019US1_SL.txt and is 152,875 bytes in size.

TECHNICAL FIELD

This invention relates to modulators of Wnt activity, e.g., Wnt enhancers, which act on TIKI proteins and inhibit TIKI-mediated cleavage of Wnt proteins, as well as methods of identifying such modulators and methods of use thereof.

BACKGROUND

Secreted morphogens such as the Wnt family of signaling proteins control animal development including axis formation, patterning and cell movements, and regulate adult tissue homeostasis, stem cell renewal and regeneration (Clevers, 2006; Logan and Nusse, 2004; MacDonald et al., 2009; Moon et al., 2004). Deregulation of Wnt signaling in humans causes birth defects, cancer, osteoporosis and other diseases (Clevers, 2006; Logan and Nusse, 2004; MacDonald et al., 2009; Moon et al., 2004). As prototypic morphogens Wnt proteins exhibit both short and long range signaling properties and govern the behavior of responding cells in a concentration gradient field (Hausmann et al., 2007; Strigini and Cohen, 2000; Zecca et al., 1996). The mechanism that regulates Wnt biogenesis and gradient formation has been intensively studied but not been fully understood. Critical for Wnt biogenesis and functions are post-translational modifications including N-glycosylation and lipidation, as have been best exemplified for the mouse Wnt3a protein (Komekado et al., 2007; Takada et al., 2006; Willert et al., 2003). O-acylation of a serine residue (S209) and N-glycosylation appear to be required for Wnt3a secretion (Komekado et al., 2007; Takada et al., 2006), whereas a distinct lipid modification, palmitoylation of a cysteine residue (C77), is important for Wnt3a activity (Willert et al., 2003). These modifications have profound influence on Wnt trafficking through the secretory pathway, extracellular transport/distribution and/or receptor binding (Cong et al., 2004; Franch-Marro et al., 2008; Komekado et al., 2007; Kurayoshi et al., 2007; Takada et al., 2006; Willert et al., 2003; Zhai et al., 2004). Whether Wnt proteins can be post-translationally modified and inactivated in development and/or tissue homeostasis is unknown.

Canonical Wnt signaling plays a central role in metazoan anterior-posterior (AP) patterning (De Robertis and Kuroda, 2004; Niehrs, 2004; Petersen and Reddien, 2009). Wnt engagement of a cell surface receptor complex composed of the serpentine Frizzled (Fz) receptor and the single-span LDL receptor-related protein 6 (LRP6) induces the stabilization of the transcription co-activator beta-catenin (He et al., 2004; MacDonald et al., 2009), thereby activating gene expression programs for AP patterning. A gradient of Wnt/beta-catenin signaling occurs along the AP axis, with the highest level posteriorly (Kiecker and Niehrs, 2001). In the *Xenopus* embryo the dorsal Spemann-Mangold Organizer promotes head/anterior development via secreting Wnt antagonists such as secreted Fz-related proteins (sFRPs) and Dickkopf-1 (Dkk1), which bind to and inhibit Wnt/Fz or LRP6 to create an anterior zone free of Wnt signaling (De Robertis and Kuroda, 2004; Harland and Gerhart, 1997; Niehrs, 2004).

SUMMARY

The present invention is based, at least in part, on the discovery that the organizer-specific transmembrane protein, Tiki1, and related Tiki2, act as inhibitors of Wnt signaling via proteolytic cleavage, oxidation and inactivation of Wnt ligands.

Thus, in some embodiments, the present invention provides antibodies or antigen-binding fragments thereof that bind to a TIKI protein, e.g., TIKI1, TIKI2, or TIKI1 and TIKI2, and inhibits TIKI-mediated cleavage of a Wnt protein.

In some embodiments, the antibodies or antigen-binding fragments thereof bind specifically to human TIKI1, human TIKI2, or both human TIKI1 and human TIKI2.

In some embodiments, the antigen-binding fragment comprises an F(ab), F(ab')2, or scFV fragment.

In some embodiments, the antibodies or antigen-binding fragments thereof inhibit cleavage of one or more of Wnt2B, 3, 3A, 4, 5A, 5B, 6, 7A, 7B, 8A, 8B, and/or 16, e.g., of Wnt3a, Wnt5a, or Wnt8.

In some embodiments, the antibodies or antigen-binding fragments thereof are chimeric, human or humanized.

In another aspect, the invention provides peptide antigens (e.g., comprising about 6, 8, 10, 12, 14, 16, 18, 20, 22, 24, 26, 28, 30, 32, 34, 36, 38, 40, 42, 44, 46, 48 or 50 amino acids) for use in generating antibodies that bind specifically to human TIKI1, TIKI2, or both TIKI1 and TIKI2, and inhibit TIKI-mediated cleavage of a Wnt, comprising amino acids corresponding to H58, E85, E205, or H331 of SEQ ID NO:2.

In some embodiments, the peptides comprise comprising amino acids corresponding to H58, E85, E205, or H331 of SEQ ID NO:2 plus 1, 2, 3, 4, 5, 6, 7, 8, 9, 10, 11, 12, 13, 14, 15, 16, 17, 18, 19, or 20, e.g., up to 25 amino acids on either side.

In another aspect, the invention provides methods for generating an inhibitory antibody that binds to TIKI1, comprising immunizing an animal with a peptide antigen described herein, and antibodies or antigen-binding fragments thereof that bind specifically to human TIKI1, TIKI2, or both TIKI1 and TIKI2, and inhibit TIKI-mediated cleavage of a Wnt, made by this method.

In another aspect, the invention provides antibodies or antigen-binding fragments thereof that bind specifically to human TIKI1, TIKI2, or both TIKI1 and TIKI2, and inhibit TIKI-mediated cleavage of a Wnt, that bind to an epitope comprising amino acids corresponding to H58, E85, E205, or H331 of SEQ ID NO:2, or 1, 2, 3, 4, 5, 6, 7, 8, 9, 10, 11, 12, 13, 14, 15, 16, 17, 18, 19, or 20, e.g., up to 25 amino acids on either side.

In another aspect, the invention provides methods of treating a subject having or at risk of developing a disorder associated with a loss of bone density, e.g., osteoporosis. The methods include administering to the subject an antibody or antigen-binding fragment thereof as described herein.

In some embodiments, the present invention provides a modulator of Wnt signaling wherein the modulator affects TIKI-mediated cleavage of a Wnt protein. In some aspects, the modulator is an antibody, a peptide, or a nucleic acid. In other aspects, the modulator is an inhibitor of TIKI cleavage. In further aspects, the inhibitor is an antibody, a small molecule or an inhibitory nucleic acid.

In some embodiments, the invention includes a method of identifying a modulator of TIKI-mediated cleavage of a Wnt protein. In some aspects, the method comprises providing a test mixture comprising a Wnt protein, a TIKI protein and a test compound and comparing the level of Wnt cleavage in the test mixture with the level of Wnt cleavage in an otherwise identical mixture not comprising the test compound, wherein a higher or lower level of Wnt protein cleavage in the test mixture compared with the level of Wnt protein cleavage in the otherwise identical mixture not comprising the test compound is an indication that the test compound is a modulator of TIKI-mediated cleavage of a Wnt protein.

In some embodiments, the present invention provides a method of identifying a modulator of TIKI-mediated cleavage of a Wnt protein. In some aspects, the method comprises contacting a cell expressing a Wnt protein and a TIKI protein with a test compound and comparing the level of Wnt cleavage in the cell with the level of Wnt cleavage in an otherwise identical cell not contacted with the test compound, wherein a higher or lower level of Wnt protein cleavage in the cell contacted with the test compound compared with the level of Wnt protein cleavage in the otherwise identical mixture not contacted with the test compound is an indication that the test compounds is a modulator of TIKI-mediated cleavage of a Wnt protein.

In some embodiments, the modulator is an inhibitor. In further aspects, the test compound is selected from the group consisting of an antibody, or antigen binding fragment thereof, a peptide, a small molecule, and an inhibitory nucleic acid.

In some embodiments, the level of Wnt cleavage is assessed using at least one of the methods selected from the group consisting of detecting Wnt signaling activity, detecting cleavage of at least one N-terminal amino acid of a Wnt protein, detecting increased mobility of the Wnt protein in a gel, detecting cleavage of the Wnt protein using liquid chromatography/mass spectometry (LC/MS), sequencing the Wnt protein, assessing the hydrophobicity of the Wnt protein using detergent partitioning, and detecting aggregation of the Wnt protein.

In some embodiments, the Wnt protein is selected from the group consisting of Wnt2B, 3, 3A, 4, 5A, 5B, 6, 7A, 7B, 8A, 8B, and 16; in some embodiments, the Wnt protein is Wnt3a.

In a further aspect, the invention provides methods for increasing Wnt signaling in a cell. In some aspects, the method comprises contacting the cell with an effective amount of a TIKI inhibitor wherein the inhibitor inhibits TIKI-mediated cleavage of the N-terminal portion of a Wnt protein, thereby increasing Wnt signaling in the cell.

In some aspects, the TIKI inhibitor is an antibody, or antigen binding fragment thereof, that specifically binds TIKI and inhibits TIKI cleavage of the N-terminal amino acids of the Wnt protein. In other aspects, the TIKI inhibitor is a small molecule that inhibits TIKI cleavage of the N-terminal amino acids of the Wnt protein. In further aspects, the Wnt protein is Wnt3a and the N-terminal amino acids comprise at least one sequence selected from the group consisting of SYPIWWSL (SEQ ID NO: 46), SYPIWWS-LAVGPQYS (SEQ ID NO: 47) and SYPIWWSLAVG-PQYSS (SEQ ID NO: 48). In other aspects, the Wnt protein is Xwnt8 and the N-terminal amino acids comprise at least one sequence selected from the group consisting of AWSVNNFLMTGPKAYLT (SEQ ID NO: 49) and AWSVNNFLMTGPKAYLTYSA (SEQ ID NO: 50).

The present invention provides a method of increasing Wnt signaling in a patient in need thereof. In some aspects, the method comprises administering a therapeutically effective amount of a TIKI inhibitor wherein the inhibitor inhibits TIKI-mediated cleavage of the N-terminal amino acids of a Wnt protein and thereby inhibits or prevents inactivation of the Wnt protein, thereby increasing Wnt signaling in the patient.

In some aspects, the TIKI inhibitor is an inhibitor of Tiki1, Tiki2, or Tiki1 and Tiki2, and further wherein the inhibitor is an antibody, or antigen binding fragment thereof, that specifically binds TIKI thereby inhibiting TIKI-mediated cleavage of the N-terminal amino acids of the Wnt protein.

The present invention provides a method of treating a disorder associated with reduced Wnt signaling. In some aspects, the method comprises administering a therapeutically effective amount of a TIKI inhibitor that inhibits cleavage by TIKI of the N-terminal amino acids of a Wnt protein and thereby inhibits or prevents inactivation of the Wnt protein, thereby increasing Wnt signaling and treating a disorder associated with reduced Wnt signaling.

The present invention provides a method of decreasing bone loss or resorption in a patient in need thereof. In some aspects, the method comprises administering a therapeutically effective amount of a TIKI inhibitor wherein the inhibitor inhibits cleavage by TIKI of the N-terminal amino acids of a Wnt protein and thereby inhibits or prevents inactivation of the Wnt protein, thereby increasing Wnt signaling and thereby decreasing bone loss or resorption. In some aspects, the TIKI inhibitor is selected from the group consisting of an antibody, or antigen binding fragment thereof that specifically binds TIKI, and an inhibitory nucleic acid. In yet another aspect, the inhibitory nucleic acid is selected from the group consisting of a siRNA, an antisense oligonucleotide, a ribozyme, and an aptamer.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 1A:
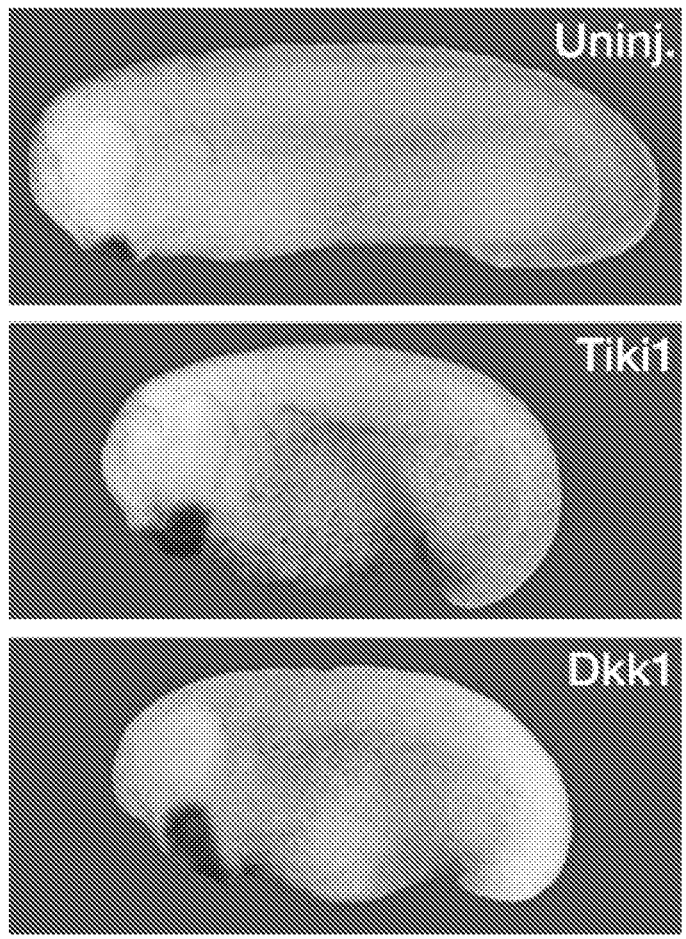
FIGS. 1A-G. Tiki1 promotes anterior development and specifically inhibits Wnt signaling.

(A) Dorsal injection of Tiki1 mRNA (100 pg) induced an enlarged head phenotype indistinguishable from that induced by Dkk1.

(B) Tiki1 schematic domain structure. SP, signal peptide; TM, transmembrane domain.

(C) Phylogenetic tree of Tiki proteins from human, *Xenopus*, zebrafish, *Nematostella, C. elegans* and *Amphimedon* based on ClustalW alignment (see FIG. 1H). The TIKI domain is also homologous to bacterial gumN (see FIG. 1I).

(D) Tiki1 inhibited Xwnt8-induced Xnr3 expression in animal caps. 2.5 or 5 pg of Xwnt8 mRNA was injected with or without 2 ng Tiki1 mRNA at the 2-cell stage, and animal caps were dissected at stage 9 for RT-PCR. EF-1alpha was a loading control. uninj: uninjected embryos; WE: whole embryos.

(E) Tiki1 (400 pg) inhibited axis duplication by Xwnt8 (10 pg) but not by constitutively activated LRP6ΔN (100 pg), Xdsh (1 ng) or beta-catenin (100 pg). Indicated mRNAs were injected into the ventral marginal zone at the 8-cell stage and the phenotype was scored at the tadpole stage. LDLR was used as a negative control. Numbers indicate embryos injected and scored.

(F) Tiki1 did not inhibit Nodal signaling. 5 or 10 pg of Xnr1 mRNA with or without 2 ng of Tiki1 mRNA were injected at the 2-cell stage and animal caps were dissected at stage 9 for RT-PCR.

(G) Tiki1 did not inhibit FGF signaling. 2 ng of Tiki1 mRNA were injected at the 2-cell stage. Animal caps were dissected at stage 8.5 from control or injected embryos, and treated with 100 or 500 ng/ml bFGF until stage 10 before RT-PCR.

FIG. 1H. ClustalW alignment of Tiki proteins from representative vertebrates, *Nematostella, C. elegans* and *Amphimedon*.

Protein sequences from NCBI: Human TIKI1 (Q86V40/LOC129293), Human TIKI2 (XP_371250/LOC388630), *C. elegans* (CAA94108/C05G5.5) and *Amphimedon queenslandica* (XP_003387010). Other proteins from *Xenopus tropicalis, Danio rerio* and *Nemostella vectensis* were derived from genomic sequences, and their cDNAs were isolated and deposited into GenBank. Black, grey, and light grey represent identical, conservative, and similar amino acid residues, respectively. GenBank accession numbers for nucleotide sequences, in order:

Human_TIKI1 JQ653415.1 (SEQ ID NO:1),
Xenopus_Tiki1 JQ653417.1 (SEQ ID NO:3),
Danio_Tiki1 JQ653419.1 (SEQ ID NO:4),
Human_TIKI2 JQ653416.1 (SEQ ID NO:2),
Xenopus_Tiki2 JQ653418.1 (SEQ ID NO:5),
Danio_Tiki2 JQ653420.1 (SEQ ID NO:6),
Nematostella_Tiki JQ653422 (SEQ ID NO:7),
C. elegans_Tiki JQ653421.1 (SEQ ID NO:8), and
Amphimedon_Tiki JQ653423.1 (SEQ ID NO:9).

Figure 1B:
Figure 1C:
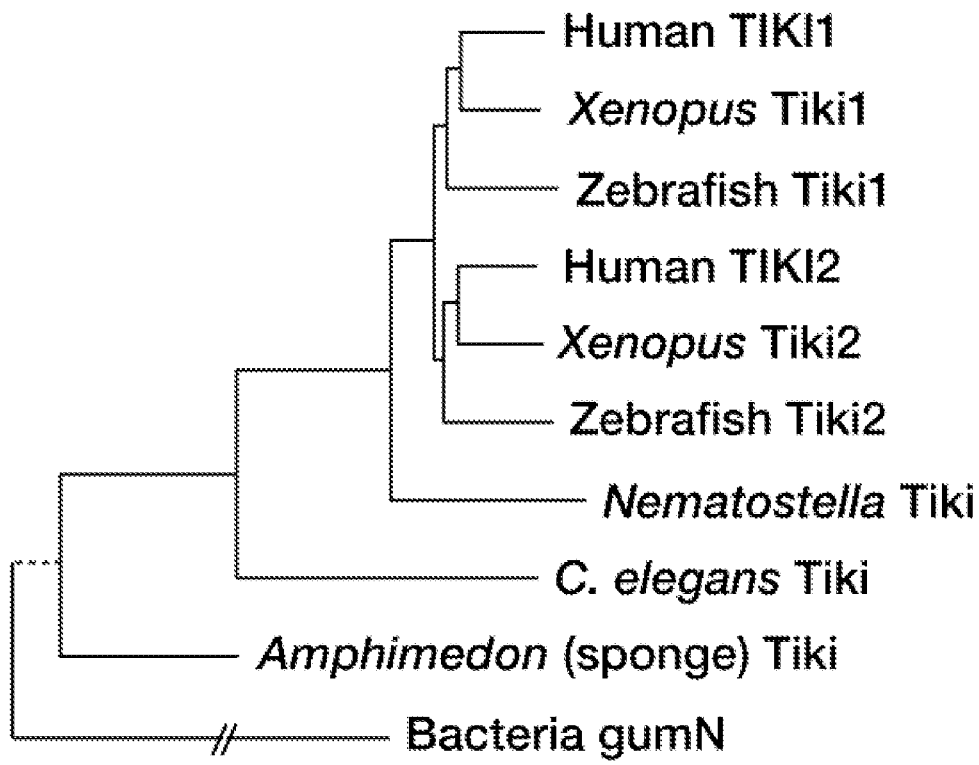
Figure 1D:
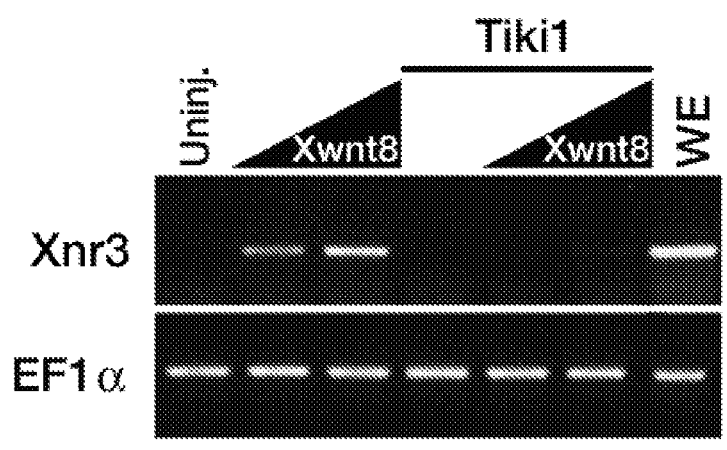
Figure 1E:
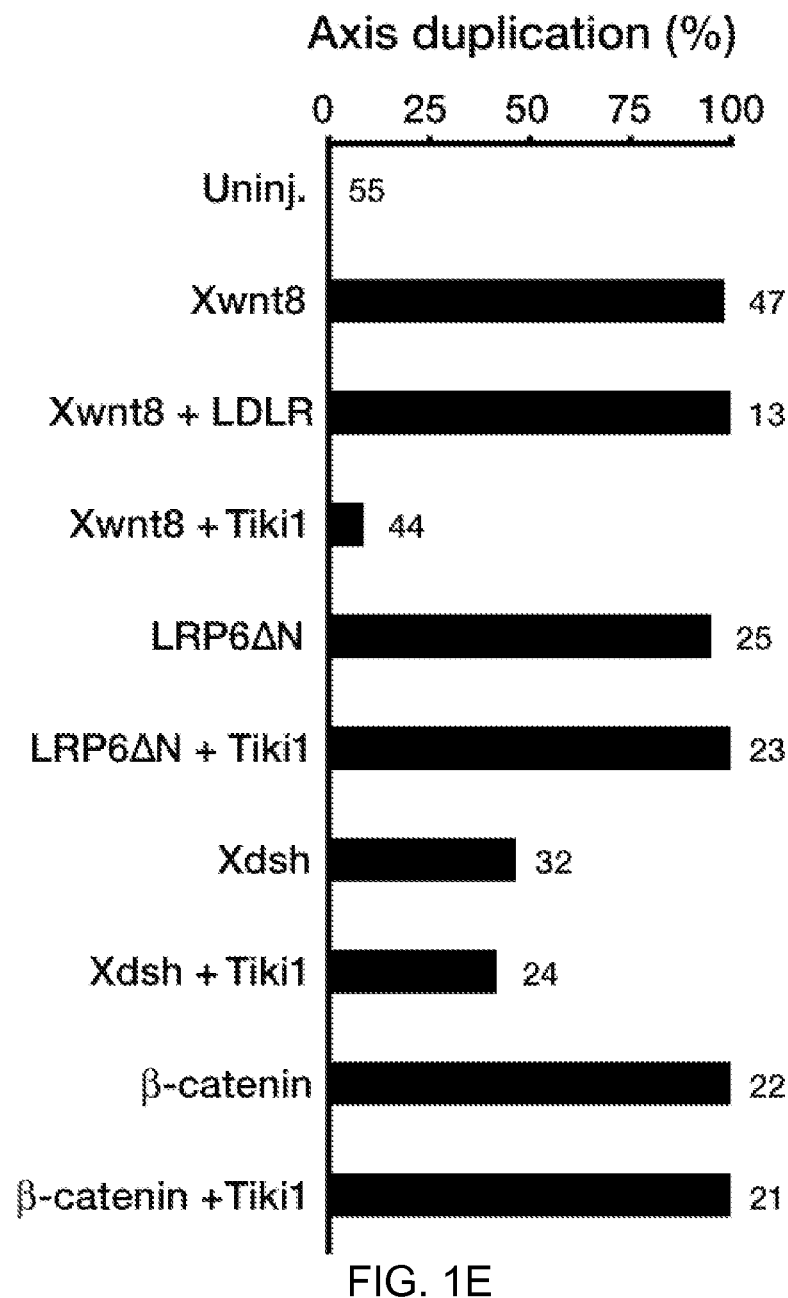
Figure 1F:
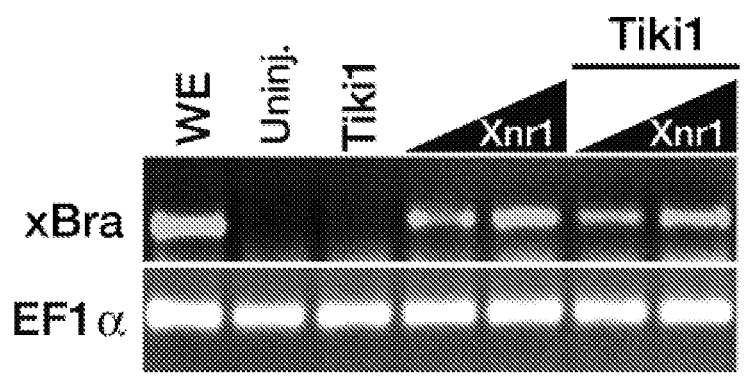
Figure 1G:
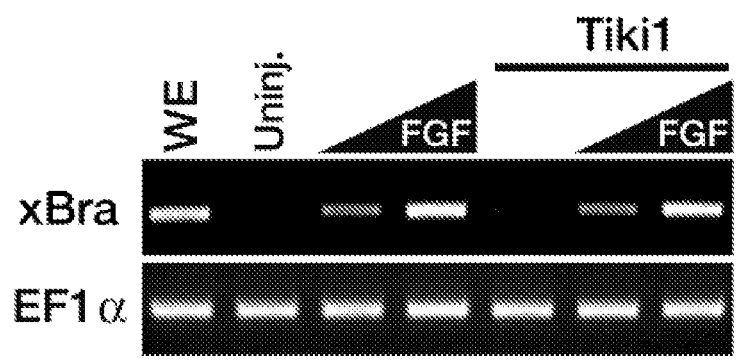
Figure 1H:
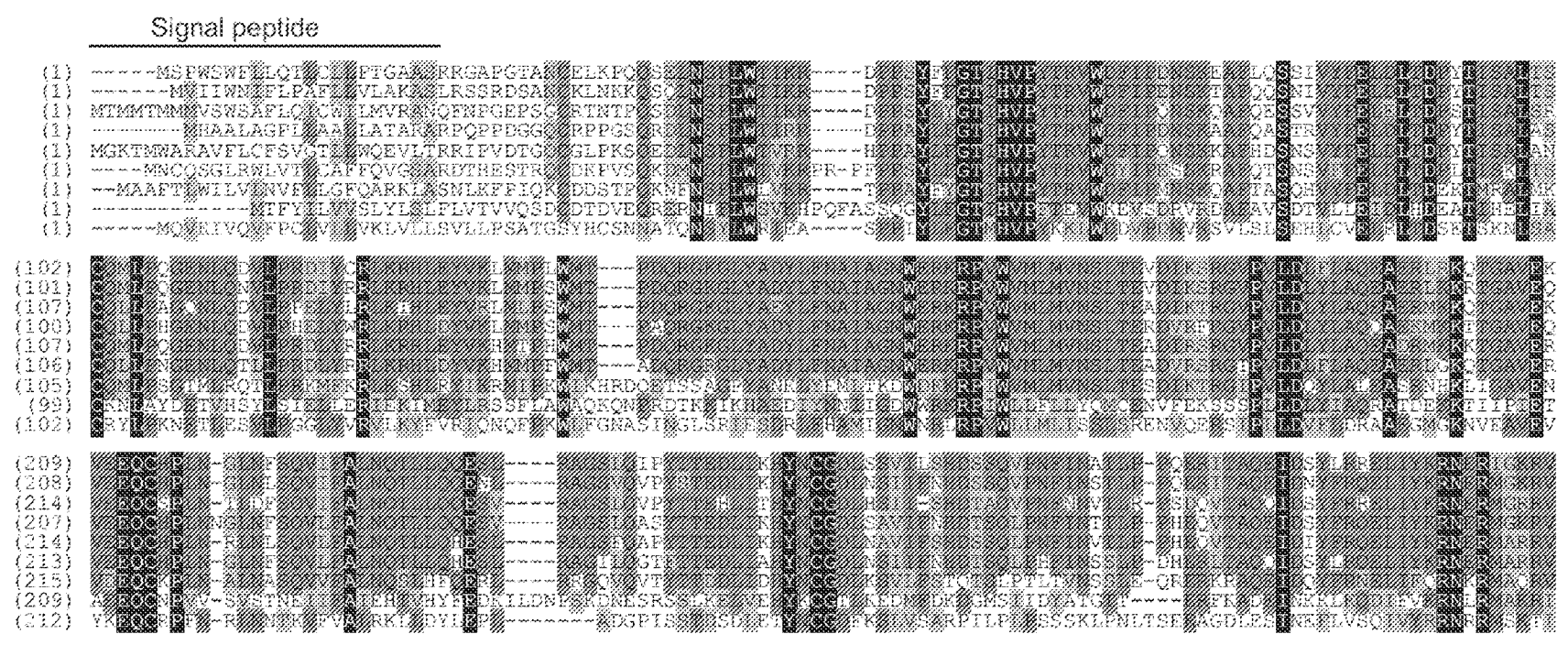
Figure 1H:
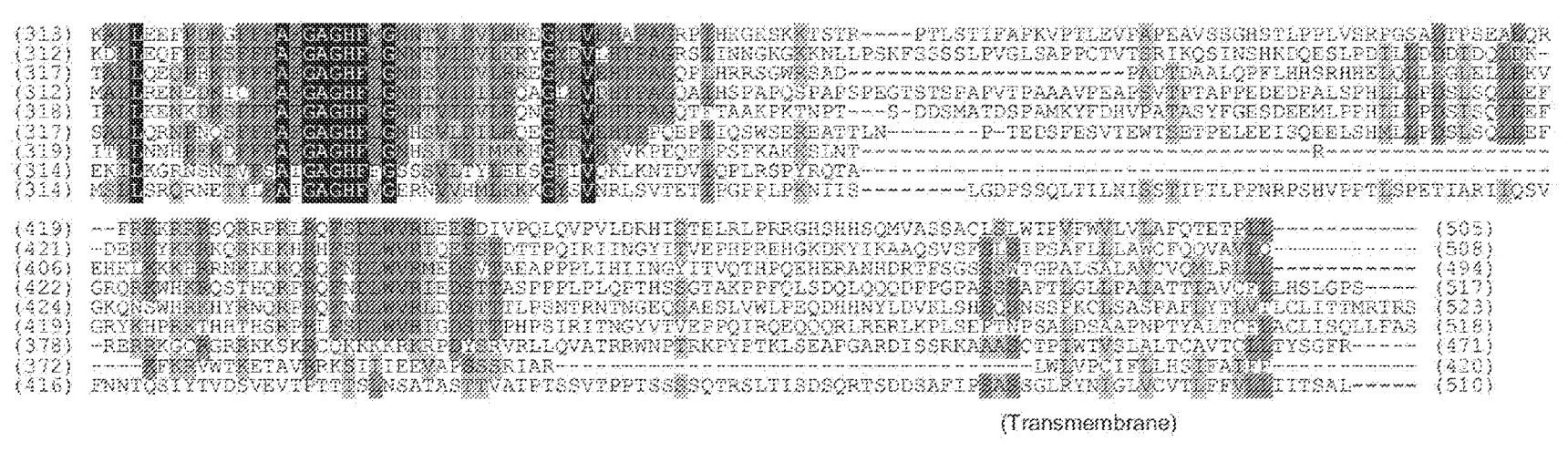
Figure 1I:
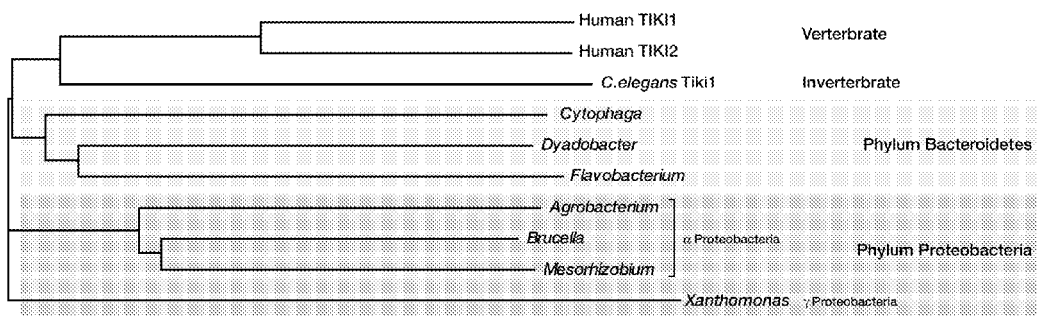
Figure 1J:
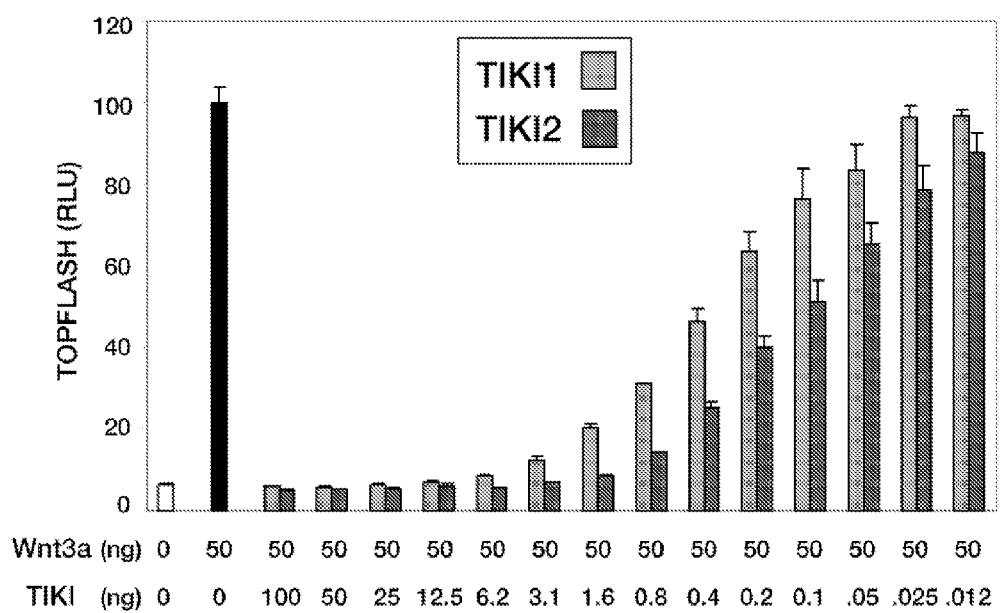
Figure 1K:
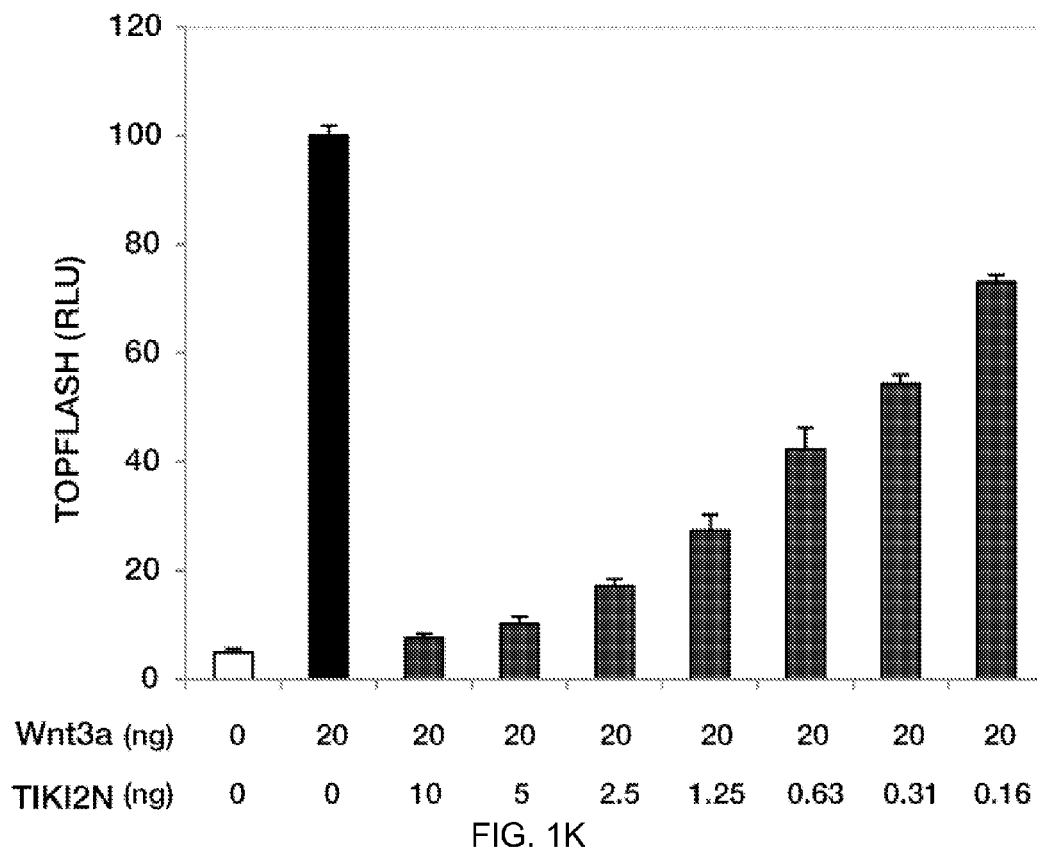

FIG. 1I-K. Tiki has bacterial homologs and inhibited Wnt signaling in mammalian cells.

(I) Phylogenetic tree showing homology between bacterial gumN proteins and Tiki proteins based on ClustalW. Highest similarities to human TIKI proteins were found in the phyla of bacteriorodates and proteobacteria (specifically α-proteobacteria). In α-proteobacteria *Xanthomonas*, the gumN gene is located near the characterized gum operon that is involved in xanthan gum biogenesis. However gumN is not required for xanthan gum biogenesis or secretion, and is absent or mutated in many *Xanthomonas* species, and thus is unlikely to be a part of the gum operon (Becker et al., 1998; Katzen et al., 1999; Lu et al., 2008). Therefore gumN, like the gumA, gumO and gumP ORFs near the *Xanthomonas* gum operon, likely represents a misnomer. In other species of bacteria, gumN-related genes are not located in any particular operons and are also of unknown functions. Therefore the "TIKI domain" represents a more appropriate name. Protein sequences used from NCBI: Human TIKI1 (Q86V40.3/LOC129293), Human TIKI2 (XP_371250.7/LOC388630), *C. elegans* (CAA94108.5/C05G5.5), *Cytophaga* (YP_678939.1), *Dyadobacter* (YP_0030877771.1), *Flavobacterium* (YP_001193165.1), *Agrobacterium* (YP_002545985.1), *Brucella* (NP_539064.1), *Mesorhizobium* (YP_675938.1), *Xanthomonas* (NP_637794.1).

(J, K) TIKI1, TIKI2 or TIKI2N each inhibited Wnt signaling in mammalian cells. The TOPFLASH reading (normalized to Renilla) in Wnt3a alone was set as 100. DNA transfection amounts are shown per well in a standard 24-well plate format. Representative data from one of three independent experiments is shown.

FIGS. 2A-M. Expression pattern and regulation of Tiki1 in early embryos (A) RT-PCR revealed that Tiki1 mRNA becomes detectable at stage 9 and is prominently expressed from stage 10 (early gastrula) to stage 30 (tadpole).

(B) Tiki1 is expressed dorsally. Stage 10 embryos were cut into four parts: animal, vegetal, dorsal and ventral, and used for RT-PCR. Xnr3 serves as a positive control.

(C to L) Whole mount in situ hybridization of Tiki1 and Dkk1 during gastrulation. Schematic drawing is on the right. C and D, vegetal view with dorsal on top; E and F, longitudinal hemi-section, dorsal on the right; G to L, dorsal view with anterior on top.

(M) Tiki1 expression is regulated by maternal Wnt signaling. Whole embryos were used for LiCl or UV treatment. 20 or 40 pg of Xwnt8 mRNA was injected into the ventral marginal zone (VMZ) at 4 to 8-cell stage and the VMZ was dissected at stage 10.5 for RT-PCR. ΔNTCF mRNA (1 or 2 ng) was injected into the dorsal marginal zone (DMZ) at 4 to 8-cell stage and the DMZ was dissected at stage 10.5 for RT-PCR. Con: control.

FIGS. 3A-D. *Xenopus* Tiki1 is required for anterior development/head formation.

(A) 500 pg mRNA for Tiki1-FLAG (targeted by MO) or HA*Tiki1 (resistant to MO) were injected with or without the Tiki1MO (5, 10, 20, 40 ng) into the animal pole at the 2-cell stage, and animal caps were dissected at stage 10 for Western blotting. MO, morpholino antisense oligonucleotide.

(B) Tiki1MO injection resulted in anterior/head defects, which were rescued by HA*Tiki1. 20 ng of control MO, Tiki1MO or Tiki1MO together with 50 pg of HA-Tiki1 mRNA was injected into two dorsal blastomeres at the 8-cell stage and the phenotype was scored at stage 42. Lateral view (left) and dorso-anterior view (right) are shown. Con, control.

(C) Statistical data of the Tiki1MO phenotype.

(D) Tiki1 is required for the head organizer. Mid-gastrula embryos (stage 10.5-11) were examined by whole mount in situ hybridization.

FIGS. 3E-I. Further characterization of Tiki1MO-injected embryos and Tiki1 inhibition of Xwnt8 expressed after mid-blastula transition.

(E) Dkk1 rescued the Tiki1MO phenotype. 20 ng of control MO, Tiki1MO, 50 pg Dkk1 mRNA, or Tiki1MO plus 50 pg of Dkk1 mRNA were injected into two dorsal blastomeres at the 8-cell stage, and the phenotype was scored at stage 30.

(F) Tiki1MO reduces Goosecoid expression in prechordal plate at stage 13. 20 ng of control MO, Tiki1MO or Tiki1MO plus 50 pg of HA*Tiki1 mRNA were injected into two dorsal blastomeres at the 8-cell stage. Injected embryos were subjected to whole mount in situ hybridization with the Gsc probe at stage 13 (dorsal view with anterior up). See Table 1 for statistical data.

(G) Tiki1MO reduced SO-specific Goosecoid expression at stage 11 but not prior to stage 10.5. Time course of Gsc expression was examined between stage 8.5 and 11. 20 ng of Tiki1MO or control MO was injected into two dorsal blastomeres at the 8-cell stage. After Injection embryos were cultured at 22° C. till indicated stages, and were subjected to whole mount in situ hybridization (vegetal view with dorsal up). See Table 2 for statistical data.

(H) Tiki1 inhibited Xwnt8 when both were expressed via injected plasmids. 100 pg of the CS107+Tiki1 plasmid were injected into two dorsal blastomeres of a 4-cell stage embryo followed by injection of 40 pg CS2+Wnt8 plasmids into the same dorsal blastomeres. Dorsal injection of the CS2+ plasmid was used as control. Anterior defects were scored at stage 40. Control (Co) embryos (Un-injected or CS2-injected) displayed normal head containing eyes and cement gland (97%, n=65). CS2+Wnt8-injected embryos display anterior defects as loss of brain, eyes and cement gland (100%, n=19) as previously reported. CS2+Wnt8 and CS107+Tiki1 co-injected embryos displayed head containing eyes and the cement gland (62.5%, n=16). CS107+Tiki1-injected embryos display enlarged head with eyes and the cement gland (100%, n=15). Statistical data of anterior deficiency phenotypes are shown in the graph. Ant def, Anterior deficiency.

(I) Tiki1 is required for anterior neural patterning. 20 ng of control MO or Tiki1MO plus fluorescein dextran (FLD, as a lineage tracer) were injected into one dorsal blastomere at the 8-cell stage. 50 pg of HA*Tiki1 mRNA were injected into the dorsal-animal blastomeres at the 4-cell stage in rescue experiments. Injected embryos were collected at stage 16 and subjected for whole mount in situ hybridization. Expression of forebrain markers BF1 and Otx2 (not shown) and the midbrain marker Ent was reduced in the Tiki1MO-injected half and was rescued by HA*Tiki1. See Table 3 for statistical data.

FIGS. 4A-J. Tiki proteins inactivate Wnt3a.

(A) Quantitative RT-PCR showing the relative expression level of TIKI1 and TIKI2 mRNA in HEK293T cells. TIKI1 and TIKI2 mRNA levels were normalized to that of beta-actin and the TIKI2 level was set as 1. Note that TIKI2 mRNA level is over 30 times more than that of TIKI1.

(B) Knocking down the endogenous TIKI2 in HEK293T cells enhanced Wnt3a activity. Wnt3a was co-transfected with indicated control (con) or TIKI2 siRNA and TOPFLASH reporter activities were examined 48 hrs post transfection. Note that the enhancement of Wnt3a activity was correlated with the knockdown efficiency of each TIKI2 siRNA.

(C) Quantitative RT-PCR analysis showing the siRNA knockdown efficiency of TIKI2 mRNA in HEK293T cells 48 hrs after the siRNA transfection, as normalized to beta-actin levels.

(D) Tiki2 knockdown effect was countered by TIKI1 expression.

(E) HeLa cells expressing HA-TIKI1 or HA-TIKI2 were labeled by a cell non-permeable biotinylation reagent. Cell surface (CS) proteins were precipitated with streptavidin agarose beads and subjected to Western blotting. Input whole cell lysates (WCL) were also analyzed. HA-TIKI proteins exhibited two forms. The slower migrating form was enriched on the cell surface, and might be more extensively glycosylated.

(F) TIKI2 inhibited beta-catenin stabilization in Wnt3a-expressing cells. Indicated L cell lines were also treated with control or Wnt3a CM for 2 hrs (lanes 3 and 4) and WCL were subjected to Western blotting. Beta-tubulin represents a loading control.

(G) Wnt3a was secreted similarly in the presence or absence of TIKI2, but exhibited faster electrophoretic migration. CM or WCL were analyzed by Western blotting.

(H) Wnt3a produced from TIKI2-expressing L cells exhibited minimal activity in activation of TOPFLASH reporter expression, tested at multiple concentrations in 2-fold sequential dilutions.

(I) Wnt3a produced from TIKI2-expressing L cells induced minimal LRP6 or Dvl2 phosphorylation, or beta-catenin stabilization. L cells were treated with control CM or increasing amounts of Wnt3a CM for 2 hrs, and WCL and the input Wnt3a CM were analyzed by Western blotting. Note that LRP6 protein levels were not altered upon Wnt3a treatment. The apparent intensity reduction of the LRP6 band was due to LRP6 phosphorylation, which perturbed recognition by the antibody raised against the LRP6 cytoplasmic domain (Tamai et al., 2004).

(J) Wnt3a secreted from TIKI2-expressing cells exhibited minimal binding to either Fz8 or LRP6. Wnt3a CM was incubated with LRP6N-IgG or mFz8CRD-IgG. The protein complexes were precipitated by protein G agarose and subjected to Western blotting.

FIGS. 4K-R. TIKI modification of Wnt3a is independent of lipidation or N-glycosylation.

(K) Western blotting shows that TIKI2 siRNAs reduced TIKI2-FLAG, but not HA-TIKI1, protein expression to different degrees. TIKI2-FLAG and HA-TIKI1 were co-transfected with control or individual TIKI2 siRNA and WCL were subjected to Western blotting 48 hrs post transfection.

(L) Wnt3a secreted from TIKI1- or TIKI2-expressing HEK293T cells exhibited faster electrophoretic migration. Note that ectopic TIKI1 protein expression was poorer than that of TIKI2.

(M) Wnt3a secreted from TIKI1- or TIKI2-expressing HEK293T cells partitioned exclusively in the aqueous phase.

(N) Tiki did not significantly affect Wnt3a acylation (C77 palmitoylation plus S209 O-acylation). Mock HEK293T cells or HEK293T cells expressing Wnt3a alone or Wnt3a together with TIKI2 were metabolically labeled by a palmitic acid analog az-15 and $^{35}$S-Methione/Cysteine. Wnt3a in the CM was enriched by immunoprecipitation and acylated Wnt3a with az-15 incorporation was detected via reacting with alk-Rho (Rhodamine) through a "click chemistry" reaction, followed by SDS-PAGE and in gel fluorescence scanning. The same gels were subjected to autoradiography to show the total Wnt3a protein ($^{35}$S-labeled). No significant alterations in Wnt3a acylation with or without TIKI2. Note that this data was largely identical to that in FIG. 5B, except that a different palmitic acid analog was used for metabolic labeling.

(O) Wnt3a or Wnt3a(C77A) CM from control KRM2N- or TIKI2N-expressing cells was analyzed by SDS-PAGE and western blotting before or after PNGF treatment (to remove N-glycosylation). The slower mobility of Wnt3a (C77A) from TIKI2-expressing cells (lane 4) was due to altered N-glycosylation likely as a secondary consequence of TIKI2 modification, as it was abolished by PNGF treatment (lane 8). KRM2N was used as a negative control and is the secreted ectodomain of the single transmembrane protein Kremen2.

(P) Wnt3a mutants deficient in N-glycosylation (N87Q/N298Q) or lipidation (C77A/S209A) showed faster migration on SDS-PAGE gel when co-expressed with TIKI2N. Because neither Wnt3a(N87Q/N298Q) nor Wnt3a(C77A/S209A) was secreted, WCL was used for Western blotting. Wnt3a(N87Q/N298Q) migrated faster in SDS-PAGE due to a lack of N-glycosylation (Komekado et al., 2007).

(Q) TIKI2 inhibited TOPFLASH reporter induced by Wnt3a(C77A) autocrine signaling. Different concentrations (in a 2-fold dilution series) of the TIKI2 expression vector were co-transfected with the expression vector for Wnt3a or Wnt3a(C77A), which exhibited some but weaker activity that was inhibited by TIKI2.

(R) Wnt3a amino-terminal deletion mutants (Δ19-43 and Δ19-144), but not a carboxyl terminal deletion mutant (Δ271-352), appear to be resistant to TIKI modification. Mature Wnt3a protein (after cleavage of the signal peptide) starts at amino acid 19. Wnt3a or its deletion mutant was each co-expressed with KRM2N or TIKI2N in HEK293T cells and the WCL were analyzed by SDS-PAGE and Western blotting. Wild type Wnt3a and the Δ271-352 deletion mutant migrated faster in the presence of TIKI2N, but the migration of neither Δ19-43 nor Δ19-144 deletion mutant was affected by TIKI2N.

Figure 5A:
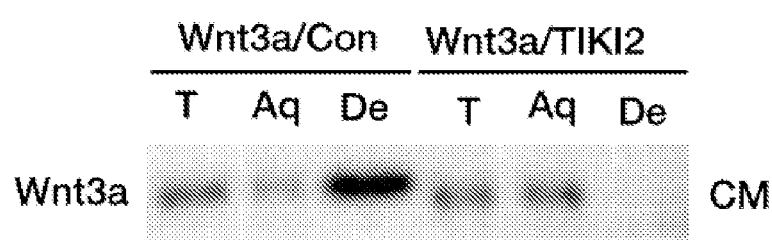
Figures 5B, 5C:
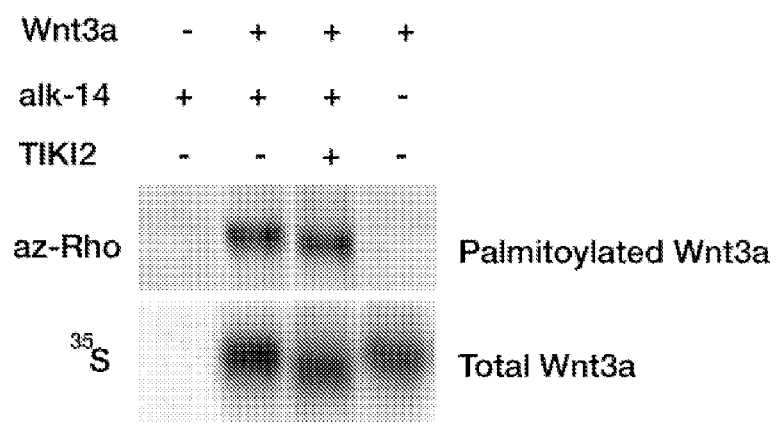
Figure 5D:
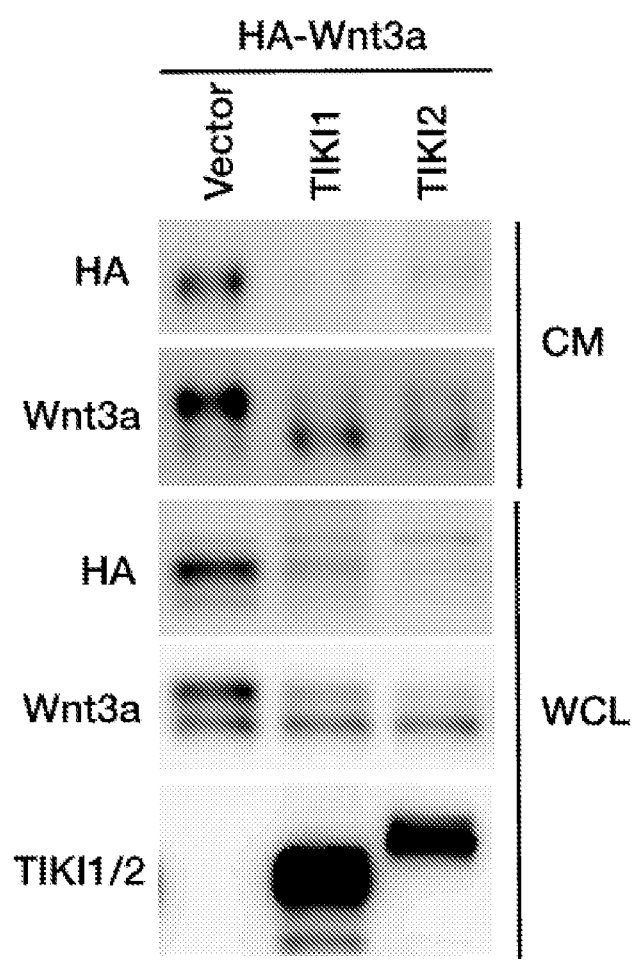
Figure 5E:
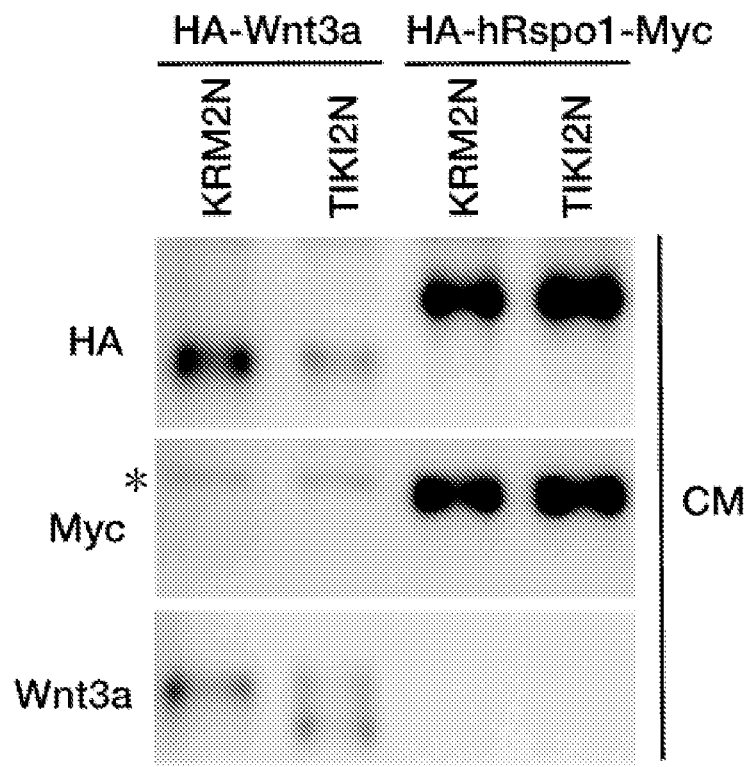
Figure 5F:
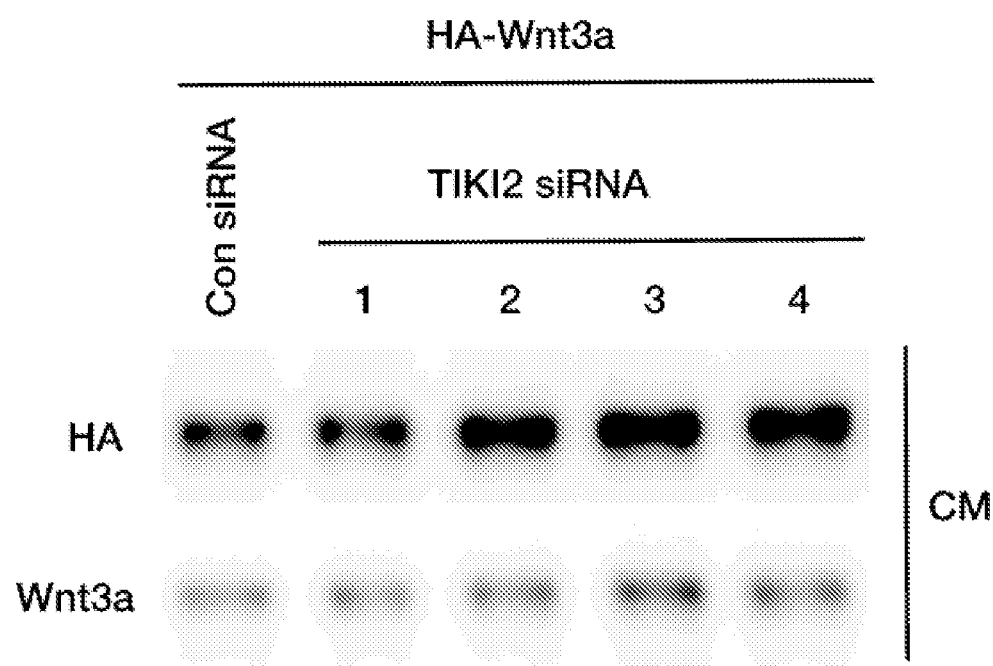
Figure 5G:
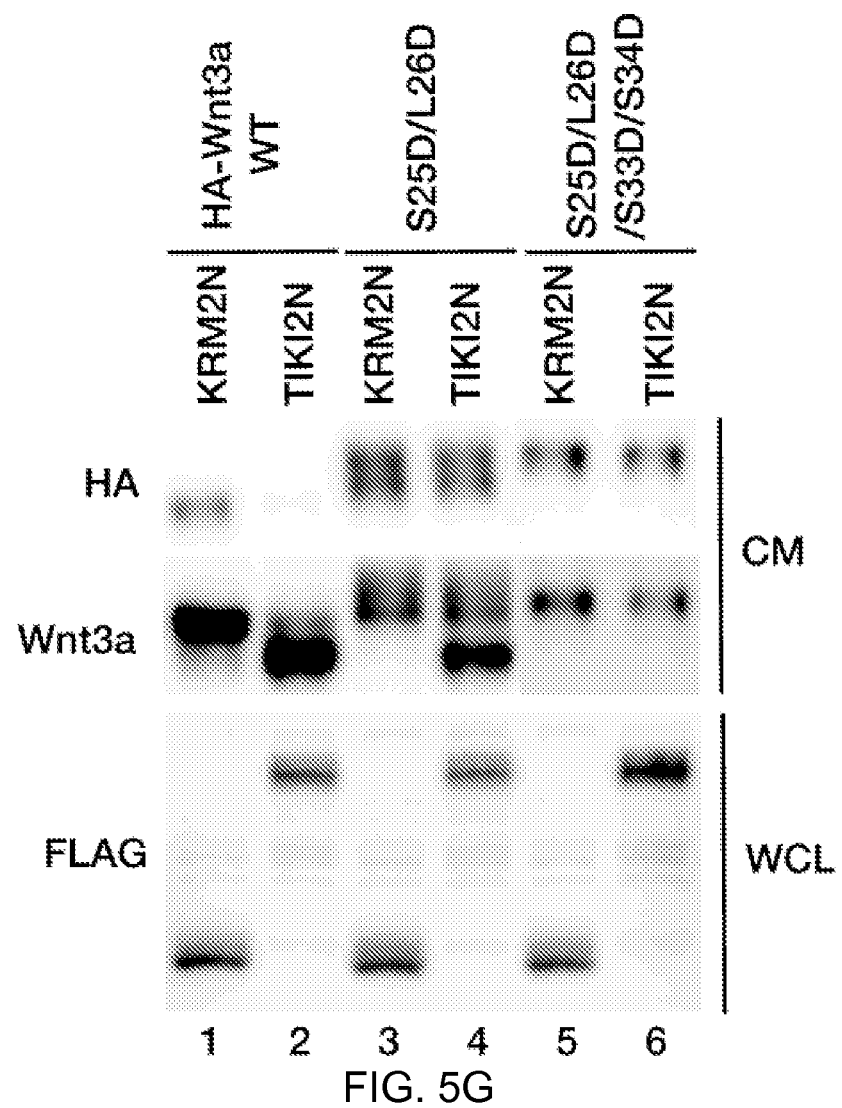
Figure 5H:
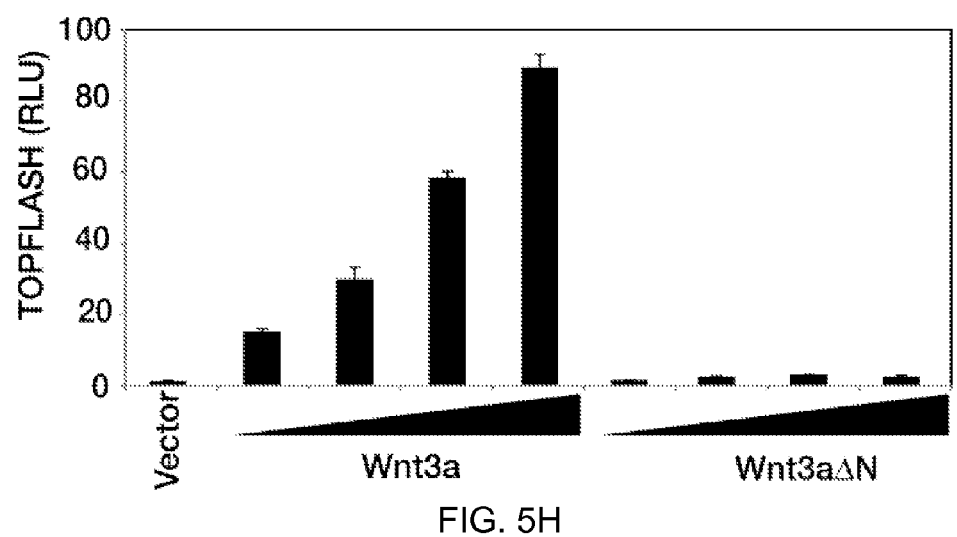
Figure 5I:
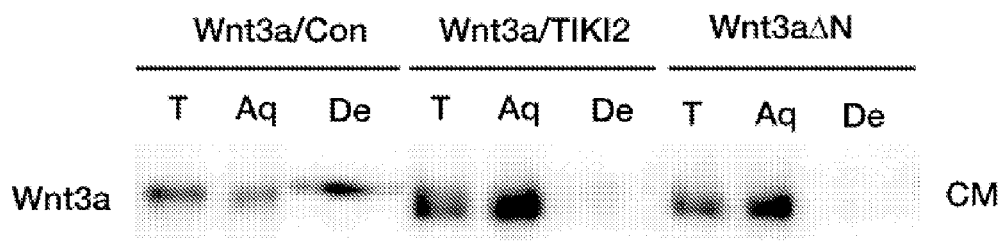
Figures 5J, 5K:
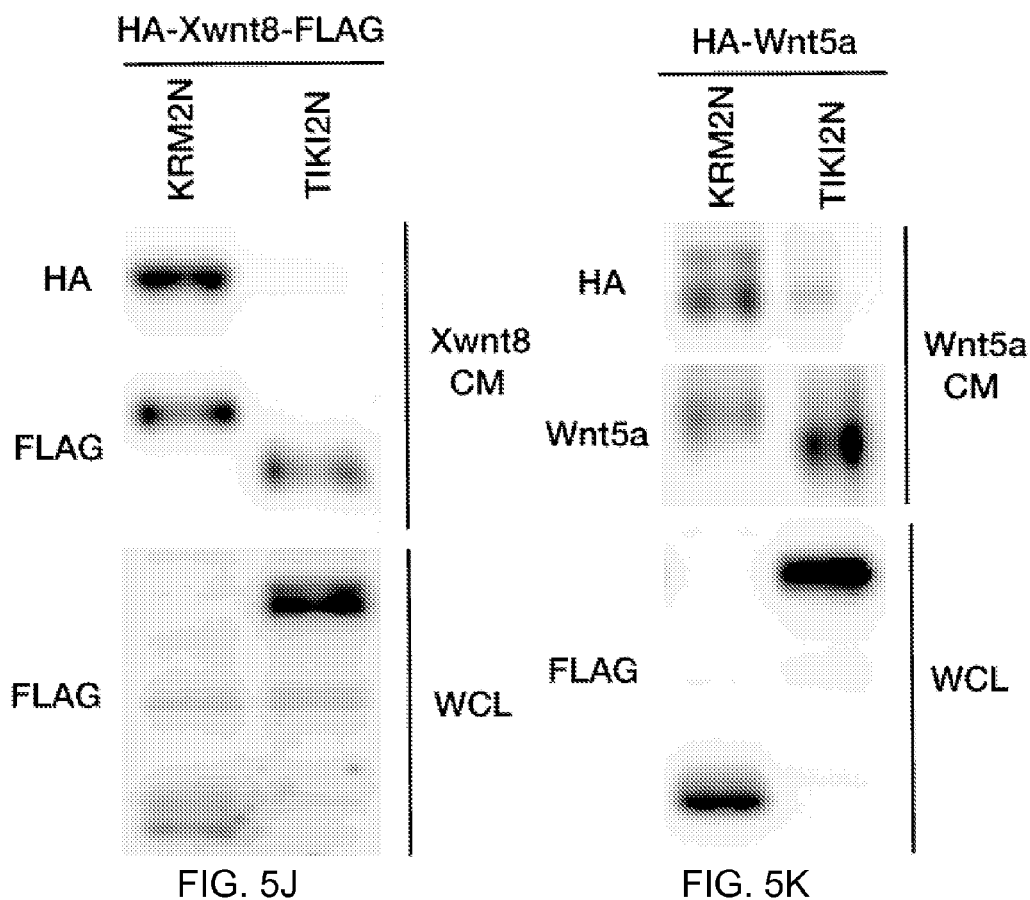
Figure 5L:
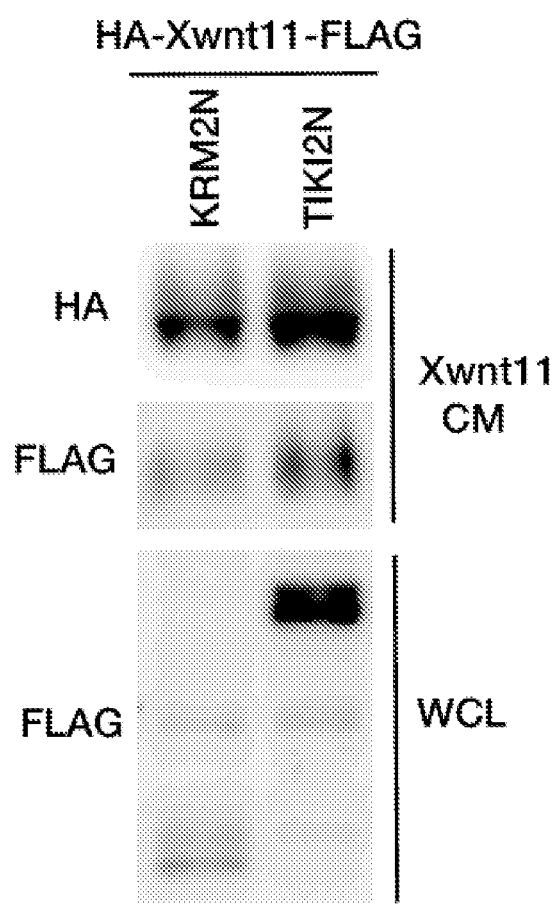
Figure 5M:
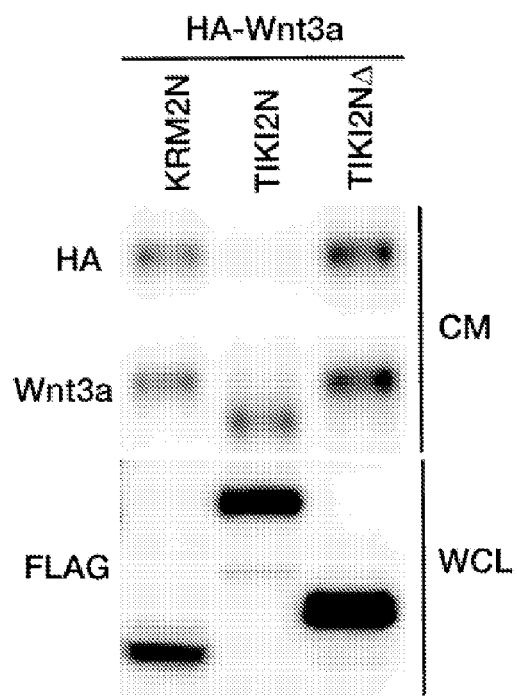
Figure 5N:
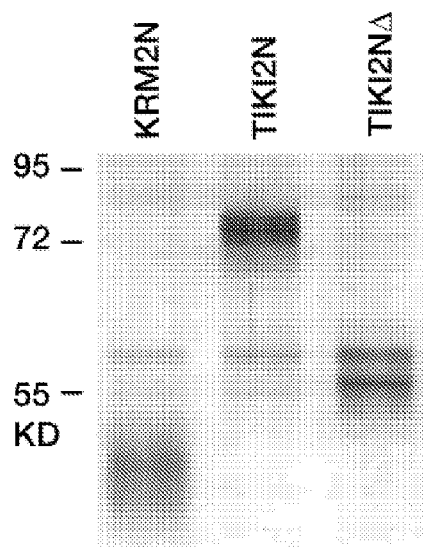
Figure 5O:
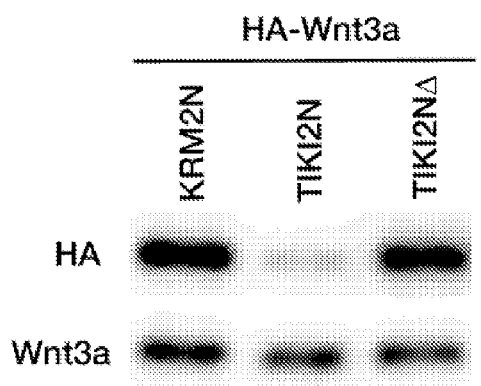
Figure 5P:
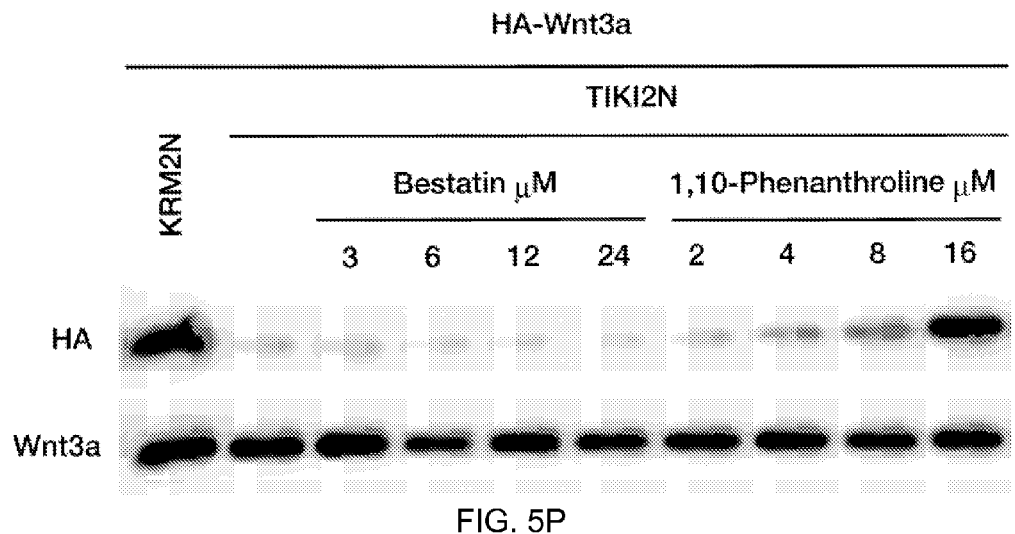
Figure 5Q:
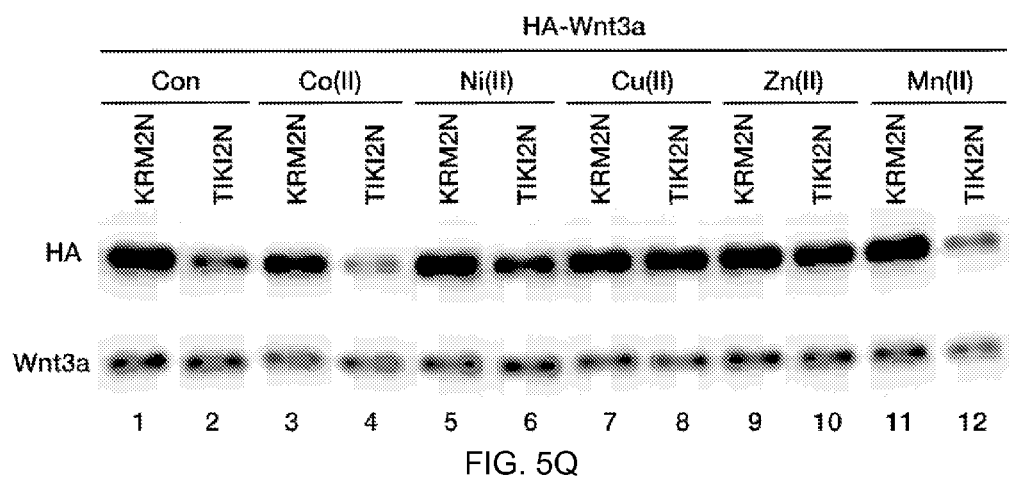
Figure 5R:
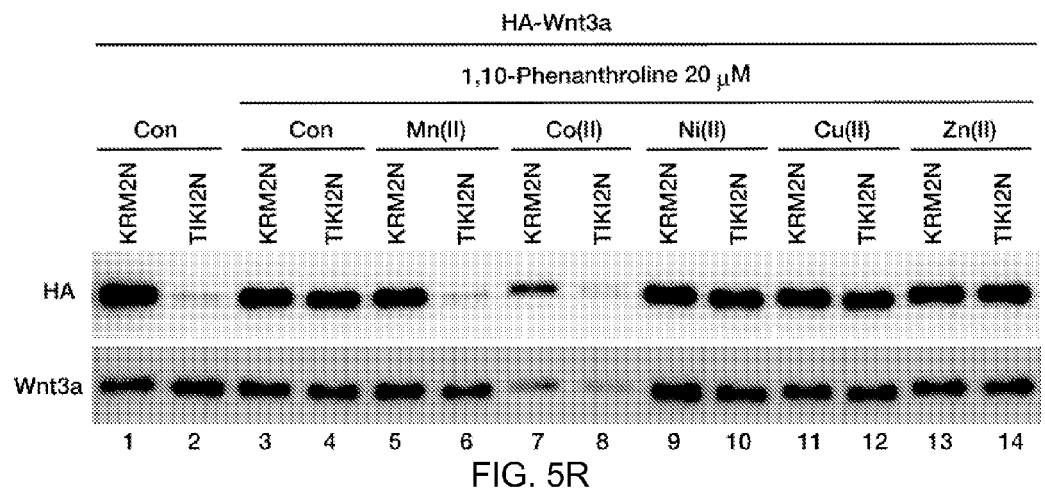

FIGS. 5A-R. Tiki inactivates Wnt3a via amino-terminal cleavage.

(A) Triton X-114 phase separation assay. Wnt3a from control cells mainly partitioned in the detergent (De) phase, but Wnt3a secreted from TIKI2-expressing cells partitioned exclusively in the aqueous (Aq) phase. T, total.

(B) Tiki did not significantly affect Wnt3a acylation (C77 palmitoylation plus S209 O-acylation). Mock HEK293T cells or HEK293T cells expressing Wnt3a alone or Wnt3a together with TIKI2 were metabolically labeled by a palmitic acid analog alk-14 and $^{35}$S-Methione/Cysteine. Wnt3a in the CM was enriched by immunoprecipitation and acylated Wnt3a with alk-14 incorporation was detected via reacting with az-Rho (Rhodamine). The same gels were subjected to autoradiography to show the total Wnt3a protein ($^{35}$S-labeled).

Figure 5S:
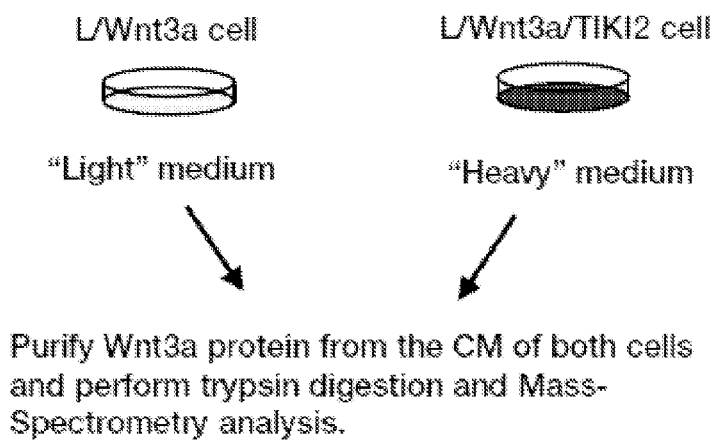
Figure 5T:
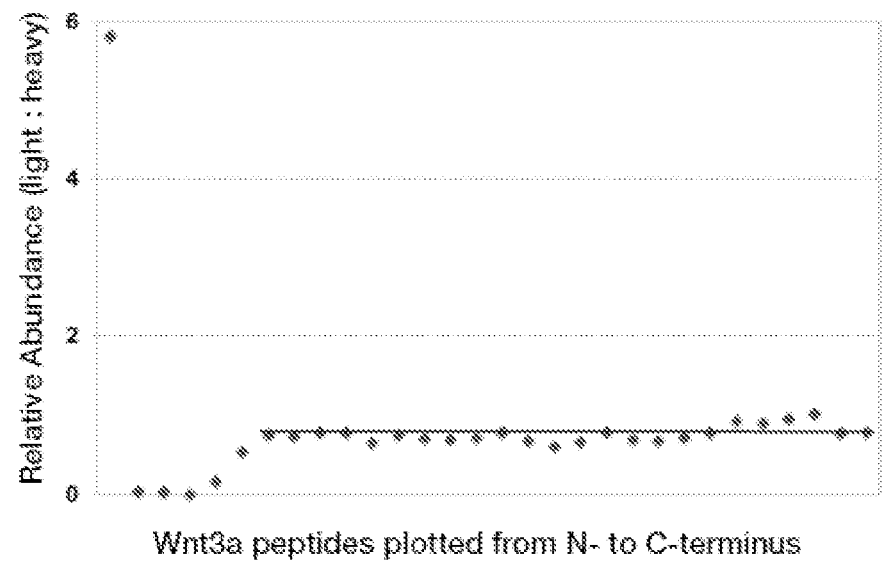
Figure 5U:
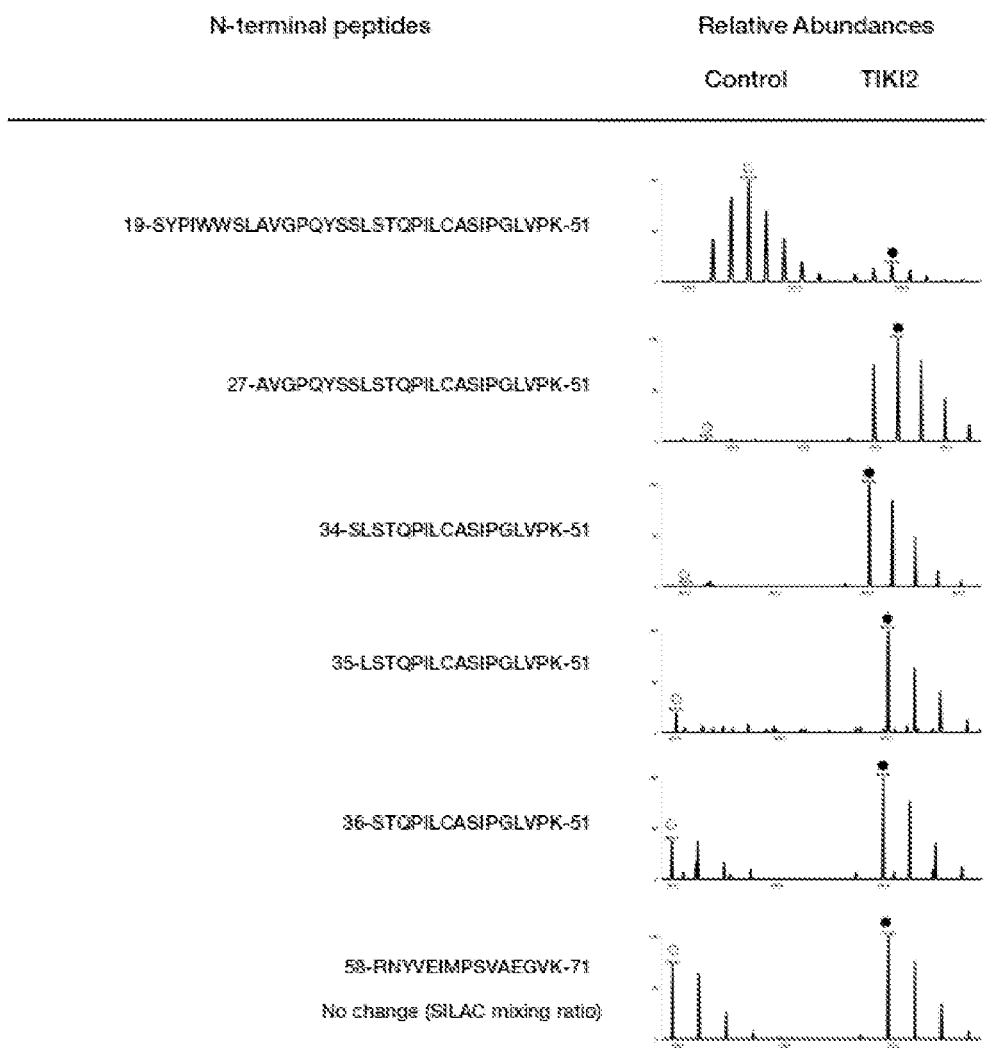

(C) Edman sequencing and/or mass spectrometry analysis indicated amino-terminal cleavage of Wnt3a and Xwnt8 in the presence of TIKI2. The top sequence shows the control Wnt3a sequence (SEQ ID NO:10); the middle sequence is Wnt3a after cleavage by TIKI2 (SEQ ID NO:11); the bottom sequence is from Xwnt8 (SEQ ID NO:12). The big arrowheads indicate the major cleavage site and small arrowheads indicate two additional minor cleavage sites in Wnt3a revealed by quantitative mass spectrometry (FIGS. 5S-U). Wnt3aΔN was engineered to be identical to TIKI-cleaved Wnt3a.

(D) TIKI modified Wnt3a by amino-terminal cleavage. Wnt3a with an amino-terminal HA tag was co-expressed with TIKI1 or TIKI2 (HA tagged) and CM or WCL was analyzed by Western blotting. The TIKI1 cDNA vector was transfected at a 10-fold higher dose than that of TIKI2.

(E) TIKI did not cleave R-spondin1. HA-Wnt3a or HA-hRspo1-Myc was co-expressed with KRM2N or TIKI2N and CM were analyzed by Western blotting. * marks a cross-reactive band in the Myc blot.

(F) Endogenous TIKI2 cleaved Wnt3a. HA-Wnt3a was co-expressed with control or individual TIKI2 siRNAs into HEK293T cells and CM were analyzed by Western blotting.

(G) Wnt3a mutants harboring cleavage site mutations are partially or completely resistant to TIKI cleavage. HA-Wnt3a, Wnt3a(S25D/L26D), or Wnt3a(S25D/L26D/S33D/S34D) was co-expressed with KRM2N or TIKI2N and CM or WCL was analyzed by Western blotting. Wnt3a (S25D/L26D) was partially resistant to TIKI2N as a lower band was observed in the Wnt3a blot in the presence of TIKI2N (lane 4), and Wnt3a(S25D/L26D/S33D/S34D) was completely resistant to TIKI2N (lane 6). The two mutants exhibited altered mobility compared to Wnt3a.

(H) Wnt3aΔN was inactive as examined by transfection in a 2-fold dilution series in TOPFLASH reporter assays.

(I) Wnt3aΔN in CM partitioned exclusively in the aqueous (Aq) phase.

(J) TIKI cleaved Xwnt8. HA-Xwnt8-FLAG was co-expressed with KRM2N or TIKI2N and CM or WCL were analyzed by Western blotting. Levels of KRM2N and TIKI2N (both FLAG-tagged) were monitored.

(K) TIKI cleaved Wnt5a. HA-Wnt5a was co-expressed with KRM2N or TIKI2N and CM or WCL were analyzed by Western blotting.

(L) TIKI did not cleave Xwnt11. HA-Xwnt11-FLAG was co-expressed with KRM2N or TIKI2N and CM or WCL were analyzed by Western blotting.

(M) Wnt3a was cleaved at the amino-terminus by (FLAG-tagged) TIKI2N, but not by KRM2N or TIKI2NΔ, co-expressed in HEK293T cells.

(N) Silver staining of purified KRM2N, TIKI2N or TIKI2NΔ used for the in vitro.

(O) TIKI2N cleaved Wnt3a in vitro. Recombinant HA-Wnt3a was incubated in vitro with KRM2N, TIKI2N or TIKI2NΔ purified from HEK293T cells, and the reaction product was subjected to Western blotting.

(P) TIKI2N activity was sensitive to 1, 10-Phenanthroline but not to Bestatin. Note that 16 μM of 1, 10-Phenanthroline was about 100 times lower than manufacturer's recommended doses.

(Q) Effects of divalent metals on TIKI2N activity. 50 μM of each divalent metals ion was applied in the in vitro reaction and incubated for 2 hrs. TIKI2N activity was enhanced by $Co^{2+}$ and $Mn^{2+}$, and was inhibited by $Ni^{2+}$, $Cu^{2+}$ and $Zn^{2+}$.

(R) Rescue of TIKI2N activity with divalent metals after inhibition with 1, 10-Phenanthroline. 20 μM of 1, 10-Phenanthroline was firstly applied in the in vitro reaction for 1 hr and 50 μM of each metal ion was added and incubated for another 2 hrs. TIKI2N activity was rescued by $Co^{2+}$ and $Mn^{2+}$ (lanes 6 and 8).

FIGS. 5S-U. Quantitative mass spectrometric analysis of control Wnt3a and TIKI2-modified Wnt3a.

(S) Description of the combined SILAC and Wnt3a purification strategy.

(T) The relative Wnt3a peptide abundance without (light) and with (heavy) TIKI2 co-expression. The mean ratio (red line) of light-to-heavy is a reflection of SILAC sample mixing, and indicates no change in peptide status with or without TIKI2 along most of the Wnt3a protein except for the amino terminus, where the mean ratio dropped precipitously.

(U) Mass Spectra and relative peak abundance of amino-terminal light and heavy Wnt3a peptides. The relative peak heights of light (grey circle) versus heavy (black circle) peptides indicate amino-terminal processing induced by TIKI2. Specifically peptide 19-51 was not observed in Wnt3a from TIKI2-expressing cells, but shorter versions were observed as presented. See Table 4 for primary spectrometry data. FIG. 5U discloses SEQ ID NOS 78-83, respectively, in order of appearance.

Figure 5V:
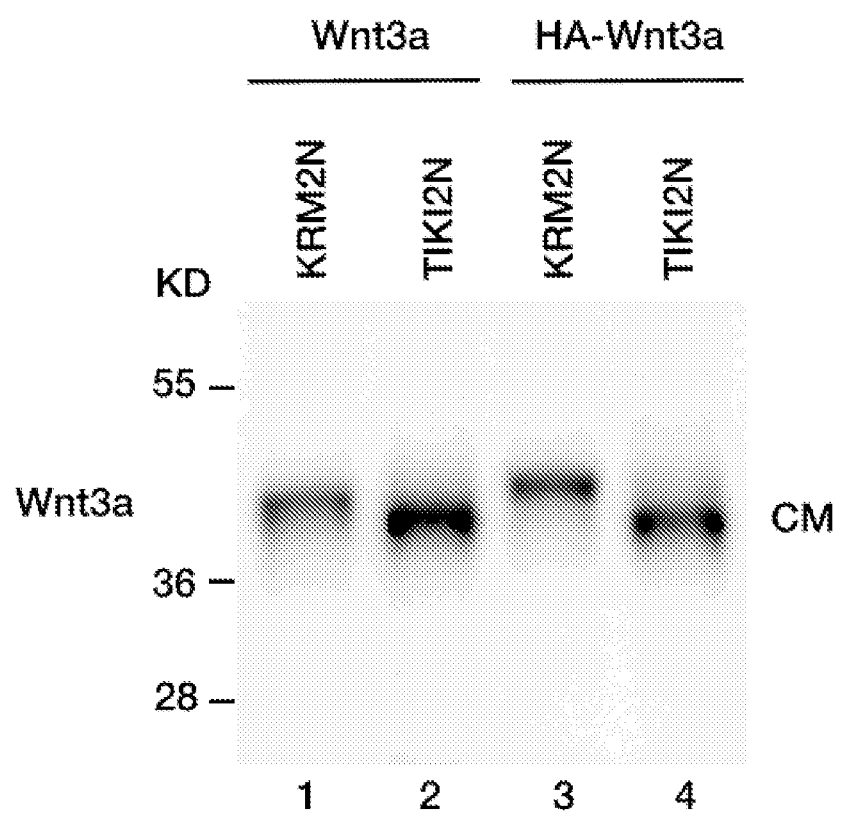

FIGS. 5V-CC. Tiki cleaves Wnt3a.

(V) The amino-terminal HA tag did not appear to affect TIKI cleavage of Wnt3a. Wnt3a or HA-Wnt3a was co-expressed with KRM2N or TIKI2N and CM were analyzed by Western blotting with an anti-Wnt3a antibody. Wnt3a or HA-Wnt3a migrated to the similar molecular weight position in the presence of TIKI2N (lanes 2 versus 4), even though HA-Wnt3a migrated slightly slower (due to the HA tag) than Wnt3a in the absence of TIKI2N (lanes 1 versus 3).

(W) HA-Wnt3a(S25D/L26D/S33D/S34D) was inactive as examined by transfection in a 2-fold dilution series in TOPFLASH reporter assays.

(X) HA-Wnt3a(S25D/L26D/S33D/S34D) formed oxidized oligomers in CM. The arrow indicates Wnt3a monomers, and * indicates Wnt3a oligomers in non-reducing gel (top). CM from HEK293T cells were separated by SDS-PAGE under the non-reducing or reducing (bottom) condition and analyzed by Western blotting with an anti-Wnt3a antibody.

(Y-BB) TIKI2, but not KRM2, interacts with Wnt3a, Xwnt8-Myc, Wnt5a, and Xwnt11. Wnt proteins were each co-expressed with KRM2N or TIKI2N (FLAG tagged) and CM were subjected to immunoprecipitation with an anti-FLAG antibody and Western blotting with indicated antibodies.

(CC) TIKI1N and TIKI1N-KDEL ("KDEL" disclosed as SEQ ID NO: 51), but not TIKI2NΔ, inhibited TOPFLASH reporter induced by Wnt3a. Different concentrations (in a 2-fold dilution series) of the TIKI1N, TIKI1N-KDEL ("KDEL" disclosed as SEQ ID NO: 51) or TIKI2NΔ expression vector were co-transfected with the expression vector for Wnt3a.

FIGS. 6A-E. Wnt3a oxidation-oligomerization due to Tiki cleavage (A-D) Secreted Wnt3a in CM. The arrow and * indicate Wnt3a monomers and oligomers in non-reducing gels, respectively (top). Note the enormous size of the upper * band. Reducing gels (bottom) were also shown.

(A) Wnt3a from TIKI2-expressing cells formed exclusively oxidized oligomers.

(B) Wnt3aΔN formed oxidized oligomers.

(C) Oxidized Wnt3a oligomers partitioned exclusively in the aqueous (Aq) phase, while Wnt3a monomers partitioned in the detergent (De) phase. T, total.

(D) Wnt3a(C77A) formed oxidized oligomers regardless of TIKI2 cleavage. The experiment shown was performed together with the one presented in (A) and a common control was used. Wnt3a(C77A) from TIKI2-expressing cells migrated slower in the reducing gel due to altered N-glycosylation secondary to TIKI cleavage (see FIG. 4O).

(E) Wnt3a, Wnt3a(C77A), and Wnt3a(S209A) behaved similarly in whole cell lysates. Each existed mainly as monomers (arrow), but also as heterogeneous oxidized species from dimers (arrowhead) to larger oligomers (*), regardless of TIKI2 cleavage.

FIGS. 6F-M. Further characterization of TIKI cleavage of Wnt3a in vitro, oxidized Wnt3a oligomers in CM, and the activity of TIKI1N-KDEL ("KDEL" disclosed as SEQ ID NO: 51).

(F) Recombinant HA-Wnt3a was incubated in vitro with purified KRM2N, TIKI2N for indicated time and the reaction product was subjected to Western blotting. Note that TIKI2N cleavage of HA-Wnt3a became obvious by 2 hrs under the in vitro condition.

(G) Recombinant HA-Wnt3a was incubated in vitro with purified KRM2N, TIKI2N at different pH conditions for 2 hrs and the reaction product was subjected to Western blotting.

(H) Recombinant HA-Wnt3a was incubated in vitro with purified KRM2N, TIKI2N in the presence or absence of increasing amount of Sigma protease inhibitors mixture (contains AEBSF, Aprotinin, Bestatin, E-64, Leupeptin and Pepstatin A) for 4 hrs and the reaction product was subjected to Western blotting. TIKI2N was resistant to the protease inhibitors.

(I) Recombinant HA-Wnt3a was incubated with Trypsin in vitro in the presence or absence of increasing amounts of Sigma protease inhibitors for 2 hrs. Note that the protease inhibitors worked as shown by blocking Trypsin digestion of HA-Wnt3a.

(J) Recombinant HA-Wnt3a was incubated in vitro with purified KRM2N, TIKI2N in the presence or absence of indicated concentrations of EDTA for 4 hrs. Note that EDTA inhibited TIKI2N activity, in particular at higher concentrations.

(K) The trace amount of Wnt3a oligomers (*) in CM contained the intact amino terminus CM from mock or HA-Wnt3a expressing HEK293T cells was analyzed by reducing and non-reducing SDS-PAGE and by Western blotting with anti-Wnt3a and anti-HA antibodies. The amino terminal HA tag was detected in oligomers.

(L) CM from mock, Wnt3a, Wnt3a(C77A) or Wnt3a (209A) expressing HEK293T cells in the presence or absence of TIKI2 expression. Wnt3a(S209A) was not secreted as reported (Takada et al., 2006).

(M) HA-Wnt3a was expressed alone or together with TIKI1N or TIKI1N-KDEL ("KDEL" disclosed as SEQ ID NO: 51) in HEK293T cells, and CM or WCL were subjected to Western blotting. Both TIKI1N and TIKI1N-KDEL ("KDEL" disclosed as SEQ ID NO: 51) cleaved Wnt3a. Note that TIKI1N was secreted into CM but TIKI1N-KDEL ("KDEL" disclosed as SEQ ID NO: 51) was not.

FIGS. 7A-F. Tiki1 inhibits Wnt/β-catenin signaling in both Wnt-producing and Wnt-responding cells.

(A) Tiki1 acts in Xwnt8-producing cells. Xwnt8 mRNA (20 pg) was co-injected with Tiki1 or LDLR mRNA (100 pg) into a single blastomere at the 8-cell stage, while 501234-Luciferase (140 pg) plus TK-Renilla (1.25 pg) reporter DNAs were injected into a neighboring blastomere.

(B) Tiki1 acts in Xwnt8-responding cells. S01234-Luciferase and TK-Renilla reporter DNAs were co-injected with Tiki1 or LDLR mRNA in a single blastomere, while Xwnt8 mRNA was injected into a neighboring blastomere.

(C) The endogenous Tiki1 acts in Wnt-producing cells. Tiki1MO or control MO (20 ng) was co-injected with CS2+Xwnt8 DNA (40 pg) into a single dorsal blastomere at the 8-cell stage, while 501234-Luciferase or S0-luciferase (100 pg) plus TK-Renilla (1.25 pg) reporter DNAs were injected into a neighboring dorsal blastomere.

(D) The endogenous Tiki1 acts in Wnt-responding cells. S01234-luciferase or S0-luciferease and TK-Renilla reporter DNAs were co-injected with Tiki1MO or control MO into a single dorsal blastomere, while CS2+Xwnt8 was injected into a neighboring dorsal blastomere. Luciferase readings were normalized to Renilla.

(E-F) Tiki1 reduces nuclear beta-catenin levels by acting in Wnt-responding cells. Tiki1 or LDLR mRNA (200 pg) together with fluorescein dextran (FLD, green) were injected into one blastomere at the 8-cell stage, while Xwnt8 mRNA (20 pg) plus RFP mRNA (800 pg, red) were injected into a neighboring blastomere. Stage 9 animal cap cells were subjected to immuno-fluorescence analysis with anti-beta-catenin antibodies. Only cells within the distance of five cell bodies from Xwnt8-expressing cells were counted in any given field. No nuclear 3-catenin-positive cells were found in areas free of Xwnt8-expressing cells. All cells exhibited positive staining for plasma membrane-bound 3-catenin Summary and statistical data were derived from three independent experiments (F). **p<0.001.

Figure 8A:
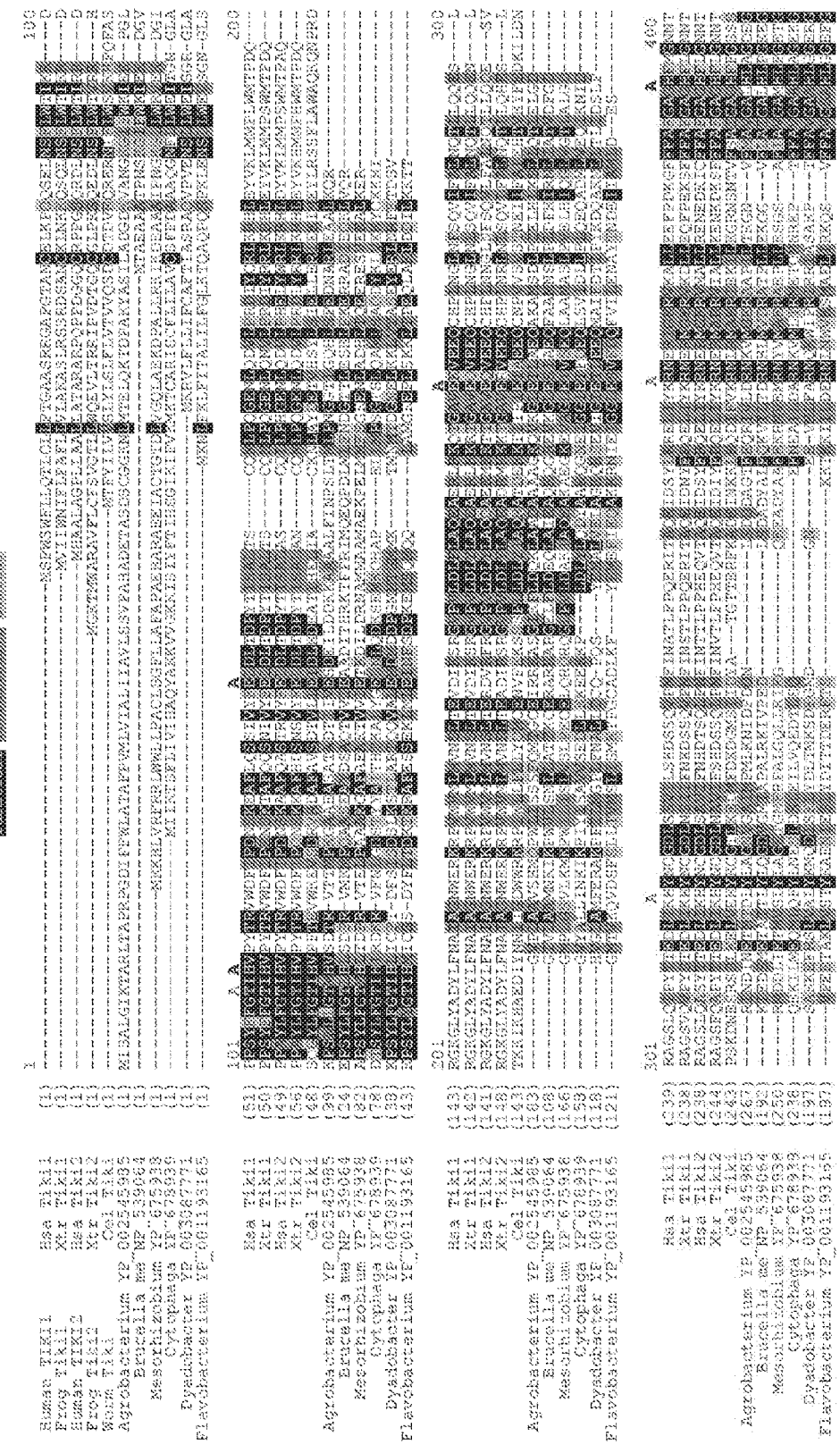

FIG. 8A. Alignment of sequences from TraB and PrgY superfamilies. The TraB superfamily includes TIKI/GumN branch and PrgY branch, distinguished by hydrophobic residues in/surrounding GxxH motifs. The PrgY proteins do not align with TIKI/GumN proteins but they have similar GxxH motifs (first GTxH and second GxxHxxG). FIG. 8A discloses SEQ ID NOS 84-94, respectively, in order of appearance.

FIG. 8B. Bar graph showing the results of a TOPFLASH assay testing TIKI2 mutations in Human TIKI2N construct (no transmembrane domain). Decreasing doses of 5, 2.5, 1.25 and 0.612 ng of the indicated TIKI2N expression plasmid were cotransfected with Wnt3a (20 ng) in HEK293T cells.

FIGS. 9A-E. Exemplary amino acid sequences of human Wnt3a (9A-9B, with amino acids L26 and S33/S34 marked; SEQ ID NOs:13-14, respectively), human Wnt5a (9C; SEQ ID NO:15), Xwnt8 (9D; SEQ ID NO:16), and HA-Wnt3a, which harbors the HA tag after the signal peptide (9E; SEQ ID NO:17).

DETAILED DESCRIPTION

The present inventors recently described a family of transmembrane Tiki proteins (see US Pre-Grant Pub. No. 20110231942, incorporated by reference in its entirety herein). The present invention is based, at least in part, on the discovery that these TIKI proteins inactivate Wnt morphogens through proteolytic cleavage.

Tiki1 is specifically expressed in the Spemann-Mangold Organizer and is required for head formation in *Xenopus* embryos. In the absence of Tiki1, expression of all head organizer genes examined is diminished, indicative of defective head organizer function, which in turn causes deficiency in anterior neural patterning. As in the absence of Tiki1 head organizer-specific Gsc expression is initiated normally but down-regulated from mid-gastrulation onward, Tiki1 appears to be required for Organizer maintenance, which is antagonized by zygotic Wnt signaling, but not for the initiation of Organizer formation, which requires maternal Wnt signaling. Tiki1 as a founding "Wnt inactivator" joins known Organizer-specific Wnt antagonists including Dkk1, Frzb/sFRP3, and others, and likely acts to ensure a "Wnt-free" zone for anterior development (De Robertis and Kuroda, 2004; Niehrs, 2004). Tiki1 functions in both Wnt-producing and Wnt-responding cells, thereby inactivating Wnt made by the organizer locally or by neighboring or posterior regions (McGrew et al., 1997). Tiki1 expression in the organizer is induced by maternal Wnt signaling, and may in certain context constitute a negative feedback loop that is common in morphogen signaling.

A Tiki-mediated Wnt inactivation mechanism may be ancient since a Tiki1 homolog is encoded in the genome of sponge *Amphimedon* and of sea anemone *Nematostella*, thereby predating the split of invertebrate and vertebrate lineages. A Tiki1 homolog is also found in the genome of nematodes, but not in *Drosophila* or other insects, suggesting loss of the Tiki gene, similar to loss of other Wnt antagonist genes, during insect evolution. Tiki proteins provocatively share homology with the TraB superfamily of putative bacterial proteins, notably the gumN subfamily, and thus represent the first example of Wnt signaling components with a prokaryotic origin. Like most or all members of the TraB family, the gumN gene product of *Xanthomonas* is characterized neither functionally nor biochemically. The homology with Tiki proteins thus suggests potential mechanisms for gumN/TraB proteins.

As described herein, Tiki proteins are likely, or at least are associated with/regulate the activity of, a metalloprotease that specifically cleaves the amino terminus of Wnt proteins, despite bearing no recognizable homology to known proteases. Tiki proteolytic activity requires $Co^{2+}$ or $Mn^{2+}$ in vitro, although other divalent metals may as well serve as co-factors in vivo. TIKI2 cleaves primarily after leucine 26 of Wnt3a (i.e., leucine 8 of mature Wnt3a), and to lesser degrees, after serines 33 and 34 (serines 15 and 16 of mature Wnt3a). TIKI2 also cleaves Xwnt8 after threonine 39 and alanine 42 (threonine 17 and alanine 20 of mature Xwnt8) and Wnt5a amino terminus, but does not appear to cleave Xwnt11, implying broad but stringent TIKI specificity towards different Wnt proteins. The Wnt amino terminus is highly variable among family members but well conserved among paralogs, hinting specific regulation of individual Wnt proteins by its amino terminus Comparison of TIKI2 cleavage sites in Wnt3a and Xwnt8 amino termini does not reveal a recognizable consensus. The finding that TIKI2 interacts with Wnt3a, Xwnt8 and Wnt5a suggests a possibility that TIKI may bind to a conserved motif/domain within Wnt proteins, thereby orienting TIKI for Wnt amino terminal proteolysis. TIKI2 also binds to but does not cleave Xwnt11, implying Wnt-binding alone is not sufficient for cleavage. Tiki specificity is also reflected in the fact that Tiki does not inhibit signaling by Nodal/TGF-beta or bFGF, and does not cleave Wnt agonist R-spondin1. Importantly TIKI fails to cleave a Wnt3a mutant that harbors amino acid substitutions at the identified proteolytic sites, implying TIKI selectivity for peptide bond hydrolysis.

Tiki cleavage results in massive Wnt3a oxidation and oligomerization through inter-molecular disulfide bond formation. These secreted and soluble Wnt3a oligomers exhibit drastically altered biophysical and biochemical properties, including the loss of hydrophobicity and receptor-binding capability. Indeed Wnt3aΔN, engineered to lack the same eight amino terminal residues removed by Tiki, is inactive and forms oxidized and hydrophilic oligomers. The present results thus suggest that the Wnt amino terminus has an unappreciated but critical role in preventing Wnt oxidation-oligomerization during Wnt biogenesis and function, a feature that is exploited by Tiki1 during anterior patterning.

Wnt lipid modifications, exemplified by C77 palmitoylation and S209 O-acylation of Wnt3a (Komekado et al., 2007; Takada et al., 2006; Willert et al., 2003), have critical but distinct roles in Wnt biogenesis and function. S209 O-acylation, likely carried out by the putative O-acyltransferase Porcupine (Hausmann et al., 2007), is essential for Wnt3a secretion (Takada et al., 2006) due to its involvement in mediating Wnt3a-binding to the transporter protein Wntless (Banziger et al., 2006; Coombs et al., 2010). On the other hand, Wnt3a C77 palmitoylation is required for activity but not secretion (Willert et al., 2003), but the molecular basis for its requirement in signaling has not been resolved. The present study suggests a potential link between Wnt palmitoylation and Wnt folding/activity. Wnt3a(C77A), which lacks palmitoylation and has been commonly employed for interrogating the role of Wnt palmitoylation in vivo (Cong et al., 2004; Franch-Marro et al., 2008; Komekado et al., 2007; Kurayoshi et al., 2007; Takada et al., 2006; Willert et al., 2003), shares similar biochemical and functional properties with Tiki-modified Wnt3a and Wnt3aΔN, as they are each hydrophilic, inactive, and form oxidized oligomers in CM. These data imply that C77 palmitoylation, like Wnt3a amino terminus, is required for keeping Wnt3a from oxidation/oligomerization during biogenesis. It has been shown that Wnt3a(C77A), like Tiki-modified Wnt3a, binds to neither Fz nor LRP6 (Cong et al., 2004). The findings that Tiki-modified Wnt3a and Wnt3a(C77A) each form oxidized oligomers appear to provide a plausible mechanism to account for their failure to engage the Wnt receptors. Alternatively it remains possible that C77 palmitoylation, and in the same vein Wnt3a amino terminus are simultaneously involved in binding to both Fz and LRP6, although such a scenario requires more convoluted molecular explanations. A recent study shows that a mutant Wingless (Wg, the *Drosophila* Wnt1) protein, Wg(C93A) that has an alanine substitution at C93 (the equivalent of C77 in Wnt3a) and thus lacks palmitoylation, is secreted but forms large-sized (>1.3M Dalton) soluble aggregates (Mulligan et al., 2012). Although it is yet to be determined whether such aggregates are formed by Wg inter-molecular disulfide bonds, a conserved role of palmitoylation in preventing oxidation-oligomerization may be shared among Wg, Wnt3a, and possibly other Wnt proteins, as suggested by the apparent similarity between Wnt3a(C77A) and Wg(C93A) oligomers. Although oxidizing oligomerization appears to be a mechanism for Wnt inactivation, the present findings do not exclude the possibility that active Wnt proteins are non-covalent oligomers (or monomers).

It is striking that the oxidized oligomers formed by Tiki-modified Wnt3a or Wnt3a(C77A), which harbors dual lipids or a single lipid, respectively, remain fully soluble aqueously (Willert et al., 2003; this study). These oxidized oligomers exhibit strict correlation with hydrophilic behavior, in sharp contrast to Wnt3a monomers (or non-covalent oligomers). These observations argue that the inactive Wnt oligomers are unlikely misfolded protein aggregates, but rather may represent an alternatively folded but ordered oligomerization state (or states) that buries the lipid adduct(s) inside, thereby shielding lipidation and behaving hydrophilic. It is intriguing how Tiki removal of the eight amino terminal residues, which do not contain a cysteine and therefore are not involved in intra-molecular disulfide bonding or sulfhydryl-mediated palmitoylation (Resh, 2006), triggers extensive Wnt3a inter-molecular oxidation. Oxidized Wnt oligomers, which are present during biogenesis (FIG. 6E), imply two or more free sulfhydryl groups per molecule, and that Wnt proteins share 22 invariable cysteine residues throughout the poly-peptide. Among other important questions are the specificity and mechanism of Tiki1 and Tiki2 towards different Wnt proteins, whether Tiki cleavage regulates other Wnt pathways, how Wnt amino terminus and palmitoylation maintain Wnt in the active state through prevention of oxidation, and whether the oxidized Wnt oligomers, given the reversible nature of oxidation, can be resolved/functionally restored by reducing enzymes or protein disulfide isomerases. The present study of Wnt cleavage by Tiki has uncovered a new dimension of Wnt regulation that depends on unsuspected but critical Wnt biogenic properties. As Wnt signaling plays essential roles in diseases including cancer and osteoporosis, TIKI1/2 as Wnt-proteolytic enzymes may represent new therapeutic targets.

Anti-Tiki1/2 Inhibitory Antibodies

The term "antibody" as used herein refers to an immunoglobulin molecule or antigen-binding portion thereof, i.e., an antigen-binding portion. Examples of antigen-binding portions of immunoglobulin molecules include F(ab) and F(ab')2 fragments, which retain the ability to bind antigen. Such fragments can be obtained commercially, or using methods known in the art. For example F(ab')2 fragments can be generated by treating the antibody with an enzyme such as pepsin, a non-specific endopeptidase that normally produces one F(ab')2 fragment and numerous small peptides of the Fc portion. The resulting F(ab')2 fragment is composed of two disulfide-connected Fab units. The Fc fragment is extensively degraded and can be separated from the F(ab')2 by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50.00 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')2 Preparation Kit (Pierce Biotechnology, Rockford, Ill.). In addition, commercially available services for generating antigen-binding fragments can be used, e.g., Bio Express, West Lebanon, N.H.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. The antibody can be coupled to a toxin or imaging agent.

Methods for making suitable antibodies are known in the art. A full-length TIKI protein or antigenic peptide fragment thereof can be used as an immunogen. In some embodiments, an antigenic peptide fragment can be used. For example, peptides comprising TELRLPRRGH (amino acids 462-471; SEQ ID NO:52) or EESDIVPQLQ (amino acids 443-452; SEQ ID NO:53) can be used to generate antibodies that bind specifically to TIKI1; and peptides comprising AVPEAPSVTP (amino acids 385-394; SEQ ID NO:54), TAPPEDEDPA (395-404; SEQ ID NO:55), or QQDPPG-PASS (481-490; SEQ ID NO:56) can be used to generate antibodies that bind specifically to TIKI2. In some embodiments, peptides including residues corresponding to H58, E85, H331, or E205 (numbered according to human TIKI2 sequence as set forth in SEQ ID NO:2), plus 1, 2, 3, 4, 5, 6, 7, 8, 9, 10, 11, 12, 13, 14, 15, 16, 17, 18, 19, 20 or more amino acids on either side, can be used. Also included herein are antibodies (e.g., monoclonal antibodies) that bind to these peptides, as well as antigen-binding fragments thereof. However, although these antigenic fragments of Tiki2 can be used to generate antibodies that can inhibit TIKI-mediated cleavage of a Wnt protein, the present invention is not limited in any way to these, or any other, fragments of TIKI (e.g., Tiki1 and Tiki2). Rather, the present invention encompasses generation of antibodies using any portion, as well as the full-length, TIKI protein since, as would be appreciated by one skilled in the art, binding of an antibody can alter protein conformation and/or sterically hinder the activity of a protein such that antibodies that bind to any portion of TIKI may inhibit TIKI-mediated cleavage of a Wnt protein even if the antibody epitope does not comprise any of these amino acid residues.

In some embodiments, the present invention provides an antibody that competes for binding of TIKI with an antibody disclosed elsewhere herein. Antibody binding and competition can be assessed using any method known in the art, including, but not limited to, ELISA, surface plasmon resonance (e.g., as measured using a BIAcore instrument), and Octet analysis (e.g., using a ForteBio instrument), among many other art-recognized methods.

Methods for making monoclonal antibodies are known in the art. Basically, the process involves obtaining antibody-secreting immune cells (lymphocytes) from the spleen of a mammal (e.g., mouse) that has been previously immunized with the antigen of interest (e.g., a cancer-related antigen) either in vivo or in vitro. The antibody-secreting lymphocytes are then fused with myeloma cells or transformed cells that are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Mammalian lymphocytes are immunized by in vivo immunization of the animal (e.g., a mouse) with an antigen. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by known techniques, for example, using polyethylene glycol ("PEG") or other fusing agents (See Milstein and Kohler, Eur. J. Immunol. 6:511 (1976), which is hereby incorporated by reference). This immortal cell line, which is preferably murine, but can also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol. 5:256-262 (1993) and Pluckthun, Immunol. Revs. 130:151-188 (1992).

Procedures for raising polyclonal antibodies are also known. Typically, such antibodies can be raised by administering the protein or polypeptide of the present invention subcutaneously to New Zealand white rabbits that have first been bled to obtain pre-immune serum. For example, the antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized, e.g., with pentobarbital 150 mg/Kg IV. This and other procedures for raising polyclonal antibodies are disclosed in Harlow, et al., editors, "Antibodies: A Laboratory Manual" (1988).

In addition to utilizing whole antibodies, the invention encompasses the use of binding portions of such antibodies. Such binding portions include Fab fragments, F(ab')2 fragments, Fv fragments, single chain Fv fragments, single chain $V_H$ fragments, and single chain $V_L$ fragments. These antibody fragments can be made by conventional procedures, such as proteolytic fragmentation procedures, as described in J. Goding, "Monoclonal Antibodies: Principles and Practice," pp. 98-118 (N.Y. Academic Press 1983).

The antibody can also be a single chain antibody. A single-chain antibody (scFV) can be engineered (see, for example, Colcher et al., Ann. N. Y. Acad. Sci. 880:263-80 (1999); and Reiter, Clin. Cancer Res. 2:245-52 (1996)). The single chain antibody can be dimerized or multimerized to generate multivalent antibodies having specificities for different epitopes of the same target protein. In some embodiments, the antibody is monovalent, e.g., as described in Abbs et al., Ther. Immunol. 1(6):325-31 (1994), incorporated herein by reference The antibody can also be a bispecific antibody or a diabody. Diabodies are bivalent, bispecific antibodies in which the $V_H$ and $V_L$ domains are expressed on a single polypeptide chain, with a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al. Structure 2:1121-1123 (1994)). See US 2012/0052074.

Chimeric, humanized, de-immunized, or human antibodies are desirable for applications which include repeated administration, e.g., therapeutic treatment of human subjects.

Chimeric antibodies generally contain portions of two different antibodies, typically of two different species. Generally, such antibodies contain human constant regions and variable regions from another species, e.g., murine variable regions. For example, mouse/human chimeric antibodies have been reported which exhibit binding characteristics of the parental mouse antibody, and effector functions associated with the human constant region. See, e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397, all of which are incorporated by reference herein. Generally, these chimeric antibodies are constructed by preparing a genomic gene library from DNA extracted from pre-existing murine hybridomas (Nishimura et al., Cancer Research, 47:999 (1987)). The library is then screened for variable region genes from both heavy and light chains exhibiting the correct antibody fragment rearrangement patterns. Alternatively, cDNA libraries are prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes can then be expressed in a cell line of choice, e.g., a murine myeloma line. Such chimeric antibodies have been used in human therapy.

Humanized antibodies are known in the art. Typically, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting the entire nonhuman variable domains onto human constant regions to generate a chimeric antibody (Morrison et al., Proc. Natl. Acad. Sci., USA 81:6801 (1984); Morrison and Oi, Adv. Immunol. 44:65 (1988) (which preserves the ligand-binding properties, but which also retains the immunogenicity of the nonhuman variable domains); (b) by grafting only the nonhuman CDRs onto human framework and constant regions with or without retention of critical framework residues (Jones et al. Nature, 321:522 (1986); Verhoeyen et al., Science 239:1539 (1988)); or (c) by transplanting the entire nonhuman variable domains (to preserve ligand-binding properties) but also "cloaking" them with a human-like surface through judicious replacement of exposed residues (to reduce antigenicity) (Padlan, Molec. Immunol. 28:489 (1991)).

Humanization by CDR grafting typically involves transplanting only the CDRs onto human fragment onto human framework and constant regions. Theoretically, this should substantially eliminate immunogenicity (except if allotypic or idiotypic differences exist). However, it has been reported that some framework residues of the original antibody also need to be preserved (Riechmann et al., Nature 332:323 (1988); Queen et al., Proc. Natl. Acad. Sci. USA 86:10,029 (1989)). The framework residues which need to be preserved can be identified by computer modeling. Alternatively, critical framework residues may potentially be identified by comparing known antibody combining site structures (Padlan, Molec. Immun. 31(3):169-217 (1994)). The invention also includes partially humanized antibodies, in which the 6 CDRs of the heavy and light chains and a limited number of structural amino acids of the murine monoclonal antibody are grafted by recombinant technology to the CDR-depleted human IgG scaffold (Jones et al., Nature 321:522-525 (1986)).

Deimmunized antibodies are made by replacing immunogenic epitopes in the murine variable domains with benign amino acid sequences, resulting in a deimmunized variable domain. The deimmunized variable domains are linked genetically to human IgG constant domains to yield a deimmunized antibody (Biovation, Aberdeen, Scotland).

Human antibodies are antibodies in which the variable and constant domain sequences are human sequences. In some embodiments, human antibodies are produced by immunizing a non-human, transgenic animal that harbors within its genome some or all (preferably all) of the human immunoglobulin heavy chain and light chain loci. In some embodiments, the non-human animal is a XENOMOUSE animal. (Abgenix, Inc., Fremont, Calif.), which are engineered mice with large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504. In some embodiments, the non-human animals have a human immunoglobulin minilocus, in which an exogenous Ig locus is mimicked through the inclusion of individual genes from the Ig locus. For example, one or more $V_H$, $D_H$, or $J_H$ genes, mu constant domain, and a second constant domain (e.g., a gamma constant domain) are formed into a construct for insertion into an animal. See, e.g., U.S. Pat. Nos. 5,545,807, 5,545,806, 5,569,825, 5,625, 126, 5,633,425, 5,661,016, 5,770,429, 5,789,650, 5,814,318, 5,591,669, 5,612,205, 5,721,367, 5,789,215, and 5,643,763. See also US 2012/0052074.

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids Res., 21:2265-2266 (1993)). Thus, these techniques are viable alternatives to traditional monoclonal antibody hybridoma techniques for isolation of monoclonal antibodies, including, but not limited to, fully human, humanized and chimeric antibodies.

An "inhibitory" antibody or antigen-binding fragment, as used herein, is an antibody or antigen-binding fragment as described above that inhibits the TIKI-mediated cleavage of a Wnt protein, e.g., of Wnt2B, 3, 3A, 4, 5A, 5B, 6, 7A, 7B, 8A, 8B, and/or 16, e.g., Wnt3a, Wnt5a, and/or Wnt8. Thus the methods for generating an antibody as described herein can include determining whether a candidate antibody inhibits Wnt cleavage, e.g., using an assay described herein or known in the art, e.g., an in vitro Wnt cleavage assay as described below.

Methods

One skilled in the art, armed with the surprising disclosure provided herein demonstrating that TIKI1/2 inhibits Wnt proteins by mediating their proteolytic cleavage would appreciate that the invention encompasses methods of identifying useful modulators of the cleavage as well as methods of treating diseases or disorders mediated by Wnt protein activity, including, but not limited to, Wnt signaling mediated or associated with bone metabolism and cell proliferation (e.g., cancer).

Methods of Treating Diseases or Disorders Mediated by Wnt Signaling

Also described herein are methods of treating a disorder associated with aberrant Wnt signalling, e.g., increased or decreased Wnt signalling. The methods include administering a composition comprising an active ingredient that binds to TIKI1/2 and inhibits TIKI-mediated cleavage of a Wnt protein. In some embodiments, the active ingredient is an antibody or antigen-binding fragment thereof that binds to TIKI1/2 and inhibits cleavage of a Wnt protein, e.g., inhibits cleavage of Wnt3a, Wnt5a, or Wnt8 (Xwnt8). In some embodiments, the active ingredient is a small molecule, an inhibitory nucleic acid or an aptamer which inhibits TIKI1/2 cleavage of a Wnt protein. In some embodiments, the small molecule is a metalloprotease inhibitor. In other embodiments, the metalloprotease inhibitor is an inhibitor of $Co^{2+}$ or $Mn^{2+}$-dependent metalloproteases, including, but not limited to, EDTA and 1,10-phenanthroline.

Disorders Associated with Increased Wnt Signalling

In some embodiments the disorder is associated with increased Wnt signalling, e.g., a disorder associated with unwanted cellular proliferation in which decreased Wnt signaling is associated with better prognosis, e.g., as described herein, by administering a therapeutically effective amount of a secreted form of a Tiki1/2 protein, e.g., as shown in FIG. 12, or a variant thereof, as described herein, that has Wnt inhibitory activity. The treatment should result in an improvement in a parameter of the disorder, e.g., a parameter related to clinical outcome. In some embodiments, the subject is a human, e.g., a human with a disorder associated with unwanted cellular proliferation, e.g., cancer, and the parameter is cellular proliferation, tumor size, metastasis, or survival.

In some embodiments, the active ingredient mediates increased cleavage of a Wnt protein resulting in decreased Wnt signaling activity. Thus, a TIKI agonist, such as, but not limited to, an antibody or protein or small molecule that increases the cleavage by TIKI1/2 of the N-terminal amino acids of a Wnt protein (e.g., Wnt3a, Wnt5a, and Xwnt8) can be used to treat a disease or disorder associated with or mediated by increased Wnt signaling. In such methods, an effective amount of a TIKI agonist is administered to a patient in need thereof to increase the cleavage of Wnt by TIKI and thereby decrease the level of Wnt signaling, thus treating a disorder associated with increased Wnt signaling.

Disorders Associated with Decreased Wnt Signalling

In some embodiments the disorder is associated with reduced Wnt signalling, e.g., a disorder associated with a loss of bone density, e.g., osteoporosis, or a cellular proliferative disorder in which enhanced Wnt signaling is associated with better prognosis, as described herein, by administering a therapeutically effective amount of an inhibitor of a TIKI1/2 protein, e.g., an inhibitory antibody identified by a method described herein. That is, the antibody, or antigen binding fragment thereof, specifically binds TIKI1/2 and inhibits TIKI-mediated cleavage of the N-terminal amino acids of a Wnt protein. Surprisingly, cleavage of a few amino acids at the N-terminus of the mature Wnt protein (i.e., the signal sequence has been removed) causes the otherwise hydrophobic (e.g., partitions into the detergent phase using nonionic detergents) monomeric Wnt protein to aggregate and partition into the hydrophilic (aqueous) phase. More importantly, cleavage of the N-terminal amino acids inhibits Wnt signaling and other Wnt protein biological activities. Therefore, an antibody, protein, or a small molecule that inhibits cleavage of the N-terminal amino acids of Wnt can mediate an increase in Wnt signaling and provide a novel therapeutic for treatment of diseases associated with decreased Wnt signalling.

Therefore, the invention encompasses a method of treating a disorder associated with reduced Wnt signalling. The method comprises administering a therapeutically effective amount of a TIKI inhibitor that inhibits TIKI-mediated cleavage of the N-terminal amino acids of a Wnt protein. Because cleavage of the amino acids otherwise inhibits Wnt signaling, inhibiting the cleavage can increase Wnt signaling thereby treating the disorder associated with reduced Wnt signaling.

In some embodiments, the TIKI inhibitor inhibits TIKI1, TIKI2 or TIKI1 and TIKI2. In some embodiments, the TIKI inhibitor is an antibody, or antigen binding fragment thereof, that specifically binds TIKI and inhibits the TIKI-mediated cleavage of a Wnt protein. In some embodiments, the inhibitor reduces or prevents cleavage of the N-terminal amino acids of a Wnt protein, such as, but not limited to, cleavage of SYPIWWSL (SEQ ID NO: 46), SYPIWWS-LAVGPQYS (SEQ ID NO: 47) and/or SYPIWWSLAVG-PQYSS (SEQ ID NO: 48) from Wnt3a and/or cleavage of AWSVNNFLMTGPKAYLT (SEQ ID NO: 49) and/or AWSVNNFLMTGPKAYLTYSA (SEQ ID NO: 50) from Wnt8.

In some embodiments, the TIKI inhibitor is an inhibitory nucleic acid, including, but not limited to, an antisense, a siRNA, a ribozyme and an aptamer. Inhibitory nucleic acids can inhibit expression of TIKI1/2 and thus reduce the cleavage of a Wnt protein by TIKI. Therefore, TIM inhibitors that can increase Wnt signaling include inhibitory nucleic acids.

The treatment, i.e., inhibition or increase of TIKI-mediated cleavage of Wnt, should result in an improvement in a parameter of the disorder, e.g., a parameter related to clinical outcome. In some embodiments, the parameter is bone density, and an improvement would be an increase in or maintenance of bone density over time. In some embodiments, the subject is a human, e.g., a human with loss of bone density, e.g., osteoporosis, and the parameter is maintenance or increase in bone density over time, e.g., with aging. In some embodiments, the subject is a human with a disorder associated with unwanted cellular proliferation, e.g., a cancer in which enhanced Wnt signaling is associated with better prognosis, and the parameter is cellular proliferation, tumor size, metastasis, or survival.

The compounds and methods described herein are useful in the treatment of disorders associated with abnormal apoptotic or differentiative processes, e.g., cellular proliferative disorders or cellular differentiative disorders, e.g., cancer.

Examples of cellular proliferative and/or differentiative disorders include cancer, e.g., carcinoma, sarcoma, metastatic disorders or hematopoietic neoplastic disorders, e.g., leukemias and lymphomas. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, e.g., a dermal endothelial, fibroblast, immune cell (e.g., mast cell or macrophage) found in a dermal layer, e.g., the papillary layer or the reticular layer.

Examples of skin disorders include psoriasis, psoriatic arthritis, dermatitis (eczema), e.g., exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis. photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

In some embodiments, the disorder is psoriasis. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

One of skill in the art will readily be able to identify those disorders that would benefit from increased or decreased Wnt signaling. For example, it is known that activation of the Wnt/beta-catenin pathway is crucial to the establishment of leukemic stem cells in chronic myeloid leukemia (Ysebaert et al., Leukemia. 2006; 20(7):1211-6). Wnt activation is also important in colorectal, desmoid, ovarian, endometrial, gastric, hepatocellular, kidney (Wilm's tumor), prostate, thyroid, uterine, and lung (e.g., non-small cell lung) cancers. See, e.g., Polakis, Genes Dev. 14:1837-1851 (2000). However, enhanced Wnt signaling is associated with better prognosis of some cancers (such as melanoma (see, e.g., Bachmann et al., Clin Cancer Res 11:8606-8614 (2005); Chien et al., PNAS 106:1193-1198 (2009); Kageshita et al., Br J Dermatol 145:210-216 (2001); and Maelandsmo et al., Clin Cancer Res 9:3383-3388 (2003)) and medulloblastoma (see, e.g., Ellison et al., J Clin Oncol 23:7951-7957 (2005); Fattet et al., J Pathol 218:86-94 (2009); and Kool et al., Plos One 3, e3088 (2008)), possibly due to enhanced differentiation by Wnt in these cancers (see also Dejmek et al., Cancer Res 65:9142-9146 (2005); and Lame and Delmas, Frontiers in Bioscience 11:733-742 (2006)). Other diseases associated with aberrant Wnt signaling may also benefit from treatment with the compounds and methods described herein, see, e.g., Moon et al., Nature Reviews Genetics 5, 691-701 (2004).

An "effective amount" or "therapeutically effective amount," as used interchangeably herein, is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Methods of Screening

Small chemical compound inhibitors are attractive drug candidates for treating osteoporosis or disorders associated with unwanted cellular proliferation, e.g., cancer. However, the known Wnt antagonists such as Sclerostin, DKK1, and SFRP1 function through protein-protein interactions and their inhibition via small molecules is difficult to achieve. In contrast, Tiki1/2 (e.g., Tiki2) appear to be ideal therapeutic targets for several reasons. First, Tiki2−/−, or even Tiki2+/−, mice show increased bone mass, suggesting that inhibition, or partial inhibition, of Tiki2 may benefit osteoporosis treatment. Second, Tiki2−/− mice are viable, suggesting that long-term Tiki inhibition may have minimal adverse effects. Third, Tiki proteins act as enzymes, which in general are 'drugable', i.e., suitable for inhibition by chemical compounds. Therefore the present invention includes methods of identifying small molecule inhibitors for Tiki1/2 for treatment of osteoporosis, or small molecule activators or mimics of Tiki1/2 for treatment of disorders associated with unwanted cellular proliferation, e.g., cancer.

Included herein are methods for screening test compounds, e.g., polypeptides, polynucleotides, inorganic or organic large or small molecule test compounds, to identify agents useful in the treatment of disorders associated with loss of bone density, e.g., osteoporosis, or disorders associated with unwanted cellular proliferation, e.g., cancer. The methods include identifying molecules that inhibit TIKI-mediated cleavage of a Wnt, e.g., Wnt3a, Wnt5a, or Wnt8.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., a bone cell or an osteoclast, or a tumor cell (e.g., a primary or cultured tumor cell), and one or more effects of the test compound is evaluated. In a cultured or primary cell for example, the ability of the test compound to modulate, e.g., inhibit, TIKI-mediated cleavage of the N-terminus of a Wnt, e.g., Wnt3a, Wnt5a, or Wnt8, is evaluated.

General methods useful in evaluating an effect on Wnt cleavage are known in the art or described herein. For example, a test compound can be evaluated in cells expressing both Tiki1/2 and a Wnt, e.g., Wnt3a, Wnt5a, or Wnt8; since cleavage of Wnt results in a decrease in Wnt activity, Wnt activity can be evaluated, e.g., by Wnt-responsive luciferase reporter assays. Such assays use a reporter gene such as the fruitfly luciferase, whose expression is under the control of Wnt-responsive DNA elements (WREs) (Molenaar et al., Cell 86 (1996), pp. 391-399. Korinek et al., Science 1997. 275, 1784-1787. Major et al., Science. 2007. 316:1043-6).

In some embodiments, antibody, or antigen binding fragment thereof, TIKI agonists and inhibitors are identified. That is, in some embodiments, an antibody that specifically binds TIKI is identified by assessing its ability to inhibit or increase TIKI-mediated cleavage of a Wnt protein using assays disclosed herein or those well-known in the art.

In some embodiments, an assay of Wnt modification, e.g., an assay for Tiki1/2-mediated cleavage of Wnt, can be used (e.g., using assays known in the art and/or described herein, see the Examples, below). In some embodiments, liquid chromatography and mass spectrometry (LC/MS) can be used to detect cleavage products of Tiki-mediated cleavage of a Wnt protein. In some embodiments, a Wnt protein comprises a detectable tag polypeptide sequence (e.g, hemagglutinin [HA] and FLAG) near the N-terminal cleavage site of Tiki-mediated cleavage such that cleavage results in loss of the tag when the Wnt protein is detected. Wnt signaling assays, such as, but not limited to, Super-TOP-FLASH as described by Major et al. (2007, Science 316:1043-1046) can be used to assess the level of Wnt signaling in the presence and absence of the test compound to determine if the test compound is a modulator (increases or decreases) Wnt signaling activity. Many other methods can be used to determine the cleavage of the N-terminal amino acids of Wnt mediated by TIKI, including, but not limited to, sequencing the Wnt protein, detecting a shift in mobility of cleaved Wnt protein by, e.g., gel electrophoresis, detecting a shift from the detergent to the aqueous phase upon detergent partitioning of Wnt using a nonionic detergent (e.g., Triton X-114), assessing the binding of Wnt to know Wnt binding proteins (e.g., Fz and LRP6, among others), and determining the presence of large oligomeric aggregates of Wnt, detecting on Wnt activity in in vivo animal models, among many others such as the methods disclosed herein and those well-known in the art.

The specificity of the effect can be confirmed by comparison of the activity of the test compound in cells that do not express Tiki1/2; a test compound that affects Wnt activity in the presence of Tiki1/2, but does not affect Wnt activity in the absence of Tiki1/2, can be considered to be a specific modulator of Tiki1/2. In addition, binding experiments to detect specific binding of a test compound to Tiki1/2 can also be used to detect specificity (Huang et al., Nature Chemical Biology 2009).

A test compound that has been screened by a method described herein and determined to modulate Tiki activity, e.g., in an in vitro screen, can be considered a candidate compound. A candidate compound that has been screened, e.g., in an in vivo model of a disorder, e.g., loss of bone density, e.g., osteoporosis, or cellular proliferative disorders, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase or maintain bone density or affect Tiki/Wnt signaling) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with loss of bone density, e.g., osteoporosis, or cellular proliferative disorders. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with loss of bone density, e.g., osteoporosis, or a cellular proliferative disorder, as described herein. The animal can be monitored for a change in the disorder, e.g., for an improvement in a parameter of the disorder, e.g., a parameter related to clinical outcome. In some embodiments, the parameter is bone density, and an improvement would be an increase in or maintenance of bone density over time. In some embodiments, the subject is a human, e.g., a human with loss of bone density, e.g., osteoporosis, and the parameter is maintenance or increase in bone density over time, e.g., with aging. In some embodiments, the subject is a human, e.g., a human with a disorder associated with unwanted cellular proliferation, e.g., cancer, and the parameter is cellular proliferation, tumor size, metastasis, or survival.

Compounds identified by methods described herein are also useful in the treatment of disorders associated with abnormal apoptotic or differentiative processes, e.g., cellular proliferative disorders or cellular differentiative disorders, e.g., cancer.

Pharmaceutical Compositions and Methods of Administration

The methods described herein include the manufacture and use of pharmaceutical compositions, which include as active ingredients compounds described herein, e.g., inhibitory antibodies or fragments thereof, as active ingredients. Also included are the pharmaceutical compositions themselves. In some embodiments, the active ingredient is an antibody or antigen-binding fragment thereof that binds to TIKI1/2 and inhibits cleavage of a Wnt protein, e.g., inhibits cleavage of Wnt3a, Wnt5a, or Wnt8.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

The pharmaceutical compositions can be included in a container, pack, or dispenser together with instructions for administration.

EXAMPLES

The invention is further described in the following examples, which do not limit the scope of the invention described in the claims.

Experimental Procedures

The following methods were used in the Examples set forth herein.

Xenopus Embryo Manipulation, cDNA Library Screening and In Situ Hybridization

Procedures for embryo manipulation, reverse transcription PCR and in situ hybridization were performed as previously described (Tamai et al., 2000). The arrayed Xenopus tropicalis full length cDNAs (Voigt et al., 2005) were used for the screening as performed previously (Kato et al., 2002). cDNA pools (in the CS107 vector) that contain 96 independent clones were transcribed in vitro using SP6 polymerase, and the resulting mRNA pools were injected into the dorsal side of the embryo at 4-cell stage at the dose of 10 ng RNA/embryo. Injected embryos were scored at stage 30-31 for enlarged or diminished anterior development. The positive pools were divided into smaller pools and the same process was repeated till a single cDNA was identified.

Plasmids

The Xenopus Tiki1 cDNA in pCS107 that contains the full coding region and parts of 5' and 3' UTR was from the library. Human TIKI1 and TIKI2 genes were amplified from a human cell line via RT-PCR and cloned into pCS2+. Also in pCS2+ are: HA*Tiki1 (which has a HA tag at the amino terminus after a heterologous signal peptide from human Fz5), HA-TIKI1/2, HA-TIKI1/2N, HA-TIKI1N-KDEL ("KDEL" disclosed as SEQ ID NO: 51), Tiki1-FLAG (which contains a part of endogenous 5' UTR and a FLAG tag at the carboxyl terminus), TIKI2N-FLAG-6×HIS ("6×HIS" disclosed as SEQ ID NO: 57) (which is the extracellular domain of TIKI2 fused with a carboxyl FLAG tag and a 6×HIS tag ("6×HIS" disclosed as SEQ ID NO: 57) and was used for tandem affinity purification (TAP)), KRM2N-FLAG-6×HIS ("6×HIS" disclosed as SEQ ID NO: 57), and TIKI2NΔ-FLAG-6×HIS ("6×HIS" disclosed as SEQ ID NO: 57) (which is the extracellular domain of TIKI2 with a deletion from residue 223 to 349), mouse Wnt3a, HA-Wnt3a (a HA tag was inserted after the signal peptide), Wnt3a(C77A), Wnt3a(N87Q/N298Q), Wnt3a(C77A/S209A), Wnt3a(S25D/L26D), Wnt3a(S25D/L26D/S33D/S34D), Wnt3aΔ19-43, Wnt3aΔ19-144, Wnt3aΔ271-352, Wnt3aΔN. The HA-TIKI1 and 2 were subcloned into pBABE-puro vector (Addgene plasmid 1764) for retroviral expression. Wnt3a(FLAG) (a FLAG tag was inserted internally between residue 250 and 251), HA-hR-spondin1-Myc (human R-spondin1 with a HA tag on the N-terminus and a Myc tag on the C-terminus), HA-Xwnt8-FLAG, HA-Xwnt11-FLAG, HA-Wnt5a were generated by PCR and subcloned into pcDNA3.1.

Antibodies, Immunoblotting and Immunofluorescence

The rabbit polyclonal anti-LRP6 antibody has been described (Tamai et al., 2004). Other antibodies were used according to manufacturer's instructions. From Cell Signaling: the rabbit monoclonal anti-Wnt3a (#2721, 1:1000), anti-HA (#3724, 1:1000), anti-Wnt5a (#2530, 1:1000) and anti-FLAG (#8146, 1:2000), from Santa Cruz: anti-Dvl2 (sc-13974, 1:1000), anti-HA (sc-7392, 1:1000), and anti-Myc (sc-40, 1:500), from BD Transduction Laboratories: anti-beta-catenin (610154, 1:2000), From Hybridoma Bank: anti-tubulin (E7, 1:5000). Anti-FLAG M2 (A2220) and anti-HA (A2095) Affinity gels are from Sigma Immunoblotting was performed as previously described (MacDonald et al., 2008). For indirect immunofluorescence experiments, HeLa cells were plated on glass coverslips in 12-well plates and transfected with HA*Tiki1 expression construct. To visualize Tiki1 proteins on the cell surface, live cells were incubated with the anti-HA antibody in the culture medium for 30 min. The coverslip was washed with PBS and fixed with 4% paraformaldehyde in PBS for 10 min at room temperature. The cells were permeabilized with 0.2% Triton X-100 in PBS for 5 min, blocked with 10% normal goat serum and then incubated with fluorescent secondary antibodies for 1 hr at room temperature. The coverslip was washed, mounted on glass slides and imaged by confocal microscopy (Carl-Zeiss LSM510). To visualize the total cellular Tiki1 protein, cells were fixed and permeabilized before incubation with primary and secondary antibodies Immunofluorescence analysis using Xenopus animal caps was done as previously described (Takada et al., 2006).

Morpholinos and RT-PCR primers

The following morpholino oligonucleotides were used: Tiki1 MO: 5'-CCAAATGATTACCATCATAGCTCAG-3' (SEQ ID NO:33); standard control MO: 5'-CCTCTTAC-CTCAGTTACAATTTATA-3' (SEQ ID NO:34) (Gene Tools, LLC). RT-PCR primers for XTiki1: Forward, 5'-CCGGCTCGAGGCAAAGGTTATCGGGAGCAA-3' (SEQ ID NO:35), Reverse, 5'-GGCCTCTAGAGGTCCGT-TAGGTCCAATTCA-3'(SEQ ID NO:36); human TIKI1: Forward, 5'-GAATAGGGAAGCGGGTGAAG-3'(SEQ ID NO:37), Reverse, 5'-GTGTTGTTGCCCATGAAATG-3' (SEQ ID NO:38); human TIKI2: Forward, 5'-TCTTCAAC-CACGACACATCC-3'(SEQ ID NO:39), Reverse, 5'-GGCGGAAGTAGCTGTCAATC-3'(SEQ ID NO:40).

Cell Culture, Transfection and Reporter Assay

HEK293T, HeLa, L and L-Wnt3a cells (from ATCC) were maintained in Dulbecco's modified Eagle's medium (DMEM; Invitrogen) supplemented with 10% fetal bovine serum (FBS) and 1% penicillin-streptomycin-glutamine (Invitrogen). Lipofectamine 2000 (Invitrogen) or Fugene6 (Roche) was used for all cell transfections. L and L-Wnt3a cells that stably express TIKI2 were generated by infecting cells with retroviruses and selected by puromycin. L cells stably expressing Wnt3a(FLAG) were established by transfecting L cells with a Wnt3a(FLAG) expressing vector and selected with neomycine. L cells stably expressing both Wnt3a(FLAG) and TIKI2 were also generated. TOPFLASH reporter assay was performed as previously described (MacDonald et al., 2008).

RNAi

To knockdown human TIKI2 in the TOPFLASH reporter assay, HEK293T cells in 24-well plates were transfected with 100 ng of TOPFLASH reporter, 5 ng of TK-Renilla reporter, 5 ng of empty vector or Wnt3a, and 20 nM of each siRNA. The reporter activities were examined 48 hrs post-transfection. The following TIKI2 siRNAs were used, TIKI2 siRNA-1: 5'-ACAAGAGGAATGAGCGCAT-3'(SEQ ID NO:41); TIKI2 siRNA-2: 5'-GAGCTTTACTGGCGCT-TGA-3'(SEQ ID NO:42); TIKI2 siRNA-3: 5'-GCACCCGT-GTCTACTTTGA-3'(SEQ ID NO:43); TIKI2 siRNA-4: 5'-TAAACTCGCTCATAGAGAG-3'(SEQ ID NO:44).

Quantitative RT-PCR

RNA was isolated using the RNeasy kit (Qiagen). First strand cDNA was prepared from 1 μg of total RNA using Superscript II First-Strand kit (Invitrogen). Power SYBR Green PCR Master Mix (Applied Biosystems) was used to amplify TIKI1 or TIKI2 and normalized to beta-actin/ ACTB. Values were fit to a standard curve and analyzed using the manufacturer's software to render the expression levels in a linear format. Expression of TIKI1 was compared to TIKI2 using a delta-delta CT method and normalized to relative TIKI2 expression.

Triton X-114 Phase Separation

Wnt3a CM was analyzed by Triton X-114 phase separation as described (Komekado et al., 2007). Briefly, Wnt3a CM was mixed with equal volume of Triton X-114 buffer (10 mM Tris-HCl, Ph 7.4, 150 mM NaCl, 4.5% Triton X-114), incubated on ice for 5 min and then at 37° C. for 5 min. After centrifugation at 2000 g for 5 min, the supernatant aqueous phase (Aq) and bottom detergent phase (De) together with the original mixture (Total) were analyzed by SDS-PAGE and Western blotting.

Protein Purification

HEK293T cells in 100 mm dishes were transfected with TIKI2N-, KRM2N-, TIKI2NΔ-FLAG-6×HIS ("6×HIS" disclosed as SEQ ID NO: 57) or HA-Wnt3a vectors. The medium containing transfection mixture was replaced with 6 ml fresh medium 24 hrs post-transfection, and incubated for another 24 hrs. To purify TIKI2N, KRM2N and TIKI2NΔ, cells were washed with PBS and lysed in ice-cold PBS containing 0.2% NP-40, 20 mM imidazole and the protease inhibitor cocktail (Roche) to make whole cell lysates (WCL). WCL was mixed with Ni-NTA agarose beads (QIAGEN) and incubated at 4° C. with rotation for 1 hr. The beads were pelleted by centrifugation and washed four times with PBS/0.2% NP-40 and the FLAG-6×HIS ("6×HIS" disclosed as SEQ ID NO: 57) fusion proteins were eluted with PBS/0.2% NP-40 containing 100 mM imidazole. The elute was diluted 3 time with PBS/0.2% NP-40 and were mixed with FLAG M2 agarose beads (Sigma). Following 2 hrs incubation with rotation at 4° C., the beads were pelleted by centrifugation and washed three times with PBS/0.2% NP-40 and one time with HEPES buffer (50 mM HEPES (pH 7.4), 100 mM NaCl, 0.2% NP-40). The FLAG fusion proteins were eluted with HEPES buffer containing 50 µg/ml 3×FLAG peptide. To purify HA-Wnt3a, the conditioned medium (CM) was collected and was cleared by centrifugation and 0.2% NP-40 was added. The CM was mixed with anti-HA agarose beads (Sigma). Following 2 hrs incubation with rotation at 4° C., the beads were pelleted by centrifugation and washed three times with PBS/0.2% NP-40 and one time with HEPES buffer (50 mM HEPES (pH 7.4), 100 mM NaCl, 0.2% NP-40). The HA-Wnt3a protein was eluted with HEPES buffer containing 300 µg/ml HA peptide.

In Vitro Treatment of Wnt3a with Purified Proteins

About 50 ng purified TIKI2N, KRM2N, or TIKI2NΔ protein was mixed with 10 ng purified HA-Wnt3a in a total volume of 10 µl HEPES buffer (50 mM HEPES (pH 7.4), 100 mM NaCl, 0.2% NP-40) and incubated at 30° C. To examine TIKI2N activity in different pH conditions, the following buffer was used instead of HEPES, 100 mM sodium acetate (pH 5.5), 100 mM Tris-HCl (pH 6, 7, 8, 9) or 50 mM CAPS (pH 10, 11). The reaction product was analyzed by SDS-PAGE and Western blotting with anti-HA and anti-Wnt3a antibodies. For mass spectrometric analysis, 200 ng of recombinant Wnt3a (from Stem RD) was incubated with about 500 ng of TIKIN or KRM2N overnight at 30° C. and separated by SDS-PAGE. The Wnt3a bands were cut, trypsin digested and subjected to mass spectrometric analyses.

Metabolic Labeling and Click-Chemistry

HEK293T cells in 100 mm tissue culture dishes were transfected with indicated plasmids. 24 hrs after transfection, cells were washed with serum-free DMEM once and then cultured in the labeling medium (methionine, cysteine-free DMEM containing 5% dialyzed FBS, 10% normal DMEM, 50 µM az-15 or alk-14, 100 µCi [$^{35}$S]-methionine/cysteine) for 12 hrs. CM was collected and cleared by centrifugation. "Click-chemistry" reaction was performed as previously described (Charron et al., 2009; Zhang et al., 2010). Briefly, Wnt3a(FLAG) was enriched from CM by anti-FLAG M2 beads. The beads were washed and re-suspended in 20 µl of PBS plus 2.25 µl freshly premixed click-chemistry reaction mixture (alk-Rho or az-Rho, 100 µM, TCEP, 1 mM, Tris[(1-benzyl-1H-1,2,3-triazol-4-yl)methyl]amine (TBTA), 100 µM, and CuSO4.5H2O, 1 mM) for 1 hr at room temperature. The beads were washed three times with ice-cold RIPA buffer (1% Triton X-100, 1% sodium deoxycholate, 0.1% SDS, 50 mM triethanolamine pH 7.4, 150 mM NaCl) and resuspended in 30 µl of SDS buffer (4% SDS, 50 mM triethanolamine, pH 7.4, 150 mM NaCl) plus 15 µl of 4×SDS loading buffer (40% glycerol, 200 mM Tris-HCl, pH 6.8, 8% SDS, 0.4% bromophenol blue, 20 mM DTT), heated for 3 min at 80° C. The samples were separated by SDS-PAGE and the gels were fixed in 40% methanol, 10% acetic acid for 5 min, washed with distilled water for 5 min and scanned on a GE Healthcare Typhoon 9400 variable-mode imager for Rhodamine-associated signal at excitation 532 nm/emission 580 nm. To detect the radioactive signals, the gels were dried and subjected to autoradiography.

Amino-Terminal Edman Sequencing

CM from L-Wnt3a(FLAG) cells or L-Wnt3a(FLAG) cells expressing TIKI2 was collected and cleared by centrifugation. Wnt3a(FLAG) was purified by anti-FLAG M2 agarose and separated by SDS-PAGE, transferred to the PVDF membrane. The PVDF membrane was stained with Ponseau S solution and the Wnt3a bands were cut and sent for sequencing on ABI 494 Protein sequencer at Tufts University Core Facility.

SILAC Labeling and Mass Spectrometric Analysis

SILAC labeling and Mass spectrometric analysis was performed as previously described (Ong et al., 2002; Singh et al., 2009). Briefly, L cells stably expressing Wnt3a (FLAG) and L cells stably expressing both Wnt3a(FLAG) and TIKI2 were cultured in arginine- and lysine-free medium supplemented with 10% dialyzed FBS, and either $^{12}C_6^{14}N_4$-arginine (Arg0) and $^{12}C_6^{14}N_2$-lysine (Lys0) or $^{13}C_6^{15}N_4$-arginine (Arg10) and $^{13}C_6^{15}N_2$-lysine (Lys8). After six doublings, cells were expanded and cultured in the labeling medium for 4 days. Wnt3a(FLAG) CM was collected and cleared, and subjected to affinity purification. The purified Wnt3a proteins were combined and separated by SDS-PAGE, followed by in gel trypsin digestion and quantitative Mass spectrometric analysis. Untagged Wnt3a was also purified from CM of L cells stably expressing Wnt3a or L cells stably expressing both Wnt3a and TIKI2 for mass spectrometric analyses and obtained identical data as Wnt3a (FLAG). Untagged Wnt3a was firstly enriched by blue Sepharose 6 beads (GE Healthcare) and directly eluted with elution buffer (20 mM Tris-HCl, 1.5M KCl, 1% CHAPS, pH 7.5). Elutes were dialyzed against PBS/1% CHAPS, concentrated and immunoprecipitated with an anti-Wnt3a antibody (Cell Signaling). The IP products were separated by SDS-PAGE and Wnt3a bands were subjected to mass spectrometric analyses. Xwnt8-Myc and HA-Xwnt8-FLAG

Example 1

Expression Cloning of Tiki1

A functional cDNA expression screen was performed using arrayed *Xenopus* cDNAs to identify novel genes involved in AP patterning and Wnt signaling. One of the isolated cDNAs caused dramatic head enlargement in embryos upon overexpression and was named Tiki1 (Tiki refers to a large headed humanoid carving in Polynesian mythology) (FIG. 1A). Tiki1 encodes a putative type I transmembrane protein of 508 residues, harboring a leading amino-terminal signal peptide, a large ectodomain, and a transmembrane domain at the carboxyl terminus (FIG. 1B). Tiki1 is the founding member of a new protein family conserved from invertebrates to vertebrates, and a Tiki1 homologue is encoded in the genome of sponge *Amphimedon queenslandica* and sea anemone *Nematostella vectensis* and thus is likely in the common ancestor before invertebrates and vertebrates diverged (FIGS. 1C and 1H). Most vertebrates including *Xenopus*, zebrafish and human have two genes, Tiki1 and Tiki2 (FIGS. 1C and 1H). Tiki proteins do not harbor any functional motifs known to metazoa, but intriguingly exhibit a conserved ectodomain of about 340 residues, referred to here as the "TIKI domain", which shares significant homology (25% identity/40% similarity) with gumN proteins of putative bacterial gene products of unknown functions (gumN proteins have recently been reclassified into the TraB superfamily, Pfam: PF01963) (FIGS. 1C and 1I).

```
Human TIKI1 (Hsa_TIKI1)
                                                         (SEQ ID NO: 45)
ATGAGTCCCTGGAGCTGGTTCCTGCTGCAGACCCTCTGCCTCCTGCCCACG

GGCGCAGCTTCGCGGCGCGGGCGCCCGGCACCGCCAACTGCGAGCTCAA

GCCCCAACAAAGCGAGCTGAATTCCTTCTTGTGGACCATTAAGCGAGACC

CACCATCTTACTTCTTTGGCACAATCCATGTCCCGTACACCCGAGTTTGGG

ACTTCATCCCCGACAACTCTAAGGAGGCTTTCCTGCAGAGCAGCATTGTGT

ACTTTGAGTTGGATCTCACAGACCCCTATACCATCTCAGCTCTCACCAGCT

GTCAGATGCTGCCACAGGGCGAGAACCTCCAAGATGTGCTCCCCAGGGAC

ATCTACTGCCGCCTCAAGCGCCACCTGGAGTATGTCAAGCTCATGATGCCC

TTGTGGATGACCCCAGACCAGCGCGGCAAGGGGCTCTACGCAGACTACCT

CTTCAATGCTATTGCCGGAAACTGGGAGCGCAAGAGGCCTGTCTGGGTGA

TGCTCATGGTCAACTCCCTGACTGAAGTGGACATTAAGTCCCGTGGAGTG

CCTGTCTTAGACCTGTTCCTTGCCCAGGAGGCTGAGCGGCTGAGGAAACA

GACTGGGGCAGTGGAAAAGGTGGAAGAGCAGTGCCATCCATTGAATGGG

TTGAACTTTTCACAGGTCATCTTTGCTTTGAACCAGACCCTCCTGCAGCAG

GAAAGCCTGCGAGCAGGCAGTCTTCAGATCCCCTACACGACGGAGGATCT

CATCAAACACTATAACTGCGGGGACCTCAGCTCCGTCATCCTCAGCCATG

ACAGCTCCCAGGTTCCCAATTTTATTAATGCCACGCTACCACCTCAGGAGC

GCATCACTGCTCAGGAGATTGACAGCTACTTACGCCGGGAGCTGATCTAC

AAGCGGAATGAGAGAATAGGGAAGCGGGTGAAGGCCCTTTTGGAGGAGT

TCCCTGACAAAGGCTTCTTCTTTGCCTTTGGAGCTGGTCATTTCATGGGCA

ACAACACAGTGCTGGATGTTTTGCGGCGTGAAGGCTATGAGGTAGAACAC

GCCCCTGCTGGACGACCCATCCACAAAGGGAAGAGTAAAAAGACCTCCAC

ACGGCCCACTCTGTCCACCATCTTTGCTCCAAAAGTCCCTACCCTGGAAGT

ACCGGCACCAGAAGCCGTATCCTCAGGGCACTCAACGCTGCCTCCCCTTG

TGTCCCGGCCTGGAAGTGCCGACACGCCCAGTGAGGCCGAACAGAGGTTC

CGGAAGAAGCGGAGGCGGTCACAGCGGAGGCCGCGACTCCGGCAATTCA

GCGATCTGTGGGTCCGCCTGGAGGAGAGTGACATAGTCCCGCAACTCCAG

GTCCCTGTCCTGGACAGGCACATCTCCACTGAACTGCGGCTCCCTCGCCGT

GGGCATTCCCACCACAGCCAGATGGTGGCCAGCAGTGCCTGCCTGTCTCT
```

CTGGACTCCTGTGTTCTGGGTGCTGGTGCTGGCTTTCCAAACAGAGACACC

CCTCCTGTAA (SEQ ID NO: 1)
MSPWSWFLLQTLCLLPTGAASRRGAPGTANCELKPQQSELNSFLWTIKRDPPS

YFFGTIHVPYTRVWDFIPDNSKEAFLQSSIVYFELDLTDPYTISALTSCQMLPQ

GENLQDVLPRDIYCRLKRHLEYVKLMMPLWMTPDQRGKGLYADYLFNAIAG

NWERKRPVWVMLMVNSLTEVDIKSRGVPVLDLFLAQEAERLRKQTGAVEK

VEEQCHPLNGLNFSQVIFALNQTLLQQESLRAGSLQIPYTTEDLIKHYNCGDLS

SVILSHDSSQVPNFINATLPPQERITAQEIDSYLRRELIYKRNERIGKRVKALLE

EFPDKGFFFAFGAGHFMGNNTVLDVLRREGYEVEHAPAGRPIHKGKSKKTST

RPTLSTIFAPKVPTLEVPAPEAVSSGHSTLPPLVSRPGSADTPSEAEQRFRKKRR

RSQRRPRLRQFSDLWVRLEESDIVPQLQVPVLDRHISTELRLPRRGHSHHSQM

VASSACLSLWTPVFWVLVLAFQTETPLL

Human TIKI2 (Hsa_TIKI2)
(SEQ ID NO: 18)
ATGCACGCCGCCCTGGCGGGGCCGCTGCTCGCCGCCCTCCTCGCCACCGCT

CGCGCCCGCCCGCAGCCCCCGGACGGAGGACAGTGCCGGCCGCCCGGATC

GCAGAGGGACTTGAACTCCTTCCTGTGGACGATTCGGCGTGATCCTCCGG

CCTACCTGTTTGGCACTATTCACGTCCCCTACACCCGCGTCTGGGACTTCA

TCCCGGACAACTCCAAGGCAGCCTTCCAGGCTAGCACCCGTGTCTACTTTG

AGCTGGACCTTACAGACCCCTACACCATCTCGGCCCTGGCCAGCTGCCAG

CTGCTGCCGCACGGGGAAAACCTGCAGGACGTGCTGCCCCACGAGCTTTA

CTGGCGCTTGAAGCGCCACCTGGACTACGTGAAGTTGATGATGCCCTCCT

GGATGACGCCCGCTCAGCGGGGCAAGGGGCTCTATGCTGACTACCTATTC

AATGCCATCGCGGGCAACTGGGAGCGCAAGAGGCCCGTCTGGGTGATGCT

CATGGTAAACTCGCTCACAGAGAGGGACGTGCGCTTCCGTGGTGTGCCCG

TGCTCGACCTCTACCTGGCCCAGCAGGCTGAGAAGATGAAGAAGACCACA

GGGGCTGTGGAGCAGGTGGAGGAGCAGTGCCATCCCCTCAACAACGGGCT

CAACTTCTCCCAGGTGCTGTTTGCCCTGAACCAAACCCTGCTGCAGCAGGA

GAGTGTGCGGGCCGGGAGCCTGCAGGCCTCCTACACCACGGAGGACCTCA

TCAAGCACTACAACTGCGGAGACCTCAGCGCAGTCATCTTCAACCACGAC

ACATCCCAGCTGCCCAACTTTATCAACACCACCCTCCCGCCACACGAGCA

GGTGACGGCCCAGGAGATTGACAGCTACTTCCGCCAGGAGCTCATCTACA

AGAGGAATGAGCGCATGGGGAAGAGGGTCATGGCGCTTCTACGGGAGAA

CGAGGACAAGATCTGCTTCTTTGCCTTCGGAGCAGGTCACTTTCTGGGGAA

CAACACAGTCATCGACATCCTGCGGCAGGCAGGGCTGGAGGTGGACCACA

CACCCGCCGGGCAGGCCATACACAGCCCTGCCCCCAGAGCCCAGCGCCC

TCTCCTGAGGGGACCTCGACGAGCCCGGCCCCAGTGACCCCAGCTGCCGC

TGTCCCCGAAGCACCCTCTGTGACCCCCACCGCCCCACCAGAGGATGAGG

ATCCAGCCCTGTCCCCACACCTCCTGCTCCCCGACAGCCTCAGCCAGCTGG

AGGAGTTTGGCCGGCAGAGGAAGTGGCACAAGAGGCAGAGCACACACCA

GCGGCCGCGGCAGTTCAATGACCTCTGGGTCCGCATCGAGGACAGCACCA

-continued

CCGCCTCACCACCCCGCTGCCCCTGCAGCCCACCCACAGCTCGGGGACC

GCCAAGCCCCCTTCCAGCTTTCAGACCAGCTACAACAGCAGGACCCGCC

AGGGCCCGCCAGCAGCTCGGCACCCACCCTGGGCCTTCTCCCCGCCATCG

CCACCACCATCGCTGTCTGCTTCCTGCTGCATAGCCTTGGGCCCTCCTGA (SEQ ID NO: 2)
MHAALAGPLLAALLATARARPQPPDGGQCRPPGSQRDLNSFLWTIRRDPPAY

LFGTIHVPYTRVWDFIPDNSKAAFQASTRVYFELDLTDPYTISALASCQLLPHG

ENLQDVLPHELYWRLKRHLDYVKLMMPSWMTPAQRGKGLYADYLFNAIAG

NWERKRPVWVMLMVNSLTERDVRFRGVPVLDLYLAQQAEKMKKTTGAVE

QVEEQCHPLNNGLNFSQVLFALNQTLLQQESVRAGSLQASYTTEDLIKHYNC

GDLSAVIFNHDTSQLPNFINTTLPPHEQVTAQEIDSYFRQELIYKRNERMGKRV

MALLRENEDKICFFAFGAGHFLGNNTVIDILRQAGLEVDHTPAGQAIHSPAPQ

SPAPSPEGTSTSPAPVTPAAAVPEAPSVTPTAPPEDEDPALSPHLLLPDSLQLE

EFGRQRKWHKRQSTHQRPRQFNDLWVRIEDSTTASPPPLPLQPTHSSGTAKPP

FQLSDQLQQQDPPGPASSSAPTLGLLPAIATTIAVCFLLHSLGPS

*Xenopus tropicalis* Tiki1
(SEQ ID NO: 19)
ATGGTAATCATTTGGAATATATTCCTGCCAGCATTCCTCCTAGTGCTGGCC

AAAGCGAGTCTCAGGAGCTCCAGGGATTCGGCAAACTGCAAGCTCAACAA

GAAACAAAGCCAACTAAACTCCTTTCTGTGGACAATAAAGCGAGATCCCC

CCTCATACTTTTTTGGCACAATTCATGTACCTTATACACGGGTATGGGACT

TTATCCCAGAAAATTCCAAGACAGCTTTCCAACAGAGCAATATTGTGTACT

TTGAATTGGACTTAACAGACCCATACACAATCTCAGCCTTGACTAGTTGCC

AGATGCTGCCCCAGGGTGAAAACTTGCAAAATGTACTGCCCAGGGATATT

TACCGAAGGTTGAAACGCCATTTGGAATATGTTAAACTTATGATGCCTTCC

TGGATGACCCCTGATCAAAGAGGAAAAGGGCTTTATGCTGACTATTTATT

CAATGCTATTGCTGGAAATTGGGAAAGGAAAAGACCTGTCTGGGTTATGC

TGATGGTGAACTCTCTAACAGAGGTCGATATCAAGTCGAGAGGAGTCCCA

GTATTGGATTTATATTTGGCTCAAGAAGCTGAGCGCCTTAAGAAAAGAAC

TGGAGCAGTAGAACAGGTAGAAGAACAATGCCACCCCCTAAATGGATTG

AACTTATCACAGGTAATATTTGCCTTAAATCAGACTCTCTTGCAACAGGAG

AACCTTCGTGCAGGCAGCGTTCAAGTTCCCTATTCCACAGAAGACCTGATC

AAGCATTACAACTGTGGAGACCTCAACTCCATTATTTTTAATCACGATTCT

TCACAAGTCCCTAATTTCATAAACTCCACTTTACCACCTCAAGAAAGAATA

ACTGCTCAAGAGATCGACAATTATTTCCGTCAAGAGCTGATTTATAAAAG

GAATGAGCGCATGGGAAAGAGGGTTAAAGATCTACTGGAGCAGTTTCCGG

AGAAAAGTTTTTTCTTTGCTTTCGGTGCAGGTCATTTCCTGGCAATAATA

CTGTCATTGATGTGTTAAAAAGGTATGGATATGATGTGCTACACACTCCTG

CTGGTCGATCCATCATCAACAATGGTAAAGGTAAGAAAAATCTGCTGCCA

TCCAAGTTTTCATCTTCATCTTTACCAGTTGGGTTATCCGCACCTCCCTGCA

CAGTTACTTCCAGAATAAAACAGTCAATAAATTCTCACAAAGACCAAGAA

TCCCTCCCTGACATACTGTTAGATGATGATATCGACCAGCTTGATAAAGAC

-continued

```
GAAAGAAAGTACAAAAAGAGGAAGCAAAGGAAAGAAAAACATCGCCATT

TCAGTGATCTCTGGGTTCGCATTCAAGAAAGCTCAACAGACACCACGCCG

CAAATCCGAATTATTAATGGATACATTACTGTGGAACCACATCCAAGAGA

ACACGGAAAAGACAAATACATTAAGGCAGCACAAAGCGTTTCTTTCAGCC

TATCGATCCCTTCTGCCTTTTTGCTGCTGGCTTGGTGTTTTCAGCAGGTGGC

AGTATTGCAGTGA
```

(SEQ ID NO: 20)

```
MVIIWNIFLPAFLLVLAKASLRSSRDSANCKLNKKQSQLNSFLWTIKRDPPSYF

FGTIHVPYTRVWDFIPENSKTAFQQSNIVYFELDLTDPYTISALTSCQMLPQGE

NLQNVLPRDIYRRLKRHLEYVKLMMPSWMTPDQRGKGLYADYLFNAIAGN

WERKRPVWVMLMVNSLTEVDIKSRGVPVLDLYLAQEAERLKKRTGAVEQV

EEQCHPLNGLNLSQVIFALNQTLLQQENLRAGSVQVPYSTEDLIKHYNCGDL

NSIIFNHDSSQVPNFINSTLPPQERITAQEIDNYFRQELIYKRNERMGKRVKDLL

EQFPEKSFFFAFGAGHFLGNNTVIDVLKRYGYDVLHTPAGRSIINNGKGKKNL

LPSKFSSSSLPVGLSAPPCTVTSRIKQSINSHKDQESLPDILLDDDIDQLDKDER

KYKKRKQRKEKHRHFSDLWVRIQESSTDTTPQIRIINGYITVEPHPREHGKDK

YIKAAQSVSFSLSIPSAFLLLAWCFQQVAVLQ
```

*Xenopus tropicalis* Tiki2 (Xtr Tiki2)

(SEQ ID NO: 21)

```
ATGGGAAAAACAATGTGGGCTAGGGCAGTGTTCCTCTGCTTCTCGGTGGG

CACGTTACTGTGGCAGGAGGTCCTGACTAGGAGAATCCCGGTGGACACCG

GTCAGTGTGGGCTGCCCAAATCGCAAGAAGATCTGAATTCCTTTCTTTGGA

CCGTAAGGAGGCATCCACCTGCCTATCTCTTTGGAACCATACATGTGCCTT

ATACAAGAGTTTGGGATTTCATACCCCAAAACTCCAAAAAGGCGTTTCAT

GACAGCAACAGTGTATACTTTGAATTGGACCTCACTGACCCATACACTATT

TCAGCTTTGGCAAACTGTCAGATGCTTCCACAGGGGGAAAAACCTGCAGGA

TGTGCTGCCCAGGGATCTGTACAGGAGACTAAAGAGGCACTTGGAGTATG

TTAAGCACATGACGCCTCACTGGATGACCCCAGACCAGAGGGGAAAGGG

CCTTTATGCTGATTACCTCTTTAATGCCATTGCTGGGAACTGGGAGAGAAA

GAGACCTGTGTGGGTGATGCTGATGGTAAATTCTTTAACAGAAGCTGATA

TCAGGTCTAGAGGTGTCCCAGTCTTGGATCTGTATTTAGCACAGGAAGCTG

ATCGAATGAAGAAGAAAACCGGGGCTGTTGAGAGGGTAGAAGAACAGTG

TCATCCTCTCAATAGGTTAAACCTTTCCCAGGTTTTGTTTGCCCTAAATCA

AACATTGTTGCAGCATGAAAGTCTACGTGCAGGAAGTTTCCAAGCTCCAT

ATACCACAGAGGATCTTATCAAACATTACAACTGTGGGGACCTCAATGCT

GTGATATTTAGCCATGATTCTTCCCAGCTCCCAAATTTTATCAACGTCACT

CTTCCCCCTCATGAACAAGTAACCGCACAAGAAATTGATATCTACTTTAGG

CAAGAACTGATCTACAAGAGGAACGAGAGGATGGCAAGGAGAGTGATTG

CACTTCTTAAGGAGAACAAGGACAAAAGTTTCTTCTTTGCTTTTGGTGCAG

GCCACTTCCTTGGAAATAACACAGTCATTGATGTTCTGAGACAAAATGGA

TATGAGGTTGAGCACACTCCAGCGGGACAGACATTTACTGCAGCAAAACC

CAAAACAAACCCAACCTCGGATGACTCCATGGCAACCGATTCTCCAGCAA
```

-continued

TGAAATATTTTGATCACGTCCCTGCGACAGCTTCCTACTTTGGCGAGTCGG

ATGAGGAGATGCTGCCCCCCCACCTCCTGTTGCCAGACAGTATTAGTCAG

CTGGAAGAGTTTGGAAAGCAGAATAGTTGGCATCGGAAGCATTACAGGA

ATCAGAGACCAAGGCAGTTCAATGACCTTTGGGTTCGTTTAGATGATAGT

ACAACAACATTGCCTTCAAACACTAGGAACACCAACGGAGAACAGTCTGC

AGAGTCACTGGTTTGGCTGCCTGAGCAGGATCATCACAATTACCTGGATG

TTAAACTGTCCCATTCACAGAGCAATTCATCTCCCAAGTGCCTATCAGCAA

GCCCTGCCTTCCTCTATACGTTAGTAACTTTGTGCCTTATAACAACAATGA

GAACACGATCA (SEQ ID NO: 22)
MGKTMWARAVFLCFSVGTLLWQEVLTRRIPVDTGQCGLPKSQEDLNSFLWT

VRRHPPAYLFGTIHVPYTRVWDFIPQNSKKAFHDSNSVYFELDLTDPYTISAL

ANCQMLPQGENLQDVLPRDLYRRLKRHLEYVKHMTPHWMTPDQRGKGLYA

DYLFNAIAGNWERKRPVWVMLMVNSLTEADIRSRGVPVLDLYLAQEADRM

KKKTGAVERVEEQCHPLNRLNLSQVLFALNQTLLQHESLRAGSFQAPYTTED

LIKHYNCGDLNAVIFSHDSSQLPNFINVTLPPHEQVTAQEIDIYFRQELIYKRNE

RMARRVIALLKENKDKSFFFAFGAGHFLGNNTVIDVLRQNGYEVEHTPAGQT

FTAAKPKTNPTSDDSMATDSPAMKYFDHVPATASYFGESDEEMLPPHLLLPD

SISQLEEFGKQNSWHRKHYRNQRPRQFNDLWVRLDDSTTTLPSNTRNTNGEQ

SAESLVWLPEQDHHNYLDVKLSHSQSNSSPKCLSASPAFLYTLVTLCLITTMR

TRS

Zebrafish Tiki1 (Dre Tiki1)
(SEQ ID NO: 23)
ATGACGATGATGACGATGATGATGGTCAGCTGGAGCGCTTTTCTGCAGAT

CTGCTGGATACTCATGGTGAGAGCAAACCAGTTCAACCCCGGAGAGCCGA

GCGGCTGCCGGACCAACACTCCACAGAGTGATCTGAACTCCTTCCTGTGG

ACGATCAAGCGGGACCCTCCGTCATATCTGTACGGCACCATCCACGTCCC

GTACACCCGCGTCTGGGACTTCATCCCGCAGAACTCCAAGCAGGCGTTCC

AGGAGAGCAGCGTGGTGTACTTTGAGCTGGAGCTGACGGACCCGTCCACC

ATCTCGGCTCTGTCCCGCTGTCAGCTGCTGCCGGCGGGCCAGAACCTGCA

GGACGTGCTGCCGCCAGAACTCTACCTGCGCCTGAAGACGCACCTGGAGT

ACGTGCGGCTGATGCTACCCTCCTGGATGACCCCTGACCAGCGGGGAAAG

GGCCTGTATGCTGAATACCTGTTCAACGCCATCGCCGGGAACTGGGAGCG

CAAGCGTCCGGTGTGGGTGATGCTGATGGTGAACTCGCTGACGGAGGCCG

ATATAAAGACCCGTGGGGTCCCGGTGCTGGACCTGTACCTGGCCCAGGAG

GCGGAGCGCATGAAGAAGCAGACCGGAGCCGTGGAGAAGGTGGAGGAGC

AGTGCAGTCCGCTAAACACACTCGACTTCTCTCAGGTGATCTTCGCTCTGA

ATCAGACGCTGCTGCAGCAGGAGAGTGTGCGGGCCGGCAGTCTGCAGGTG

CCCTACACAACTGAACACCTGATCACACACTACAACTGTGGAGACCTGCA

CTCCATCATCAGCCACGACACCGCACAGGTGCCGAACTTCAACAATGTGA

CTCTGCGTCCCAGCGATCAGGTGACGGCGCAGCAGATCGACAGCTACTTC

AGACGCGAGCTGATCTACAAGCGTAATGAGCGCATGGGCCGCCGCGTCAC

```
AGCCCTGCTGCAGGAACAGCCACACAAAACTTTCTTCTTCGCATTCGGAG

CAGGGCATTTTCTGGGGAATAACTCTGTGATTGACGTCCTGCGGAGAGAA

GGATACGAGGTAGAACACACACCTGCTGGACAACCACTGCACAGACGGTC

AGGCTGGAGGTCTGCAGATCCCGCAGACACAGACGCAGCGCTGCAGCCGT

TCCTCCACCACAGCAGGCATCATGAGCTGCAGCTTCTGGAGGGTCTGGAG

CTGCTGGAGAAGGTGGAGCACAAGCTGAAGAAGAAACACCGCAGAAACA

AGCTGAAGAAACAGCGGCAGTTCAACGACCTGTGGGTGCGCATGGAGGA

CAGTGTGACAGCCGAGGCTCCGCCCCCTCTCATCCACATCATCAACGGTTA

CATCACAGTCCAGACACACCCACAGGACCACGAGAGAGCCAATCACGAC

AGGACGTTTTCAGGCTCCTCCTCCTGGACAGGCCCCGCCCTCAGTGCGCTG

GCTGTGTGTGTTCAGATGCTCAGACTGCTGCTGTGA
```
                                                    (SEQ ID NO: 24)
```
MTMMTMMMVSWSAFLQICWILMVRANQFNPGEPSGCRTNTPQSDLNSFLW

TIKRDPPSYLYGTIHVPYTRVWDFIPQNSKQAFQESSVVYFELELTDPSTISALS

RCQLLPAGQNLQDVLPPELYLRLKTHLEYVRLMLPSWMTPDQRGKGLYAEY

LFNAIAGNWERKRPVWVMLMVNSLTEADIKTRGVPVLDLYLAQEAERMKK

QTGAVEKVEEQCSPLNTLDFSQVIFALNQTLLQQESVRAGSLQVPYTTEHLIT

HYNCGDLHSITSHDTAQVPNFNNVTLRPSDQVTAQQIDSYFRRELIYKRNERM

GRRVTALLQEQPHKTFFFAFGAGHFLGNNSVIDVLRREGYEVEHTPAGQPLH

RRSGWRSADPADTDAALQPFLHHSRHHELQLLEGLELLEKVEHKLKKKHRR

NKLKKQRQFNDLWVRMEDSVTAEAPPPLIHIINGYITVQTHPQDHERANHDR

TFSGSSSWTGPALSALAVCVQMLRLLL
```
(No predicted transmembrane region, but has a predicted GPI
anchor site (underlined))

Zebrafish Tiki2 (Dre Tiki2)
                                                    (SEQ ID NO: 25)
```
ATGAACTGTCAGTCGGGACTGCGATGGTTGGTAACTTTATGCGCTTTCTTT

CAAGTGGGCTCTGCCCGGGACACGCACGAGAGCACGCGGCAATGTGACA

AGCCCGTATCGCAGAAAGACATGAACTCCTTCCTGTGGACCGTGAAGCGG

CCTCGTCCTTTTCCACCGTCGTATCTGTTTGGCACAATCCACGTCCCGTAC

ACTCGAGTGTGGGACTATATCCCAGAGAGCTCAAAACGTGCCTTTCAGAC

CAGCAACAGTGTATTCTTTGAACTGGATCTCACAGATCCTTTAACCATCTC

CAAACTCACCAGCTGCCAGCTTCTGCCCAATGGAGAAAACCTCCAGACGC

TACTGCCACGGGATCTCTACCGCCGCCTCAAGCGCCACCTGGACTACGTC

AAACACATGATGCCCTTCTGGATGACAGCAGACCAGCGCGGCCGAGGACT

TTATGCCGACTACCTCTTCAACGCCATTGCGGGGAACTGGGAACGCAAGA

GGCCTGTATGGGTGATGCTAATGGTGAACTCGCTGACGGAAGCAGACGTC

CGGTCACGGGGAACCCCCGTGCTCGACCTGTTCTTGGCACAGGAGGCAGA

GCGTCTCGGAAGCAGACAGGTGCTGTGGAGAGGGTGGAGGAACAGTGC

CATCCCCTGAATGGACTGAACTTCTCACAGGTGTTGTTTGCCCTGAACCAG

ACTCTACTGCAGCATGAGAGTTTGCGTGCAGGCATTCTGCAGGGCACCTTT

ACTACAGAGGACCTCATTGCACACTACAATTGTGGAGACCTCAACTCCAT

CATCTTCAATCATGACACATCCCAGCTTCCGCATTTCATCAACAGTTCTCT
```

-continued

```
GCCAGATCATGAGCGCTTGACGGCGCAGCAGATCGACAGTTACCTGCGGC

AGGAGCTCATTTACAAACGCAATGAACGAATGGCCCGCCGCGTCTCCGCC

CTCCTTCAGAGAAACCCCAACCAGAGCTTCTTTTTCGCTTTTGGAGCTGGT

CATTTCCTGGGGAATCATAGTGTACTGGACATTCTGCGGCAGGAGGGCTA

TGAGGTGGAGCACACACCACCACAAGAGCCCATCATACAGAGCTGGTCTG

AGCGGGAGGCGACCACACTGAATCCCACCGAAGACAGCTTCGAGTCAGTG

ACAGAATGGACATCAGAGACTCCTGAGCTGGAGGAGATCAGCCAGGAAG

AACTCTCCCATATGCTGCTGCCTGACAGTCTCAGCCAGCTAGAGGAATTTG

GCCGCTACAAGCATCCTCGTAAAACCCATCATACGCACAGTCGACCTCGG

CTGTTCAGCGACCTGTGGGTGCGCATAGGAGACAGCACGACTCCACACCC

AAGCATAAGGATAACCAATGGCTATGTGACGGTGGAGCCTCCTCAGATAC

GACAGGAACAGCAACAAAGACTCAGAGAAAGACTGAAGCCTCTCAGTGAG

CCCACAAACCCCAGCGCACTTGACTCCGCTGCTCCAAACCCAACATATGC

GCTGACTTGTTTTTTGGCCTGTCTCATTTCACAACTGCTTTTTGCTTCCTAA
```

(SEQ ID NO: 26)
```
MNCQSGLRWLVTLCAFFQVGSARDTHESTRQCDKPVSQKDMNSFLWTVKRP

RPFPPSYLFGTIHVPYTRVWDYIPESSKRAFQTSNSVFFELDLTDPLTISKLTSC

QLLPNGENLQTLLPRDLYRRLKRHLDYVKHMMPFWMTADQRGRGLYADYL

FNAIAGNWERKRPVWVMLMVNSLTEADVRSRGTPVLDLFLAQEAERLGKQT

GAVERVEEQCHPLNGLNFSQVLFALNQTLLQHESLRAGILQGTFTTEDLIAHY

NCGDLNSIIFNHDTSQLPHFINSSLPDHERLTAQQIDSYLRQELIYKRNERMAR

RVSALLQRNPNQSFFFAFGAGHFLGNHSVLDILRQEGYEVEHTPPQEPIIQSWS

EREATTLNPTEDSFESVTEWTSETPELEEISQEELSHMLLPDSLSQLEEFGRYK

HPRKTHHTHSRPRLFSDLWVRIGDSTTPHPSIRITNGYVTVEPPQIRQEQQQRL

RERLKPLSEPTNPSALDSAAPNPTYALTCFLACLISQLLFAS
```

Worm Tiki (*C. elegans* Tiki)

(SEQ ID NO: 27)
```
ATGACCTTTTATATACTAGTTGTATCTTTATATTTATCATTGTTTCTAGTAA

CTGTTGTACAGTCCGATTGTGATACCGATGTTGAACAGAGGGAAAGAAAT

ATATTCTTGTGGTCAGTAAAACATCCCCAGTTCGCATCATCTCAGGGATAT

CTTTTTGGTACAATTCATGTGCCATTCACCGAGGTTTGGAAGGAAGTGAGC

GACCGAGTGCGTGATGCATTTGCGGTGTCAGACACAGTTCTCTTGGAAATT

GATTTACATGATGAAGCAACAATTCATGAGTTGATAGCTTGTAAGAACTT

GGCATATGATGAGACTGTGCACTCTTATCTTTCCATTGAATTATTGGAAAG

AATAGAGAAATTATGGAATATCTTCGCTCAAGTTTCCTTGCCTGGGCCCA

GAAACAAAATCCACGGGACACAAAGAAGATAAAGCATGCTGAAGATATC

TACAACAATATCATAGGAGATTGGTGGAGAAAACGCCCAATTTGGTTATT

ATTTCTGCTCTATCAAATGTGCGAAAATGTGTTTGAAAAAAGTTCAAGTCC

ATTACTAGATTTGTACATTGCACAAAGAGCCACCGACGAGAAGAAGACAA

TTATCCCGATTGAAACCGCCGAGGAGCAATGCAATCCAGTTGTTTCAGTTT

CTACCAATGAAATTATCTTTGCAATAGAGCATACTGTGCACTATTTTGAAG

ATAAAATCTTGGACAATCCATCAAAGGATAATGAGTCTAGAAGCAGTTTG
```

-continued

```
AAAGAGCTCGTCGAACATTATAAGTGTGGGACTCTGAAGGAAGATATGTT

TGATAAAGATGGAATGTCTATAATTGACTATGCAACTGGAACAACAGAAC

GGTTTAAAGCTGACGAGATCAACAAAAAGTTGAAGCAGGATATTTTTGTA

AAACGAAATTTGAGAATGGCCAAACGGATAGAGAAGATTTTGAAGGGTC

GAAATAGTAACACTGTATTTTCTGCAATAGGCGCTGGACACTTTTTTGGAA

GCAGTAGTGTGTTAACATATCTTGAAGAGAGCGGATTTATAGTTCAGAAG

TTAAAAAATACAGATGTGATTCAACCCCTACGATCTCCCTACCGTCAAACC

GCAAAGTTCAAACGTGTATGGACCAAGGAAACCGCAGTTCGTCGAAAATC

AATAATCATCGAAGAAGTAGCACCATCGTCCAGTCGAATTGCTAGATTATG

GCTAGTTCCGTGTATTTTTCTTTTACATTCCATCTTTGCCATTTTCCCATGA
```

(Signal peptide)

(SEQ ID NO: 28)

<u>MTFYILVVSLYLSLFLVTVVQS</u>DCDTDVEQRERNIFLWSVKHPQFASSQGYLFGTIH

VPFTEVWKEVSDRVRDAFAVSDTVLLEIDLHDEATIHELIACKNLAYDETVHSYLSI

ELLERIEKIMEYLRSSFLAWAQKQNPRDTKKIKHAEDIYNNIIGDWWRKRPIWLLFL

LYQMCENVFEKSSSPLLDLYIAQRATDEKKTIIPIETAEEQCNPVVSVSTNETIFAI

EHTVHYFEDKILDNPSKDNESRSSLKELVEHYKCGTLKEDMFDKDGMSTIDYATGTT

ERFKADEINKKLKQDIFVKRNLRMAKRIEKILKGRNSNTVESAIGAGHFEGSSSVLT

YLEESGFIVQKLKNTDVIQPLRSPYRQTAKFKRVWTKETAVRRKSIIIEE<u>VAPSSSR

IARLWLVPCIFLLHSIFAIFP</u>

(transmembrane)

*Nematostella* Tiki (SEQ ID NO: 29)

```
ATGGCAGCCTTTACTTTATGGATATTGGTGCTTAATGTTTTCCTGTTGGGTT

TTCAAGCCCGCAAGTTAGCGAGTAATTTAAAGTTTCCGATACAGAAATGT

GATGATTCTACGCCTCAGAAGAATTTCAATTCATTCCTATGGCTTGTCAAG

CGAACGCCACCGGCGTATTTTTATGGAACAATCCACGTCCCGTACACAAG

AGTGTGGGATTTTATCCCTATGAACAGCAAACAAGCATTCACTGCAAGTC

AGCACGTCTATTTCGAGCTCGATCTTACGGACGAGAAAACTATGAGAGCT

TTAATGAAATGTCAAATGCTCCCGTCTGGGACAATGCTCAGACAGACTTT

ACCGCGCAAGATGTTTAAGAGATTGAAATCTCATTTACGTTACATCAAAA

GAATGATTCCTAAATGGATTAAACACCGCGATCAAGAGACTTCGAGCGCC

GGTCCTTACGCCAATAAGCTTTACGAGATGCTTACCAAAGACTGGGATAA

AAAGCGACCTATTTGGGTCATGTTGATGGTGAATTCATTAACCGAGAGTG

ATATTAAAACTCGTGGAATTCCCGTATTGGACCAGTACCTGGCCTTGGAG

GCAAGCAGAAATCACAAACTAATCGGTGCTGTAGAAAATGTTGATGAACA

ATGTAAACCACTCAACGCCTTAAACGCCTCACAGGTAGTATTTGCTCTTAA

TCAGTCTCTTCACTTTCAAGAGCGGTTGCGCAGAGGCCAAGTCCAAGTAA

CGTACACAACAGACGATCTGATCGATCATTATAATTGCGGGGACCTGAAG

TCAGTTTTGTTCTCGACTCAGACCAGTCTGCCTACCCTGACCGTGAATTCC

TCTTTAGAGCAAAGGGAACGGAAACGAGCCCAGGAAATAGACCAGTACT

TTCGCAATGAACTGATTTTCCAGAGGAATAAGCGAATGGCGCAAAGAGTT

ATAACACTGCTTAATAATCACCCAGAAAAAGACTTCTTTTTCGCGTTCGGC
```

-continued

GCAGGTCACTTTCTTGGTAATCACAGTATTATAGATATAATGAAGAAACA

CGGTTATGATGTGGAATACGTCAAACCGGAGCAAGAGCTACCAAGCTTCA

AAGCCAAGAAATCGCTGAATACCCGGCGAGAAAGGCGCAAAGGCTGCAG

GGGCAGGAGAAAAAGAGCAAACGATGTCAGAAGAAAAAGAAACGGAA

GCGCCCTGACTATAGCCGAGTTAGACTTCTTCAGGTCGCTACTAGACGGTG

GAACCCTACAAGAAAGCCGTACCCTACCAAACTATCTGAGGCACCTGGCG

CCAGAGACATTTCCTCGCGGAAAGCTGCTGCATCTTGCACCCCAATCTGG

ACTGTTTCACTTGCTCTTACATGTGCTGTCACTTGCCTGTTGACGTACAGC

GGTTTTCGGTAA (SEQ ID NO: 30)
MAAFTLWILVLNVFLLGFQARKLASNLKFPIQKCDDSTPQKNFNSFLWLVKR

TPPAYFYGTIHVPYTRVWDFIPMNSKQAFTASQHVYFELDLTDEKTMRALMK

CQMLP SGTMLRQTLPRKMFKRLKSHLRYIKRMIPKWIKHRDQETSSAGPYAN

KLYEMLTKDWDKKRPIWVMLMVNSLTESDIKTRGIPVLDQYLALEASRNHK

LIGAVENVDEQCKPLNALNASQVVFALNQSLHFQERLRRGQVQVTYTTDDLI

DHYNCGDLKSVLFSTQTSLPTLTVNSSLEQRERKRAQEIDQYFRNELIFQRNK

RMAQRVITLLNNHPEKDFFFAFGAGHFLGNHSIIDIMKKHGYDVEYVKPEQEL

PSFKAKKSLNTRRERRKGCRGRRKKSKRCQKKKKRKRPDYSRVRLLQVATR

RWNPTRKPYPTKLSEAPGARDISSRKAAASCTPIWTVSLALTCAVTCLLTYSG

FR

*Amphimedon* Tiki
(SEQ ID NO: 31)
ATGCAAGTGAAGATAGTACAAGTTTTTCCATGCTTGGTACTGCTAGTAAA

GCTAGTGCTTCTCTCTGTTCTACTGCCATCAGCTACAGGATCATACCACTG

CAGTAACAATGCCACTCAAAATTCTTATTTGTGGCGTATTGAGGCATCCCC

TCCAATCTACCTCTTTGGCACAATGCATGTTCCCTACAAGAAACTTTGGGA

TGATGTCCCTGATAATGTAAAGAGTGTTCTCAGCCTCTCGGAGCACCTCTG

TGTAGAGCTACGCCTCACCGACTCAGAAACCTCAAAAAACCTTTCTGCGT

GTCGATACCTTCCAAAAAATGAAACACTAGAGAGTGTACTCCCTGGAGGC

CTCTATGTACGCGTGTTGAAGTACTTTGTCCGGATTCAGAACCAGTTCCCA

AAGTGGTTGTTTGGTAATGCGAGTATCAACGGTCTCTCGAGGATAGAGAG

TGATCGTCTCTTCCATGCTATGATTGGGAACTGGAACAGGCTCAGACCTGT

GTGGCTCCTAATGCTCATCAGCTCTTTATCCAGAGAGAACGTCCAAGAGA

GGAGCATTCCCCTTCTTGATGTGTTTCTAGATCGTGCTGCCGAGGGCATGG

GAAAGAATGTAGAAGCAGTCGAAGTATACAAAGAGCAGTGTCGACCATTT

AACAGACTTAATAATACAAAGGTATTCGTCGCTTTAAGGAAACTCTTAGA

TTACCTTGAGCCGTTAGCCGATGGCCCTATATCGTCCACCGACTCAGACCT

TGAGACCTACAACTGTGGCGACTTCAAGAGTCTAGTCTCAGCGAGGCCCA

TACTCCCACTCCCTAGCTCTTCAAAACTCCCAAACCTCACGTCAGAGGAGG

CCGGAGATCTTGAGAGTATCAACGAGTTTCTCGTTAGTCAGATAGTTTATA

GACGAAACAGACGAATGAGTAAAACGATTATGAGCCTTTTGAGTAGACAG

AGAAATGAGACTTACCTCTTTGCCATTGGAGCAGGTCATTTTGTGGGTGAA

-continued

```
AGGAATGTAGTACACATGCTGAAGAAGAAAGGCTACAGTGTAAATAGGC

TATCAGTTACTGAGACTATTCCTGGTCCTCCACTTCCCAAAAACATTATAT

CTCTGGGTGATCCTTCATCGCAGCTTACCATATTAAATATATCCAGTACAA

TCCCAACTCTACCACCGAACAGACCATCTCATGTCCCTCCCACTCTCTCTC

CTGAAACCATTGCCAGGATCATACAATCAGTTTTCAATAACACACAGTCA

ATATACACAGTTGACTCGGTTGAAGTCACACCCACCACTACATCTTTAAAT

TCAGCAACTGCATCAACCACTGTCGCCACACCCACCTCATCAGTGACTCCT

CCCACTTCAAGCAGTAGTCAAACACGTAGTTTAACTATTAGTGATAGTCA

AAGAACTAGTGATGATAGTGCATTCATTCCAAGTGCTTCATCAGGTTTAAG

ATATAATATAGGACTAGTTTGTGTAACTTTATTTTTTGTGTTGTTAATAATC

ACATCAGCTTTGTGA
```

(SEQ ID NO: 32)
```
MQVKIVQVFPCLVLLVKLVLLSVLLPSATGSYHCSNNATQNSYLWRIEASPPI

YLFGTMHVPYKKLWDDVPDNVKSVLSLSEHLCVELRLTDSETSKNLSACRYL

PKNETLESVLPGGLYVRVLKYFVRIQNQFPKWLFGNASINGLSRIESDRLFHA

MIGNWNRLRPVWLLMLISSLSRENVQERSIPLLDVFLDRAAEGMGKNVEAVE

VYKEQCRPFNRLNNTKVFVALRKLLDYLEPLADGPISSTDSDLETYNCGDFKS

LVSARPILPLPSSSKLPNLTSEEAGDLESINEFLVSQIVYRRNRRMSKTIMSLLS

RQRNETYLFAIGAGHFVGERNVVHMLKKKGYSVNRLSVTETIPGPPLPKNIIS

LGDPSSQLTILNISSTIPTLPPNRPSHVPPTLSPETIARIIQSVFNNTQSIYTVDSVE

VTPTTTSLNSATASTTVATPTSSVTPPTSSSSQTRSLTISDSQRTSDDSAFIPSAS

SGLRYNIGLVCVTLFFVLLIITSAL
```

Example 2

Tiki1 Antagonizes Wnt Function

The enlarged head phenotype by Tiki1 overexpression is indistinguishable from that by Dkk1 (FIG. 1A), a Wnt/LRP6 antagonist (Bafico et al., 2001; Glinka et al., 1998; MacDonald et al., 2009; Mao et al., 2001; Semenov et al., 2001). Indeed Tiki1 antagonized Wnt function in embryos, and inhibited axis duplication and induction of Xnr3 (a Wnt/beta-catenin target gene) by *Xenopus* wnt8 (Xwnt8), but not by beta-catenin or Dishevelled, another Wnt downstream component, and importantly not by a constitutively activated LRP6ΔN (Tamai et al., 2004) (FIGS. 1D and 1E). Thus Tiki1 likely acts at or upstream of Wnt receptors. Tiki1 did not affect signaling by other secreted factors such as Nodal, a member of the TGF-beta (transforming growth factor-beta) family, or bFGF (basic fibroblast growth factor) (FIGS. 1F and 1G), attesting its specificity as a Wnt antagonist. *Xenopus* Tiki2, and human TIKI1 and TIKI2 also behaved as Wnt antagonists in embryos, HEK293T cells (FIG. 1J) and mouse L cells (see below). TIKI1N and TIKI2N, which is a secreted form of the respective ectodomain harboring the conserved TIKI domain (FIGS. 1B and 1H), were fully functional and interchangeable with TIKI1/2 in embryos and cultured cells (FIG. 1K).

Example 3

Organizer-Specific Expression of Tiki1

Figure 2A:
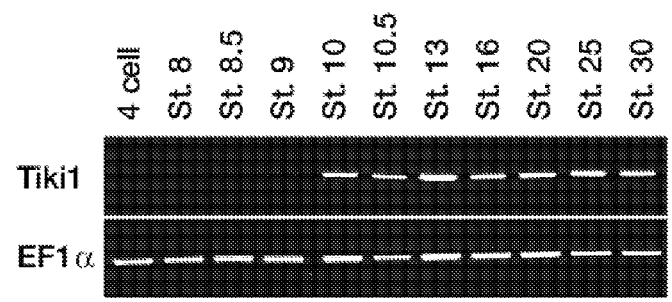
Figure 2B:
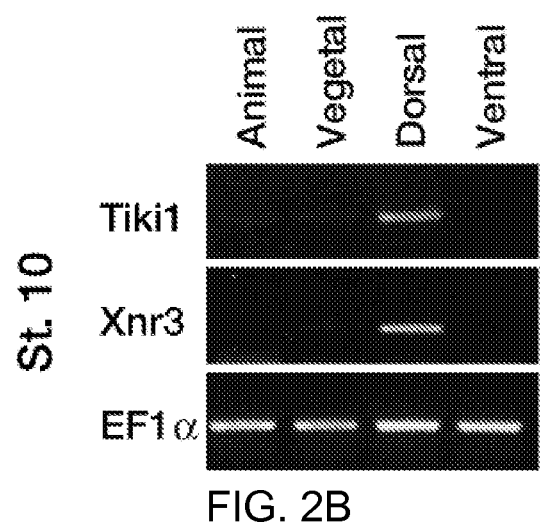

Tiki1 expression was investigated during *Xenopus* early development. RT-PCR revealed that Tiki1 mRNA becomes detectable at stage 9 and is prominently expressed from stage 10 (early gastrula) to stage 30 (tadpole) (FIG. 2A), and interestingly is restricted to the dorsal segment of the gastrula embryo (FIG. 2B). Whole mount in situ hybridization showed that at stage 10 Tiki1 is expressed exclusively in the forming dorsal blastopore lip, the Organizer, in a pattern similar to that of Dkk1 (FIGS. 2C and 2D). Longitudinal hemi-sectioning of the stage 10.5 embryo revealed that Tiki1 is excluded from the dorsal margin of the Organizer and overlapped with Dkk1 expression in the prechordal mesoderm and endomesoderm (FIGS. 2E and 2F). At stage 11 Tiki1 and Dkk1 are strongly expressed in the anterior domain of the prospective prechordal plate (FIGS. 2G and 2H). By blastopore closure Tiki1 expression domain becomes distinct from that of Dkk1, as Tiki1 is restricted to the anterior midline (FIG. 2I) while Dkk1 displays a wing-shaped expression domain straddling Tiki1 (FIG. 2J). At the early neurula stage Tiki1 is expressed in the midline anterior to the tip of the notochord in cells of the endoderm and overlying neural ectoderm (FIG. 2K) while Dkk1 has a more broad expression pattern in the prospective ventral forebrain (FIG. 2L). Therefore Tiki1 is zygotically and specifically expressed in the Organizer, in particular in the head organizer region responsible for anterior patterning.

Figure 2M:
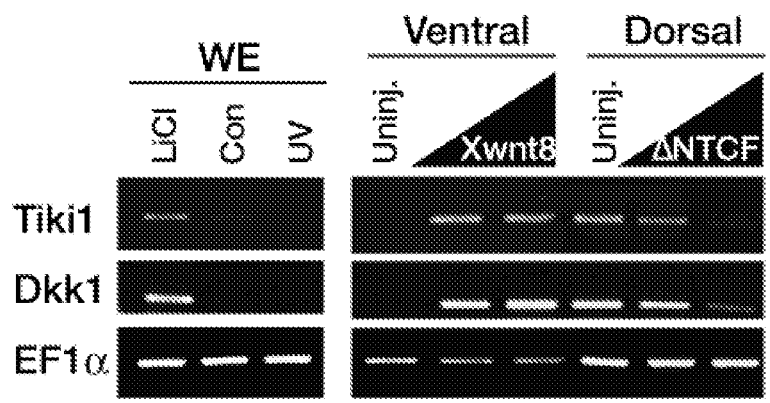

Organizer formation requires maternal Wnt/β-catenin signaling (De Robertis and Kuroda, 2004; Harland and Gerhart, 1997), which is necessary and sufficient for Tiki1 (and Dkk1) expression. Ectopic Xwnt8 induced Tiki1 and Dkk1 expression ventrally, whereas a dominant negative TCF (T cell factor, a DNA-binding transcription factor that mediates beta-catenin signaling), ΔNTCF (Molenaar et al., 1996), suppressed the endogenous Tiki1 and Dkk1 dorsal expression (FIG. 2M). Furthermore LiCl, which stabilizes β-catenin thus dorsalizes embryos, induced Tiki1 and Dkk1 expression, while ultraviolet irradiation, which through microtubule disruption causes defective maternal Wnt signaling thus ventralizes embryos (Harland and Gerhart, 1997), suppressed Tiki1 and Dkk1 expression (FIG. 2M). Thus Tiki1 exhibits similar regulation as Dkk1 in the Organizer.

Example 4

Tiki1 is Required for Head Development

Figure 3A:
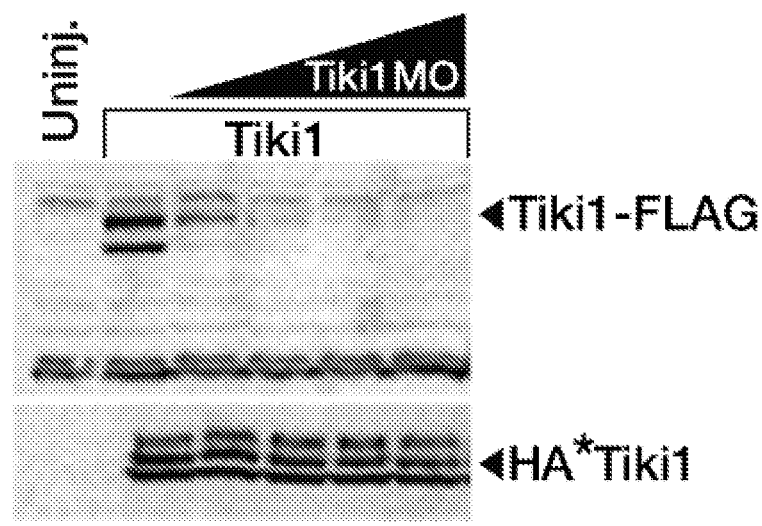
Figure 3B:
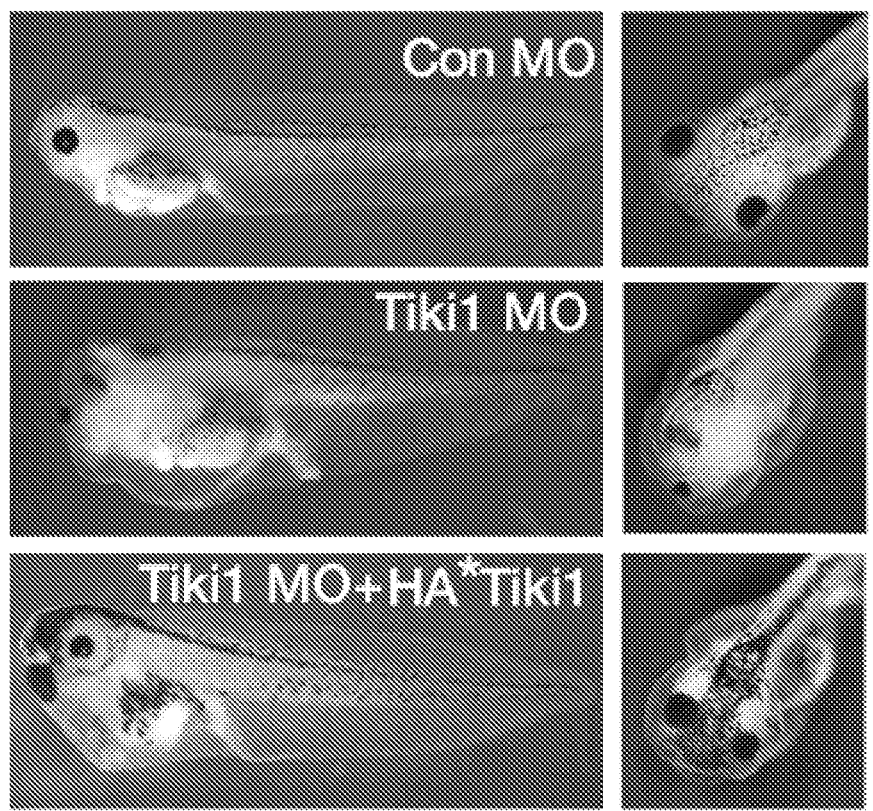
Figure 3C:
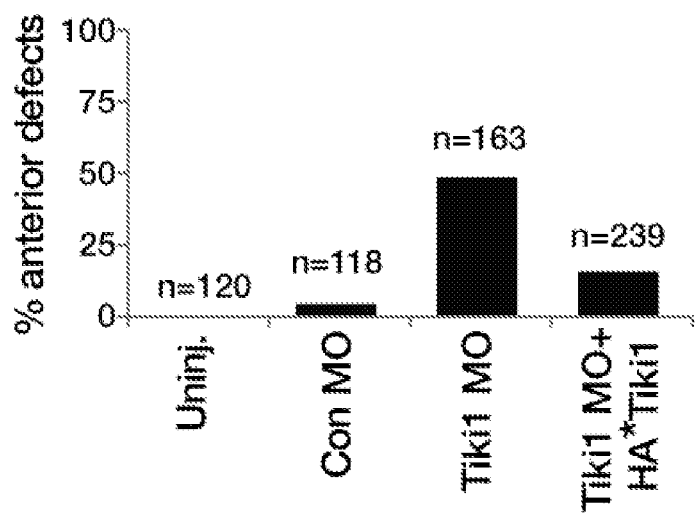

Loss-of-function experiments were performed via Tiki1 protein depletion using a morpholino antisense oligonucleotide against Tiki1 (Tiki1MO), which specifically blocked the synthesis of the exogenously expressed Tiki1 (Tiki1-FLAG, tagged) in embryos (FIG. 3A). Tiki1MO was unable to block the synthesis of HA*Tiki1, whose mRNA was engineered to lack the MO complementary sequence, attesting Tiki1MO targeting specificity (FIG. 3A). 20 ng of Tiki1MO were injected into two dorsal blastomeres of 8-cell stage embryos. Strikingly roughly 50% of Tiki1MO-injected embryos developed anterior defects exhibiting loss of forebrain structures, including diminished or loss of the cement gland and eyes, or exhibiting eyes fused at the midline reminiscent of cyclopia (FIGS. 3B and 3C). Co-injection of HA*Tiki1 mRNA rescued Tiki1MO phenotypes (FIGS. 3B and 3C). Supporting a role of Tiki1 in Wnt inhibition during head formation, Dkk1 mRNA injection also rescued Tiki1MO anterior deficiency phenotypes (FIG. 3E).

Figure 3D:
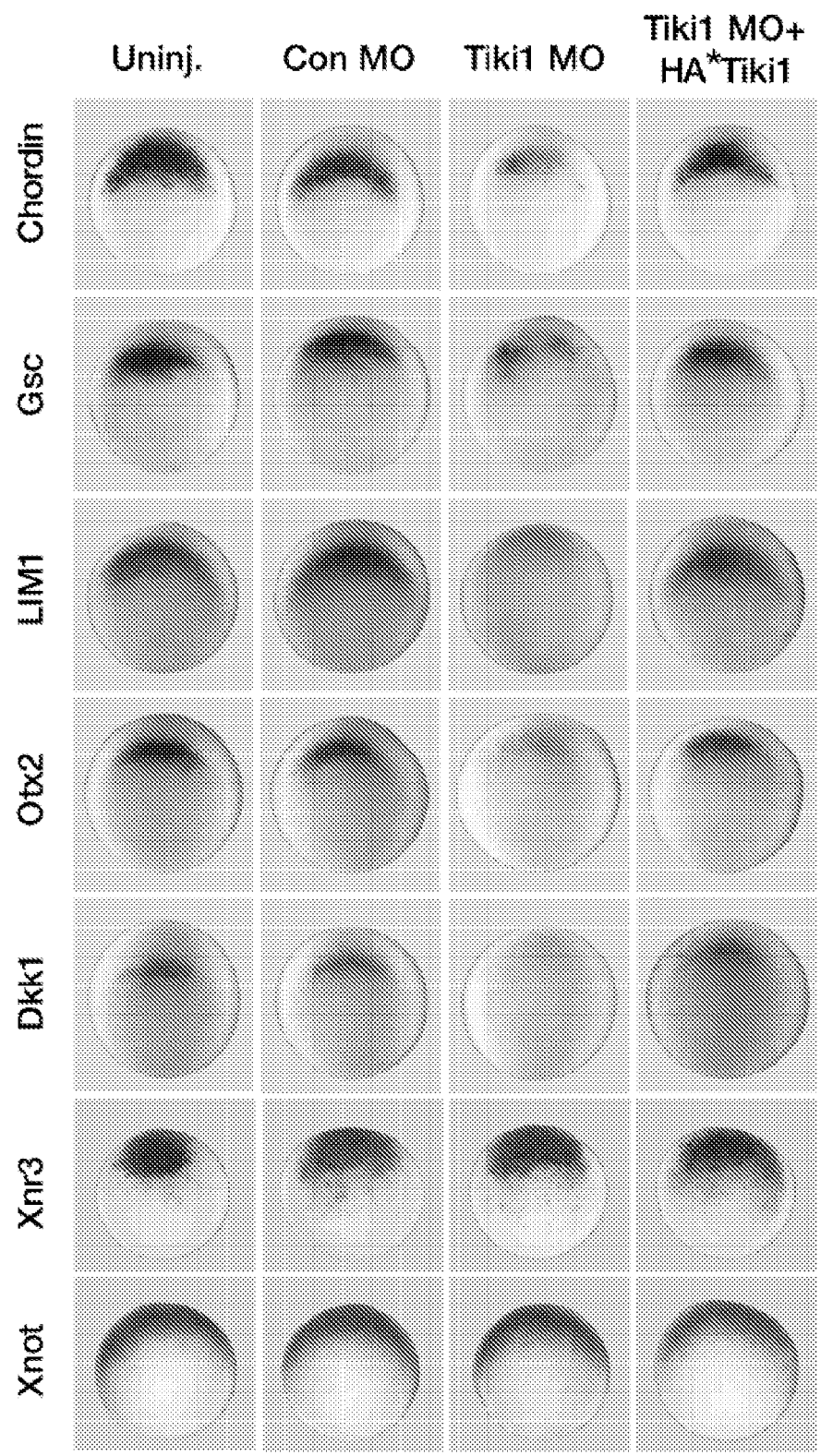
Figure 3E:
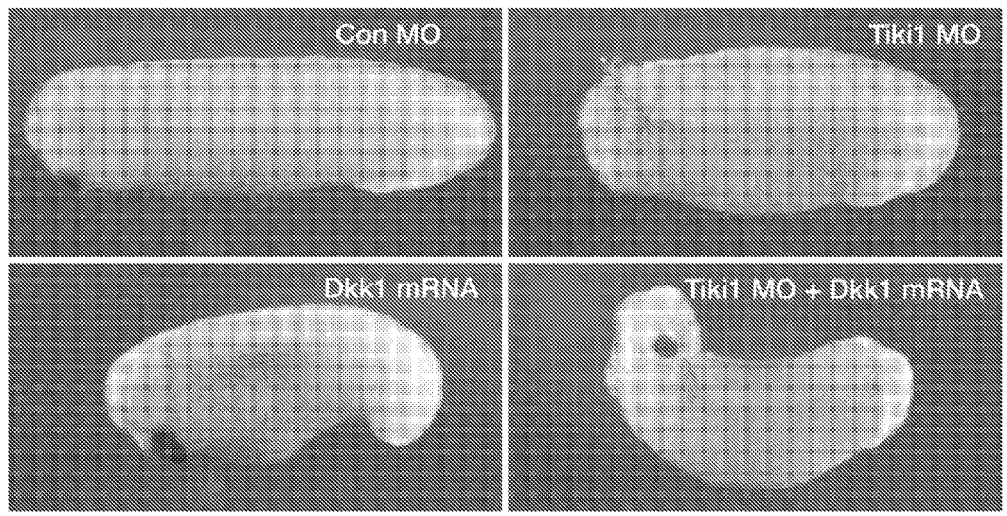
Figure 3F:
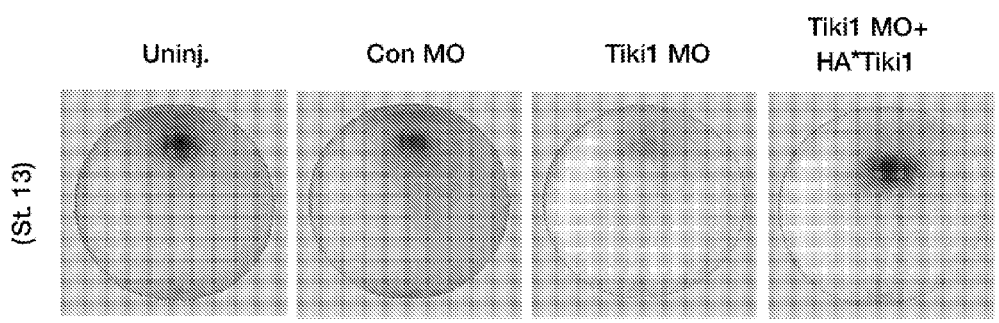

Further, injection of Tiki1MO in two dorsal blastomeres of 8-cell stage embryos suppressed the expression of head organizer genes including Goosecoid (Gsc), Lim1, Otx2, and Dkk1 in gastrula stage embryos (stages 10.5-11) (FIG. 3D and Table 1). Tiki1MO also inhibited the expression of Organizer gene Chordin, but not of other Organizer or dorsally expressed genes Xnr3 and Xnot (FIG. 3D and Table 1), which are not involved in head organizer function. Tiki1MO also reduced Gsc expression in prechordal plate, the descendent of the head organizer, at the neurula stage (FIG. 3F and Table 1). HA*Tiki1 mRNA injection rescued the effect of Tiki1MO on all head organizer genes examined (FIG. 3D and Table 1). Control MO-injected embryos showed normal expression of all markers examined, similar to uninjected embryos (FIG. 3D and Table 1). Tiki1 MO did not affect Gsc expression in early-mid gastrula prior to stage 10.5 (FIG. 3G and Table 2), which relies on maternal Wnt/beta-catenin signaling (Cho et al., 1991; Christian and Moon, 1993). These results show that Tiki1 is specifically required for maintenance of the head organizer via antagonizing zygotic Wnt signaling. Consistently, Tiki1 inhibited Xwnt8 posterizing effect when both were co-expressed dorsally via injected plasmids, which zygotically express Tiki1 and Xwnt8, respectively, after mid-blastula transition (FIG. 3H).

TABLE 1

Statistical data for FIGS. 3D and 3F.
Whole embryos displaying the described change in gene expression:

| | Uninjected | | | | Control MO | | | | Tiki1 MO | | | | Tiki1 MO + HA-Tiki1 | | | |
|---|---|---|---|---|---|---|---|---|---|---|---|---|---|---|---|---|
| | | Percentage (%) | | | | Percentage (%) | | | | Percentage (%) | | | | Percentage (%) | | |
| Gene | n | Absent | Reduced | NC* | n | Absent | Reduced | NC* | n | Absent | Reduced | NC* | n | Absent | Reduced | NC* |
| Chd | 25 | 0 | 0 | 100 | 34 | 0 | 3 | 97 | 39 | 0 | 36 | 64 | 31 | 0 | 23 | 77 |
| Gsc | 29 | 0 | 10 | 90 | 30 | 0 | 3 | 97 | 45 | 0 | 66 | 34 | 31 | 0 | 23 | 77 |
| Lim1 | 17 | 0 | 0 | 100 | 40 | 0 | 0 | 100 | 35 | 28 | 54 | 18 | 37 | 3 | 19 | 78 |
| Otx2 | 35 | 0 | 0 | 100 | 37 | 5 | 3 | 92 | 40 | 7 | 60 | 33 | 33 | 0 | 30 | 70 |
| Dkk1 | 31 | 0 | 0 | 100 | 40 | 0 | 3 | 97 | 47 | 25 | 40 | 35 | 31 | 6 | 16 | 78 |
| Xnr3 | 24 | 0 | 4 | 96 | 31 | 0 | 0 | 100 | 27 | 0 | 7 | 93 | 42 | 0 | 5 | 95 |
| Xnot | 20 | 0 | 0 | 100 | 30 | 0 | 0 | 100 | 32 | 0 | 13 | 87 | 39 | 0 | 0 | 100 |
| Gsc st.13 | 38 | 0 | 0 | 100 | 31 | 0 | 0 | 100 | 45 | 35 | 32 | 33 | 38 | 13 | 0 | 87 |

*NC = No Change

TABLE 2

Figure 3G:
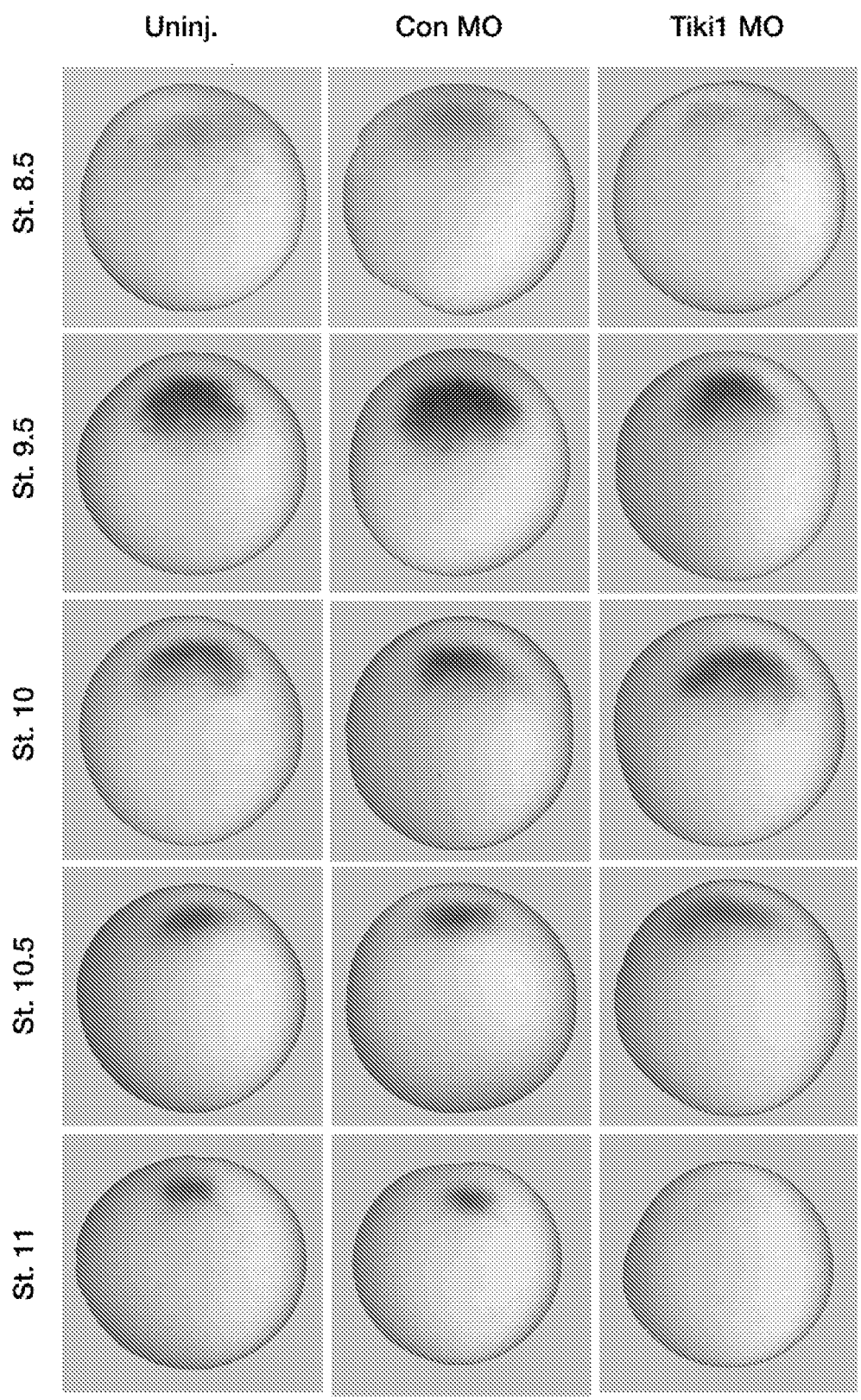
Figure 3H:
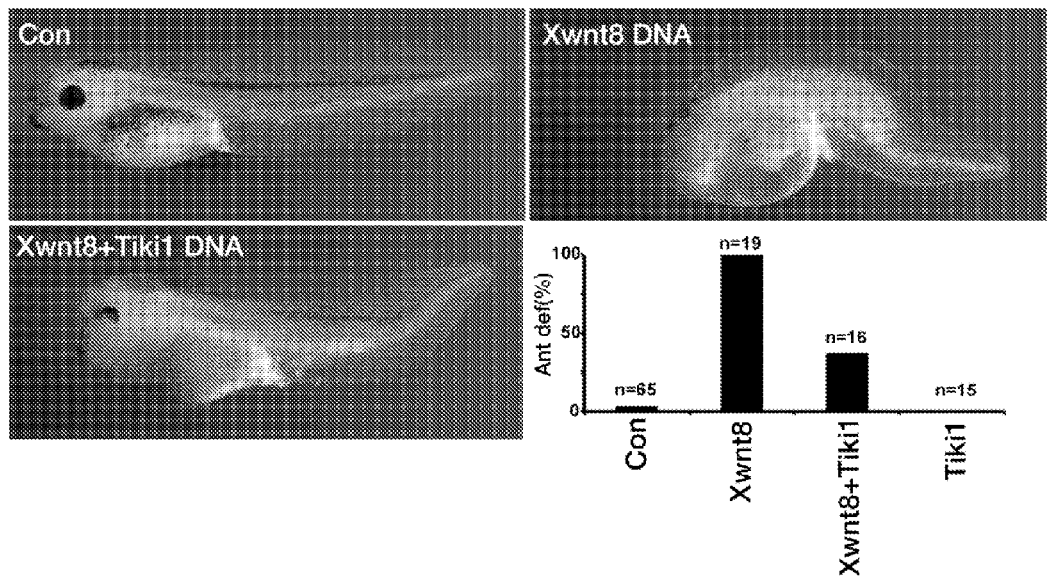

Statistical data for FIG. 3G.
Whole embryos displaying the described change in Goosecoid expression:

| | stage 8.5 | | | | stage 9.5 | | | | stage 10 | | | |
|---|---|---|---|---|---|---|---|---|---|---|---|---|
| | | Percentage (%) | | | | Percentage (%) | | | | Percentage (%) | | |
| Condition | n | Absent | Reduced | NC | n | Absent | Reduced | NC | n | Absent | Reduced | NC |
| Uninj. | 15 | 0 | 0 | 100 | 16 | 0 | 0 | 100 | 26 | 0 | 0 | 100 |
| Control MO | 13 | 0 | 0 | 100 | 28 | 14 | 0 | 86 | 26 | 8 | 0 | 92 |
| Tiki1 MO | 12 | 0 | 0 | 100 | 30 | 13 | 0 | 87 | 22 | 15 | 0 | 85 |

TABLE 2-continued

Statistical data for FIG. 3G.
Whole embryos displaying the described change in Goosecoid expression:

| | | stage 10.5 | | | | stage 11 | | |
|---|---|---|---|---|---|---|---|---|
| | | | Percentage (%) | | | | Percentage (%) | |
| Condition | n | Absent | Reduced | NC | n | Absent | Reduced | NC |
| Uninj. | 26 | 0 | 8 | 92 | 28 | 0 | 4 | 96 |
| Control MO | 28 | 0 | 11 | 89 | 32 | 0 | 3 | 97 |
| Tiki1 MO | 20 | 5 | 15 | 80 | 44 | 48 | 25 | 27 |

* NC = No Change

Figure 3I:
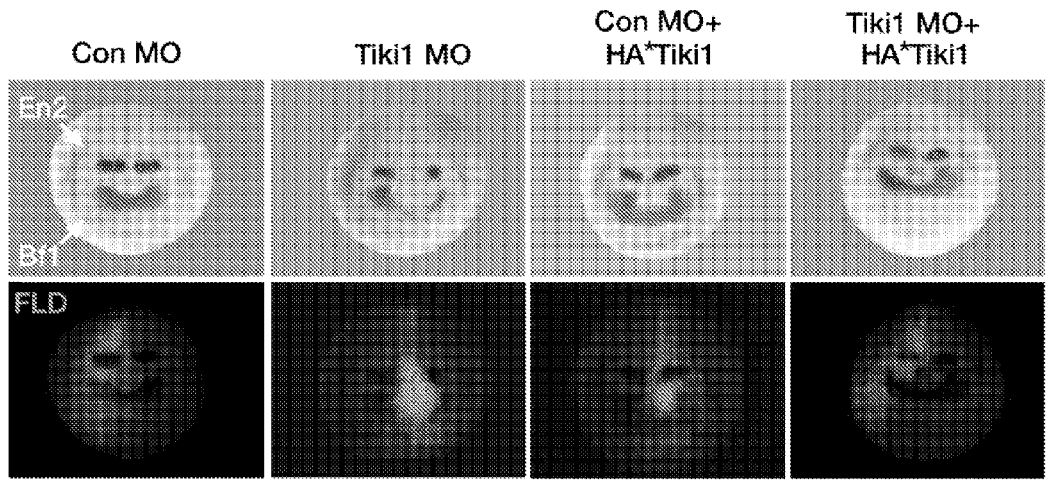

The fact that Tiki1 is specifically expressed in, and is required for function of, the head organizer implies that Tiki1 has a role in anterior neural patterning. Tiki1MO were injected with fluorescein dextran (FLD, as a lineage tracer) into one dorsal-animal blastomere at the 8-cell stage and analyzed expression of anterior neural markers at stage 16. Tiki1MO suppressed, in the injected half of the embryo, the expression of forebrain marker BF1 and Otx2 (FIG. 3I and Table 3). Tiki1MO also reduced the expression of the midbrain marker Ent, but did not affect the posterior neural marker Hoxb9 (Table 3). HA*Tiki1 mRNA injection rescued the expression of BF1, Otx2, and Ent in Tiki1MO-injected embryos (FIG. 3I and Table 3). These results show that Tiki1 function is required for anterior neural patterning, consistent with its essential role in the head organizer.

correlated strictly with the extent of reduction of TIKI2 mRNA and the tagged TIKI2 protein by the siRNAs (FIG. 4C and FIG. 4K); furthermore, the TIKI2 siRNA effect was rescued by ectopic TIKI1 expression (FIG. 4D), both attesting siRNA knockdown specificity. These results suggest that the endogenous TIKI protein(s) acts to restrain Wnt signaling in HEK293T and likely other cultured cells.

Example 6

Wnt Inactivation by Tiki Proteins

The mechanism by which Tiki proteins antagonize Wnt signaling was investigated. Upon overexpression in HEK293T or HeLa cells, Tiki1/TIKI1 and TIKI2 were

TABLE 3

Statistical data for FIG. 3I
Whole embryos displaying the described change in gene expression:

| | Control MO | | | | | Tiki1 MO | | | |
|---|---|---|---|---|---|---|---|---|---|
| | | Percentage (%) | | | | | Percentage (%) | | |
| Gene | n | Absent | Reduced | NC* | increased | n | Absent | Reduced | NC* | increased |
| BF1 | 45 | 0 | 5 | 95 | 0 | 35 | 63 | 23 | 14 | 0 |
| Otx2 | 37 | 0 | 0 | 100 | 0 | 42 | 35 | 30 | 35 | 0 |
| En-2 | 45 | 0 | 2 | 98 | 0 | 35 | 40 | 25 | 35 | 0 |
| HoxB9 | 23 | 0 | 0 | 100 | 0 | 21 | 0 | 0 | 100 | 0 |

| | Control MO + HA-Tiki1 | | | | | Tiki1 MO + HA-Tiki1 | | | |
|---|---|---|---|---|---|---|---|---|---|
| | | Percentage (%) | | | | | Percentage (%) | | |
| Gene | n | Absent | Reduced | NC* | increased | n | Absent | Reduced | NC* | Increased |
| BF1 | 37 | 0 | 0 | 22 | 78 | 48 | 0 | 23 | 4 | 73 |
| Otx2 | 28 | 0 | 0 | 14 | 86 | 45 | 0 | 13 | 11 | 76 |
| En-2 | 37 | 0 | 0 | 54 | 46 | 48 | 0 | 15 | 45 | 40 |
| HoxB9 | — | — | — | — | — | 25 | 0 | 0 | 100 | 0 |

*NC = No Change

Example 5

TIM Expression and Function in Cultured Human Cells

Figure 4A:
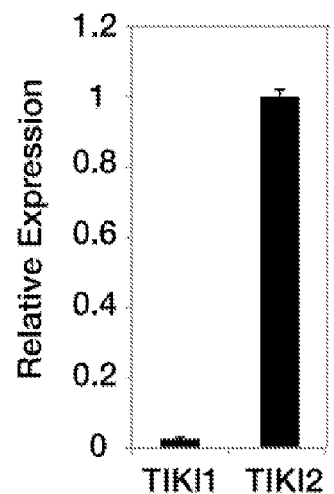
Figure 4B:
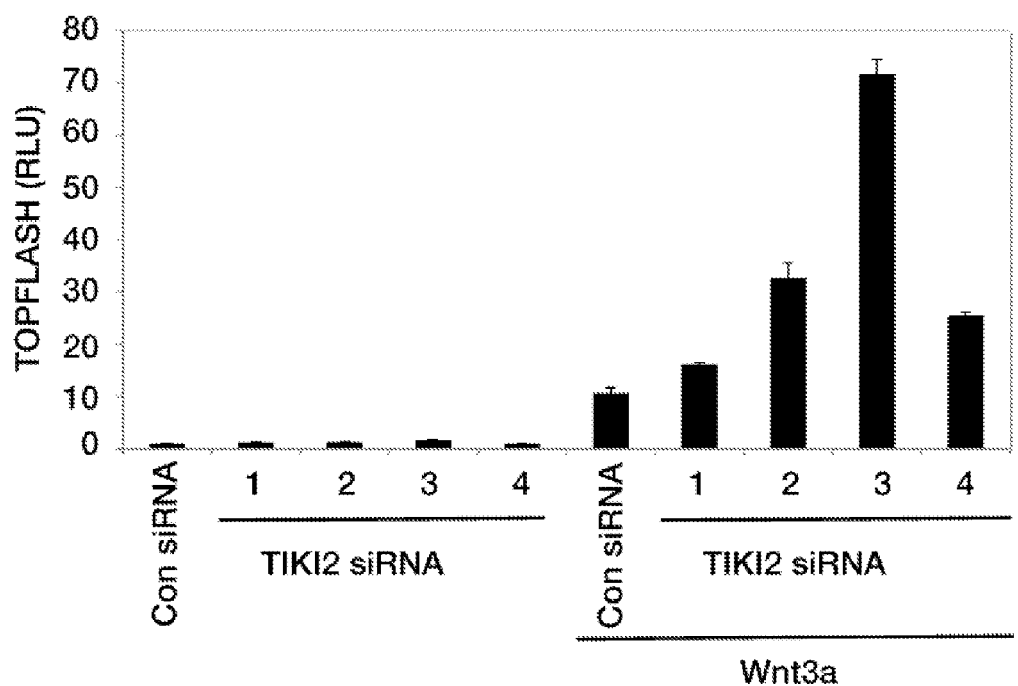
Figure 4C:
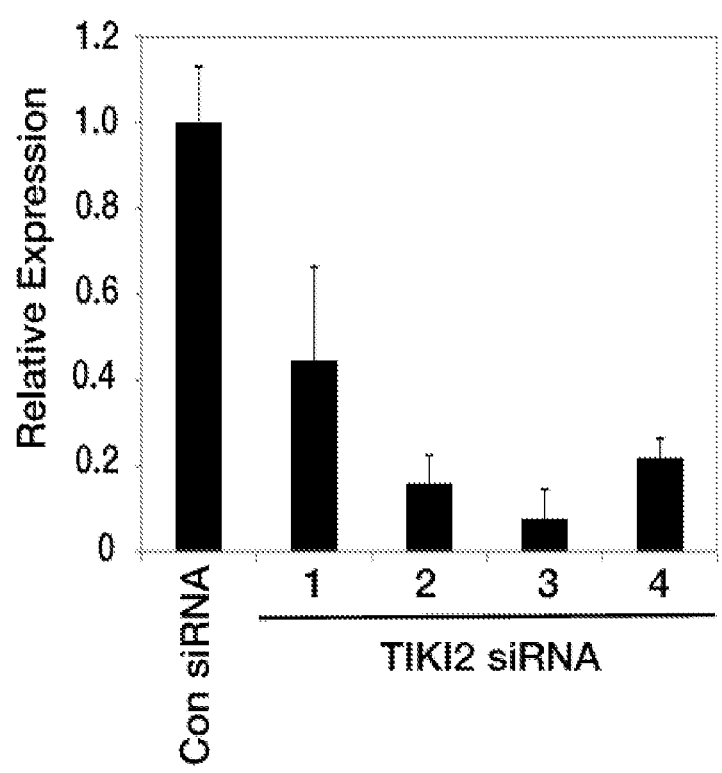
Figure 4D:
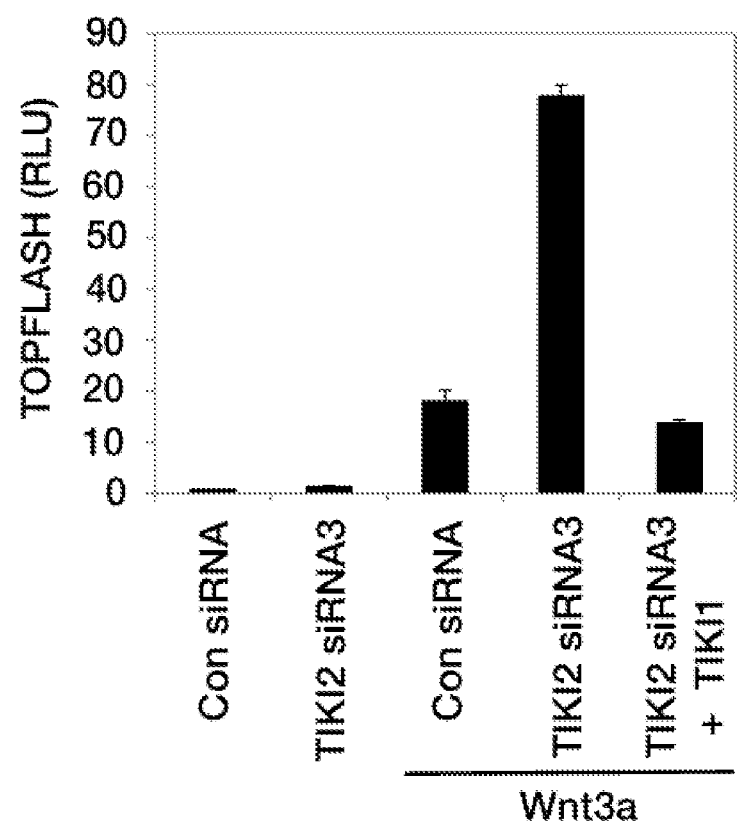
Figure 4E:
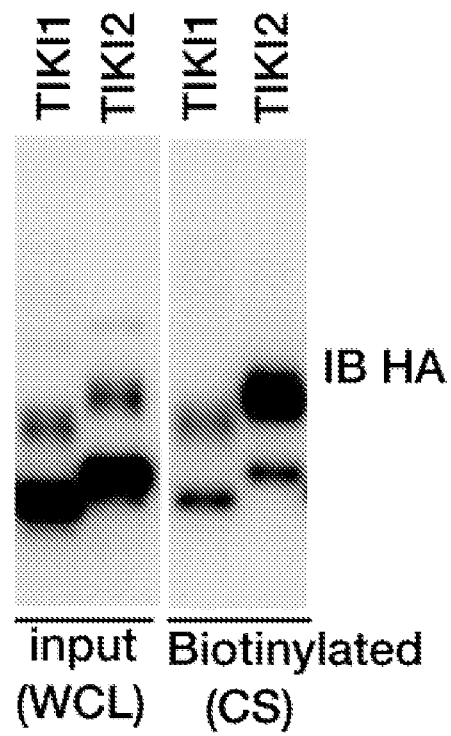
Figure 4F:
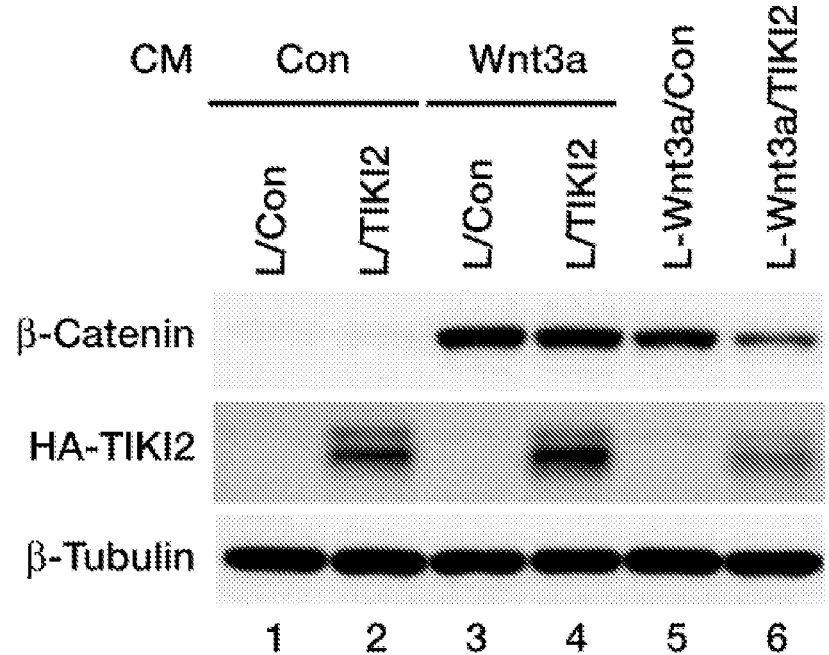
Figure 4G:
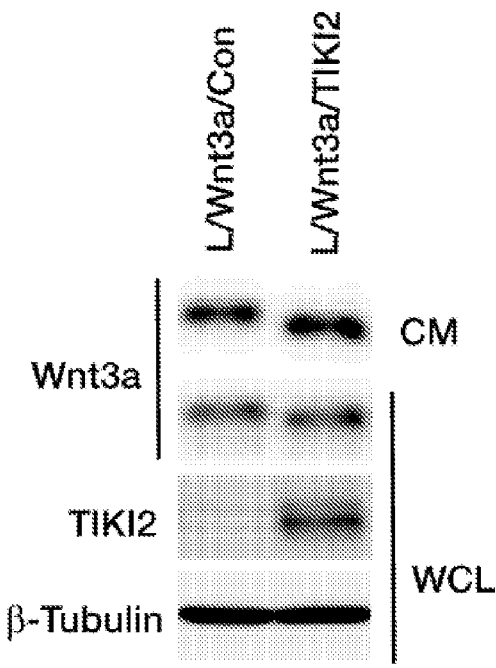
Figure 4H:
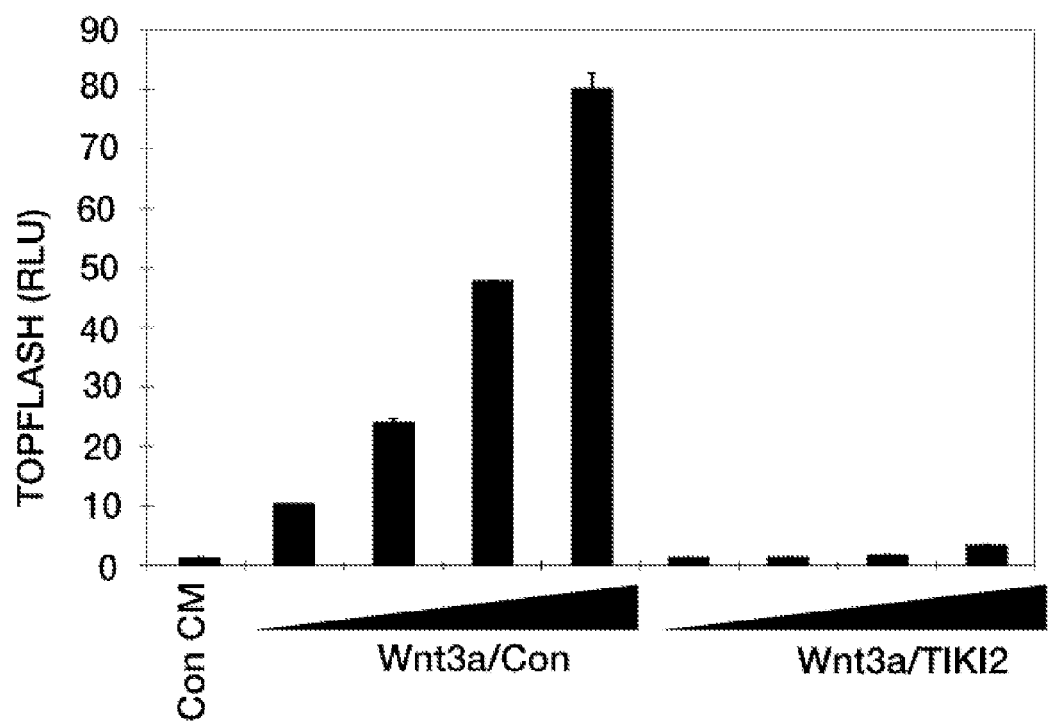
Figure 4I:
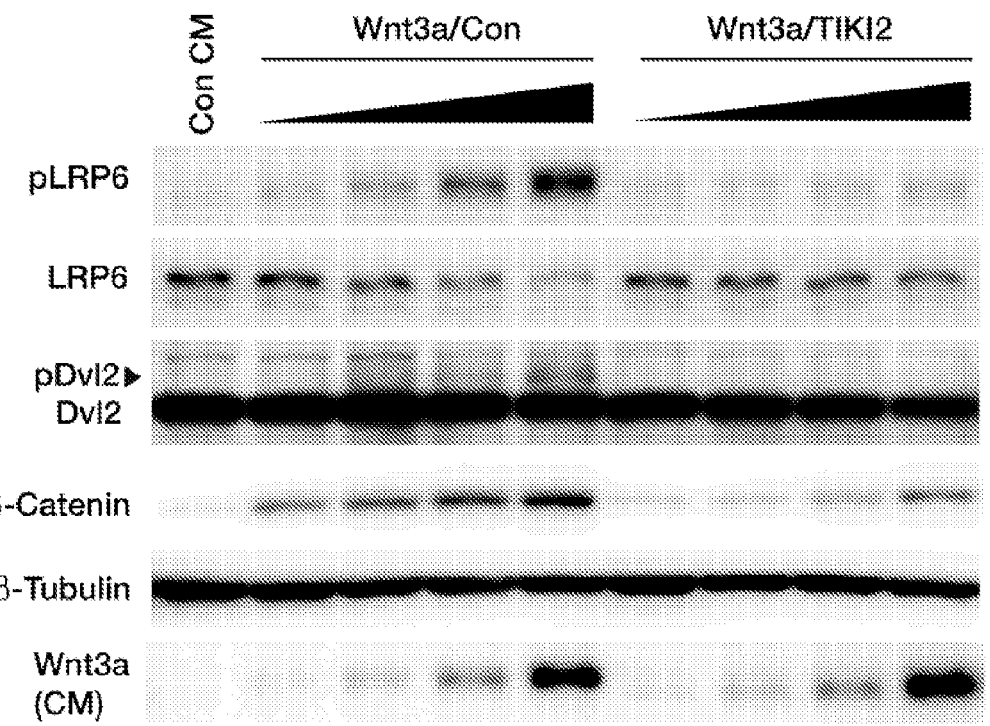
Figure 4J:
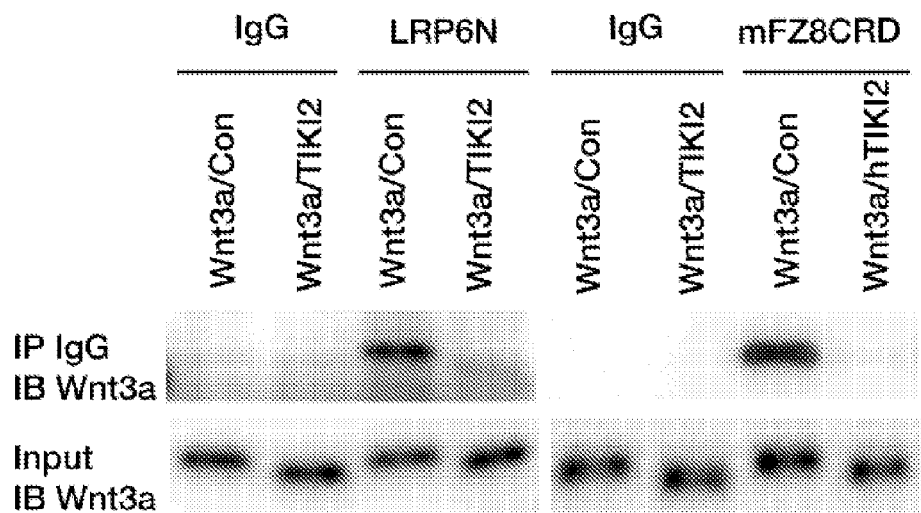

Tiki genes exhibit specific expression patterns during embryogenesis (FIG. 2 and data not shown). Unexpectedly, human HEK293T and HeLa cells, which are commonly used for Wnt signaling studies, express mRNAs for TIKI2, and TIKI1 plus TIKI2, respectively (FIG. 4A and additional data). Depletion of TIKI2 in HEK293T cells via different siRNAs each enhanced Wnt3a-induced reporter expression by up to 7 folds (FIG. 4B), and the enhancement levels detected at the plasma and internal secretory membranes via imaging and cell surface biotinylation. TIKI2 was stably expressed in L cells or Wnt3a-expressing L cells (TIKI1 was poorly expressed in L cells ectopically, data not shown). TIKI2 expression inhibited beta-catenin stabilization in Wnt3a-producing cells (FIG. 4E, lanes 5 and 6), but apparently not in cells treated with Wnt3a conditioned media (CM) (FIG. 4E, lanes 3 and 4). Interestingly, Wnt3a produced in L cells was secreted normally into CM in the presence of TIKI2, but exhibited faster electrophoretic migration both prior to (as detected in whole cell lysates, WCL) and after secretion (in CM) (FIG. 4I). Similar results were observed for Wnt3a produced in HEK293T cells that co-express either TIKI1 or TIKI2 (FIG. 4L). Importantly Wnt3a secreted from TIKI-expressing cells exhibited minimal activity, as it neither induced the expression of the Wnt-responsive reporter (FIG. 4G), phosphorylation of LRP6 and Dishevelled, nor did it promote beta-catenin stabilization (FIG. 4K). Most revealingly Wnt3a secreted from TIKI2-expressing cells failed to bind to either Fz or LRP6 as examined using the extracellular domain of mouse Fz8 (mFz8CRD-IgG) or LRP6 (LRP6N-IgG) (Tamai et al., 2000) (FIG. 4J). These data suggest that TIKI proteins result in a Wnt3a post-translational modification that minimizes Wnt3a activity but not secretion.

Example 7

Elimination of Wnt Hydrophobicity by Tiki Proteins

Figure 4N:
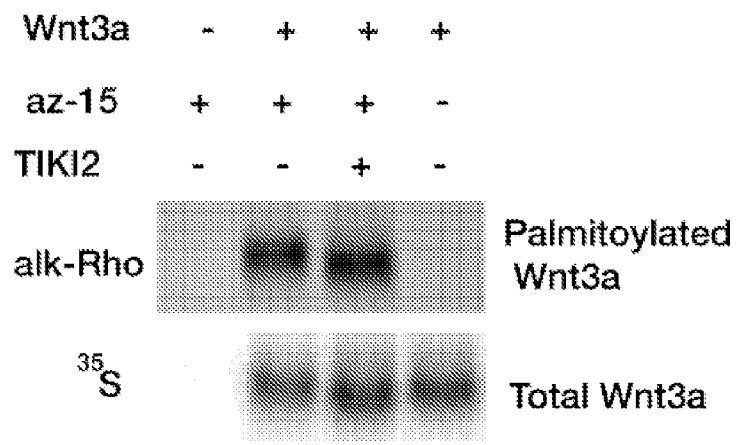
Figure 4O:
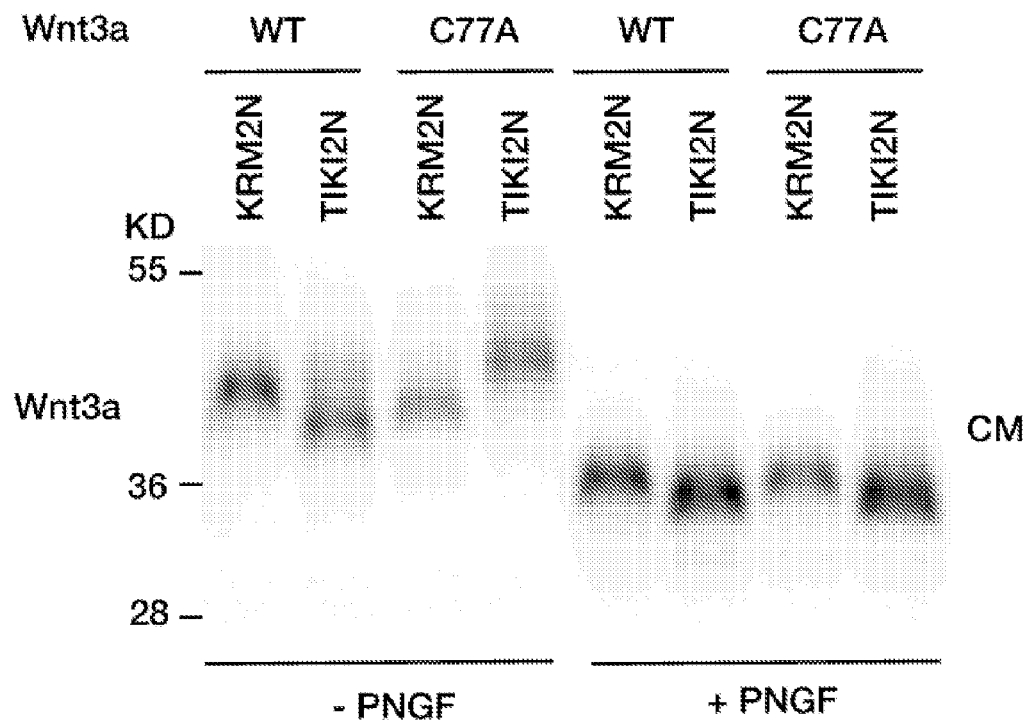
Figure 4P:
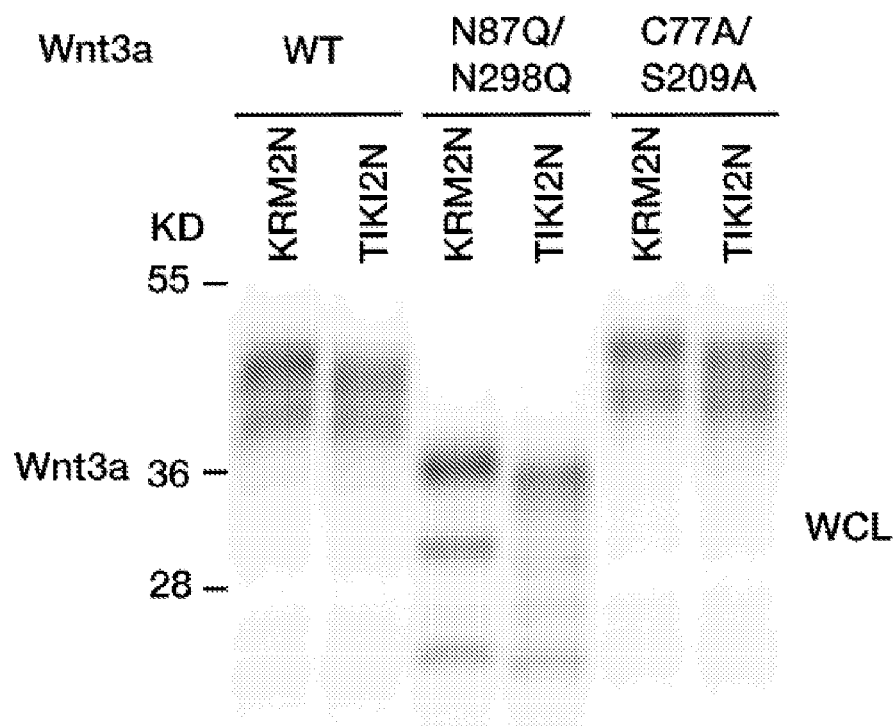
Figure 4Q:
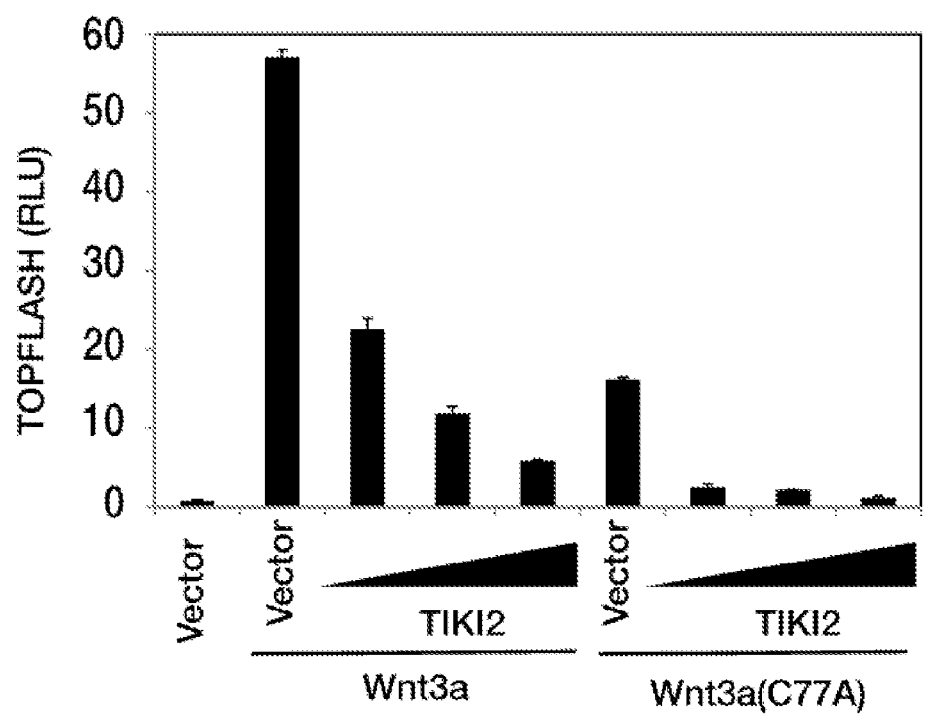
Figure 4R:
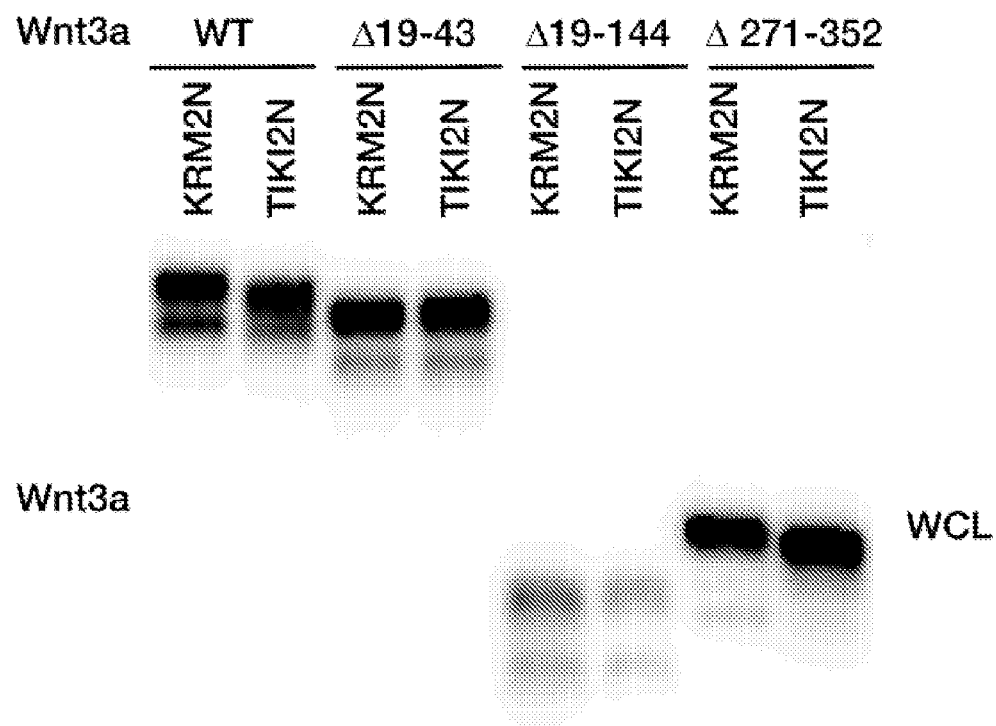

Palmitoylation at C77 appears to be required for Wnt3a binding to Fz and LRP6 and thus full signaling activity (Cong et al., 2004; Komekado et al., 2007; Willert et al., 2003). The inactivity of Tiki-modified Wnt3a is reminiscent of the Wnt3a(C77A) mutant, which harbors alanine substitution of C77 and thus lacks palmitoylation (Cong et al., 2004; Komekado et al., 2007; Willert et al., 2003). In a detergent-aqueous phase separation assay Wnt3a (palmitoylated) partitions in Triton X-114 detergent whereas Wnt3a (C77A) is soluble aqueously (Komekado et al., 2007; Willert et al., 2003). Wnt3a from TIKI1- or TIKI2-expressing cells partitioned exclusively in the aqueous phase (FIGS. 5A and 4M), further resembling Wnt3a(C77A). Unexpectedly however, metabolic labeling failed to detect notable differences in Wnt3a palmitate incorporation with or without TIKI2 (FIGS. 5B and 4N). Furthermore, Wnt3a(C77A), and in fact Wnt3a(C77A/S209A) that harbors alanine substitutions at both C77 and S209 and therefore lacks lipidation at these two residues, were modified by TIKI2 as judged by electrophoretic mobility changes (FIGS. 4O and 4P), and the residual signaling activity of Wnt3a(C77A) in an autocrine assay was still inhibited by TIKI2 (FIG. 4Q). TIKI2 also modified Wnt3a(N87Q/N298Q), which has glutamine substitutions at the two glycosylated asparagines and therefore lacks N-glycosylation (Komekado et al., 2007) (FIG. 4P). Thus despite complete elimination of Wnt3a hydrophobicity, Tiki modification of Wnt3a appears to be unrelated to C77 palmitoylation or S209 acylation, or to N-glycosylation.

Example 8

Wnt Amino-Terminal Cleavage by Tiki Proteins

Figure 5W:
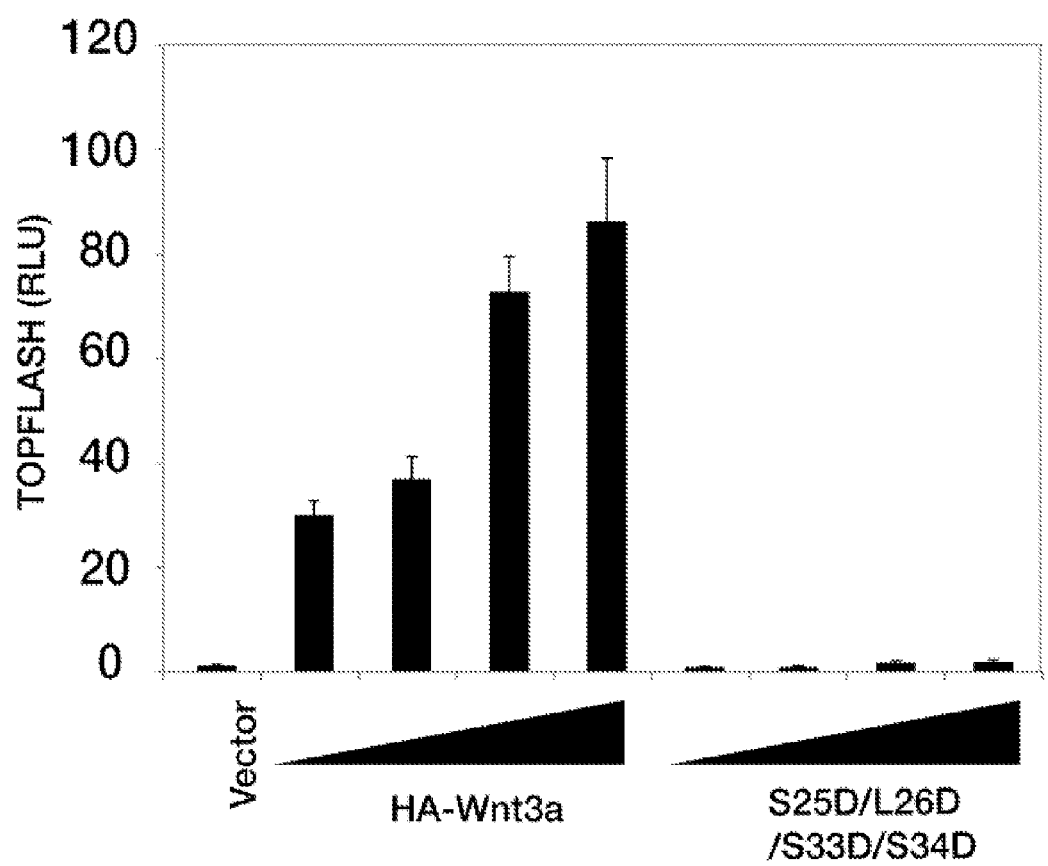
Figure 5X:
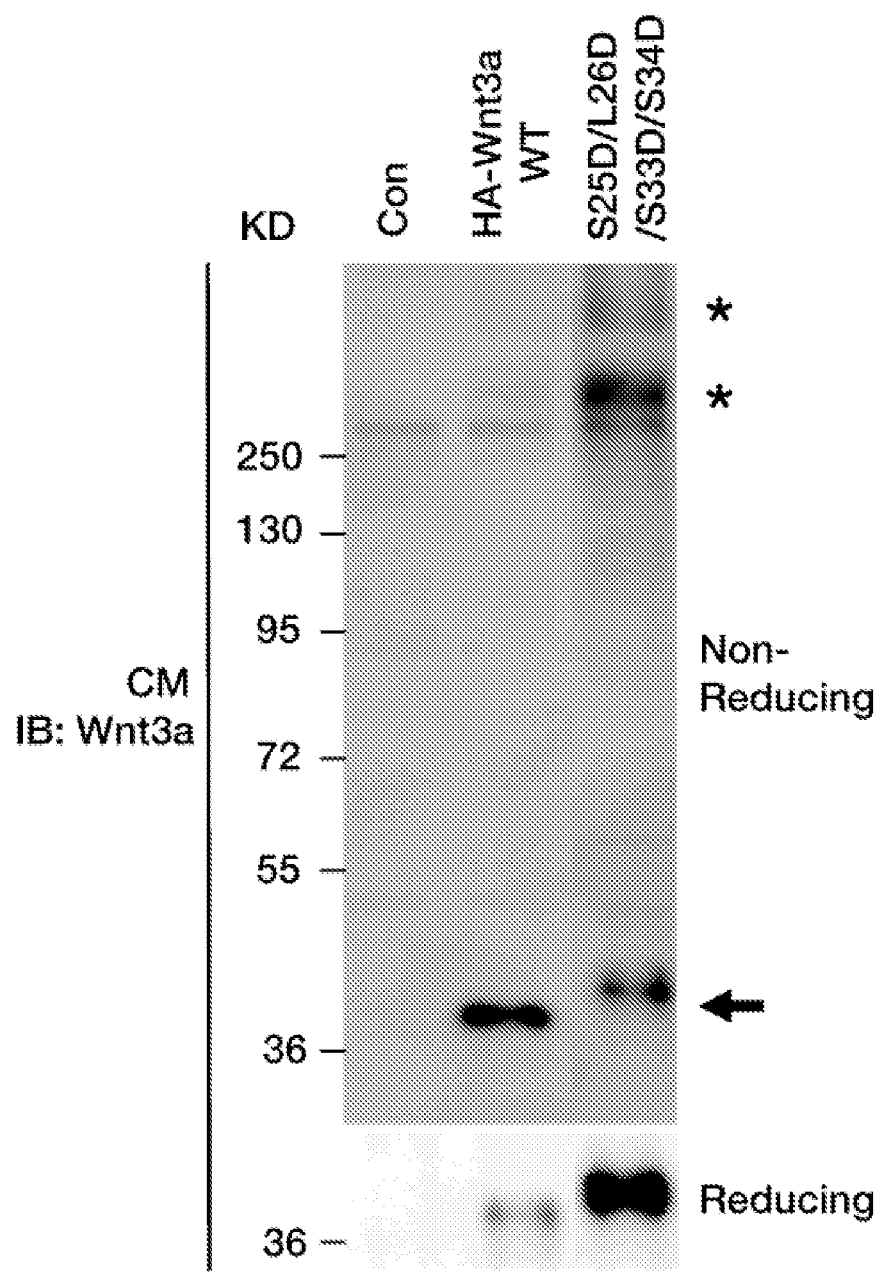

Wnt3a mutants deleted of the amino-terminal region were invariably resistant to Tiki modification (FIG. 4R), suggesting that Tiki may act on Wnt3a amino terminal region. Edman sequencing of TIKI2-modified Wnt3a was performed, which demonstrated that eight amino-terminal residues, SYPIWWSL, had been removed from the mature Wnt3a (i.e., after signal peptide removal) (FIG. 5C). A quantitative mass spectrometry (MS) approach was taken to further analyze this amino-terminal processing. Wnt3a was expressed alone or with TIKI2 in light or heavy labeled SILAC (stable isotope labeling by amino acids in cell culture) medium (Ong et al., 2002), respectively, and purified, combined and trypsinized for MS following the FLEXIQuant quantification strategy (Singh et al., 2009) (FIG. 5S). The relative peptide peak ratios of Wnt3a with and without TIKI2 modification, confirmed the complete cleavage of the 8 residues in TIKI2-modified Wnt3a, but also revealed two additional cleavage sites of lesser abundance, which are 7 and 8 residues downstream of the main cleavage site (FIGS. 5C, 5T and 5U). The relative peptide peak ratios for the remaining protein sequence between Wnt3a and TIKI2-modified Wnt3a were largely unperturbed, suggesting that TIKI2 might not affect the rest of Wnt3a protein (FIG. 5T and Table 4). HA-Wnt3a, which harbors the HA tag after the signal peptide, was then generated (FIG. 9E). Remarkably TIKI1 and TIKI2 resulted in removal of the amino terminal HA epitope from Wnt3a while leaving the rest of Wnt3a apparently intact (FIG. 5D). The HA tag did not seem to have any influence on Wnt3a cleavage by TIKI2, because HA-Wnt3a migrated indistinguishably as the untagged Wnt3a after TIKI2 cleavage (FIG. 5V, lanes 2 and 4), even though HA-Wnt3a migrated slightly slower (due to the HA tag) than untagged Wnt3a in the absence of TIKI2 (FIG. 5V, lanes 1 and 3). TIKI2 did not cleave the HA tag in HA-R-spondin1 (Wei et al., 2007), a secreted Wnt agonist that harbors the HA tag after the signal peptide (FIG. 5E). Conversely siRNA knockdown of the endogenous TIKI2 reduced the cleavage of HA-Wnt3a in HEK293T cells, as shown by increased retention of the HA epitope (FIG. 5F). These results demonstrate that Tiki specifically resulted in amino terminal cleavage of Wnt3a (but not Rspo1), fully consistent with data from Edman sequencing and the SILAC-FLEXIQuant MS analysis. To further confirm TIKI cleavage specificity, the two residues straddling the main and minor cleavage sites in Wnt3a were altered (FIG. 5C). These HA-Wnt3a mutants, Wnt3a(S25D/L26D) and Wnt3a(S25D/L26D/S33D/S34D), were partially and completely resistant to TIKI2 proteolysis, respectively (FIG. 5G, lanes 4 and 6 versus lane 2), demonstrating unambiguously that TIKI2 acts through these residues. Wnt3aΔN, which lacks the exact 8 residues removed by TIKI2 (FIG. 5C), was then generated. Wnt3aΔN was secreted normally but partitioned in the aqueous phase and exhibited minimal activity (FIGS. 5H and 5I), thereby behaving indistinguishably from Tiki-modified Wnt3a (FIG. 4G). These results together indicate that Tiki promotes cleavage of Wnt3a amino terminus, which has an essential role in Wnt3a activity. Further supporting the importance of Wnt3a amino terminus, Wnt3a(S25D/L26D/S33D/S34D) was completely inactive in signaling despite secreting normally (FIGS. 5W and 5X, the bottom panel).

TABLE 4

Absolute and relative quantification of Wnt3a peptides from a SILAC labeling experiment.

| Start | End | Sequence | SEQ ID NO. | Exp_MZ | absolute intensities | ratio of light to heavy |
|---|---|---|---|---|---|---|
| 19 | 51 | G.SYPIWWSLAVGPQYSSLSTQ PILCASIPGLVPK.Q | | 1206.64087 | 865584 | |

TABLE 4-continued

Absolute and relative quantification of Wnt3a peptides from a SILAC labeling experiment.

| Start | End | Sequence | SEQ ID NO. | Exp_MZ | absolute intensities | ratio of light to heavy |
|---|---|---|---|---|---|---|
| 19 | 51 | G.SYPIWWSLAVGPQYSSLSTQPILCASIPGLVPK.Q | | 1209.307537 | 149142 | 5.803757493 |
| 27 | 51 | L.AVGPQYSSLSTQPILCASIPGLVPK.Q | | 1292.705285 | 52305 | |
| 27 | 51 | L.AVGPQYSSLSTQPILCASIPGLVPK.Q | | 1296.705285 | 1441629 | 0.036281873 |
| 27 | 51 | L.AVGPQYSSLSTQPILCASIPGLVPK.Q | | 862.1395663 | 232187 | |
| 27 | 51 | L.AVGPQYSSLSTQPILCASIPGLVPK.Q | | 864.806233 | 8861061 | 0.02620307 |
| 34 | 51 | S.SLSTQPILCASIPGLVPK.Q | | 941.036242 | 0 | |
| 34 | 51 | S.SLSTQPILCASIPGLVPK.Q | | 945.036242 | 1812629 | 0 |
| 35 | 51 | S.LSTQPILCASIPGLVPK.Q | | 897.521679 | 26740 | |
| 35 | 51 | S.LSTQPILCASIPGLVPK.Q | | 901.521679 | 169069 | 0.158160278 |
| 36 | 51 | L.STQPILCASIPGLVPK.Q | | 840.978854 | 158109 | |
| 36 | 51 | L.STQPILCASIPGLVPK.Q | | 844.978854 | 308576 | 0.512382687 |
| 58 | 71 | R.NYVEIMPSVAEGVK.A | | 768.393065 | 5745243 | |
| 58 | 71 | R.NYVEIMPSVAEGVK.A | | 772.399918 | 7848144 | 0.73205117 |
| 58 | 71 | R.NYVEIMPSVAEGVK.A | | 776.39033 | 4724167 | |
| 58 | 71 | R.NYVEIMPSVAEGVK.A | | 780.396849 | 6595475 | 0.716273961 |
| 72 | 82 | K.AGIQECQHQFR.G | | 687.322066 | 1529081 | |
| 72 | 82 | K.AGIQECQHQFR.G | | 692.326109 | 2007448 | 0.761703915 |
| 108 | 126 | R.ESAFVHAIASAGVAFAVTR.S | | 635.673746 | 3660772 | |
| 108 | 126 | R.ESAFVHAIASAGVAFAVTR.S | | 639.009553 | 4803189 | 0.762154477 |
| 108 | 126 | R.ESAFVHAIASAGVAFAVTR.S | | 953.007109 | 196229 | |
| 108 | 126 | R.ESAFVHAIASAGVAFAVTR.S | | 957.509854 | 309802 | 0.633401334 |
| 127 | 141 | R.SCAEGSAAICGCSSR.L | | 786.814185 | 1387711 | |
| 127 | 141 | R.SCAEGSAAICGCSSR.L | | 791.818052 | 1905076 | 0.728428157 |
| 152 | 167 | K.WGGCSEDIEFGGMVSR.E | | 901.878486 | 1171350 | |
| 152 | 167 | K.WGGCSEDIEFGGMVSR.E | | 906.882212 | 1708268 | 0.685694516 |
| 193 | 202 | R.QAIASHMHLK.C | | 576.302664 | 353588 | |
| 193 | 202 | R.QAIASHMHLK.C | | 580.309352 | 527038 | 0.670896596 |
| 205 | 215 | K.CHGLSGSCEVK.T | | 617.271701 | 72955 | |
| 205 | 215 | K.CHGLSGSCEVK.T | | 621.271701 | 105026 | 0.694637518 |
| 216 | 225 | K.TCWWSQPDFR.T | | 691.801719 | 11635373 | |

TABLE 4-continued

Absolute and relative quantification of Wnt3a peptides from a SILAC labeling experiment.

| Start | End | Sequence | SEQ ID NO. | Exp_MZ | absolute intensities | ratio of light to heavy |
|---|---|---|---|---|---|---|
| 216 | 225 | K.TCWWSQPDFR.T | | 696.801719 | 15267161 | 0.762117659 |
| 226 | 245 | R.TIGDFLKDKYDSASEMVVEK.H | | 759.37808 | 1072528 | |
| 226 | 245 | R.TIGDFLKDKYDSASEMVVEK.H | | 767.392103 | 1625008 | 0.660013981 |
| 226 | 245 | R.TIGDFLKDKYDSASEMVVEK.H | | 764.709096 | 1302174 | |
| 226 | 245 | R.TIGDFLKDKYDSASEMVVEK.H | | 772.709096 | 2251469 | 0.578366391 |
| 233 | 245 | K.DKYDSASEMVVEK.H | | 750.848054 | 866498 | |
| 233 | 245 | K.DKYDSASEMVVEK.H | | 758.848054 | 1348852 | 0.642396645 |
| 233 | 245 | K.DKYDSASEMVVEK.H | | 500.900667 | 1094931 | |
| 233 | 245 | K.DKYDSASEMVVEK.H | | 506.2340003 | 1431170 | 0.765060056 |
| 233 | 245 | K.DKYDSASEMVVEK.H | | 758.845513 | 878145 | |
| 233 | 245 | K.DKYDSASEMVVEK.H | | 766.859868 | 1300947 | 0.675004439 |
| 233 | 245 | K.DKYDSASEMVVEK.H | | 506.2412157 | 1178239 | |
| 233 | 245 | K.DKYDSASEMVVEK.H | | 511.574549 | 1802018 | 0.65384419 |
| 235 | 245 | K.YDSASEMVVEK.H | | 629.286293 | 198679 | |
| 235 | 245 | K.YDSASEMVVEK.H | | 633.293243 | 283374 | 0.701119369 |
| 235 | 245 | K.YDSASEMVVEK.H | | 637.284089 | 329568 | |
| 235 | 245 | K.YDSASEMVVEK.H | | 641.291357 | 437246 | 0.753735883 |
| 270 | 293 | R.DLVYYEASPNFCEPNPETGSFGTR.D | | 917.741667 | 8837561 | |
| 270 | 293 | R.DLVYYEASPNFCEPNPETGSFGTR.D | | 921.0750003 | 9718110 | 0.909390921 |
| 270 | 293 | R.DLVYYEASPNFCEPNPETGSFGTR.D | | 1376.108877 | 3686677 | |
| 270 | 293 | R.DLVYYEASPNFCEPNPETGSFGTR.D | | 1381.112801 | 4175599 | 0.882909733 |
| 296 | 314 | R.TCNVSSHGIDGCDLLCCGR.G | | 727.969128 | 59355 | |
| 296 | 314 | R.TCNVSSHGIDGCDLLCCGR.G | | 731.3024613 | 63325 | 0.93730754 |
| 327 | 344 | K.CHCVFHWCCYVSCQECTR.V | | 850.65542 | 325324 | |
| 327 | 344 | K.CHCVFHWCCYVSCQECTR.V | | 853.9887533 | 325891 | 0.998260154 |
| 327 | 344 | K.CHCVFHWCCYVSCQECTR.V | | 638.245234 | 696604 | |

TABLE 4-continued

Absolute and relative quantification of Wnt3a peptides
from a SILAC labeling experiment.

| Start | End | Sequence | SEQ ID NO. | Exp_MZ | absolute intensities | ratio of light to heavy |
|---|---|---|---|---|---|---|
| 327 | 344 | K.CHCVFHWCCYVSCQECT R.V | | 640.745234 | 926222 | 0.752091831 |
| 345 | 352 | R.VYDVHTCK.- | | 511.241251 | 715121 | |
| 345 | 352 | R.VYDVHTCK.- | | 515.248758 | 934026 | 0.765632862 |

Light and heavy Wnt3a peptides were derived from control and TIKI2-expressing cells, respectively. Peptides are sorted from the amino to carboxyl terminus, with amino acid ranges indicated in the first column. Peptides in bold highlight specific fragments from TIKI2-modified Wnt3a.

Example 9

Tiki Cleavage of Multiple Wnt Proteins

Tiki1 or Tiki2 inhibits Xwnt8 function in embryos (FIGS. 1A-G, 3H and additional data shown). Xwnt8 was also cleaved by TIKI2, as demonstrated by removal of the amino terminal HA tag (after the signal peptide) from HA-Xwnt8-FLAG, which also had a carboxyl terminal FLAG tag for protein detection (FIG. 5J). MS analyses of both Xwnt8-Myc and HA-Xwnt8-FLAG cleaved by TIKI2 suggested identically two amino terminal cleavage sites, resulting in removal of 17 and 20 residues of mature Xwnt8, respectively (FIG. 5C and additional data). TIKI2 also cleaved HA-Wnt5a at the amino terminus (FIG. 5K), but the low amount of Wnt5a production/secretion has thus far hindered identification of the TIKI2 cleavage site(s). TIKI2 did not cleave HA-Xwnt11-FLAG (FIG. 5L), implying intriguing specificity towards different Wnt proteins.

Figures 5Y, 5Z:
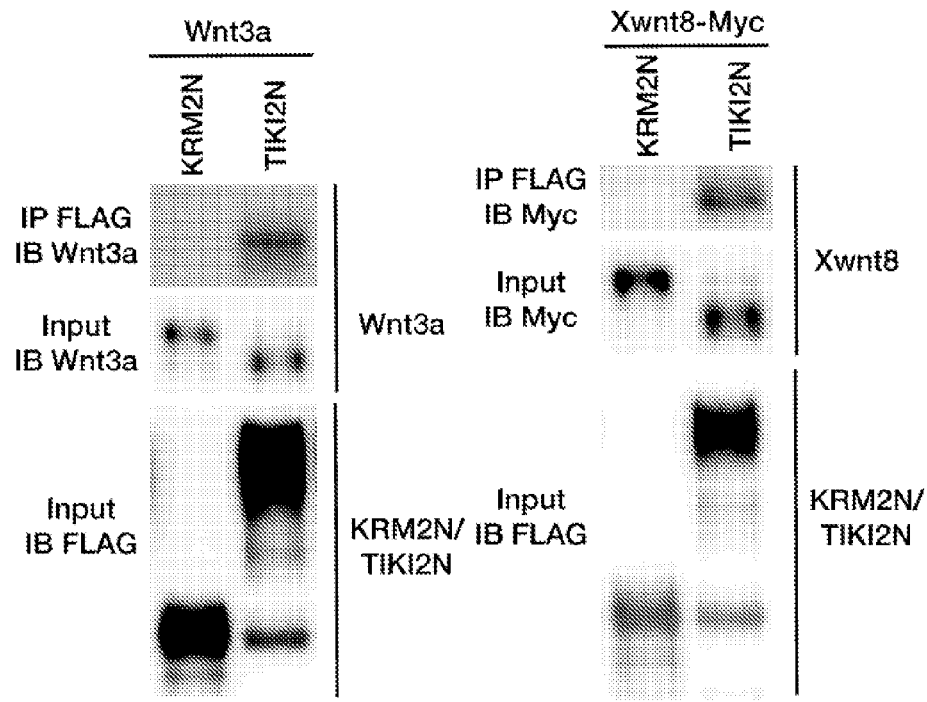
Figures 5A, 5B:
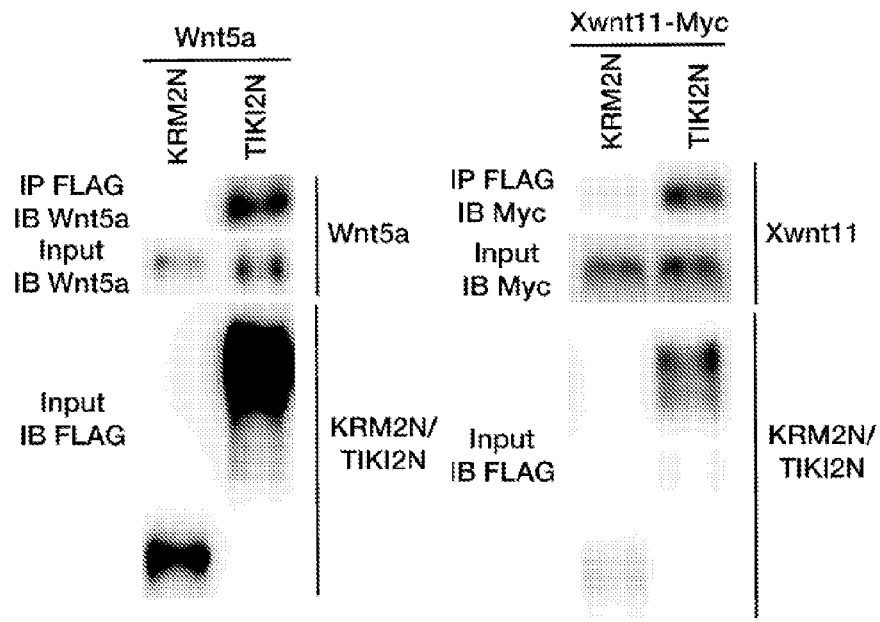
Figure 5C:
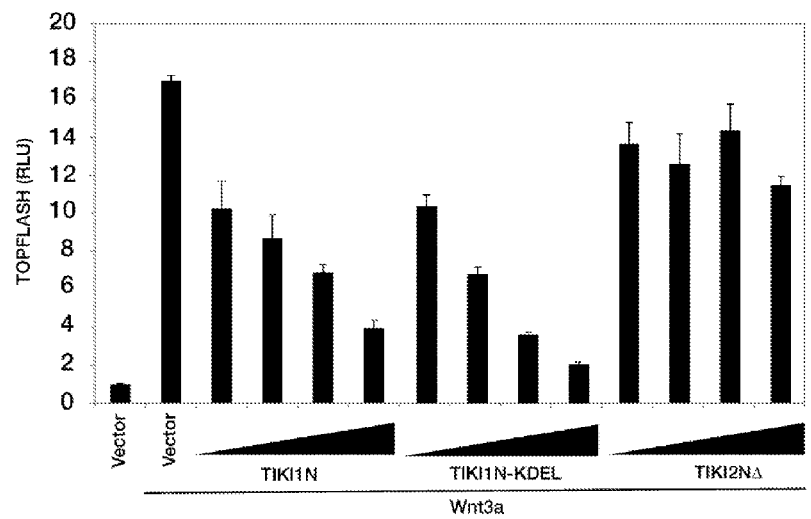

Amino terminal residues are highly variable among Wnt family members but are well conserved among paralogs in vertebrates. Consequently TIKI2 cleavage sites in Wnt3a and Xwnt8 do not reveal recognizable consensus motifs (FIG. 5C). To glimpse into this apparent paradox, TIKI2, but not KRM2 (human Kremen2), bound to Wnt3a, Xwnt8, and Wnt5a in co-immunoprecipitation assays (FIGS. 5Y-AA). This was not unanticipated since enzyme-substrate pairs (see below) often exhibit physical interactions. Intriguingly TIKI2, but not KRM2, also bound to Xwnt11 but did not cleave Xwnt11 (FIG. 5BB). Thus, TIKI may interact with conserved residues/motifs within Wnt proteins, thereby orientating itself for cleaving Wnt amino terminus.

Further experiments were performed to examine TIKI cleavage of 19 human Wnts. Each human Wnt with an amino terminal HA tag and a carboxyl terminal V5 tag was expressed alone or together with human TIKI2 in 293T cells and the resulting CM and whole cell extracts were analyzed by western blotting with anti-HA and anti-V5 antibodies. TIKI cleavable Wnts showed reduced signal on anti-HA blots and mobility change on anti-V5 blots.

TIKI cleavable Wnts included Wnt2B, 3, 3A, 4, 5A, 5B, 6, 7A, 7B, 8A, 8B, and 16.

Wnts that appeared to be resistant to TIKI cleavage in these experiments included Wnt1, 2, 9A, 9B, 10A, 10B, and 11.

Example 10

Tiki Proteins are Likely Metalloproteases

TIKI2N was sufficient for Wnt3a inhibition (FIG. 1K) and cleavage in cells (FIGS. 5E, 5G, 5M and 4O, 4P and 4R).

Recombinant TIKI2N was purified via a tandem affinity procedure (FIG. 5N), which upon in vitro incubation with purified HA-Wnt3a, triggered Wnt3a cleavage and the disappearance of the HA epitope (FIG. 5O). KRM2N, which corresponds to the ectodomain of the transmembrane Kremen2 protein (Mao et al., 2002), or TIKI2NΔ, a deletion mutant that lacks a segment of the TIKI domain and neither modified Wnt3a in cells nor inhibited Wnt signaling (FIGS. 5M and 5CC), failed to do so in the in vitro assay (FIG. 5O). MS analyses of recombinant human WNT3A cleaved by TIKI2N in vitro indicated cleavage at identical (major and minor) amino terminal sites as observed in cells. These results suggest that Tiki is, or is at least associated with, a Wnt protease.

Figures 6A, 6B, 6D:
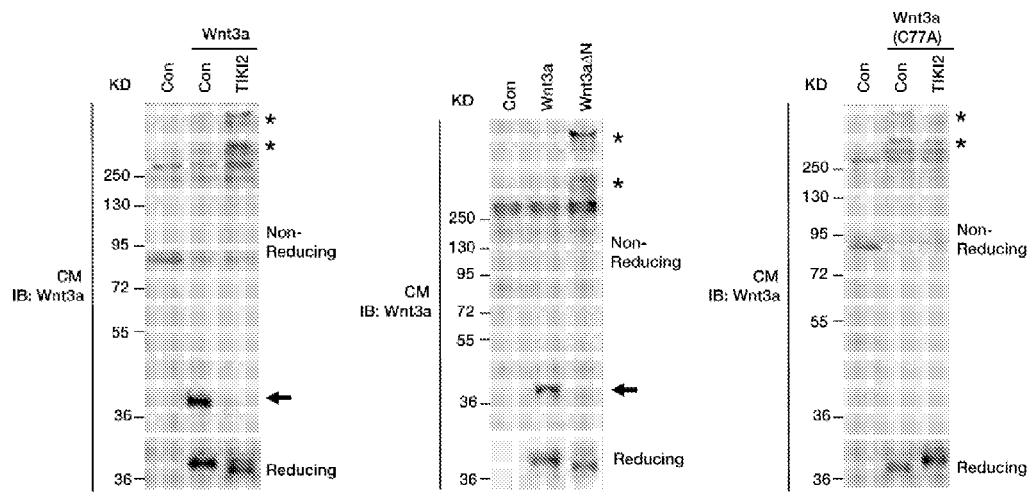
Figure 6C:
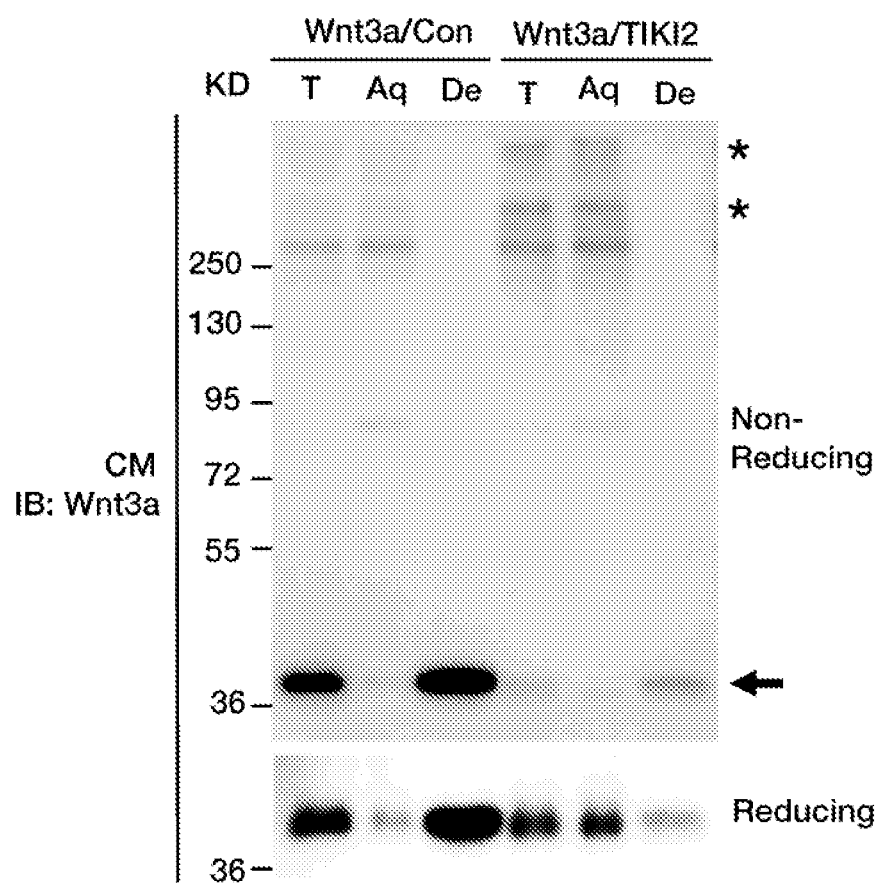

TIKI protease activity was characterized under in vitro conditions. TIKI2N cleavage of HA-Wnt3a became obvious at 2 hours (FIG. 6F), and exhibited preference for neutral to slightly basic pH between 7 to 9 (FIG. 6G). Different protease inhibitors were applied to survey which protease family TIKI might belong to. TIKI2N was neither sensitive to Bestatin, an aminopeptidase-specific inhibitor, nor to a mixture of broad specificity inhibitors for serine, cysteine, aspartic proteases and aminopeptidases (FIGS. 5P and 6H-I). Remarkably however, TIKI2N activity was potently inhibited by a metalloprotease inhibitor, 1,10-phenanthroline, which is a divalent metal chelator and was applied at concentrations 100-500 folds lower than recommended doses (FIG. 5P). TIKI2N was also inhibited, albeit more mildly, by EDTA, another metalloprotease inhibitor and divalent metal chelator (FIG. 6J) (Barrett, 1998; Overall and Blobel, 2007). Metalloproteases are defined by their dependence on divalent metals as co-factors (Barrett, 1998). Indeed TIKI2N cleavage of HA-Wnt3a in vitro was enhanced by $Co^{2+}$ and $Mn^{2+}$ (FIG. 5Q, lanes 4 and 12), but not by $Ni^{2+}$, $Cu^{2+}$, or $Zn^{2+}$, which in fact inhibited TIKI2N activity (FIG. 5Q, lanes 6, 8, and 10). Importantly, $Co^{2+}$ or $Mn^{2+}$ fully restored TIKI2N enzymatic activity that was inhibited by 1,10-phenanthroline (FIG. 5R, lanes 6 and 8). Thus Tiki proteins are likely $Co^{2+}$- or $Mn^{2+}$-dependent metalloproteases.

Example 12

Wnt Oxidation-Oligomerization Induced by Tiki Cleavage

Tiki cleavage-induced elimination of Wnt3a hydrophobicity (FIGS. 5A and 4M) was puzzling but intriguing. In an experiment to examine disulfide bond formation of Wnt3a, Tiki-modified Wnt3a, but not control Wnt3a, existed in CM mostly as large (>400 kD) oligomers that were linked by inter-molecular disulfide bonds and could be reduced to monomers under the reducing condition (FIG. 6A). Despite being fully soluble, these Wnt3a oligomers appeared to be massive in size since a significant fraction showed minimal migration in gel (FIG. 6A). This oxidized Wnt oligomerization was secondary to Tiki cleavage, since Wnt3aΔN formed, in the absence of Tiki expression, similar large and soluble oligomers that could be fully reduced (FIG. 6B), as did Wnt3a(S25D/L26D/S33D/S34D), which is inactive (FIG. 5X). Interestingly oxidized Wnt3a oligomers partitioned exclusively aqueously whereas monomeric (or non-covalently oligomeric) Wnt3a partitioned in detergent (FIG. 6C), implying that lipid adducts may have been tightly buried inside the oxidized Wnt oligomer. Control Wnt3a appeared to exhibit traces of similar oxidized oligomers (FIGS. 6A-C), which contained intact Wnt3a as demonstrated by the amino terminal HA tag (FIG. 6K), hinting that Wnt3a may have intrinsic oxidation-oligomerization propensity and its amino terminus may act to minimize such oligomerization/inactivation. However, the possibility that the trace amount of oxidized oligomers of control Wnt3a was caused by overexpression cannot be ruled out.

Figure 6E:
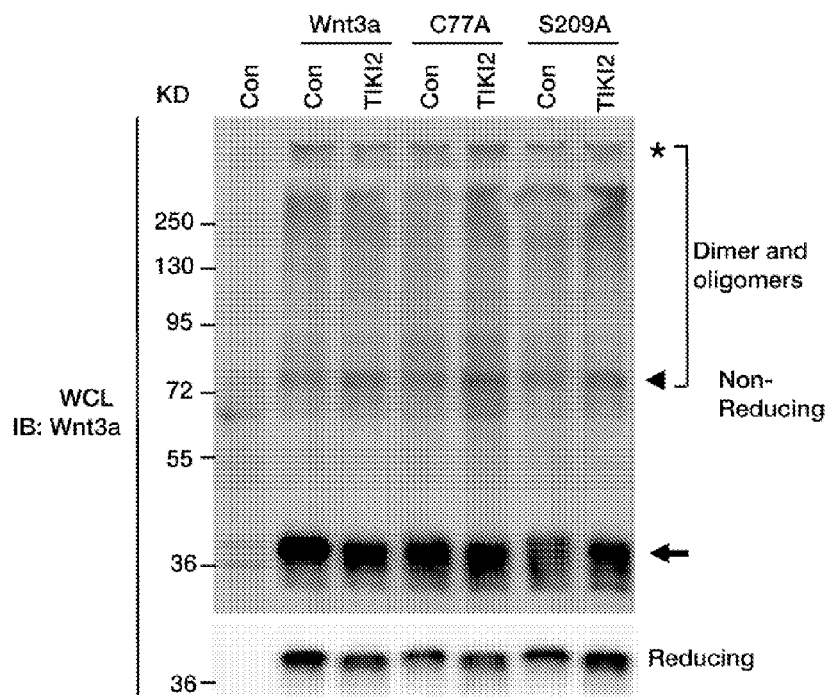
Figure 6F:
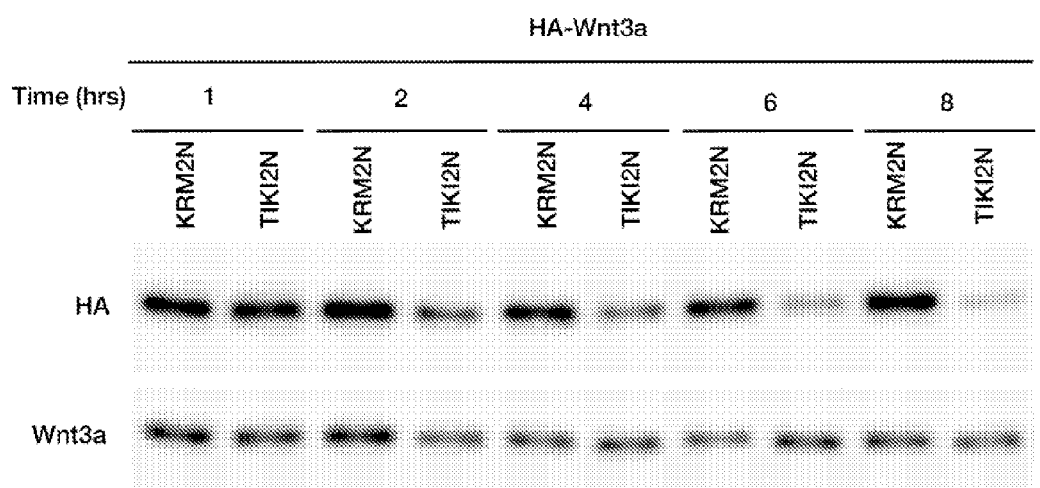
Figure 6G:
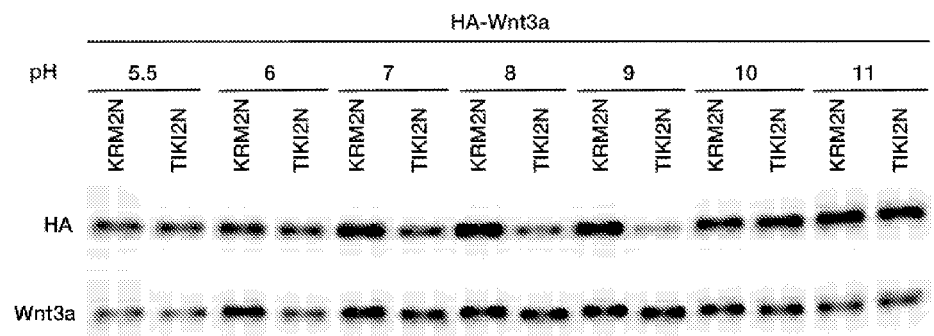
Figure 6H:
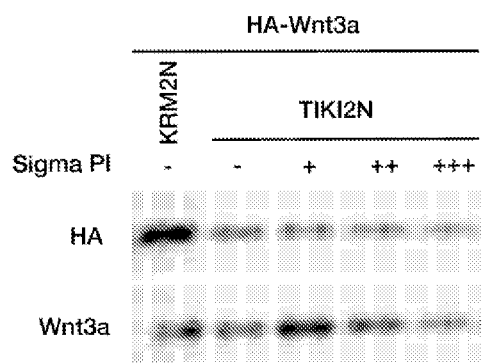
Figure 6I:
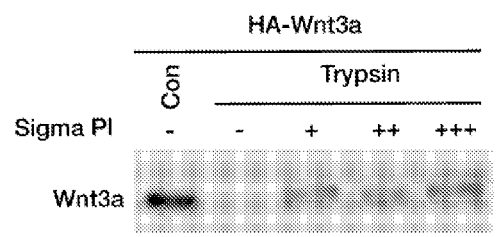
Figure 6J:
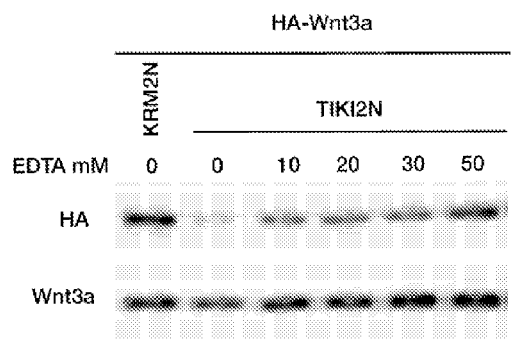
Figure 6K:
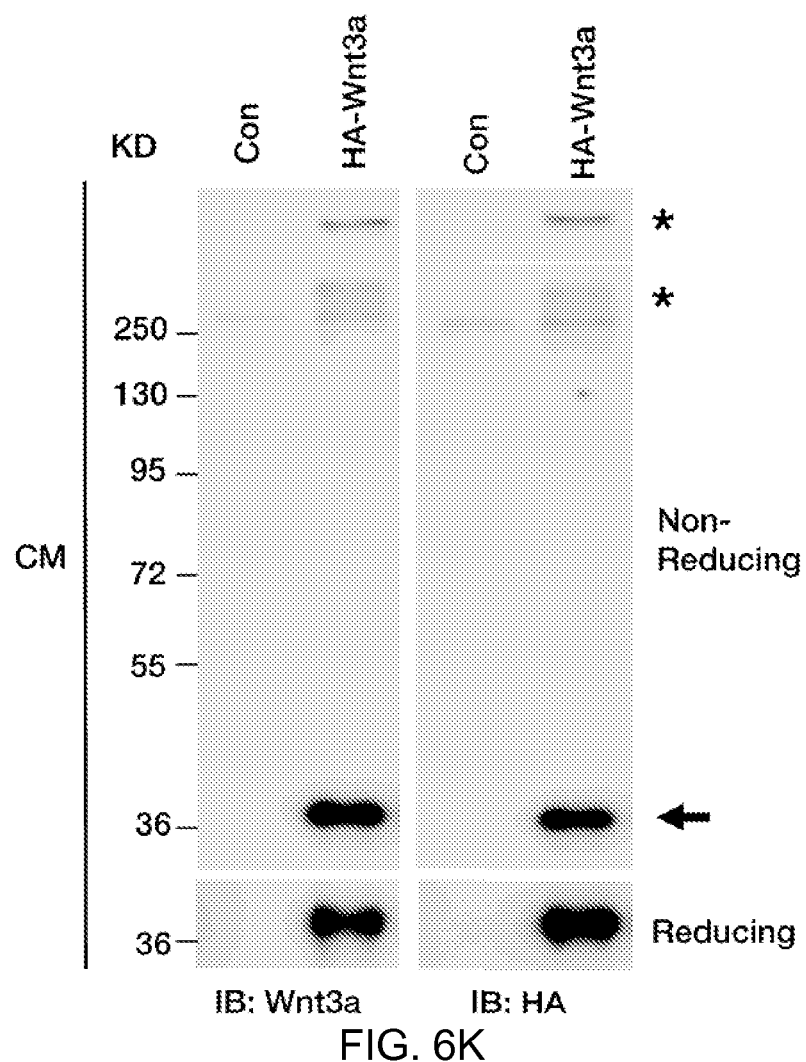
Figure 6L:
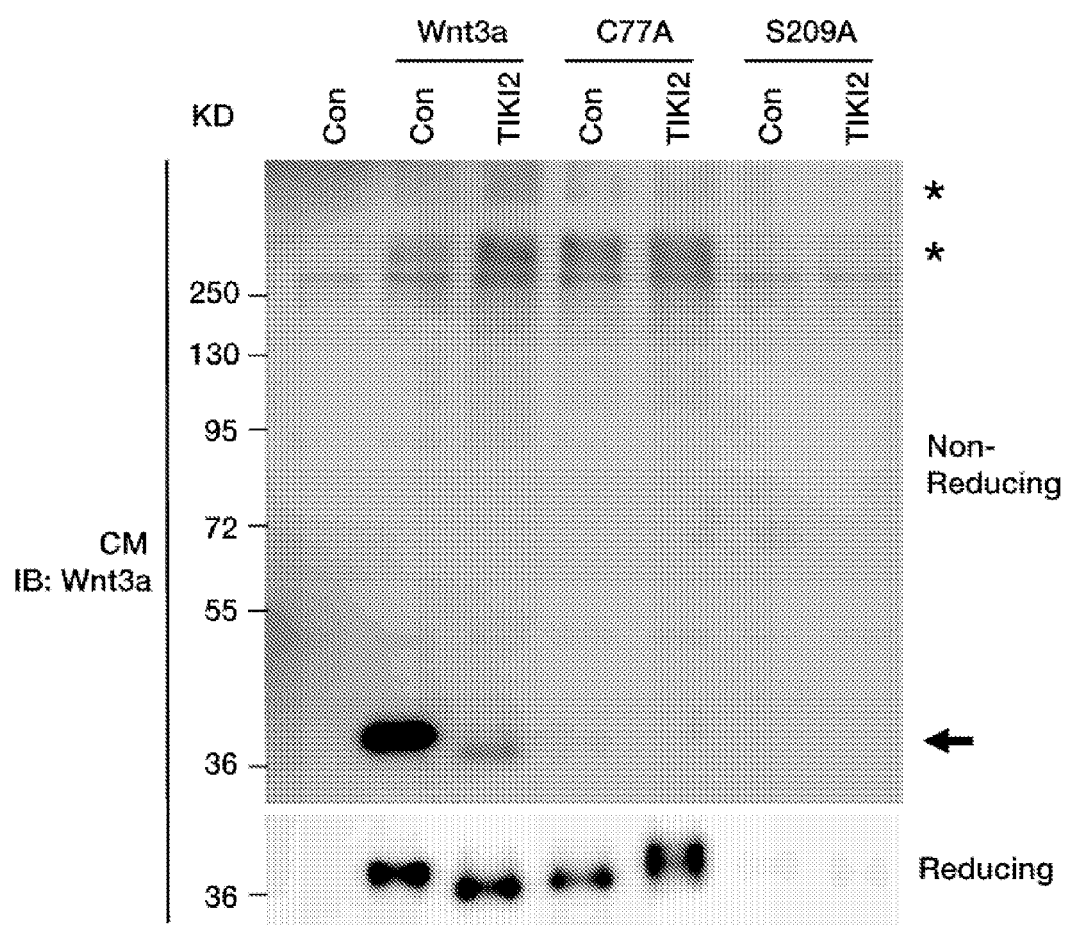
Figure 6M:
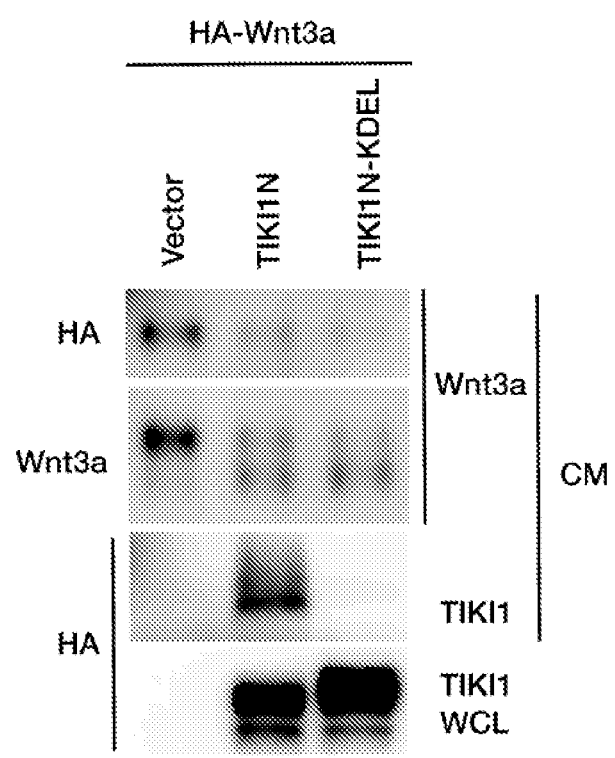

Tiki-modified Wnt3a, Wnt3aΔN, and Wnt3a(C77A) bare strong similarity in their hydrophilic behavior and incapability to signal. Interestingly, Wnt3a(C77A) also formed oxidized oligomers in CM regardless of Tiki co-expression (FIG. 6D). Although it is unknown whether oxidized oligomers of Tiki-modified Wnt3a/Wnt3aΔN or Wnt3a(C77A) were formed via disulfide bonds between the same cysteines, these data suggest that Wnt3a palmitoylation at C77 may be required for minimizing Wnt3a oxidation-oligomerization during biogenesis, a role shared by Wnt3a amino terminus that is removable by Tiki. However, while Tiki-modified Wnt3a and Wnt3aΔN are severely impaired in both autocrine and paracrine signaling assays (FIGS. 4G, 5H, and 1J and 1K), Wnt3a(C77A) retains residual autocrine signaling activity (FIG. 4P) (Willert et al., 2003), implying some quantitative or qualitative difference in the roles that Wnt3a amino terminus and palmitoylation play in maintaining Wnt3a activity.

Where these Wnt oligomers were formed during Wnt biogenesis was then examined Surprisingly in whole cell lysates there was little, if any, difference among Wnt3a, Wnt3a(C77A), and Wnt3a(S209A) that lacks O-acylation, regardless of TIKI2 cleavage, since each existed mainly as monomers (or non-covalent oligomers) and also as heterogeneous oxidized oligomers from likely dimers to larger multimers (FIG. 6E). These results may be consistent with the suspicion that Wnt3a has the intrinsic ability to form oxidized oligomers during biogenesis, but this oxidation process is resolved/reduced and thus minimized by Wnt3a amino terminus and C77 palmitoylation during or after secretion, resulting in only trace amounts of oxidized Wnt3a (wild type) oligomers in CM. But for TIKI-cleaved Wnt3a or Wnt3a(C77A), this propensity may be exacerbated during or after secretion, resulting in predominantly massive oxidized oligomers in CM. Wnt3a(S209A) was not secreted (FIG. 6L) as reported (Takada et al., 2006).

Example 13

Tiki Acts in Both Wnt-Producing and Wnt-Responding Cells

Figure 7A:
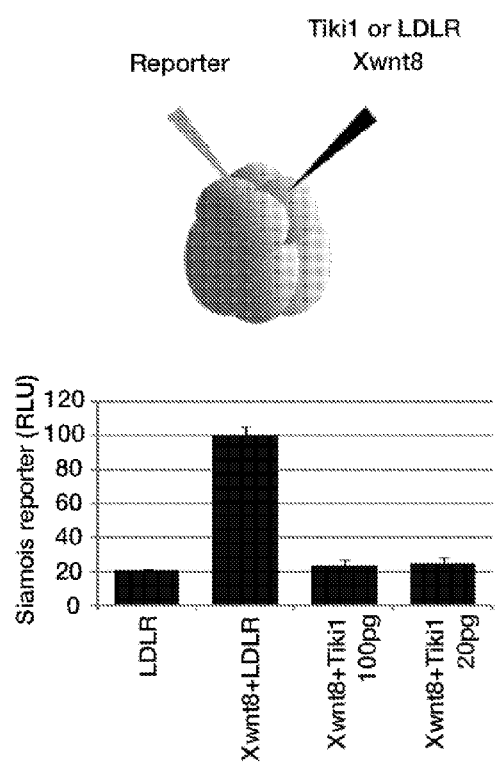
Figure 7B:
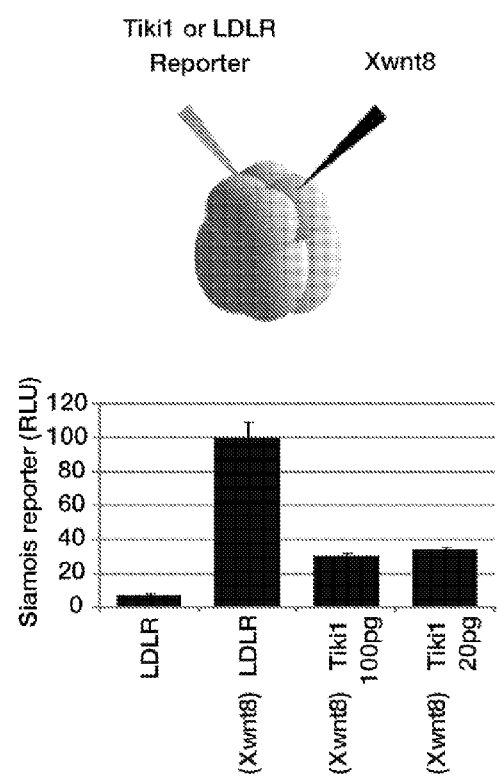

Cellular localization studies suggest that Tiki may act in the secretory pathway and on the plasma membrane. Consistent with both scenarios, Tiki1N (FIG. 1K) and Tiki1N-KDEL ("KDEL," SEQ ID NO: 51), which harbors the ER-retention KDEL sequence ("KDEL," SEQ ID NO: 51) at the carboxyl terminus of Tiki1N and was hardly secreted (FIG. 6M), each potently inhibited Wnt signaling (FIG. 5CC). Tiki showed inhibitory effect in Wnt-producing cells, but apparently not in Wnt-responding cells (FIG. 4H). Excessive Wnt3a proteins added acutely might have activated signaling prior to, or overwhelmed, Tiki function. Therefore whether Tiki was able to block signaling in Wnt-producing and -responding cells under more physiological settings in embryos was investigated. Wnt-responsive reporter assays were performed via Tiki overexpression or knockdown. Firstly, at the 8-cell stage, two animal blastomeres were injected separately with Xwnt8 mRNA or with S01234-luciferase DNA (FIG. 7A), which is driven by the promoter of the *Xenopus Siamois* gene, a direct Wnt target gene (Brannon et al., 1997). Animal blastomeres were chosen since their progenies do not express Tiki1 endogenously (FIGS. 2A-M). Xwnt8 induced luciferase expression from the reporter (FIG. 7A), but not from a control reporter, S0-luciferase, in which all TCF-binding sites were mutated (Brannon et al., 1997). Co-injection of Xwnt8 with Tiki1, but not with the control LDLR, inhibited the reporter expression (FIG. 7A). Therefore Tiki1 could inhibit Wnt activity in Wnt-producing cells in embryos as seen in mammalian cells. The co-injection scheme was then altered by injecting Xwnt8 in one animal blastomere and co-injecting Tiki1 (or LDLR) mRNA together with the S01234-luciferase reporter in a neighboring blastomere (FIG. 7B). Under these conditions Tiki1, but not LDLR, inhibited Xwnt8-induced reporter expression in Wnt-responding cells (FIG. 7B).

The same question was addressed complementarily via Tiki1MO knockdown in dorsal blastomeres whose progenies expresses Tiki1 endogenously. At the 8-cell stage, an Xwnt8 expression plasmid (which transcribes Xwnt8 after mid-blastula transition) plus the Tiki1MO (or control MO) were co-injected into a single blastomere (i.e., to knock down Tiki1 in Xwnt8-producing cells), and the S01234-luciferase plasmid was injected into the neighboring blastomere. Alternatively the Xwnt8 plasmid was injected into a single blastomere, and the 501234-luciferase reporter plus Tiki1MO or control MO was co-injected into the neighboring blastomere (i.e., to knock down Tiki1 in Xwnt8-responding cells). Xwnt8 specifically induced 501234-luciferase, but not control S0-luciferase, and the XWnt8 response was enhanced by Tiki1MO under both conditions (FIGS. 7C and 7D), Thus the endogenous Tiki1 in the Organizer acts in both Wnt-producing and Wnt-responding cells.

Tiki1 inhibition of Wnt-induced nuclear beta-catenin accumulation was monitored. Xwnt8 plus RFP (red fluorescent protein) mRNA was injected into an animal blastomere of 8-cell stage embryos, and injected Tiki1 or LDLR mRNA together with fluorescein dextran (FLD) into a neighboring blastomere (FIG. 7E), and nuclear β-catenin examined in animal cap cells at stage 9. Xwnt8-expressing cells were traced by RFP, whereas Wnt-responding cells that expressed Tiki1 or LDLR were traced by FLD, and naive cells descended from uninjected blastomeres lacked FLD or RFP fluorescence. Nuclear beta-catenin was observed in Xwnt8-expressing cells due to autocrine signaling, and in cells that expressed LDLR in response to paracrine Wnt signaling. By contrast, much fewer Tiki1-expressing cells (FIG. 7K) exhibited nuclear beta-catenin. Quantification showed that 75% of LDLR-expressing and naive cells versus 30% of Tiki1-expressing cells displayed nuclear beta-catenin (FIG. 7F), further supporting that Tiki1 functions in Wnt-responding cells.

These results indicate that Tiki is a versatile Wnt inactivator that functions in Wnt-producing cells, possibly via acting in the secretory pathway and at the plasma membrane and in Wnt-responding cells via acting at the plasma membrane.

Example 14

Mutational Analysis of Conserved Residues

Residues that are evolutionarily conserved are typically considered good candidates for playing a role in function. Thus, amino acids conserved (either identical or conservatively substituted) from humans to bacteria were replaced in TIKI2 with alanines using standard molecular biological methods for site directed mutagenesis. FIG. 8A shows an alignment of sequences from TraB and PrgY families. The TraB superfamily includes TIKI/GumN branch and PrgY branch, distinguished by hydrophobic residues in/surrounding GxxH motifs. The PrgY proteins do not align with TIKI/GumN proteins but they have similar GxxH motifs (first GTxH and second GxxHxxG). TIKI proteins usually have a hydrophobic I in the x position of first GTxH motif, while PrgY has either S or A in this position. TIKI proteins have more Fs preceding GxxHxxG while PrgY have more Vs. Secondary structure predictions suggest both GxxH motifs are at end of beta strand, with H residue at a turn.

A Wnt-responsive reporter (TOP-FLASH) assay was performed to test mutations at T56A, H58A, E85A, E205A, H256A, R303A, H331A in a Human TIKI2N construct (no transmembrane domain). Decreasing doses of 5, 2.5, 1.25 and 0.612 ng of the indicated TIKI2N expression plasmid were co-transfected with Wnt3a (20 ng) in HEK293T cells. The results, shown in FIG. 8B, indicate that the H58A, E85A, H331A, and E205A TIKI mutants are inactive, so likely represent potential active sites. T56A, H256A, and R303A had no effect on TIM activity, and so are likely to be less important sites for function.

Example 14

HTS for Tiki2 Inhibitors that Inhibit Cleavage of Wnt

A high throughput screen (HTS) is used to identify compounds that enhance LRP5/6 signaling as potential therapeutics for osteoporosis or cellular proliferative disorders. A Wnt responsive cell line is employed that carries a Super-TOPFLASH(STF) luciferase reporter (Wnt-responsive) (Major et al. Science. 2007. 316:1043-6). These STF cells grow as an adherent monolayer making them ideally suited for 384-well-plate screening format. In addition, these STF cells possess a low level of basal Wnt signaling that can be readily induced by the addition of Wnt3a, which in a 6-hour treatment resulted in 30-40 fold induction of the STF reporter (not shown). Different conditions are tested and an acceptable z' score of 0.5 or above (z' measures HTS quality and reproducibility (Zhang et al. J Biomol Screen. 1999. 4:67-73)) is achieved.

To screen for Tiki1/2 inhibitors, clonal lines are established of the above STF cells that express Wnt3a (which are referred to as STF-Wnt3a) using a retroviral Wnt3a expression vector. Individual clones are selected showing the highest levels of luciferase activity while preserving adherent monolayer growth. Next, clonal lines are established of STF-Wnt3a cells expressing Tiki1 and/or 2 via another retroviral vector (under different selection). Lastly, it will be confirmed that Tiki1/2 shRNA knockdown in the STF-Wnt3a/Tiki2 cells will lead to derepression of the STF luciferase reporter, mimicking the effects of a potential small molecule Tiki1/2 inhibitor. These multiple steps ensure that the STF cells are responsive to Wnt3a, which is inactivated by Tiki2, which is further inhibitable by potential compound inhibitors. Importantly, because the assay is based on increases of STF reporter expression, non-specific compounds that cause cell toxicity/death are excluded by definition.

A pilot scale screen is conducted treating STF-Wnt3a/Tiki2 cells with the standard 10 micro M compounds for 6 or 12 hrs to optimize the screening condition. According to experience a ratio of about 0.5 percent positive hits is reasonable. Once optimal conditions are established, the entire ICCB chemical library collection is screened through triplicate readings for each compound.

After the primary screen and subtractions of compounds that are not specific for Tiki2, compounds are selected using secondary confirmation screens. A dose response curve is performed for each compound (1 nM to 1 micro M) using the same STF-Wnt3a/Tiki2 cells in 384-well plate format. The compounds that successfully activate STF-Wnt3a/Tiki2 in the confirmation assay are tested further in immunostaining for nuclear beta-catenin, which is induced by Wnt3a in these STF cells (Major et al. Science. 2007. 316:1043-6). Thus, STF-Wnt3a/Tiki2 cells will have low nuclear beta-catenin, and inhibition of Tiki2 will restore/increase nuclear beta-catenin These assays are performed in 384-well plate format using the high-content imaging HTS system at ICCB. These assays together will allow the selected of the strongest candidates, which are used to demonstrate whether these compounds inhibit Tiki2 directly. Because Tiki2 causes cleavage of the N-terminal amino acids of mature Wnt3a, and causes Wnt3a to exhibit faster mobility in electrophoresis (FIG. 5C) and to partition in aqueous phase upon Triton X-114 partitioning (FIG. 6A,B), Tiki2 inhibitors should restore Wnt3a mobility and partitioning in detergent phase and lack of cleavage of the N-terminal amino acids of Wnt. These secondary screens together identify potent and functional Tiki2 inhibitor compounds.

Further functional validation of Tiki inhibitors is done as follows. Once candidate Tiki inhibitors are identified, their specificity is evaluated. For example, in some embodiments it is confirmed that these compounds will not directly affect Sclerostin or DKK1 inhibition of Wnt3a. Also examined is whether these compounds affect other signaling pathways, such as Hedgehog, TGF beta, BMP, and EGF/FGF. These assays can be performed using pathway-specific luciferase reporters and/or phospho-Abs (for Smad, MAPK, etc) in mammalian cell lines.

Once the specificity of candidate Tiki2 inhibitors is established, these compounds are tested in primary osteoblasts from WT and Tiki2−/− mice. Because Tiki2 is expressed in osteoblasts and Tiki2−/− mice exhibit high bone mass, Tiki2−/− osteoblasts may proliferate or differentiate into bone more robustly than the WT ones. Ideally, Tiki2 inhibitors will mimic the effects of Tiki2 deletion, and further, these compounds should have little or no effects on Tiki2−/− osteoblasts. These experiments should further demonstrate the specificity of the compounds and may validate their potential in stimulating osteoblast proliferation/differentiation in vitro.

The effect of these Tiki2 inhibitors is examined in human Saos-2 cells, which are Wnt-responsive and are commonly used for their osteoblast-like properties (Suzuki et al., J Cell Biochem. 2008. 104:304-17). It is anticipated that Tiki2 inhibition leads to increased proliferation/differentiation of these cells. These studies are compared to those using primary osteoblasts from WT and Tiki2−/− mice, substantiating similar regulation of osteoblast properties by Tiki2 between mice and men.

The most promising Tiki2 inhibitors are tested in mice. The fact that Sclerostin blocking Abs promote bone formation in an aging rat model (Li et al., 2009, J. Bone Miner. Res. 24:578-588) implies that Wnt stimulation of bone growth continues into late adulthood. Thus, Tiki2 inhibition, and thereby production of more active Wnts, will likely benefit bone mass throughout life. The effect of Tiki2 inhibitors is compared in mice with the results from the Tiki2 deletion mutants. Tiki2 compound inhibitors that increase bone mass in mice are selected for further therapeutic development.

REFERENCES

Bafico, A., Liu, G., Yaniv, A., Gazit, A., and Aaronson, S. A. (2001). Novel mechanism of Wnt signalling inhibition mediated by Dickkopf-1 interaction with LRP6/Arrow. Nat Cell Biol 3, 683-686.

Banziger, C., Soldini, D., Schutt, C., Zipperlen, P., Hausmann, G., and Basler, K. (2006). Wntless, a conserved membrane protein dedicated to the secretion of Wnt proteins from signaling cells. Cell 125, 509-522.

Barrett, A. J., Rawlings, N. D., and Woessner, J. F. (1998). Handbook of Proteolytic Enzymes (Academic Press, San Diego).

Brannon, M., Gomperts, M., Sumoy, L., Moon, R. T., and Kimelman, D. (1997). A beta-catenin/XTcf-3 complex binds to the siamois promoter to regulate dorsal axis specification in *Xenopus*. Genes & development 11, 2359-2370.

Charron, G., Zhang, M. M., Yount, J. S., Wilson, J., Raghavan, A. S., Shamir, E., and Hang, H. C. (2009). Robust fluorescent detection of protein fatty-acylation with chemical reporters. Journal of the American Chemical Society 131, 4967-4975.

Cho, K. W., Blumberg, B., Steinbeisser, H., and De Robertis, E. M. (1991). Molecular nature of Spemann's organizer: the role of the *Xenopus* homeobox gene goosecoid. Cell 67, 1111-1120.

Christian, J. L., and Moon, R. T. (1993). Interactions between Xwnt-8 and Spemann organizer signaling pathways generate dorsoventral pattern in the embryonic mesoderm of *Xenopus*. Genes & development 7, 13-28.

Clevers, H. (2006). Wnt/beta-catenin signaling in development and disease. Cell 127, 469-480.

Cong, F., Schweizer, L., and Varmus, H. (2004). Wnt signals across the plasma membrane to activate the beta-catenin pathway by forming oligomers containing its receptors, Frizzled and LRP. Development (Cambridge, England) 131, 5103-5115.

Coombs, G. S., Yu, J., Canning, C. A., Veltri, C. A., Covey, T. M., Cheong, J. K., Utomo, V., Banerjee, N., Zhang, Z. H., Jadulco, R. C., et al. (2010). WLS-dependent secretion of WNT3A requires Ser209 acylation and vacuolar acidification. Journal of cell science 123, 3357-3367.

De Robertis, E. M., and Kuroda, H. (2004). Dorsal-ventral patterning and neural induction in *Xenopus* embryos. Annual review of cell and developmental biology 20, 285-308.

Franch-Marro, X., Wendler, F., Griffith, J., Maurice, M. M., and Vincent, J. P. (2008). In vivo role of lipid adducts on Wingless. Journal of cell science 121, 1587-1592.

Glinka, A., Wu, W., Delius, H., Monaghan, A. P., Blumenstock, C., and Niehrs, C. (1998). Dickkopf-1 is a member of a new family of secreted proteins and functions in head induction. Nature 391, 357-362.

Harland, R., and Gerhart, J. (1997). Formation and function of Spemann's organizer. Annual review of cell and developmental biology 13, 611-667.

Hausmann, G., Banziger, C., and Basler, K. (2007). Helping Wingless take flight: how WNT proteins are secreted. Nature reviews 8, 331-336.

He, X., Semenov, M., Tamai, K., and Zeng, X. (2004). LDL receptor-related proteins 5 and 6 in Wnt/beta-catenin signaling: arrows point the way. Development (Cambridge, England) 131, 1663-1677.

Kato, Y., Habas, R., Katsuyama, Y., Naar, A. M., and He, X. (2002). A component of the ARC/Mediator complex required for TGF beta/Nodal signalling. Nature 418, 641-646.

Kiecker, C., and Niehrs, C. (2001). A morphogen gradient of Wnt/beta-catenin signalling regulates anteroposterior neural patterning in *Xenopus*. Development (Cambridge, England) 128, 4189-4201.

Komekado, H., Yamamoto, H., Chiba, T., and Kikuchi, A. (2007). Glycosylation and palmitoylation of Wnt-3a are coupled to produce an active form of Wnt-3a. Genes Cells 12, 521-534.

Kurayoshi, M., Yamamoto, H., Izumi, S., and Kikuchi, A. (2007). Post-translational palmitoylation and glycosylation of Wnt-5a are necessary for its signalling. Biochem J 402, 515-523.

Logan, C. Y., and Nusse, R. (2004). The Wnt signaling pathway in development and disease. Annual review of cell and developmental biology 20, 781-810.

MacDonald, B. T., Tamai, K., and He, X. (2009). Wnt/beta-catenin signaling: components, mechanisms, and diseases. Dev Cell 17, 9-26.

MacDonald, B. T., Yokota, C., Tamai, K., Zeng, X., and He, X. (2008). Wnt signal amplification via activity, cooperativity, and regulation of multiple intracellular PPPSP motifs in the Wnt co-receptor LRP6. The Journal of biological chemistry 283, 16115-16123.

Mao, B., Wu, W., Davidson, G., Marhold, J., Li, M., Mechler, B. M., Delius, H., Hoppe, D., Stannek, P., Walter, C., et al. (2002). Kremen proteins are Dickkopf receptors that regulate Wnt/beta-catenin signalling. Nature 417, 664-667.

Mao, B., Wu, W., Li, Y., Hoppe, D., Stannek, P., Glinka, A., and Niehrs, C. (2001). LDL-receptor-related protein 6 is a receptor for Dickkopf proteins. Nature 411, 321-325.

McGrew, L. L., Hoppler, S., and Moon, R. T. (1997). Wnt and FGF pathways cooperatively pattern anteroposterior neural ectoderm in *Xenopus*. Mechanisms of development 69, 105-114.

Molenaar, M., van de Wetering, M., Oosterwegel, M., Peterson-Maduro, J., Godsave, S., Korinek, V., Roose, J., Destree, O., and Clevers, H. (1996). XTcf-3 transcription factor mediates beta-catenin-induced axis formation in *Xenopus* embryos. Cell 86, 391-399.

Moon, R. T., Kohn, A. D., De Ferrari, G. V., and Kaykas, A. (2004). WNT and beta-catenin signalling: diseases and therapies. Nat Rev Genet 5, 691-701.

Mulligan, K. A., Fuerer, C., Ching, W., Fish, M., Willert, K., and Nusse, R. (2012). Secreted Wingless-interacting molecule (Swim) promotes long-range signaling by maintaining Wingless solubility. Proceedings of the National Academy of Sciences of the United States of America 109, 370-377.

Niehrs, C. (2004). Regionally specific induction by the Spemann-Mangold organizer. Nat Rev Genet 5, 425-434.

Ong, S. E., Blagoev, B., Kratchmarova, I., Kristensen, D. B., Steen, H., Pandey, A., and Mann, M. (2002). Stable isotope labeling by amino acids in cell culture, SILAC, as a simple and accurate approach to expression proteomics. Mol Cell Proteomics 1, 376-386.

Overall, C. M., and Blobel, C. P. (2007). In search of partners: linking extracellular proteases to substrates. Nature reviews 8, 245-257.

Petersen, C. P., and Reddien, P. W. (2009). Wnt signaling and the polarity of the primary body axis. Cell 139, 1056-1068.

Resh, M. D. (2006). Trafficking and signaling by fatty-acylated and prenylated proteins. Nature chemical biology 2, 584-590.

Semenov, M. V., Tamai, K., Brott, B. K., Kuhl, M., Sokol, S., and He, X. (2001). Head inducer Dickkopf-1 is a ligand for Wnt coreceptor LRP6. Curr Biol 11, 951-961.

Singh, S., Springer, M., Steen, J., Kirschner, M. W., and Steen, H. (2009). FLEXIQuant: a novel tool for the absolute quantification of proteins, and the simultaneous identification and quantification of potentially modified peptides. Journal of proteome research 8, 2201-2210.

Strigini, M., and Cohen, S. M. (2000). Wingless gradient formation in the *Drosophila* wing. Curr Biol 10, 293-300.

Takada, R., Satomi, Y., Kurata, T., Ueno, N., Norioka, S., Kondoh, H., Takao, T., and Takada, S. (2006). Monounsaturated fatty acid modification of Wnt protein: its role in Wnt secretion. Dev Cell 11, 791-801.

Tamai, K., Semenov, M., Kato, Y., Spokony, R., Liu, C., Katsuyama, Y., Hess, F., Saint-Jeannet, J. P., and He, X. (2000). LDL-receptor-related proteins in Wnt signal transduction. Nature 407, 530-535.

Tamai, K., Zeng, X., Liu, C., Zhang, X., Harada, Y., Chang, Z., and He, X. (2004). A mechanism for Wnt coreceptor activation. Mol Cell 13, 149-156.

Voigt, J., Chen, J. A., Gilchrist, M., Amaya, E., and Papalopulu, N. (2005). Expression cloning screening of a unique and full-length set of cDNA clones is an efficient method for identifying genes involved in *Xenopus* neurogenesis. Mechanisms of development 122, 289-306.

Wei, Q., Yokota, C., Semenov, M. V., Doble, B., Woodgett, J., and He, X. (2007). R-spondin1 is a high affinity ligand for LRP6 and induces LRP6 phosphorylation and beta-catenin signaling. The Journal of biological chemistry 282, 15903-15911.

Willert, K., Brown, J. D., Danenberg, E., Duncan, A. W., Weissman, I. L., Reya, T., Yates, J. R., 3rd, and Nusse, R. (2003). Wnt proteins are lipid-modified and can act as stem cell growth factors. Nature 423, 448-452.

Zecca, M., Basler, K., and Struhl, G. (1996). Direct and long-range action of a wingless morphogen gradient. Cell 87, 833-844.

Zhai, L., Chaturvedi, D., and Cumberledge, S. (2004). *Drosophila* wnt-1 undergoes a hydrophobic modification and is targeted to lipid rafts, a process that requires porcupine. The Journal of biological chemistry 279, 33220-33227.

Zhang, M. M., Tsou, L. K., Charron, G., Raghavan, A. S., and Hang, H. C. (2010). Tandem fluorescence imaging of dynamic S-acylation and protein turnover. Proceedings of the National Academy of Sciences of the United States of America 107, 8627-8632.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated antibody or antigen-binding fragment thereof that binds to a TIKI protein and inhibits TIKI-mediated cleavage of a Wnt protein.

2. The antibody or antigen-binding fragment thereof of claim 1 that binds specifically to human TIKI1, human TIKI2, or both human TIKI1 and human TIKI2.

3. The antigen-binding fragment of claim 1, wherein the fragment comprises an F(ab), F(ab')$_2$, or scFv fragment.

4. The antibody or antigen-binding fragment of claim 1 that inhibits cleavage of one or more of Wnt2B, 3, 3A, 4, 5A, 5B, 6, 7A, 7B, 8A, 8B, or 16.

5. The antibody or antigen-binding fragment of claim 1, wherein the antibody or antigen-binding fragment is murine, chimeric, human or humanized.

6. A method of generating an inhibitory antibody that binds to TIKI, comprising
   immunizing an animal with a peptide antigen comprising 10 amino acids of SEQ ID NO:2 including at least one amino acid selected from H58, E85, E205, or H331 of SEQ ID NO:2;
   obtaining the inhibitory antibody from the animal; and
   determining that the inhibitory antibody inhibits TIKI-mediated cleavage of a Wnt protein.

7. An antibody or antigen-binding fragment thereof that binds specifically to human TIKI1, TIKI2, or both TIKI1 and TIKI2, and inhibits TIKI-mediated cleavage of a Wnt, made by the method of claim 6.

8. An antibody or antigen-binding fragment thereof that binds specifically to human TIKI1, TIKI2, or both TIKI1 and TIKI2, and inhibits TIKI-mediated cleavage of a Wnt, wherein the antibody binds to an epitope comprising at least one amino acid corresponding to H58, E85, E205 and H331 of SEQ ID NO:2.

9. A method of treating a subject having or at risk of developing a disorder associated with a loss of bone density, the method comprising administering to the subject an antibody or antigen-binding fragment thereof that binds to a TIKI protein and inhibits TIKI-mediated cleavage of a Wnt protein.

10. The method of claim 9, wherein the Wnt protein is Wnt3a and comprises at least one sequence selected from the group consisting of SYPIWWSL (SEQ ID NO:46), SYPIWWSLAVGPQYS (SEQ ID NO:47) and SYPIWWS-LAVGPQYSS (SEQ ID NO:48).

11. The method of claim 9, wherein the Wnt protein is Wnt8 and comprises at least one sequence selected from the group consisting of AWSVNNFLMTGPKAYLT (SEQ ID NO:49) and AWSVNNFLMTGPKAYLTYSA (SEQ ID NO:50).

12. A method of decreasing bone loss or resorption, or increasing bone growth and/or density, in a patient in need thereof, the method comprising administering a therapeutically effective amount of a TIKI inhibitor wherein the TIKI inhibitor is an antibody or antigen binding fragment thereof that specifically binds TIKI and inhibits TIKI-mediated cleavage of a Wnt protein and thereby inhibits or prevents inactivation of the Wnt protein, thereby increasing Wnt signaling and thereby decreasing bone loss or resorption.

\* \* \* \* \*

UNITED STATES PATENT AND TRADEMARK OFFICE
CERTIFICATE OF CORRECTION

PATENT NO. : 9,534,059 B2
APPLICATION NO. : 14/391971
DATED : January 3, 2017
INVENTOR(S) : Xi He, Xinjun Zhang and Bryan MacDonald Page 1 of 1

It is certified that error appears in the above-identified patent and that said Letters Patent is hereby corrected as shown below:

In the Specification

Column 1, Line 17, please delete "RO1 GM057603; RO1 GM05760351, and R01 AR60359-01" and insert -- GM057603 and AR060359 --.

Signed and Sealed this
Fifth Day of May, 2020

Andrei Iancu
*Director of the United States Patent and Trademark Office*

SEQUENCE LISTING

```
<160> NUMBER OF SEQ ID NOS: 94

<210> SEQ ID NO 1
<211> LENGTH: 505
<212> TYPE: PRT
<213> ORGANISM: Homo sapiens

<400> SEQUENCE: 1

Met Ser Pro Trp Ser Trp Phe Leu Leu Gln Thr Leu Cys Leu Leu Pro
1               5                   10                  15

Thr Gly Ala Ala Ser Arg Arg Gly Ala Pro Gly Thr Ala Asn Cys Glu
            20                  25                  30

Leu Lys Pro Gln Gln Ser Glu Leu Asn Ser Phe Leu Trp Thr Ile Lys
        35                  40                  45

Arg Asp Pro Pro Ser Tyr Phe Phe Gly Thr Ile His Val Pro Tyr Thr
    50                  55                  60

Arg Val Trp Asp Phe Ile Pro Asp Asn Ser Lys Glu Ala Phe Leu Gln
65                  70                  75                  80
```

```
Ser Ser Ile Val Tyr Phe Glu Leu Asp Leu Thr Asp Pro Tyr Thr Ile
                85                  90                  95

Ser Ala Leu Thr Ser Cys Gln Met Leu Pro Gln Gly Glu Asn Leu Gln
                100                 105                 110

Asp Val Leu Pro Arg Asp Ile Tyr Cys Arg Leu Lys Arg His Leu Glu
                115                 120                 125

Tyr Val Lys Leu Met Met Pro Leu Trp Met Thr Pro Asp Gln Arg Gly
        130                 135                 140

Lys Gly Leu Tyr Ala Asp Tyr Leu Phe Asn Ala Ile Ala Gly Asn Trp
145                 150                 155                 160

Glu Arg Lys Arg Pro Val Trp Val Met Leu Met Val Asn Ser Leu Thr
                165                 170                 175

Glu Val Asp Ile Lys Ser Arg Gly Val Pro Val Leu Asp Leu Phe Leu
                180                 185                 190

Ala Gln Glu Ala Glu Arg Leu Arg Lys Gln Thr Gly Ala Val Glu Lys
            195                 200                 205

Val Glu Glu Gln Cys His Pro Leu Asn Gly Leu Asn Phe Ser Gln Val
        210                 215                 220

Ile Phe Ala Leu Asn Gln Thr Leu Leu Gln Gln Glu Ser Leu Arg Ala
225                 230                 235                 240

Gly Ser Leu Gln Ile Pro Tyr Thr Thr Glu Asp Leu Ile Lys His Tyr
                245                 250                 255

Asn Cys Gly Asp Leu Ser Ser Val Ile Leu Ser His Asp Ser Ser Gln
                260                 265                 270

Val Pro Asn Phe Ile Asn Ala Thr Leu Pro Pro Gln Glu Arg Ile Thr
            275                 280                 285

Ala Gln Glu Ile Asp Ser Tyr Leu Arg Arg Glu Leu Ile Tyr Lys Arg
        290                 295                 300

Asn Glu Arg Ile Gly Lys Arg Val Lys Ala Leu Leu Glu Glu Phe Pro
305                 310                 315                 320

Asp Lys Gly Phe Phe Phe Ala Phe Gly Ala Gly His Phe Met Gly Asn
                325                 330                 335

Asn Thr Val Leu Asp Val Leu Arg Arg Glu Gly Tyr Glu Val Glu His
            340                 345                 350

Ala Pro Ala Gly Arg Pro Ile His Lys Gly Lys Ser Lys Lys Thr Ser
        355                 360                 365

Thr Arg Pro Thr Leu Ser Thr Ile Phe Ala Pro Lys Val Pro Thr Leu
    370                 375                 380

Glu Val Pro Ala Pro Glu Ala Val Ser Ser Gly His Ser Thr Leu Pro
385                 390                 395                 400

Pro Leu Val Ser Arg Pro Gly Ser Ala Asp Thr Pro Ser Glu Ala Glu
                405                 410                 415

Gln Arg Phe Arg Lys Lys Arg Arg Ser Gln Arg Arg Pro Arg Leu
            420                 425                 430

Arg Gln Phe Ser Asp Leu Trp Val Arg Leu Glu Glu Ser Asp Ile Val
        435                 440                 445

Pro Gln Leu Gln Val Pro Val Leu Asp Arg His Ile Ser Thr Glu Leu
    450                 455                 460

Arg Leu Pro Arg Arg Gly His Ser His Ser Gln Met Val Ala Ser
465                 470                 475                 480

Ser Ala Cys Leu Ser Leu Trp Thr Pro Val Phe Trp Val Leu Val Leu
                485                 490                 495
```

```
Ala Phe Gln Thr Glu Thr Pro Leu Leu
                500             505

<210> SEQ ID NO 2
<211> LENGTH: 517
<212> TYPE: PRT
<213> ORGANISM: Homo sapiens

<400> SEQUENCE: 2

Met His Ala Ala Leu Ala Gly Pro Leu Ala Leu Leu Ala Thr
1               5                   10                  15

Ala Arg Ala Arg Pro Gln Pro Asp Gly Gln Cys Arg Pro Pro
            20                  25                  30

Gly Ser Gln Arg Asp Leu Asn Ser Phe Leu Trp Thr Ile Arg Arg Asp
            35                  40                      45

Pro Pro Ala Tyr Leu Phe Gly Thr Ile His Val Pro Tyr Thr Arg Val
    50                      55                      60

Trp Asp Phe Ile Pro Asp Asn Ser Lys Ala Ala Phe Gln Ala Ser Thr
65                      70                  75                  80

Arg Val Tyr Phe Glu Leu Asp Leu Thr Asp Pro Tyr Thr Ile Ser Ala
                85                  90                      95

Leu Ala Ser Cys Gln Leu Leu Pro His Gly Glu Asn Leu Gln Asp Val
                100                 105                 110

Leu Pro His Glu Leu Tyr Trp Arg Leu Lys Arg His Leu Asp Tyr Val
            115                 120                 125

Lys Leu Met Met Pro Ser Trp Met Thr Pro Ala Gln Arg Gly Lys Gly
130                 135                 140

Leu Tyr Ala Asp Tyr Leu Phe Asn Ala Ile Ala Gly Asn Trp Glu Arg
145                 150                 155                 160

Lys Arg Pro Val Trp Val Met Leu Met Val Asn Ser Leu Thr Glu Arg
                165                 170                 175

Asp Val Arg Phe Arg Gly Val Pro Val Leu Asp Leu Tyr Leu Ala Gln
            180                 185                 190

Gln Ala Glu Lys Met Lys Lys Thr Thr Gly Ala Val Glu Gln Val Glu
            195                 200                 205

Glu Gln Cys His Pro Leu Asn Asn Gly Leu Asn Phe Ser Gln Val Leu
        210                 215                 220

Phe Ala Leu Asn Gln Thr Leu Leu Gln Gln Glu Ser Val Arg Ala Gly
225                 230                 235                 240

Ser Leu Gln Ala Ser Tyr Thr Thr Glu Asp Leu Ile Lys His Tyr Asn
                245                 250                 255

Cys Gly Asp Leu Ser Ala Val Ile Phe Asn His Asp Thr Ser Gln Leu
            260                 265                 270

Pro Asn Phe Ile Asn Thr Thr Leu Pro Pro His Glu Gln Val Thr Ala
        275                 280                 285

Gln Glu Ile Asp Ser Tyr Phe Arg Gln Glu Leu Ile Tyr Lys Arg Asn
    290                 295                 300

Glu Arg Met Gly Lys Arg Val Met Ala Leu Leu Arg Glu Asn Glu Asp
305                 310                 315                 320

Lys Ile Cys Phe Phe Ala Phe Gly Ala Gly His Phe Leu Gly Asn Asn
                325                 330                 335

Thr Val Ile Asp Ile Leu Arg Gln Ala Gly Leu Glu Val Asp His Thr
            340                 345                 350

Pro Ala Gly Gln Ala Ile His Ser Pro Ala Pro Gln Ser Pro Ala Pro
        355                 360                 365
```

```
Ser Pro Glu Gly Thr Ser Thr Ser Pro Ala Pro Val Thr Pro Ala Ala
    370                 375                 380

Ala Val Pro Glu Ala Pro Ser Val Thr Pro Thr Ala Pro Pro Glu Asp
385                 390                 395                 400

Glu Asp Pro Ala Leu Ser Pro His Leu Leu Pro Asp Ser Leu Ser
                405                 410                 415

Gln Leu Glu Glu Phe Gly Arg Gln Arg Lys Trp His Lys Arg Gln Ser
                420                 425                 430

Thr His Gln Arg Pro Arg Gln Phe Asn Asp Leu Trp Val Arg Ile Glu
            435                 440                 445

Asp Ser Thr Thr Ala Ser Pro Pro Leu Pro Leu Gln Pro Thr His
    450                 455                 460

Ser Ser Gly Thr Ala Lys Pro Pro Phe Gln Leu Ser Asp Gln Leu Gln
465                 470                 475                 480

Gln Gln Asp Pro Pro Gly Pro Ala Ser Ser Ala Pro Thr Leu Gly
                485                 490                 495

Leu Leu Pro Ala Ile Ala Thr Thr Ile Ala Val Cys Phe Leu Leu His
                500                 505                 510

Ser Leu Gly Pro Ser
            515

<210> SEQ ID NO 3
<211> LENGTH: 508
<212> TYPE: PRT
<213> ORGANISM: Xenopus tropicalis

<400> SEQUENCE: 3

Met Val Ile Ile Trp Asn Ile Phe Leu Pro Ala Phe Leu Leu Val Leu
1               5                   10                  15

Ala Lys Ala Ser Leu Arg Ser Ser Arg Asp Ser Ala Asn Cys Lys Leu
                20                  25                  30

Asn Lys Lys Gln Ser Gln Leu Asn Ser Phe Leu Trp Thr Ile Lys Arg
            35                  40                  45

Asp Pro Pro Ser Tyr Phe Phe Gly Thr Ile His Val Pro Tyr Thr Arg
    50                  55                  60

Val Trp Asp Phe Ile Pro Glu Asn Ser Lys Thr Ala Phe Gln Gln Ser
65                  70                  75                  80

Asn Ile Val Tyr Phe Glu Leu Asp Leu Thr Asp Pro Tyr Thr Ile Ser
                85                  90                  95

Ala Leu Thr Ser Cys Gln Met Leu Pro Gln Gly Glu Asn Leu Gln Asn
                100                 105                 110

Val Leu Pro Arg Asp Ile Tyr Arg Arg Leu Lys Arg His Leu Glu Tyr
            115                 120                 125

Val Lys Leu Met Met Pro Ser Trp Met Thr Pro Asp Gln Arg Gly Lys
130                 135                 140

Gly Leu Tyr Ala Asp Tyr Leu Phe Asn Ala Ile Ala Gly Asn Trp Glu
145                 150                 155                 160

Arg Lys Arg Pro Val Trp Val Met Leu Met Val Asn Ser Leu Thr Glu
                165                 170                 175

Val Asp Ile Lys Ser Arg Gly Val Pro Val Leu Asp Leu Tyr Leu Ala
            180                 185                 190

Gln Glu Ala Glu Arg Leu Lys Lys Arg Thr Gly Ala Val Glu Gln Val
        195                 200                 205

Glu Glu Gln Cys His Pro Leu Asn Gly Leu Asn Leu Ser Gln Val Ile
```

```
                210                 215                 220
Phe Ala Leu Asn Gln Thr Leu Gln Gln Glu Asn Leu Arg Ala Gly
225                 230                 235                 240

Ser Val Gln Val Pro Tyr Ser Thr Glu Asp Leu Ile Lys His Tyr
                245                 250                 255

Cys Gly Asp Leu Asn Ser Ile Ile Phe Asn His Asp Ser Ser Gln Val
                260                 265                 270

Pro Asn Phe Ile Asn Ser Thr Leu Pro Pro Gln Glu Arg Ile Thr Ala
            275                 280                 285

Gln Glu Ile Asp Asn Tyr Phe Arg Gln Glu Leu Ile Tyr Lys Arg Asn
290                 295                 300

Glu Arg Met Gly Lys Arg Val Lys Asp Leu Leu Glu Gln Phe Pro Glu
305                 310                 315                 320

Lys Ser Phe Phe Phe Ala Phe Gly Ala Gly His Phe Leu Gly Asn Asn
                325                 330                 335

Thr Val Ile Asp Val Leu Lys Arg Tyr Gly Tyr Asp Val Leu His Thr
                340                 345                 350

Pro Ala Gly Arg Ser Ile Ile Asn Asn Gly Lys Gly Lys Lys Asn Leu
            355                 360                 365

Leu Pro Ser Lys Phe Ser Ser Ser Leu Pro Val Gly Leu Ser Ala
370                 375                 380

Pro Pro Cys Thr Val Thr Ser Arg Ile Lys Gln Ser Ile Asn Ser His
385                 390                 395                 400

Lys Asp Gln Glu Ser Leu Pro Asp Ile Leu Asp Asp Ile Asp
                405                 410                 415

Gln Leu Asp Lys Asp Glu Arg Lys Tyr Lys Arg Lys Gln Arg Lys
                420                 425                 430

Glu Lys His Arg His Phe Ser Asp Leu Trp Val Arg Ile Gln Glu Ser
            435                 440                 445

Ser Thr Asp Thr Thr Pro Gln Ile Arg Ile Ile Asn Gly Tyr Ile Thr
            450                 455                 460

Val Glu Pro His Pro Arg Glu His Gly Lys Asp Lys Tyr Ile Lys Ala
465                 470                 475                 480

Ala Gln Ser Val Ser Phe Ser Leu Ser Ile Pro Ser Ala Phe Leu Leu
                485                 490                 495

Leu Ala Trp Cys Phe Gln Gln Val Ala Val Leu Gln
            500                 505

<210> SEQ ID NO 4
<211> LENGTH: 494
<212> TYPE: PRT
<213> ORGANISM: Danio rerio

<400> SEQUENCE: 4

Met Thr Met Met Thr Met Met Met Val Ser Trp Ser Ala Phe Leu Gln
1               5                   10                  15

Ile Cys Trp Ile Leu Met Val Arg Ala Asn Gln Phe Asn Pro Gly Glu
                20                  25                  30

Pro Ser Gly Cys Arg Thr Asn Thr Pro Gln Ser Asp Leu Asn Ser Phe
            35                  40                  45

Leu Trp Thr Ile Lys Arg Asp Pro Ser Tyr Leu Tyr Gly Thr Ile
    50                  55                  60

His Val Pro Tyr Thr Arg Val Trp Asp Phe Ile Pro Gln Asn Ser Lys
65                  70                  75                  80
```

```
Gln Ala Phe Gln Glu Ser Ser Val Val Tyr Phe Glu Leu Glu Leu Thr
                85                  90                  95
Asp Pro Ser Thr Ile Ser Ala Leu Ser Arg Cys Gln Leu Leu Pro Ala
            100                 105                 110
Gly Gln Asn Leu Gln Asp Val Leu Pro Pro Glu Leu Tyr Leu Arg Leu
        115                 120                 125
Lys Thr His Leu Glu Tyr Val Arg Leu Met Leu Pro Ser Trp Met Thr
    130                 135                 140
Pro Asp Gln Arg Gly Lys Gly Leu Tyr Ala Glu Tyr Leu Phe Asn Ala
145                 150                 155                 160
Ile Ala Gly Asn Trp Glu Arg Lys Arg Pro Val Trp Val Met Leu Met
                165                 170                 175
Val Asn Ser Leu Thr Glu Ala Asp Ile Lys Thr Arg Gly Val Pro Val
            180                 185                 190
Leu Asp Leu Tyr Leu Ala Gln Glu Ala Glu Arg Met Lys Lys Gln Thr
        195                 200                 205
Gly Ala Val Glu Lys Val Glu Gln Cys Ser Pro Leu Asn Thr Leu
    210                 215                 220
Asp Phe Ser Gln Val Ile Phe Ala Leu Asn Gln Thr Leu Leu Gln Gln
225                 230                 235                 240
Glu Ser Val Arg Ala Gly Ser Leu Gln Val Pro Tyr Thr Thr Glu His
                245                 250                 255
Leu Ile Thr His Tyr Asn Cys Gly Asp Leu His Ser Ile Ile Ser His
            260                 265                 270
Asp Thr Ala Gln Val Pro Asn Phe Asn Asn Val Thr Leu Arg Pro Ser
        275                 280                 285
Asp Gln Val Thr Ala Gln Gln Ile Asp Ser Tyr Phe Arg Arg Glu Leu
    290                 295                 300
Ile Tyr Lys Arg Asn Glu Arg Met Gly Arg Arg Val Thr Ala Leu Leu
305                 310                 315                 320
Gln Glu Gln Pro His Lys Thr Phe Phe Phe Ala Phe Gly Ala Gly His
                325                 330                 335
Phe Leu Gly Asn Asn Ser Val Ile Asp Val Leu Arg Arg Glu Gly Tyr
            340                 345                 350
Glu Val Glu His Thr Pro Ala Gly Gln Pro Leu His Arg Arg Ser Gly
        355                 360                 365
Trp Arg Ser Ala Asp Pro Ala Asp Thr Asp Ala Ala Leu Gln Pro Phe
    370                 375                 380
Leu His His Ser Arg His His Glu Leu Gln Leu Leu Glu Gly Leu Glu
385                 390                 395                 400
Leu Leu Glu Lys Val Glu His Lys Leu Lys Lys His Arg Arg Asn
                405                 410                 415
Lys Leu Lys Lys Gln Arg Gln Phe Asn Asp Leu Trp Val Arg Met Glu
            420                 425                 430
Asp Ser Val Thr Ala Glu Ala Pro Pro Leu Ile His Ile Ile Asn
        435                 440                 445
Gly Tyr Ile Thr Val Gln Thr His Pro Gln Asp His Glu Arg Ala Asn
    450                 455                 460
His Asp Arg Thr Phe Ser Gly Ser Ser Trp Thr Gly Pro Ala Leu
465                 470                 475                 480
Ser Ala Leu Ala Val Cys Val Gln Met Leu Arg Leu Leu Leu
                485                 490
```

```
<210> SEQ ID NO 5
<211> LENGTH: 523
<212> TYPE: PRT
<213> ORGANISM: Xenopus tropicalis

<400> SEQUENCE: 5

Met Gly Lys Thr Met Trp Ala Arg Ala Val Phe Leu Cys Phe Ser Val
1               5                   10                  15

Gly Thr Leu Leu Trp Gln Glu Val Leu Thr Arg Arg Ile Pro Val Asp
            20                  25                  30

Thr Gly Gln Cys Gly Leu Pro Lys Ser Gln Glu Asp Leu Asn Ser Phe
        35                  40                  45

Leu Trp Thr Val Arg Arg His Pro Pro Ala Tyr Leu Phe Gly Thr Ile
    50                  55                  60

His Val Pro Tyr Thr Arg Val Trp Asp Phe Ile Pro Gln Asn Ser Lys
65                  70                  75                  80

Lys Ala Phe His Asp Ser Asn Ser Val Tyr Phe Glu Leu Asp Leu Thr
                85                  90                  95

Asp Pro Tyr Thr Ile Ser Ala Leu Ala Asn Cys Gln Met Leu Pro Gln
            100                 105                 110

Gly Glu Asn Leu Gln Asp Val Leu Pro Arg Asp Leu Tyr Arg Arg Leu
        115                 120                 125

Lys Arg His Leu Glu Tyr Val Lys His Met Thr Pro His Trp Met Thr
130                 135                 140

Pro Asp Gln Arg Gly Lys Gly Leu Tyr Ala Asp Tyr Leu Phe Asn Ala
145                 150                 155                 160

Ile Ala Gly Asn Trp Glu Arg Lys Arg Pro Val Trp Val Met Leu Met
                165                 170                 175

Val Asn Ser Leu Thr Glu Ala Asp Ile Arg Ser Arg Gly Val Pro Val
            180                 185                 190

Leu Asp Leu Tyr Leu Ala Gln Glu Ala Asp Arg Met Lys Lys Lys Thr
        195                 200                 205

Gly Ala Val Glu Arg Val Glu Glu Gln Cys His Pro Leu Asn Arg Leu
    210                 215                 220

Asn Leu Ser Gln Val Leu Phe Ala Leu Asn Gln Thr Leu Leu Gln His
225                 230                 235                 240

Glu Ser Leu Arg Ala Gly Ser Phe Gln Ala Pro Tyr Thr Thr Glu Asp
                245                 250                 255

Leu Ile Lys His Tyr Asn Cys Gly Asp Leu Asn Ala Val Ile Phe Ser
            260                 265                 270

His Asp Ser Ser Gln Leu Pro Asn Phe Ile Asn Val Thr Leu Pro Pro
        275                 280                 285

His Glu Gln Val Thr Ala Gln Glu Ile Asp Ile Tyr Phe Arg Gln Glu
    290                 295                 300

Leu Ile Tyr Lys Arg Asn Glu Arg Met Ala Arg Arg Val Ile Ala Leu
305                 310                 315                 320

Leu Lys Glu Asn Lys Asp Lys Ser Phe Phe Ala Phe Gly Ala Gly
                325                 330                 335

His Phe Leu Gly Asn Asn Thr Val Ile Asp Val Leu Arg Gln Asn Gly
            340                 345                 350

Tyr Glu Val Glu His Thr Pro Ala Gly Gln Thr Phe Thr Ala Ala Lys
        355                 360                 365

Pro Lys Thr Asn Pro Thr Ser Asp Asp Ser Met Ala Thr Asp Ser Pro
    370                 375                 380
```

-continued

```
Ala Met Lys Tyr Phe Asp His Val Pro Ala Thr Ala Ser Tyr Phe Gly
385                 390                 395                 400

Glu Ser Asp Glu Glu Met Leu Pro Pro His Leu Leu Leu Pro Asp Ser
            405                 410                 415

Ile Ser Gln Leu Glu Glu Phe Gly Lys Gln Asn Ser Trp His Arg Lys
        420                 425                 430

His Tyr Arg Asn Gln Arg Pro Arg Gln Phe Asn Asp Leu Trp Val Arg
    435                 440                 445

Leu Asp Asp Ser Thr Thr Thr Leu Pro Ser Asn Thr Arg Asn Thr Asn
450                 455                 460

Gly Glu Gln Ser Ala Glu Ser Leu Val Trp Leu Pro Glu Gln Asp His
465                 470                 475                 480

His Asn Tyr Leu Asp Val Lys Leu Ser His Ser Gln Ser Asn Ser Ser
                485                 490                 495

Pro Lys Cys Leu Ser Ala Ser Pro Ala Phe Leu Tyr Thr Leu Val Thr
            500                 505                 510

Leu Cys Leu Ile Thr Thr Met Arg Thr Arg Ser
        515                 520

<210> SEQ ID NO 6
<211> LENGTH: 518
<212> TYPE: PRT
<213> ORGANISM: Danio rerio

<400> SEQUENCE: 6

Met Asn Cys Gln Ser Gly Leu Arg Trp Leu Val Thr Leu Cys Ala Phe
1               5                   10                  15

Phe Gln Val Gly Ser Ala Arg Asp Thr His Glu Ser Thr Arg Gln Cys
            20                  25                  30

Asp Lys Pro Val Ser Gln Lys Asp Met Asn Ser Phe Leu Trp Thr Val
        35                  40                  45

Lys Arg Pro Arg Pro Phe Pro Pro Ser Tyr Leu Phe Gly Thr Ile His
50                  55                  60

Val Pro Tyr Thr Arg Val Trp Asp Tyr Ile Pro Glu Ser Ser Lys Arg
65                  70                  75                  80

Ala Phe Gln Thr Ser Asn Ser Val Phe Glu Leu Asp Leu Thr Asp
            85                  90                  95

Pro Leu Thr Ile Ser Lys Leu Thr Ser Cys Gln Leu Leu Pro Asn Gly
        100                 105                 110

Glu Asn Leu Gln Thr Leu Leu Pro Arg Asp Leu Tyr Arg Arg Leu Lys
    115                 120                 125

Arg His Leu Asp Tyr Val Lys His Met Met Pro Phe Trp Met Thr Ala
130                 135                 140

Asp Gln Arg Gly Arg Gly Leu Tyr Ala Asp Tyr Leu Phe Asn Ala Ile
145                 150                 155                 160

Ala Gly Asn Trp Glu Arg Lys Arg Pro Val Trp Val Met Leu Met Val
                165                 170                 175

Asn Ser Leu Thr Glu Ala Asp Val Arg Ser Arg Gly Thr Pro Val Leu
            180                 185                 190

Asp Leu Phe Leu Ala Gln Glu Ala Glu Arg Leu Gly Lys Gln Thr Gly
        195                 200                 205

Ala Val Glu Arg Val Glu Glu Gln Cys His Pro Leu Asn Gly Leu Asn
    210                 215                 220

Phe Ser Gln Val Leu Phe Ala Leu Asn Gln Thr Leu Leu Gln His Glu
225                 230                 235                 240
```

```
Ser Leu Arg Ala Gly Ile Leu Gln Gly Thr Phe Thr Thr Glu Asp Leu
            245                 250                 255

Ile Ala His Tyr Asn Cys Gly Asp Leu Asn Ser Ile Ile Phe Asn His
            260                 265                 270

Asp Thr Ser Gln Leu Pro His Phe Ile Asn Ser Ser Leu Pro Asp His
            275                 280                 285

Glu Arg Leu Thr Ala Gln Gln Ile Asp Ser Tyr Leu Arg Gln Glu Leu
            290                 295                 300

Ile Tyr Lys Arg Asn Glu Arg Met Ala Arg Arg Val Ser Ala Leu Leu
305                 310                 315                 320

Gln Arg Asn Pro Asn Gln Ser Phe Phe Phe Ala Phe Gly Ala Gly His
            325                 330                 335

Phe Leu Gly Asn His Ser Val Leu Asp Ile Leu Arg Gln Glu Gly Tyr
            340                 345                 350

Glu Val Glu His Thr Pro Pro Gln Glu Pro Ile Ile Gln Ser Trp Ser
            355                 360                 365

Glu Arg Glu Ala Thr Thr Leu Asn Pro Thr Glu Asp Ser Phe Glu Ser
            370                 375                 380

Val Thr Glu Trp Thr Ser Glu Thr Pro Glu Leu Glu Glu Ile Ser Gln
385                 390                 395                 400

Glu Glu Leu Ser His Met Leu Leu Pro Asp Ser Leu Ser Gln Leu Glu
            405                 410                 415

Glu Phe Gly Arg Tyr Lys His Pro Arg Lys Thr His His Thr His Ser
            420                 425                 430

Arg Pro Arg Leu Phe Ser Asp Leu Trp Val Arg Ile Gly Asp Ser Thr
            435                 440                 445

Thr Pro His Pro Ser Ile Arg Ile Thr Asn Gly Tyr Val Thr Val Glu
            450                 455                 460

Pro Pro Gln Ile Arg Gln Gln Gln Arg Leu Arg Glu Arg Leu
465                 470                 475                 480

Lys Pro Leu Ser Glu Pro Thr Asn Pro Ser Ala Leu Asp Ser Ala Ala
            485                 490                 495

Pro Asn Pro Thr Tyr Ala Leu Thr Cys Phe Leu Ala Cys Leu Ile Ser
            500                 505                 510

Gln Leu Leu Phe Ala Ser
        515

<210> SEQ ID NO 7
<211> LENGTH: 471
<212> TYPE: PRT
<213> ORGANISM: Nematostella vectensis

<400> SEQUENCE: 7

Met Ala Ala Phe Thr Leu Trp Ile Leu Val Leu Asn Val Phe Leu Leu
1               5                   10                  15

Gly Phe Gln Ala Arg Lys Leu Ala Ser Asn Leu Lys Phe Pro Ile Gln
            20                  25                  30

Lys Cys Asp Asp Ser Thr Pro Gln Lys Asn Phe Asn Ser Phe Leu Trp
        35                  40                  45

Leu Val Lys Arg Thr Pro Pro Ala Tyr Tyr Gly Thr Ile His Val
        50                  55                  60

Pro Tyr Thr Arg Val Trp Asp Phe Ile Pro Met Asn Ser Lys Gln Ala
65                  70                  75                  80

Phe Thr Ala Ser Gln His Val Tyr Phe Glu Leu Asp Leu Thr Asp Glu
```

```
                    85                  90                  95
Lys Thr Met Arg Ala Leu Met Lys Cys Gln Met Leu Pro Ser Gly Thr
                100                 105                 110

Met Leu Arg Gln Thr Leu Pro Arg Lys Met Phe Lys Arg Leu Lys Ser
                115                 120                 125

His Leu Arg Tyr Ile Lys Arg Met Ile Pro Lys Trp Ile Lys His Arg
                130                 135                 140

Asp Gln Glu Thr Ser Ser Ala Gly Pro Tyr Ala Asn Lys Leu Tyr Glu
145                 150                 155                 160

Met Leu Thr Lys Asp Trp Asp Lys Lys Arg Pro Ile Trp Val Met Leu
                165                 170                 175

Met Val Asn Ser Leu Thr Glu Ser Asp Ile Lys Thr Arg Gly Ile Pro
                180                 185                 190

Val Leu Asp Gln Tyr Leu Ala Leu Glu Ala Ser Arg Asn His Lys Leu
                195                 200                 205

Ile Gly Ala Val Glu Asn Val Asp Glu Gln Cys Lys Pro Leu Asn Ala
                210                 215                 220

Leu Asn Ala Ser Gln Val Val Phe Ala Leu Asn Gln Ser Leu His Phe
225                 230                 235                 240

Gln Glu Arg Leu Arg Arg Gly Gln Val Gln Val Thr Tyr Thr Thr Asp
                245                 250                 255

Asp Leu Ile Asp His Tyr Asn Cys Gly Asp Leu Lys Ser Val Leu Phe
                260                 265                 270

Ser Thr Gln Thr Ser Leu Pro Thr Leu Thr Val Asn Ser Ser Leu Glu
                275                 280                 285

Gln Arg Glu Arg Lys Arg Ala Gln Glu Ile Asp Gln Tyr Phe Arg Asn
                290                 295                 300

Glu Leu Ile Phe Gln Arg Asn Lys Arg Met Ala Gln Arg Val Ile Thr
305                 310                 315                 320

Leu Leu Asn Asn His Pro Glu Lys Asp Phe Phe Ala Phe Gly Ala
                325                 330                 335

Gly His Phe Leu Gly Asn His Ser Ile Ile Asp Ile Met Lys Lys His
                340                 345                 350

Gly Tyr Asp Val Glu Tyr Val Lys Pro Glu Gln Glu Leu Pro Ser Phe
                355                 360                 365

Lys Ala Lys Lys Ser Leu Asn Thr Arg Arg Glu Arg Arg Lys Gly Cys
                370                 375                 380

Arg Gly Arg Arg Lys Lys Ser Lys Arg Cys Gln Lys Lys Lys Arg
385                 390                 395                 400

Lys Arg Pro Asp Tyr Ser Arg Val Arg Leu Leu Gln Val Ala Thr Arg
                405                 410                 415

Arg Trp Asn Pro Thr Arg Lys Pro Tyr Pro Thr Lys Leu Ser Glu Ala
                420                 425                 430

Pro Gly Ala Arg Asp Ile Ser Ser Arg Lys Ala Ala Ala Ser Cys Thr
                435                 440                 445

Pro Ile Trp Thr Val Ser Leu Ala Leu Thr Cys Ala Val Thr Cys Leu
                450                 455                 460

Leu Thr Tyr Ser Gly Phe Arg
465                 470

<210> SEQ ID NO 8
<211> LENGTH: 420
<212> TYPE: PRT
<213> ORGANISM: Caenorhabditis elegans
```

<400> SEQUENCE: 8

| Met | Thr | Phe | Tyr | Ile | Leu | Val | Val | Ser | Leu | Tyr | Leu | Ser | Leu | Phe | Leu |
|---|---|---|---|---|---|---|---|---|---|---|---|---|---|---|---|
| 1 | | | | 5 | | | | | 10 | | | | | 15 | |

| Val | Thr | Val | Val | Gln | Ser | Asp | Cys | Asp | Thr | Asp | Val | Glu | Gln | Arg | Glu |
|---|---|---|---|---|---|---|---|---|---|---|---|---|---|---|---|
| | | | 20 | | | | | 25 | | | | | 30 | | |

| Arg | Asn | Ile | Phe | Leu | Trp | Ser | Val | Lys | His | Pro | Gln | Phe | Ala | Ser | Ser |
|---|---|---|---|---|---|---|---|---|---|---|---|---|---|---|---|
| | | 35 | | | | | 40 | | | | | 45 | | | |

| Gln | Gly | Tyr | Leu | Phe | Gly | Thr | Ile | His | Val | Pro | Phe | Thr | Glu | Val | Trp |
|---|---|---|---|---|---|---|---|---|---|---|---|---|---|---|---|
| | 50 | | | | | 55 | | | | | 60 | | | | |

| Lys | Glu | Val | Ser | Asp | Arg | Val | Arg | Asp | Ala | Phe | Ala | Val | Ser | Asp | Thr |
|---|---|---|---|---|---|---|---|---|---|---|---|---|---|---|---|
| 65 | | | | 70 | | | | | 75 | | | | | 80 | |

| Val | Leu | Leu | Glu | Ile | Asp | Leu | His | Asp | Glu | Ala | Thr | Ile | His | Glu | Leu |
|---|---|---|---|---|---|---|---|---|---|---|---|---|---|---|---|
| | | | | 85 | | | | | 90 | | | | | 95 | |

| Ile | Ala | Cys | Lys | Asn | Leu | Ala | Tyr | Asp | Glu | Thr | Val | His | Ser | Tyr | Leu |
|---|---|---|---|---|---|---|---|---|---|---|---|---|---|---|---|
| | | | 100 | | | | | 105 | | | | | 110 | | |

| Ser | Ile | Glu | Leu | Leu | Glu | Arg | Ile | Glu | Lys | Ile | Met | Glu | Tyr | Leu | Arg |
|---|---|---|---|---|---|---|---|---|---|---|---|---|---|---|---|
| | | | 115 | | | | | 120 | | | | | 125 | | |

| Ser | Ser | Phe | Leu | Ala | Trp | Ala | Gln | Lys | Gln | Asn | Pro | Arg | Asp | Thr | Lys |
|---|---|---|---|---|---|---|---|---|---|---|---|---|---|---|---|
| | 130 | | | | | 135 | | | | | 140 | | | | |

| Lys | Ile | Lys | His | Ala | Glu | Asp | Ile | Tyr | Asn | Asn | Ile | Ile | Gly | Asp | Trp |
|---|---|---|---|---|---|---|---|---|---|---|---|---|---|---|---|
| 145 | | | | 150 | | | | | 155 | | | | | 160 | |

| Trp | Arg | Lys | Arg | Pro | Ile | Trp | Leu | Leu | Phe | Leu | Leu | Tyr | Gln | Met | Cys |
|---|---|---|---|---|---|---|---|---|---|---|---|---|---|---|---|
| | | | | 165 | | | | | 170 | | | | | 175 | |

| Glu | Asn | Val | Phe | Glu | Lys | Ser | Ser | Pro | Leu | Leu | Asp | Leu | Tyr | Ile |
|---|---|---|---|---|---|---|---|---|---|---|---|---|---|---|
| | | | 180 | | | | | 185 | | | | | 190 | |

| Ala | Gln | Arg | Ala | Thr | Asp | Glu | Lys | Lys | Thr | Ile | Ile | Pro | Ile | Glu | Thr |
|---|---|---|---|---|---|---|---|---|---|---|---|---|---|---|---|
| | | 195 | | | | | 200 | | | | | 205 | | | |

| Ala | Glu | Glu | Gln | Cys | Asn | Pro | Val | Val | Ser | Val | Ser | Thr | Asn | Glu | Ile |
|---|---|---|---|---|---|---|---|---|---|---|---|---|---|---|---|
| | 210 | | | | | 215 | | | | | 220 | | | | |

| Ile | Phe | Ala | Ile | Glu | His | Thr | Val | His | Tyr | Phe | Glu | Asp | Lys | Ile | Leu |
|---|---|---|---|---|---|---|---|---|---|---|---|---|---|---|---|
| 225 | | | | 230 | | | | | 235 | | | | | 240 | |

| Asp | Asn | Pro | Ser | Lys | Asp | Asn | Glu | Ser | Arg | Ser | Ser | Leu | Lys | Glu | Leu |
|---|---|---|---|---|---|---|---|---|---|---|---|---|---|---|---|
| | | | | 245 | | | | | 250 | | | | | 255 | |

| Val | Glu | His | Tyr | Lys | Cys | Gly | Thr | Leu | Lys | Glu | Asp | Met | Phe | Asp | Lys |
|---|---|---|---|---|---|---|---|---|---|---|---|---|---|---|---|
| | | | 260 | | | | | 265 | | | | | 270 | | |

| Asp | Gly | Met | Ser | Ile | Ile | Asp | Tyr | Ala | Thr | Gly | Thr | Thr | Glu | Arg | Phe |
|---|---|---|---|---|---|---|---|---|---|---|---|---|---|---|---|
| | | 275 | | | | | 280 | | | | | 285 | | | |

| Lys | Ala | Asp | Glu | Ile | Asn | Lys | Lys | Leu | Lys | Gln | Asp | Ile | Phe | Val | Lys |
|---|---|---|---|---|---|---|---|---|---|---|---|---|---|---|---|
| | 290 | | | | | 295 | | | | | 300 | | | | |

| Arg | Asn | Leu | Arg | Met | Ala | Lys | Arg | Ile | Glu | Lys | Ile | Leu | Lys | Gly | Arg |
|---|---|---|---|---|---|---|---|---|---|---|---|---|---|---|---|
| 305 | | | | 310 | | | | | 315 | | | | | 320 | |

| Asn | Ser | Asn | Thr | Val | Phe | Ser | Ala | Ile | Gly | Ala | Gly | His | Phe | Phe | Gly |
|---|---|---|---|---|---|---|---|---|---|---|---|---|---|---|---|
| | | | | 325 | | | | | 330 | | | | | 335 | |

| Ser | Ser | Ser | Val | Leu | Thr | Tyr | Leu | Glu | Glu | Ser | Gly | Phe | Ile | Val | Gln |
|---|---|---|---|---|---|---|---|---|---|---|---|---|---|---|---|
| | | | 340 | | | | | 345 | | | | | 350 | | |

| Lys | Leu | Lys | Asn | Thr | Asp | Val | Ile | Gln | Pro | Leu | Arg | Ser | Pro | Tyr | Arg |
|---|---|---|---|---|---|---|---|---|---|---|---|---|---|---|---|
| | | | 355 | | | | | 360 | | | | | 365 | | |

| Gln | Thr | Ala | Lys | Phe | Lys | Arg | Val | Trp | Thr | Lys | Glu | Thr | Ala | Val | Arg |
|---|---|---|---|---|---|---|---|---|---|---|---|---|---|---|---|
| | 370 | | | | | 375 | | | | | 380 | | | | |

| Arg | Lys | Ser | Ile | Ile | Ile | Glu | Glu | Val | Ala | Pro | Ser | Ser | Ser | Arg | Ile |
|---|---|---|---|---|---|---|---|---|---|---|---|---|---|---|---|
| 385 | | | | 390 | | | | | 395 | | | | | 400 | |

| Ala | Arg | Leu | Trp | Leu | Val | Pro | Cys | Ile | Phe | Leu | Leu | His | Ser | Ile | Phe |
|---|---|---|---|---|---|---|---|---|---|---|---|---|---|---|---|

Ala Ile Phe Pro
        420

<210> SEQ ID NO 9
<211> LENGTH: 510
<212> TYPE: PRT
<213> ORGANISM: Amphimedon queenslandica

<400> SEQUENCE: 9

Met Gln Val Lys Ile Val Gln Val Phe Pro Cys Leu Val Leu Leu Val
1               5                   10                  15

Lys Leu Val Leu Leu Ser Val Leu Leu Pro Ser Ala Thr Gly Ser Tyr
            20                  25                  30

His Cys Ser Asn Asn Ala Thr Gln Asn Ser Tyr Leu Trp Arg Ile Glu
        35                  40                  45

Ala Ser Pro Pro Ile Tyr Leu Phe Gly Thr Met His Val Pro Tyr Lys
    50                  55                  60

Lys Leu Trp Asp Asp Val Pro Asp Asn Val Lys Ser Val Leu Ser Leu
65                  70                  75                  80

Ser Glu His Leu Cys Val Glu Leu Arg Leu Thr Asp Ser Glu Thr Ser
                85                  90                  95

Lys Asn Leu Ser Ala Cys Arg Tyr Leu Pro Lys Asn Glu Thr Leu Glu
            100                 105                 110

Ser Val Leu Pro Gly Gly Leu Tyr Val Arg Val Leu Lys Tyr Phe Val
        115                 120                 125

Arg Ile Gln Asn Gln Phe Pro Lys Trp Leu Phe Gly Asn Ala Ser Ile
    130                 135                 140

Asn Gly Leu Ser Arg Ile Glu Ser Asp Arg Leu Phe His Ala Met Ile
145                 150                 155                 160

Gly Asn Trp Asn Arg Leu Arg Pro Val Trp Leu Leu Met Leu Ile Ser
                165                 170                 175

Ser Leu Ser Arg Glu Asn Val Gln Glu Arg Ser Ile Pro Leu Leu Asp
            180                 185                 190

Val Phe Leu Asp Arg Ala Ala Glu Gly Met Gly Lys Asn Val Glu Ala
        195                 200                 205

Val Glu Val Tyr Lys Glu Gln Cys Arg Pro Phe Asn Arg Leu Asn Asn
    210                 215                 220

Thr Lys Val Phe Val Ala Leu Arg Lys Leu Leu Asp Tyr Leu Glu Pro
225                 230                 235                 240

Leu Ala Asp Gly Pro Ile Ser Ser Thr Asp Ser Asp Leu Glu Thr Tyr
                245                 250                 255

Asn Cys Gly Asp Phe Lys Ser Leu Val Ser Ala Arg Pro Ile Leu Pro
            260                 265                 270

Leu Pro Ser Ser Ser Lys Leu Pro Asn Leu Thr Ser Glu Glu Ala Gly
        275                 280                 285

Asp Leu Glu Ser Ile Asn Glu Phe Leu Val Ser Gln Ile Val Tyr Arg
    290                 295                 300

Arg Asn Arg Arg Met Ser Lys Thr Ile Met Ser Leu Leu Ser Arg Gln
305                 310                 315                 320

Arg Asn Glu Thr Tyr Leu Phe Ala Ile Gly Ala Gly His Phe Val Gly
                325                 330                 335

Glu Arg Asn Val Val His Met Leu Lys Lys Lys Gly Tyr Ser Val Asn
            340                 345                 350

```
Arg Leu Ser Val Thr Glu Thr Ile Pro Gly Pro Leu Pro Lys Asn
            355                 360                 365
Ile Ile Ser Leu Gly Asp Pro Ser Ser Gln Leu Thr Ile Leu Asn Ile
    370                 375                 380
Ser Ser Thr Ile Pro Thr Leu Pro Pro Asn Arg Pro Ser His Val Pro
385                 390                 395                 400
Pro Thr Leu Ser Pro Glu Thr Ile Ala Arg Ile Ile Gln Ser Val Phe
                405                 410                 415
Asn Asn Thr Gln Ser Ile Tyr Thr Val Asp Ser Val Glu Val Thr Pro
            420                 425                 430
Thr Thr Thr Ser Leu Asn Ser Ala Thr Ala Ser Thr Val Ala Thr
        435                 440                 445
Pro Thr Ser Ser Val Thr Pro Pro Thr Ser Ser Ser Gln Thr Arg
    450                 455                 460
Ser Leu Thr Ile Ser Asp Ser Gln Arg Thr Ser Asp Asp Ser Ala Phe
465                 470                 475                 480
Ile Pro Ser Ala Ser Ser Gly Leu Arg Tyr Asn Ile Gly Leu Val Cys
                485                 490                 495
Val Thr Leu Phe Phe Val Leu Leu Ile Ile Thr Ser Ala Leu
                500                 505                 510
```

<210> SEQ ID NO 10
<211> LENGTH: 35
<212> TYPE: PRT
<213> ORGANISM: Homo sapiens

<400> SEQUENCE: 10

```
Ser Tyr Pro Ile Trp Trp Ser Leu Ala Val Gly Pro Gln Tyr Ser Ser
1               5                   10                  15
Leu Ser Thr Gln Pro Ile Leu Cys Ala Ser Ile Pro Gly Leu Val Pro
                20                  25                  30
Lys Gln Leu
        35
```

<210> SEQ ID NO 11
<211> LENGTH: 27
<212> TYPE: PRT
<213> ORGANISM: Homo sapiens

<400> SEQUENCE: 11

```
Ala Val Gly Pro Gln Tyr Ser Ser Leu Ser Thr Gln Pro Ile Leu Cys
1               5                   10                  15
Ala Ser Ile Pro Gly Leu Val Pro Lys Gln Leu
                20                  25
```

<210> SEQ ID NO 12
<211> LENGTH: 34
<212> TYPE: PRT
<213> ORGANISM: Homo sapiens

<400> SEQUENCE: 12

```
Ala Trp Ser Val Asn Asn Phe Leu Met Thr Gly Pro Lys Ala Tyr Leu
1               5                   10                  15
Thr Tyr Ser Ala Ser Val Ala Val Gly Ala Gln Asn Gly Ile Glu Glu
                20                  25                  30
Cys Lys
```

<210> SEQ ID NO 13

```
<211> LENGTH: 385
<212> TYPE: PRT
<213> ORGANISM: Homo sapiens

<400> SEQUENCE: 13

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

Asn Pro Gly Ser Arg Ala Gly Asn Ser Ala His Gln Pro Pro His Pro
        355                 360                 365

Gln Pro Pro Val Arg Phe His Pro Pro Leu Arg Arg Ala Gly Lys Val
370                 375                 380

Pro
```

<210> SEQ ID NO 14
<211> LENGTH: 352
<212> TYPE: PRT
<213> ORGANISM: Homo sapiens

<400> SEQUENCE: 14

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 15
<211> LENGTH: 381

<212> TYPE: PRT
<213> ORGANISM: Homo sapiens

<400> SEQUENCE: 15

```
Pro Leu Gln Lys Ser Ile Gly Ile Leu Ser Pro Val Ala Leu Gly
1               5                   10                  15

Met Ala Gly Ser Ala Met Ser Ser Lys Phe Phe Leu Val Ala Leu Ala
            20                  25                  30

Ile Phe Phe Ser Phe Ala Gln Val Val Ile Glu Ala Asn Ser Trp Trp
        35                  40                  45

Ser Leu Gly Met Asn Asn Pro Val Gln Met Ser Glu Val Tyr Ile Ile
    50                  55                  60

Gly Ala Gln Pro Leu Cys Ser Gln Leu Ala Gly Leu Ser Gln Gly Gln
65                  70                  75                  80

Lys Lys Leu Cys His Leu Tyr Gln Asp His Met Gln Tyr Ile Gly Glu
                85                  90                  95

Gly Ala Lys Thr Gly Ile Lys Glu Cys Gln Tyr Gln Phe Arg His Arg
            100                 105                 110

Arg Trp Asn Cys Ser Thr Val Asp Asn Thr Ser Val Phe Gly Arg Val
        115                 120                 125

Met Gln Ile Gly Ser Arg Glu Thr Ala Phe Thr Tyr Ala Val Ser Ala
    130                 135                 140

Ala Gly Val Val Asn Ala Met Ser Arg Ala Cys Arg Glu Gly Glu Leu
145                 150                 155                 160

Ser Thr Cys Gly Cys Ser Arg Ala Ala Arg Pro Lys Asp Leu Pro Arg
                165                 170                 175

Asp Trp Leu Trp Gly Gly Cys Gly Asp Asn Ile Asp Tyr Gly Tyr Arg
            180                 185                 190

Phe Ala Lys Glu Phe Val Asp Ala Arg Glu Arg Glu Arg Ile His Ala
        195                 200                 205

Lys Gly Ser Tyr Glu Ser Ala Arg Ile Leu Met Asn Leu His Asn Asn
    210                 215                 220

Glu Ala Gly Arg Arg Thr Val Tyr Asn Leu Ala Asp Val Ala Cys Lys
225                 230                 235                 240

Cys His Gly Val Ser Gly Ser Cys Ser Leu Lys Thr Cys Trp Leu Gln
                245                 250                 255

Leu Ala Asp Phe Arg Lys Val Gly Asp Ala Leu Lys Glu Lys Tyr Asp
            260                 265                 270

Ser Ala Ala Ala Met Arg Leu Asn Ser Arg Gly Lys Leu Val Gln Val
        275                 280                 285

Asn Ser Arg Phe Asn Ser Pro Thr Thr Gln Asp Leu Val Tyr Ile Asp
    290                 295                 300

Pro Ser Pro Asp Tyr Cys Val Arg Asn Glu Ser Thr Gly Ser Leu Gly
305                 310                 315                 320

Thr Gln Gly Arg Leu Cys Asn Lys Thr Ser Glu Gly Met Asp Gly Cys
                325                 330                 335

Glu Leu Met Cys Cys Gly Arg Gly Tyr Asp Gln Phe Lys Thr Val Gln
            340                 345                 350

Thr Glu Arg Cys His Cys Lys Phe His Trp Cys Cys Tyr Val Lys Cys
        355                 360                 365

Lys Lys Cys Thr Glu Ile Val Asp Gln Phe Val Cys Lys
    370                 375                 380
```

<210> SEQ ID NO 16

```
<211> LENGTH: 358
<212> TYPE: PRT
<213> ORGANISM: Homo sapiens

<400> SEQUENCE: 16

Met Gln Asn Thr Thr Leu Phe Ile Leu Ala Thr Leu Ile Phe Cys
1               5                   10                  15

Pro Phe Phe Thr Ala Ser Ala Trp Ser Val Asn Asn Phe Leu Met Thr
            20                  25                  30

Gly Pro Lys Ala Tyr Leu Thr Tyr Ser Ala Ser Val Ala Val Gly Ala
            35                  40                  45

Gln Asn Gly Ile Glu Glu Cys Lys Tyr Gln Phe Ala Trp Glu Arg Trp
50                  55                  60

Asn Cys Pro Glu Ser Thr Leu Gln Leu Ala Thr His Asn Gly Leu Arg
65                  70                  75                  80

Ser Ala Thr Arg Glu Thr Ser Phe Val His Ala Ile Ser Ser Ala Gly
                85                  90                  95

Val Met Tyr Thr Leu Thr Arg Asn Cys Ser Met Gly Asp Phe Asp Asn
            100                 105                 110

Cys Gly Cys Asp Asp Ser Arg Asn Gly Arg Ile Gly Gly Arg Gly Trp
            115                 120                 125

Val Trp Gly Gly Cys Ser Asp Asn Ala Glu Phe Gly Glu Arg Ile Ser
130                 135                 140

Lys Leu Phe Val Asp Gly Leu Glu Thr Gly Gln Asp Ala Arg Ala Leu
145                 150                 155                 160

Met Asn Leu His Asn Asn Glu Ala Gly Arg Leu Ala Val Lys Glu Thr
                165                 170                 175

Met Lys Arg Thr Cys Lys Cys His Gly Ile Ser Gly Ser Cys Ser Ile
            180                 185                 190

Gln Thr Cys Trp Leu Gln Leu Ala Glu Phe Arg Asp Ile Gly Asn His
            195                 200                 205

Leu Lys Ile Lys His Asp Gln Ala Leu Lys Leu Glu Met Asp Lys Arg
210                 215                 220

Lys Met Arg Ser Gly Asn Ser Ala Asp Asn Arg Gly Ala Ile Ala Asp
225                 230                 235                 240

Ala Phe Ser Ser Val Ala Gly Ser Glu Leu Ile Phe Leu Glu Asp Ser
                245                 250                 255

Pro Asp Tyr Cys Leu Lys Asn Ile Ser Leu Gly Leu Gln Gly Thr Glu
            260                 265                 270

Gly Arg Glu Cys Leu Gln Ser Gly Lys Asn Leu Ser Gln Trp Glu Arg
            275                 280                 285

Arg Ser Cys Lys Arg Leu Cys Thr Asp Cys Gly Leu Arg Val Glu Glu
290                 295                 300

Lys Lys Thr Glu Ile Ile Ser Ser Cys Asn Cys Lys Phe His Trp Cys
305                 310                 315                 320

Cys Thr Val Lys Cys Glu Gln Cys Lys Gln Val Val Ile Lys His Phe
                325                 330                 335

Cys Ala Arg Arg Glu Arg Asp Ser Asn Met Leu Asn Thr Lys Arg Lys
            340                 345                 350

Asn Arg Gly His Arg Arg
            355

<210> SEQ ID NO 17
<211> LENGTH: 361
<212> TYPE: PRT
```

<213> ORGANISM: Homo sapiens

<400> SEQUENCE: 17

```
Met Ala Pro Leu Gly Tyr Leu Val Leu Cys Ser Leu Lys Gln Ala
1               5                   10                  15

Leu Gly Tyr Pro Tyr Asp Val Pro Asp Tyr Ala Ser Tyr Pro Ile Trp
            20                  25                  30

Trp Ser Leu Ala Val Gly Pro Gln Tyr Ser Ser Leu Ser Thr Gln Pro
        35                  40                  45

Ile Leu Cys Ala Ser Ile Pro Gly Leu Val Pro Lys Gln Leu Arg Phe
50                  55                  60

Cys Arg Asn Tyr Val Glu Ile Met Pro Ser Val Ala Glu Gly Val Lys
65                  70                  75                  80

Ala Gly Ile Gln Glu Cys Gln His Gln Phe Arg Gly Arg Arg Trp Asn
                85                  90                  95

Cys Thr Thr Val Ser Asn Ser Leu Ala Ile Phe Gly Pro Val Leu Asp
            100                 105                 110

Lys Ala Thr Arg Glu Ser Ala Phe Val His Ala Ile Ala Ser Ala Gly
        115                 120                 125

Val Ala Phe Ala Val Thr Arg Ser Cys Ala Glu Gly Ser Ala Ala Ile
130                 135                 140

Cys Gly Cys Ser Ser Arg Leu Gln Gly Ser Pro Gly Glu Gly Trp Lys
145                 150                 155                 160

Trp Gly Gly Cys Ser Glu Asp Ile Glu Phe Gly Gly Met Val Ser Arg
                165                 170                 175

Glu Phe Ala Asp Ala Arg Glu Asn Arg Pro Asp Ala Arg Ser Ala Met
            180                 185                 190

Asn Arg His Asn Asn Glu Ala Gly Arg Gln Ala Ile Ala Ser His Met
        195                 200                 205

His Leu Lys Cys Lys Cys His Gly Leu Ser Gly Ser Cys Glu Val Lys
210                 215                 220

Thr Cys Trp Trp Ser Gln Pro Asp Phe Arg Thr Ile Gly Asp Phe Leu
225                 230                 235                 240

Lys Asp Lys Tyr Asp Ser Ala Ser Glu Met Val Val Glu Lys His Arg
                245                 250                 255

Glu Ser Arg Gly Trp Val Glu Thr Leu Arg Pro Arg Tyr Thr Tyr Phe
            260                 265                 270

Lys Val Pro Thr Glu Arg Asp Leu Val Tyr Tyr Glu Ala Ser Pro Asn
        275                 280                 285

Phe Cys Glu Pro Asn Pro Glu Thr Gly Ser Phe Gly Thr Arg Asp Arg
290                 295                 300

Thr Cys Asn Val Ser Ser His Gly Ile Asp Gly Cys Asp Leu Leu Cys
305                 310                 315                 320

Cys Gly Arg Gly His Asn Ala Arg Thr Glu Arg Arg Glu Lys Cys
                325                 330                 335

His Cys Val Phe His Trp Cys Cys Tyr Val Ser Cys Gln Glu Cys Thr
            340                 345                 350

Arg Val Tyr Asp Val His Thr Cys Lys
        355                 360
```

<210> SEQ ID NO 18
<211> LENGTH: 1554
<212> TYPE: DNA
<213> ORGANISM: Homo sapiens

<400> SEQUENCE: 18

```
atgcacgccg ccctggcggg gccgctgctc gccgccctcc tcgccaccgc tcgcgcccgc    60
ccgcagcccc cggacggagg acagtgccgg ccgcccggat cgcagaggga cttgaactcc   120
ttcctgtgga cgattcggcg tgatcctccg gcctacctgt ttggcactat tcacgtcccc   180
tacacccgcg tctgggactt catcccggac aactccaagg cagccttcca ggctagcacc   240
cgtgtctact ttgagctgga ccttacagac ccctacacca tctcggccct ggccagctgc   300
cagctgctgc cgcacgggga aaacctgcag gacgtgctgc cccacgagct ttactggcgc   360
ttgaagcgcc acctggacta cgtgaagttg atgatgccct cctggatgac gcccgctcag   420
cggggcaagg ggctctatgc tgactaccta ttcaatgcca tcgcgggcaa ctgggagcgc   480
aagaggcccg tctgggtgat gctcatggta aactcgctca cagagaggga cgtgcgcttc   540
cgtggtgtgc ccgtgctcga cctctacctg gcccagcagg ctgagaagat gaagaagacc   600
acaggggctg tggagcaggt ggaggagcag tgccatcccc tcaacaacgg gctcaacttc   660
tcccaggtgc tgtttgccct gaaccaaacc ctgctgcagc aggagagtgt gcgggccggg   720
agcctgcagg cctcctacac cacggaggac ctcatcaagc actacaactg cggagacctc   780
agcgcagtca tcttcaacca cgacacatcc cagctgccca ctttatcaa caccaccctc   840
ccgccacacg agcaggtgac ggcccaggag attgacagct acttccgcca ggagctcatc   900
tacaaggaga tgagcgcat ggggaagagg gtcatgcgc ttctacggga gaacgaggac   960
aagatctgct tctttgcctt cggagcaggt cactttctgg ggaacaacac agtcatcgac  1020
atcctgcggc aggcagggct ggaggtggac cacacacccg ccgggcaggc catacacagc  1080
cctgcccccc agagcccagc gccctctcct gaggggacct cgacgagccc ggccccagtg  1140
accccagctg ccgctgtccc cgaagcaccc tctgtgaccc ccaccgcccc accagaggat  1200
gaggatccag ccctgtcccc acacctcctg ctccccgaca gcctcagcca gctggaggag  1260
tttggccggc agaggaagtg gcacaagagg cagagcacac accagcggcc gcggcagttc  1320
aatgacctct gggtccgcat cgaggacagc accaccgcct caccaccccc gctgcccctg  1380
cagcccaccc acagctcggg gaccgccaag cccccccttcc agctttcaga ccagctacaa  1440
cagcaggacc cgccagggcc cgccagcagc tcggcaccca ccctgggcct tctccccgcc  1500
atcgccacca ccatcgctgt ctgcttcctg ctgcatagcc ttgggccctc ctga        1554
```

<210> SEQ ID NO 19
<211> LENGTH: 1527
<212> TYPE: DNA
<213> ORGANISM: Xenopus tropicalis

<400> SEQUENCE: 19

```
atggtaatca tttggaatat attcctgcca gcattcctcc tagtgctggc caaagcgagt    60
ctcaggagct ccagggattc ggcaaactgc aagctcaaca agaaacaaag ccaactaaac   120
tcctttctgt ggacaataaa gcgagatccc ccctcatact tttttggcac aattcatgta   180
ccttatacac gggtatggga ctttatccca gaaaattcca agacagcttt ccaacagagc   240
aatattgtgt actttgaatt ggacttaaca gacccataca caatctcagc cttgactagt   300
tgccagatgc tgccccaggg tgaaaacttg caaaatgtac tgcccaggga tatttaccga   360
aggttgaaac gccatttgga atatgttaaa cttatgatgc cttcctggat gaccctgat   420
caaagaggaa aagggcttta tgctgactat ttattcaatg ctattgctgg aaattgggaa   480
aggaaaagac ctgtctgggt tatgctgatg gtgaactctc taacagaggt cgatatcaag   540
```

-continued

```
tcgagaggag tcccagtatt ggatttatat ttggctcaag aagctgagcg ccttaagaaa      600
agaactggag cagtagaaca ggtagaagaa caatgccacc ccctaaatgg attgaactta      660
tcacaggtaa tatttgcctt aaatcagact ctcttgcaac aggagaacct tcgtgcaggc      720
agcgttcaag ttccctattc cacagaagac ctgatcaagc attacaactg tggagacctc      780
aactccatta tttttaatca cgattcttca caagtcccta atttcataaa ctccacttta      840
ccacctcaag aaagaataac tgctcaagag atcgacaatt atttccgtca agagctgatt      900
tataaaagga atgagcgcat gggaaagagg gttaaagatc tactggagca gtttccggag      960
aaaagttttt tctttgcttt cggtgcaggt catttcctgg gcaataatac tgtcattgat     1020
gtgttaaaaa ggtatggata tgatgtgcta cacactcctg ctggtcgatc catcatcaac     1080
aatggtaaag gtaagaaaaa tctgctgcca tccaagtttt catcttcatc tttaccagtt     1140
gggttatccg cacctccctg cacagttact tccagaataa aacagtcaat aaattctcac     1200
aaagaccaag aatccctccc tgacatactg ttagatgatg atatcgacca gcttgataaa     1260
gacgaaagaa agtacaaaaa gaggaagcaa aggaaagaaa acatcgcca tttcagtgat      1320 ctctgggttc gcattcaaga aagctcaaca gacaccacgc cgcaaatccg aattattaat     1380
ggatacatta ctgtggaacc acatccaaga gaacacggaa aagacaaata cattaaggca     1440
gcacaaagcg tttctttcag cctatcgatc ccttctgcct ttttgctgct ggcttggtgt     1500
tttcagcagg tggcagtatt gcagtga                                         1527
```

<210> SEQ ID NO 20
<211> LENGTH: 508
<212> TYPE: PRT
<213> ORGANISM: Xenopus tropicalis

<400> SEQUENCE: 20

```
Met Val Ile Ile Trp Asn Ile Phe Leu Pro Ala Phe Leu Leu Val Leu
1               5                   10                  15

Ala Lys Ala Ser Leu Arg Ser Ser Arg Asp Ser Ala Asn Cys Lys Leu
            20                  25                  30

Asn Lys Lys Gln Ser Gln Leu Asn Ser Phe Leu Trp Thr Ile Lys Arg
        35                  40                  45

Asp Pro Pro Ser Tyr Phe Phe Gly Thr Ile His Val Pro Tyr Thr Arg
    50                  55                  60

Val Trp Asp Phe Ile Pro Glu Asn Ser Lys Thr Ala Phe Gln Gln Ser
65                  70                  75                  80

Asn Ile Val Tyr Phe Glu Leu Asp Leu Thr Asp Pro Tyr Thr Ile Ser
                85                  90                  95

Ala Leu Thr Ser Cys Gln Met Leu Pro Gln Gly Glu Asn Leu Gln Asn
            100                 105                 110

Val Leu Pro Arg Asp Ile Tyr Arg Arg Leu Lys Arg His Leu Glu Tyr
        115                 120                 125

Val Lys Leu Met Met Pro Ser Trp Met Thr Pro Asp Gln Arg Gly Lys
    130                 135                 140

Gly Leu Tyr Ala Asp Tyr Leu Phe Asn Ala Ile Ala Gly Asn Trp Glu
145                 150                 155                 160

Arg Lys Arg Pro Val Trp Val Met Leu Met Val Asn Ser Leu Thr Glu
                165                 170                 175

Val Asp Ile Lys Ser Arg Gly Val Pro Val Leu Asp Leu Tyr Leu Ala
            180                 185                 190
```

```
Gln Glu Ala Glu Arg Leu Lys Lys Arg Thr Gly Ala Val Glu Gln Val
            195                 200                 205

Glu Glu Gln Cys His Pro Leu Asn Gly Leu Asn Leu Ser Gln Val Ile
        210                 215                 220

Phe Ala Leu Asn Gln Thr Leu Leu Gln Gln Glu Asn Leu Arg Ala Gly
225                 230                 235                 240

Ser Val Gln Val Pro Tyr Ser Thr Glu Asp Leu Ile Lys His Tyr Asn
                245                 250                 255

Cys Gly Asp Leu Asn Ser Ile Ile Phe Asn His Asp Ser Ser Gln Val
            260                 265                 270

Pro Asn Phe Ile Asn Ser Thr Leu Pro Pro Gln Glu Arg Ile Thr Ala
        275                 280                 285

Gln Glu Ile Asp Asn Tyr Phe Arg Gln Glu Leu Ile Tyr Lys Arg Asn
    290                 295                 300

Glu Arg Met Gly Lys Arg Val Lys Asp Leu Leu Glu Gln Phe Pro Glu
305                 310                 315                 320

Lys Ser Phe Phe Phe Ala Phe Gly Ala Gly His Phe Leu Gly Asn Asn
                325                 330                 335

Thr Val Ile Asp Val Leu Lys Arg Tyr Gly Tyr Asp Val Leu His Thr
            340                 345                 350

Pro Ala Gly Arg Ser Ile Ile Asn Asn Gly Lys Gly Lys Lys Asn Leu
        355                 360                 365

Leu Pro Ser Lys Phe Ser Ser Ser Leu Pro Val Gly Leu Ser Ala
    370                 375                 380

Pro Pro Cys Thr Val Thr Ser Arg Ile Lys Gln Ser Ile Asn Ser His
385                 390                 395                 400

Lys Asp Gln Glu Ser Leu Pro Asp Ile Leu Leu Asp Asp Ile Asp
                405                 410                 415

Gln Leu Asp Lys Asp Glu Arg Lys Tyr Lys Lys Arg Lys Gln Arg Lys
            420                 425                 430

Glu Lys His Arg His Phe Ser Asp Leu Trp Val Arg Ile Gln Glu Ser
        435                 440                 445

Ser Thr Asp Thr Thr Pro Gln Ile Arg Ile Ile Asn Gly Tyr Ile Thr
    450                 455                 460

Val Glu Pro His Pro Arg Glu His Gly Lys Asp Lys Tyr Ile Lys Ala
465                 470                 475                 480

Ala Gln Ser Val Ser Phe Ser Leu Ser Ile Pro Ser Ala Phe Leu Leu
                485                 490                 495

Leu Ala Trp Cys Phe Gln Gln Val Ala Val Leu Gln
            500                 505

<210> SEQ ID NO 21
<211> LENGTH: 1569
<212> TYPE: DNA
<213> ORGANISM: Xenopus tropicalis

<400> SEQUENCE: 21
atgggaaaaa caatgtgggc tagggcagtg ttcctctgct tctcggtggg cacgttactg      60
tggcaggagg tcctgactag gagaatcccg gtggacaccg tcagtgtgg gctgcccaaa      120 tcgcaagaag atctgaattc ctttctttgg accgtaagga ggcatccacc tgcctatctc      180
tttggaacca tacatgtgcc ttatacaaga gtttgggatt tcatacccca aaactccaaa      240
aaggcgtttc atgacagcaa cagtgtatac tttgaattgg acctcactga cccatacact      300
atttcagctt tggcaaactg tcagatgctt ccacaggggg aaaacctgca ggatgtgctg      360
```

-continued

```
cccagggatc tgtacaggag actaaagagg cacttggagt atgttaagca catgacgcct    420
cactggatga ccccagacca gaggggaaag ggcctttatg ctgattacct ctttaatgcc    480
attgctggga actgggagag aaagagacct gtgtgggtga tgctgatggt aaattcttta    540
acagaagctg atatcaggtc tagaggtgtc ccagtcttgg atctgtattt agcacaggaa    600
gctgatcgaa tgaagaagaa accggggct gttgagaggg tagaagaaca gtgtcatcct     660
ctcaataggt taaacctttc ccaggttttg tttgccctaa atcaaacatt gttgcagcat    720
gaaagtctac gtgcaggaag tttccaagct ccatatacca cagaggatct tatcaaacat    780
tacaactgtg gggacctcaa tgctgtgata tttagccatg attcttccca gctcccaaat    840
tttatcaacg tcactcttcc ccctcatgaa caagtaaccg cacaagaaat tgatatctac    900
tttaggcaag aactgatcta caagaggaac gagaggatgg caaggagagt gattgcactt    960
cttaaggaga acaaggacaa aagtttcttc tttgcttttg gtgcaggcca cttccttgga   1020
aataacacag tcattgatgt tctgagacaa aatggatatg aggttgagca cactccagcg   1080
ggacagacat ttactgcagc aaaacccaaa acaaacccaa cctcggatga ctccatggca   1140
accgattctc cagcaatgaa atattttgat cacgtccctg cgacagcttc ctactttggc   1200
gagtcggatg aggagatgct gcccccccac ctcctgttgc cagacagtat tagtcagctg   1260
gaagagtttg gaaagcagaa tagttggcat cggaagcatt acaggaatca gagaccaagg   1320
cagttcaatg acctttgggt tcgtttagat gatagtacaa caacattgcc ttcaaacact   1380
aggaacacca acgagaaaca gtctgcagag tcactggttt ggctgcctga gcaggatcat   1440
cacaattacc tggatgttaa actgtcccat tcacagagca attcatctcc caagtgccta   1500
tcagcaagcc ctgccttcct ctatacgtta gtaactttgt gccttataac aacaatgaga   1560
acacgatca                                                          1569
```

<210> SEQ ID NO 22
<211> LENGTH: 523
<212> TYPE: PRT
<213> ORGANISM: Xenopus tropicalis

<400> SEQUENCE: 22

```
Met Gly Lys Thr Met Trp Ala Arg Ala Val Phe Leu Cys Phe Ser Val
 1               5                  10                  15

Gly Thr Leu Leu Trp Gln Glu Val Leu Thr Arg Arg Ile Pro Val Asp
            20                  25                  30

Thr Gly Gln Cys Gly Leu Pro Lys Ser Gln Glu Asp Leu Asn Ser Phe
        35                  40                  45

Leu Trp Thr Val Arg Arg His Pro Pro Ala Tyr Leu Phe Gly Thr Ile
    50                  55                  60

His Val Pro Tyr Thr Arg Val Trp Asp Phe Ile Pro Gln Asn Ser Lys
65                  70                  75                  80

Lys Ala Phe His Asp Ser Asn Ser Val Tyr Phe Glu Leu Asp Leu Thr
                85                  90                  95

Asp Pro Tyr Thr Ile Ser Ala Leu Ala Asn Cys Gln Met Leu Pro Gln
            100                 105                 110

Gly Glu Asn Leu Gln Asp Val Leu Pro Arg Asp Leu Tyr Arg Arg Leu
        115                 120                 125

Lys Arg His Leu Glu Tyr Val Lys His Met Thr Pro His Trp Met Thr
    130                 135                 140

Pro Asp Gln Arg Gly Lys Gly Leu Tyr Ala Asp Tyr Leu Phe Asn Ala
```

```
         145                 150                 155                 160
    Ile Ala Gly Asn Trp Glu Arg Lys Arg Pro Val Trp Val Met Leu Met
                    165                 170                 175

Val Asn Ser Leu Thr Glu Ala Asp Ile Arg Ser Arg Gly Val Pro Val
                    180                 185                 190

Leu Asp Leu Tyr Leu Ala Gln Glu Ala Asp Arg Met Lys Lys Lys Thr
                    195                 200                 205

Gly Ala Val Glu Arg Val Glu Glu Gln Cys His Pro Leu Asn Arg Leu
        210                 215                 220

Asn Leu Ser Gln Val Leu Phe Ala Leu Asn Gln Thr Leu Leu Gln His
    225                 230                 235                 240

Glu Ser Leu Arg Ala Gly Ser Phe Gln Ala Pro Tyr Thr Thr Glu Asp
                    245                 250                 255

Leu Ile Lys His Tyr Asn Cys Gly Asp Leu Asn Ala Val Ile Phe Ser
                    260                 265                 270

His Asp Ser Ser Gln Leu Pro Asn Phe Ile Asn Val Thr Leu Pro Pro
                    275                 280                 285

His Glu Gln Val Thr Ala Gln Glu Ile Asp Ile Tyr Phe Arg Gln Glu
                    290                 295                 300

Leu Ile Tyr Lys Arg Asn Glu Arg Met Ala Arg Val Ile Ala Leu
    305                 310                 315                 320

Leu Lys Glu Asn Lys Asp Lys Ser Phe Phe Ala Phe Gly Ala Gly
                    325                 330                 335

His Phe Leu Gly Asn Asn Thr Val Ile Asp Val Leu Arg Gln Asn Gly
                    340                 345                 350

Tyr Glu Val Glu His Thr Pro Ala Gly Gln Thr Phe Thr Ala Ala Lys
                    355                 360                 365

Pro Lys Thr Asn Pro Thr Ser Asp Asp Ser Met Ala Thr Asp Ser Pro
                    370                 375                 380

Ala Met Lys Tyr Phe Asp His Val Pro Ala Thr Ala Ser Tyr Phe Gly
    385                 390                 395                 400

Glu Ser Asp Glu Glu Met Leu Pro Pro His Leu Leu Leu Pro Asp Ser
                    405                 410                 415

Ile Ser Gln Leu Glu Glu Phe Gly Lys Gln Asn Ser Trp His Arg Lys
                    420                 425                 430

His Tyr Arg Asn Gln Arg Pro Arg Gln Phe Asn Asp Leu Trp Val Arg
                    435                 440                 445

Leu Asp Asp Ser Thr Thr Thr Leu Pro Ser Asn Thr Arg Asn Thr Asn
    450                 455                 460

Gly Glu Gln Ser Ala Glu Ser Leu Val Trp Leu Pro Glu Gln Asp His
    465                 470                 475                 480

His Asn Tyr Leu Asp Val Lys Leu Ser His Ser Gln Ser Asn Ser Ser
                    485                 490                 495

Pro Lys Cys Leu Ser Ala Ser Pro Ala Phe Leu Tyr Thr Leu Val Thr
                    500                 505                 510

Leu Cys Leu Ile Thr Thr Met Arg Thr Arg Ser
    515                 520

<210> SEQ ID NO 23
<211> LENGTH: 1485
<212> TYPE: DNA
<213> ORGANISM: Danio rerio

<400> SEQUENCE: 23
```

| | |
|---|---:|
| atgacgatga tgacgatgat gatggtcagc tggagcgctt ttctgcagat ctgctggata | 60 |
| ctcatggtga gagcaaacca gttcaacccc ggagagccga gcggctgccg gaccaacact | 120 |
| ccacagagtg atctgaactc cttcctgtgg acgatcaagc gggaccctcc gtcatatctg | 180 |
| tacggcacca tccacgtccc gtacacccgc gtctgggact tcatcccgca gaactccaag | 240 |
| caggcgttcc aggagagcag cgtggtgtac tttgagctgg agctgacgga cccgtccacc | 300 |
| atctcggctc tgtcccgctg tcagctgctg ccggcgggcc agaacctgca ggacgtgctg | 360 |
| ccgccagaac tctacctgcg cctgaagacg cacctggagt acgtgcggct gatgctaccc | 420 |
| tcctggatga cccctgacca gcggggaaag ggcctgtatg ctgaataccc tgttcaacgcc | 480 |
| atcgccggga actgggagcg caagcgtccg gtgtgggtga tgctgatggt gaactcgctg | 540 |
| acggaggccg atataaagac ccgtggggtc ccggtgctgg acctgtacct ggcccaggag | 600 |
| gcggagcgca tgaagaagca gaccggagcc gtggagaagg tggaggagca gtgcagtccg | 660 |
| ctaaacacac tcgacttctc tcaggtgatc ttcgctctga atcagacgct gctgcagcag | 720 |
| gagagtgtgc gggccggcag tctgcaggtg ccctacacaa ctgaacacct gatcacacac | 780 |
| tacaactgtg gagacctgca ctccatcatc agccacgaca ccgcacaggt gccgaacttc | 840 |
| aacaatgtga ctctgcgtcc cagcgatcag gtgacggcgc agcagatcga cagctacttc | 900 |
| agacgcgagc tgatctacaa agtaatgag cgcatgggcc gccgcgtcac agccctgctg | 960 |
| caggaacagc cacacaaaac tttcttcttc gcattcggag cagggcattt tctggggaat | 1020 |
| aactctgtga ttgacgtcct gcggagagaa ggatacgagg tagaacacac acctgctgga | 1080 |
| caaccactgc acagacggtc aggctggagg tctgcagatc ccgcagacac agacgcagcg | 1140 |
| ctgcagccgt tcctccacca cagcaggcat catgagctgc agcttctgga gggtctggag | 1200 |
| ctgctggaga aggtggagca caagctgaag aagaaacacc gcagaaacaa gctgaagaaa | 1260 |
| cagcggcagt tcaacgacct gtgggtgcgc atggaggaca gtgtgacagc cgaggctccg | 1320 |
| cccccctctca tccacatcat caacggttac atcacagtcc agacacaccc acaggaccac | 1380 |
| gagagagcca atcacgacag gacgtttttca ggctcctcct cctggacagg cccgcccctc | 1440 |
| agtgcgctgg ctgtgtgtgt tcagatgctc agactgctgc tgtga | 1485 |

<210> SEQ ID NO 24
<211> LENGTH: 494
<212> TYPE: PRT
<213> ORGANISM: Danio rerio

<400> SEQUENCE: 24

Met Thr Met Met Thr Met Met Val Ser Trp Ser Ala Phe Leu Gln
1               5                   10                  15

Ile Cys Trp Ile Leu Met Val Arg Ala Asn Gln Phe Asn Pro Gly Glu
            20                  25                  30

Pro Ser Gly Cys Arg Thr Asn Thr Pro Gln Ser Asp Leu Asn Ser Phe
        35                  40                  45

Leu Trp Thr Ile Lys Arg Asp Pro Pro Ser Tyr Leu Tyr Gly Thr Ile
    50                  55                  60

His Val Pro Tyr Thr Arg Val Trp Asp Phe Ile Pro Gln Asn Ser Lys
65                  70                  75                  80

Gln Ala Phe Gln Glu Ser Ser Val Val Tyr Phe Glu Leu Glu Leu Thr
                85                  90                  95

Asp Pro Ser Thr Ile Ser Ala Leu Ser Arg Cys Gln Leu Leu Pro Ala
            100                 105                 110

```
Gly Gln Asn Leu Gln Asp Val Leu Pro Pro Glu Leu Tyr Leu Arg Leu
            115                 120                 125

Lys Thr His Leu Glu Tyr Val Arg Leu Met Leu Pro Ser Trp Met Thr
130                 135                 140

Pro Asp Gln Arg Gly Lys Gly Leu Tyr Ala Glu Tyr Leu Phe Asn Ala
145                 150                 155                 160

Ile Ala Gly Asn Trp Glu Arg Lys Arg Pro Val Trp Val Met Leu Met
                165                 170                 175

Val Asn Ser Leu Thr Glu Ala Asp Ile Lys Thr Arg Gly Val Pro Val
            180                 185                 190

Leu Asp Leu Tyr Leu Ala Gln Glu Ala Glu Arg Met Lys Lys Gln Thr
        195                 200                 205

Gly Ala Val Glu Lys Val Glu Glu Gln Cys Ser Pro Leu Asn Thr Leu
    210                 215                 220

Asp Phe Ser Gln Val Ile Phe Ala Leu Asn Gln Thr Leu Leu Gln Gln
225                 230                 235                 240

Glu Ser Val Arg Ala Gly Ser Leu Gln Val Pro Tyr Thr Thr Glu His
                245                 250                 255

Leu Ile Thr His Tyr Asn Cys Gly Asp Leu His Ser Ile Ile Ser His
            260                 265                 270

Asp Thr Ala Gln Val Pro Asn Phe Asn Asn Val Thr Leu Arg Pro Ser
        275                 280                 285

Asp Gln Val Thr Ala Gln Ile Asp Ser Tyr Phe Arg Arg Glu Leu
    290                 295                 300

Ile Tyr Lys Arg Asn Glu Arg Met Gly Arg Arg Val Thr Ala Leu Leu
305                 310                 315                 320

Gln Glu Gln Pro His Lys Thr Phe Phe Phe Ala Phe Gly Ala His
                325                 330                 335

Phe Leu Gly Asn Asn Ser Val Ile Asp Val Leu Arg Arg Glu Gly Tyr
            340                 345                 350

Glu Val Glu His Thr Pro Ala Gly Gln Pro Leu His Arg Arg Ser Gly
        355                 360                 365

Trp Arg Ser Ala Asp Pro Ala Asp Thr Asp Ala Ala Leu Gln Pro Phe
    370                 375                 380

Leu His His Ser Arg His His Glu Leu Gln Leu Leu Glu Gly Leu Glu
385                 390                 395                 400

Leu Leu Glu Lys Val Glu His Lys Leu Lys Lys His Arg Arg Asn
                405                 410                 415

Lys Leu Lys Lys Gln Arg Gln Phe Asn Asp Leu Trp Val Arg Met Glu
            420                 425                 430

Asp Ser Val Thr Ala Glu Ala Pro Pro Leu Ile His Ile Ile Asn
        435                 440                 445

Gly Tyr Ile Thr Val Gln Thr His Pro Gln Asp His Glu Arg Ala Asn
    450                 455                 460

His Asp Arg Thr Phe Ser Gly Ser Ser Trp Thr Gly Pro Ala Leu
465                 470                 475                 480

Ser Ala Leu Ala Val Cys Val Gln Met Leu Arg Leu Leu Leu
                485                 490
```

<210> SEQ ID NO 25
<211> LENGTH: 1557
<212> TYPE: DNA
<213> ORGANISM: Danio rerio

<400> SEQUENCE: 25

```
atgaactgtc agtcgggact gcgatggttg gtaactttat gcgctttctt tcaagtgggc    60
tctgcccggg acacgcacga gagcacgcgg caatgtgaca gcccgtatc gcagaaagac    120
atgaactcct tcctgtggac cgtgaagcgg cctcgtcctt ttccaccgtc gtatctgttt    180
ggcacaatcc acgtcccgta cactcgagtg tgggactata tcccagagag ctcaaaacgt    240
gcctttcaga ccagcaacag tgtattcttt gaactggatc tcacagatcc tttaaccatc    300
tccaaactca ccagctgcca gcttctgccc aatggagaaa acctccagac gctactgcca    360
cgggatctct accgccgcct caagcgccac ctggactacg tcaaacacat gatgcccttc    420
tggatgacag cagaccagcg cggccgagga ctttatgccg actacctctt caacgccatt    480
gcggggaact gggaacgcaa gaggcctgta tgggtgatgc taatggtgaa ctcgctgacg    540
gaagcagacg tccggtcacg gggaaccccc gtgctcgacc tgttcttggc acaggaggca    600
gagcgtctcg ggaagcagac aggtgctgtg gagagggtgg aggaacagtg ccatcccctg    660
aatggactga acttctcaca ggtgttgttt gccctgaacc agactctact gcagcatgag    720
agtttgcgtg caggcattct gcagggcacc tttactacag aggacctcat tgcacactac    780
aattgtggag acctcaactc catcatcttc aatcatgaca catcccagct tccgcatttc    840
atcaacagtt ctctgccaga tcatgagcgc ttgacggcgc agcagatcga cagttacctg    900
cggcaggagc tcatttacaa acgcaatgaa cgaatggccc gccgcgtctc cgccctcctt    960
cagagaaacc ccaaccagag cttctttttc gcttttggag ctggtcattt cctggggaat    1020
catagtgtac tggacattct gcggcaggag ggctatgagg tggagcacac accaccacaa    1080
gagcccatca tacagagctg gtctgagcgg gaggcgacca cactgaatcc caccgaagac    1140
agcttcgagt cagtgacaga atggacatca gagactcctg agctggagga gatcagccag    1200
gaagaactct cccatatgct gctgcctgac agtctcagcc agctagagga atttggccgc    1260
tacaagcatc ctcgtaaaac ccatcatacg cacagtcgac ctcggctgtt cagcgacctg    1320
tgggtgcgca taggagacag cacgactcca cacccaagca taaggataac caatggctat    1380
gtgacggtgg agcctcctca gatacgcacg gaacagcaac aaagactcag agaaagactg    1440
aagcctctca gtgagcccac aaaccccagc gcacttgact ccgctgctcc aaacccaaca    1500
tatgcgctga cttgtttttt ggcctgtctc atttcacaac tgcttttgc ttcctaa       1557
```

<210> SEQ ID NO 26
<211> LENGTH: 518
<212> TYPE: PRT
<213> ORGANISM: Danio rerio

<400> SEQUENCE: 26

```
Met Asn Cys Gln Ser Gly Leu Arg Trp Leu Val Thr Leu Cys Ala Phe
1               5                   10                  15

Phe Gln Val Gly Ser Ala Arg Asp Thr His Glu Ser Thr Arg Gln Cys
            20                  25                  30

Asp Lys Pro Val Ser Gln Lys Asp Met Asn Ser Phe Leu Trp Thr Val
        35                  40                  45

Lys Arg Pro Arg Pro Phe Pro Pro Ser Tyr Leu Phe Gly Thr Ile His
    50                  55                  60

Val Pro Tyr Thr Arg Val Trp Asp Tyr Ile Pro Glu Ser Ser Lys Arg
65                  70                  75                  80

Ala Phe Gln Thr Ser Asn Ser Val Phe Phe Glu Leu Asp Leu Thr Asp
                85                  90                  95
```

-continued

```
Pro Leu Thr Ile Ser Lys Leu Thr Ser Cys Gln Leu Leu Pro Asn Gly
            100                 105                 110

Glu Asn Leu Gln Thr Leu Leu Pro Arg Asp Leu Tyr Arg Arg Leu Lys
        115                 120                 125

Arg His Leu Asp Tyr Val Lys His Met Met Pro Phe Trp Met Thr Ala
    130                 135                 140

Asp Gln Arg Gly Arg Gly Leu Tyr Ala Asp Tyr Leu Phe Asn Ala Ile
145                 150                 155                 160

Ala Gly Asn Trp Glu Arg Lys Arg Pro Val Trp Val Met Leu Met Val
                165                 170                 175

Asn Ser Leu Thr Glu Ala Asp Val Arg Ser Arg Gly Thr Pro Val Leu
            180                 185                 190

Asp Leu Phe Leu Ala Gln Glu Ala Glu Arg Leu Gly Lys Gln Thr Gly
        195                 200                 205

Ala Val Glu Arg Val Glu Glu Gln Cys His Pro Leu Asn Gly Leu Asn
    210                 215                 220

Phe Ser Gln Val Leu Phe Ala Leu Asn Gln Thr Leu Leu Gln His Glu
225                 230                 235                 240

Ser Leu Arg Ala Gly Ile Leu Gln Gly Thr Phe Thr Thr Glu Asp Leu
                245                 250                 255

Ile Ala His Tyr Asn Cys Gly Asp Leu Asn Ser Ile Ile Phe Asn His
            260                 265                 270

Asp Thr Ser Gln Leu Pro His Phe Ile Asn Ser Ser Leu Pro Asp His
        275                 280                 285

Glu Arg Leu Thr Ala Gln Gln Ile Asp Ser Tyr Leu Arg Gln Glu Leu
    290                 295                 300

Ile Tyr Lys Arg Asn Glu Arg Met Ala Arg Arg Val Ser Ala Leu Leu
305                 310                 315                 320

Gln Arg Asn Pro Asn Gln Ser Phe Phe Phe Ala Phe Gly Ala Gly His
                325                 330                 335

Phe Leu Gly Asn His Ser Val Leu Asp Ile Leu Arg Gln Glu Gly Tyr
            340                 345                 350

Glu Val Glu His Thr Pro Pro Gln Glu Pro Ile Ile Gln Ser Trp Ser
        355                 360                 365

Glu Arg Glu Ala Thr Thr Leu Asn Pro Thr Glu Asp Ser Phe Glu Ser
    370                 375                 380

Val Thr Glu Trp Thr Ser Glu Thr Pro Glu Leu Glu Glu Ile Ser Gln
385                 390                 395                 400

Glu Glu Leu Ser His Met Leu Pro Asp Ser Leu Ser Gln Leu Glu
                405                 410                 415

Glu Phe Gly Arg Tyr Lys His Pro Arg Lys Thr His His Thr His Ser
            420                 425                 430

Arg Pro Arg Leu Phe Ser Asp Leu Trp Val Arg Ile Gly Asp Ser Thr
        435                 440                 445

Thr Pro His Pro Ser Ile Arg Ile Thr Asn Gly Tyr Val Thr Val Glu
    450                 455                 460

Pro Pro Gln Ile Arg Gln Glu Gln Gln Arg Leu Arg Glu Arg Leu
465                 470                 475                 480

Lys Pro Leu Ser Glu Pro Thr Asn Pro Ser Ala Leu Asp Ser Ala Ala
                485                 490                 495

Pro Asn Pro Thr Tyr Ala Leu Thr Cys Phe Leu Ala Cys Leu Ile Ser
            500                 505                 510

Gln Leu Leu Phe Ala Ser
```

<210> SEQ ID NO 27
<211> LENGTH: 1263
<212> TYPE: DNA
<213> ORGANISM: Caenorhabditis elegans

<400> SEQUENCE: 27

```
atgaccttttatatactagttgtatctttatatttatcattgtttctagtaactgttgta        60
cagtccgattgtgataccgatgttgaacagagggaaagaaatatattcttgtggtcagta       120
aaacatccccagttcgcatcatctcagggatatcttttggtacaattcatgtgccattc       180
accgaggttt ggaaggaagt gagcgaccga gtgcgtgatg catttgcggt gtcagacaca    240
gttctcttgg aaattgattt acatgatgaa gcaacaattc atgagttgat agcttgtaag    300
aacttggcat atgatgagac tgtgcactct tatctttcca ttgaattatt ggaaagaata    360
gagaaaatta tggaatatct tcgctcaagt ttccttgcct gggcccagaa acaaaatcca    420
cgggacacaa agaagataaa gcatgctgaa gatatctaca caatatcat ggagattgg      480
tggagaaaac gcccaatttg gttattattt ctgctctatc aaatgtgcga aatgtgttt     540
gaaaaaagtt caagtccatt actagatttg tacattgcac aaagagccac cgacgagaag    600
aagacaatta tcccgattga aaccgccgag gagcaatgca atccagttgt ttcagtttct    660
accaatgaaa ttatctttgc aatagagcat actgtgcact attttgaaga taaaatcttg    720
gacaatccat caaggataa tgagtctaga agcagtttga agagctcgt cgaacattat      780
aagtgtggga ctctgaagga agatatgttt gataaagatg gaatgtctat aattgactat    840
gcaactggaa caacagaacg gtttaaagct gacgagatca caaaaagtt gaagcaggat     900
atttttgtaa aacgaaattt gagaatggcc aaacggatag agaagatttt gaagggtcga    960
aatagtaaca ctgtatttc tgcaataggc gctggacact ttttggaag cagtagtgtg     1020
ttaacatatc ttgaagagag cggatttata gttcagaagt taaaaaatac agatgtgatt    1080
caaccccctac gatctcccta ccgtcaaacc gcaaagttca acgtgtatg gaccaaggaa    1140
accgcagttc gtcgaaaatc aataatcatc gaagaagtag caccatcgtc cagtcgaatt    1200
gctagattat ggctagttcc gtgtattttt cttttacatt ccatctttgc cattttccca    1260
tga                                                                 1263
```

<210> SEQ ID NO 28
<211> LENGTH: 420
<212> TYPE: PRT
<213> ORGANISM: Caenorhabditis elegans

<400> SEQUENCE: 28

```
Met Thr Phe Tyr Ile Leu Val Val Ser Leu Tyr Leu Ser Leu Phe Leu
 1               5                  10                  15

Val Thr Val Val Gln Ser Asp Cys Asp Thr Asp Val Glu Gln Arg Glu
            20                  25                  30

Arg Asn Ile Phe Leu Trp Ser Val Lys His Pro Gln Phe Ala Ser Ser
        35                  40                  45

Gln Gly Tyr Leu Phe Gly Thr Ile His Val Pro Phe Thr Glu Val Trp
    50                  55                  60

Lys Glu Val Ser Asp Arg Val Arg Asp Ala Phe Ala Val Ser Asp Thr
65                  70                  75                  80

Val Leu Leu Glu Ile Asp Leu His Asp Glu Ala Thr Ile His Glu Leu
                85                  90                  95
```

```
Ile Ala Cys Lys Asn Leu Ala Tyr Asp Glu Thr Val His Ser Tyr Leu
            100                 105                 110

Ser Ile Glu Leu Leu Glu Arg Ile Glu Lys Ile Met Glu Tyr Leu Arg
            115                 120                 125

Ser Ser Phe Leu Ala Trp Ala Gln Lys Gln Asn Pro Arg Asp Thr Lys
        130                 135                 140

Lys Ile Lys His Ala Glu Asp Ile Tyr Asn Asn Ile Ile Gly Asp Trp
145                 150                 155                 160

Trp Arg Lys Arg Pro Ile Trp Leu Leu Phe Leu Leu Tyr Gln Met Cys
                165                 170                 175

Glu Asn Val Phe Glu Lys Ser Ser Pro Leu Leu Asp Leu Tyr Ile
            180                 185                 190

Ala Gln Arg Ala Thr Asp Glu Lys Lys Thr Ile Ile Pro Ile Glu Thr
            195                 200                 205

Ala Glu Glu Gln Cys Asn Pro Val Val Ser Val Ser Thr Asn Glu Ile
210                 215                 220

Ile Phe Ala Ile Glu His Thr Val His Tyr Phe Glu Asp Lys Ile Leu
225                 230                 235                 240

Asp Asn Pro Ser Lys Asp Asn Glu Ser Arg Ser Ser Leu Lys Glu Leu
                245                 250                 255

Val Glu His Tyr Lys Cys Gly Thr Leu Lys Glu Asp Met Phe Asp Lys
            260                 265                 270

Asp Gly Met Ser Ile Ile Asp Tyr Ala Thr Gly Thr Glu Arg Phe
        275                 280                 285

Lys Ala Asp Glu Ile Asn Lys Leu Lys Gln Asp Ile Phe Val Lys
            290                 295                 300

Arg Asn Leu Arg Met Ala Lys Arg Ile Glu Lys Ile Leu Lys Gly Arg
305                 310                 315                 320

Asn Ser Asn Thr Val Phe Ser Ala Ile Gly Ala Gly His Phe Phe Gly
                325                 330                 335

Ser Ser Ser Val Leu Thr Tyr Leu Glu Glu Ser Gly Phe Ile Val Gln
            340                 345                 350

Lys Leu Lys Asn Thr Asp Val Ile Gln Pro Leu Arg Ser Pro Tyr Arg
        355                 360                 365

Gln Thr Ala Lys Phe Lys Arg Val Trp Thr Lys Glu Thr Ala Val Arg
370                 375                 380

Arg Lys Ser Ile Ile Ile Glu Glu Val Ala Pro Ser Ser Arg Ile
385                 390                 395                 400

Ala Arg Leu Trp Leu Val Pro Cys Ile Phe Leu Leu His Ser Ile Phe
                405                 410                 415

Ala Ile Phe Pro
            420

<210> SEQ ID NO 29
<211> LENGTH: 1416
<212> TYPE: DNA
<213> ORGANISM: Nematostella vectensis

<400> SEQUENCE: 29
atggcagcct ttactttatg gatattggtg cttaatgttt tcctgttggg ttttcaagcc    60
cgcaagttag cgagtaattt aaagtttccg atacagaaat gtgatgattc tacgcctcag   120
aagaatttca attcattcct atggcttgtc aagcgaacgc caccggcgta ttttatgga   180 acaatccacg tcccgtacac aagagtgtgg gattttatcc ctatgaacag caaacaagca   240
```

```
ttcactgcaa gtcagcacgt ctatttcgag ctcgatctta cggacgagaa aactatgaga    300
gctttaatga aatgtcaaat gctcccgtct gggacaatgc tcagacagac tttaccgcgc    360
aagatgttta agagattgaa atctcattta cgttacatca aaagaatgat tcctaaatgg    420
attaaacacc gcgatcaaga gacttcgagc gccggtcctt acgccaataa gctttacgag    480
atgcttacca aagactggga taaaaagcga cctatttggg tcatgttgat ggtgaattca    540
ttaaccgaga gtgatattaa aactcgtgga attcccgtat tggaccagta cctggccttg    600
gaggcaagca gaaatcacaa actaatcggt gctgtagaaa atgttgatga acaatgtaaa    660
ccactcaacg cctaaaacgc ctcacaggta gtatttgctc ttaatcagtc tcttcacttt    720
caagagcggt tgcgcagagg ccaagtccaa gtaacgtaca aacagacga tctgatcgat    780 cattataatt gcggggacct gaagtcagtt ttgttctcga ctcagaccag tctgcctacc    840
ctgaccgtga attcctcttt agagcaaagg gaacggaaac gagcccagga aatagaccag    900
tactttcgca atgaactgat tttccagagg aataagcgaa tggcgcaaag agttataaca    960
ctgcttaata atcacccaga aaaagacttc tttttcgcgt tcggcgcagg tcactttctt   1020
ggtaatcaca gtattataga tataatgaag aaacacggtt atgatgtgga atacgtcaaa   1080
ccggagcaag agctaccaag cttcaaagcc aagaaatcgc tgaatacccg gcgagaaagg   1140
cgcaaaggct gcaggggcag gagaaaaaag agcaaacgat gtcagaagaa aaagaaacgg   1200
aagcgccctg actatagccg agttagactt cttcaggtcg ctactagacg gtggaaccct   1260
acaagaaagc cgtaccctac caaactatct gaggcacctg cgccagaga catttcctcg   1320 cggaaagctg ctgcatcttg cacccccaatc tggactgttt cacttgctct tacatgtgct   1380
gtcacttgcc tgttgacgta cagcggtttt cggtaa                              1416
```

<210> SEQ ID NO 30
<211> LENGTH: 471
<212> TYPE: PRT
<213> ORGANISM: Nematostella vectensis

<400> SEQUENCE: 30

```
Met Ala Ala Phe Thr Leu Trp Ile Leu Val Leu Asn Val Phe Leu Leu
1               5                   10                  15

Gly Phe Gln Ala Arg Lys Leu Ala Ser Asn Leu Lys Phe Pro Ile Gln
            20                  25                  30

Lys Cys Asp Asp Ser Thr Pro Gln Lys Asn Phe Asn Ser Phe Leu Trp
        35                  40                  45

Leu Val Lys Arg Thr Pro Pro Ala Tyr Phe Tyr Gly Thr Ile His Val
    50                  55                  60

Pro Tyr Thr Arg Val Trp Asp Phe Ile Pro Met Asn Ser Lys Gln Ala
65                  70                  75                  80

Phe Thr Ala Ser Gln His Val Tyr Phe Glu Leu Asp Leu Thr Asp Glu
                85                  90                  95

Lys Thr Met Arg Ala Leu Met Lys Cys Gln Met Leu Pro Ser Gly Thr
            100                 105                 110

Met Leu Arg Gln Thr Leu Pro Arg Lys Met Phe Lys Arg Leu Lys Ser
        115                 120                 125

His Leu Arg Tyr Ile Lys Arg Met Ile Pro Lys Trp Ile Lys His Arg
    130                 135                 140

Asp Gln Glu Thr Ser Ser Ala Gly Pro Tyr Ala Asn Lys Leu Tyr Glu
145                 150                 155                 160
```

```
Met Leu Thr Lys Asp Trp Asp Lys Lys Arg Pro Ile Trp Val Met Leu
            165                 170                 175
Met Val Asn Ser Leu Thr Glu Ser Asp Ile Lys Thr Arg Gly Ile Pro
        180                 185                 190
Val Leu Asp Gln Tyr Leu Ala Leu Glu Ala Ser Arg Asn His Lys Leu
    195                 200                 205
Ile Gly Ala Val Glu Asn Val Asp Glu Gln Cys Lys Pro Leu Asn Ala
210                 215                 220
Leu Asn Ala Ser Gln Val Phe Ala Leu Asn Gln Ser Leu His Phe
225                 230                 235                 240
Gln Glu Arg Leu Arg Arg Gly Gln Val Gln Val Thr Tyr Thr Thr Asp
            245                 250                 255
Asp Leu Ile Asp His Tyr Asn Cys Gly Asp Leu Lys Ser Val Leu Phe
        260                 265                 270
Ser Thr Gln Thr Ser Leu Pro Thr Leu Thr Val Asn Ser Ser Leu Glu
    275                 280                 285
Gln Arg Glu Arg Lys Arg Ala Gln Glu Ile Asp Gln Tyr Phe Arg Asn
290                 295                 300
Glu Leu Ile Phe Gln Arg Asn Lys Arg Met Ala Gln Arg Val Ile Thr
305                 310                 315                 320
Leu Leu Asn Asn His Pro Glu Lys Asp Phe Phe Ala Phe Gly Ala
            325                 330                 335
Gly His Phe Leu Gly Asn His Ser Ile Ile Asp Ile Met Lys Lys His
        340                 345                 350
Gly Tyr Asp Val Glu Tyr Val Lys Pro Glu Gln Glu Leu Pro Ser Phe
    355                 360                 365
Lys Ala Lys Lys Ser Leu Asn Thr Arg Arg Glu Arg Arg Lys Gly Cys
370                 375                 380
Arg Gly Arg Arg Lys Lys Ser Lys Arg Cys Gln Lys Lys Lys Arg
385                 390                 395                 400
Lys Arg Pro Asp Tyr Ser Arg Val Arg Leu Leu Gln Val Ala Thr Arg
            405                 410                 415
Arg Trp Asn Pro Thr Arg Lys Pro Tyr Pro Thr Lys Leu Ser Glu Ala
        420                 425                 430
Pro Gly Ala Arg Asp Ile Ser Ser Arg Lys Ala Ala Ser Cys Thr
    435                 440                 445
Pro Ile Trp Thr Val Ser Leu Ala Leu Thr Cys Ala Val Thr Cys Leu
450                 455                 460
Leu Thr Tyr Ser Gly Phe Arg
465                 470

<210> SEQ ID NO 31
<211> LENGTH: 1533
<212> TYPE: DNA
<213> ORGANISM: Amphimedon queenslandica

<400> SEQUENCE: 31
atgcaagtga agatagtaca agttttcca tgcttggtac tgctagtaaa gctagtgctt      60
ctctctgttc tactgccatc agctacagga tcataccact gcagtaacaa tgccactcaa     120
aattcttatt tgtggcgtat tgaggcatcc cctccaatct acctctttgg cacaatgcat     180
gttccctaca agaaactttg ggatgatgtc cctgataatg taaagagtgt tctcagcctc     240
tcggagcacc tctgtgtaga gctacgcctc accgactcag aaacctcaaa aaacctttct     300
gcgtgtcgat accttccaaa aaatgaaaca ctagagagtg tactccctgg aggcctctat     360
```

-continued

```
gtacgcgtgt tgaagtactt tgtccggatt cagaaccagt tcccaaagtg gttgtttggt      420
aatgcgagta tcaacggtct ctcgaggata gagagtgatc gtctcttcca tgctatgatt      480
gggaactgga acaggctcag acctgtgtgg ctcctaatgc tcatcagctc tttatccaga      540
gagaacgtcc aagagaggag cattcccctt cttgatgtgt ttctagatcg tgctgccgag      600
ggcatgggaa agaatgtaga agcagtcgaa gtatacaaag agcagtgtcg accatttaac      660
agacttaata atacaaaggt attcgtcgct ttaaggaaac tcttagatta ccttgagccg      720
ttagccgatg gccctatatc gtccaccgac tcagaccttg agacctacaa ctgtggcgac      780
ttcaagagtc tagtctcagc gaggcccata ctcccactcc ctagctcttc aaaactccca      840
aacctcacgt cagaggaggc cggagatctt gagagtatca acgagtttct cgttagtcag      900
atagtttata gacgaaacag acgaatgagt aaaacgatta tgagcctttt gagtagacag      960
agaaatgaga cttacctctt tgccattgga gcaggtcatt ttgtgggtga aggaatgta      1020 gtacacatgc tgaagaagaa aggctacagt gtaaataggc tatcagttac tgagactatt     1080
cctggtcctc cacttcccaa aaacattata tctctgggtg atccttcatc gcagcttacc     1140
atattaaata tatccagtac aatcccaact ctaccaccga acagaccatc tcatgtccct     1200
cccactctct ctcctgaaac cattgccagg atcatacaat cagttttcaa taacacacag     1260
tcaatataca cagttgactc ggttgaagtc acacccacca ctacatcttt aaattcagca     1320
actgcatcaa ccactgtcgc cacacccacc tcatcagtga ctcctcccac ttcaagcagt     1380
agtcaaacac gtagtttaac tattagtgat agtcaaagaa ctagtgatga tagtgcattc     1440
attccaagtg cttcatcagg tttaagatat aatataggac tagtttgtgt aactttattt     1500
tttgtgttgt taataatcac atcagctttg tga                                  1533
```

<210> SEQ ID NO 32
<211> LENGTH: 510
<212> TYPE: PRT
<213> ORGANISM: Amphimedon queenslandica

<400> SEQUENCE: 32

```
Met Gln Val Lys Ile Val Gln Val Phe Pro Cys Leu Val Leu Leu Val
1               5                   10                  15

Lys Leu Val Leu Leu Ser Val Leu Leu Pro Ser Ala Thr Gly Ser Tyr
            20                  25                  30

His Cys Ser Asn Asn Ala Thr Gln Asn Ser Tyr Leu Trp Arg Ile Glu
        35                  40                  45

Ala Ser Pro Pro Ile Tyr Leu Phe Gly Thr Met His Val Pro Tyr Lys
    50                  55                  60

Lys Leu Trp Asp Asp Val Pro Asp Asn Val Lys Ser Val Leu Ser Leu
65                  70                  75                  80

Ser Glu His Leu Cys Val Glu Leu Arg Leu Thr Asp Ser Glu Thr Ser
                85                  90                  95

Lys Asn Leu Ser Ala Cys Arg Tyr Leu Pro Lys Asn Glu Thr Leu Glu
            100                 105                 110

Ser Val Leu Pro Gly Gly Leu Tyr Val Arg Val Leu Lys Tyr Phe Val
        115                 120                 125

Arg Ile Gln Asn Gln Phe Pro Lys Trp Leu Phe Gly Asn Ala Ser Ile
    130                 135                 140

Asn Gly Leu Ser Arg Ile Glu Ser Asp Arg Leu Phe His Ala Met Ile
145                 150                 155                 160
```

```
Gly Asn Trp Asn Arg Leu Arg Pro Val Trp Leu Leu Met Leu Ile Ser
                165                 170                 175

Ser Leu Ser Arg Glu Asn Val Gln Glu Arg Ser Ile Pro Leu Leu Asp
            180                 185                 190

Val Phe Leu Asp Arg Ala Ala Glu Gly Met Gly Lys Asn Val Glu Ala
        195                 200                 205

Val Glu Val Tyr Lys Glu Gln Cys Arg Pro Phe Asn Arg Leu Asn Asn
210                 215                 220

Thr Lys Val Phe Val Ala Leu Arg Lys Leu Leu Asp Tyr Leu Glu Pro
225                 230                 235                 240

Leu Ala Asp Gly Pro Ile Ser Ser Thr Asp Ser Asp Leu Glu Thr Tyr
                245                 250                 255

Asn Cys Gly Asp Phe Lys Ser Leu Val Ser Ala Arg Pro Ile Leu Pro
            260                 265                 270

Leu Pro Ser Ser Ser Lys Leu Pro Asn Leu Thr Ser Glu Glu Ala Gly
        275                 280                 285

Asp Leu Glu Ser Ile Asn Glu Phe Leu Val Ser Gln Ile Val Tyr Arg
    290                 295                 300

Arg Asn Arg Arg Met Ser Lys Thr Ile Met Ser Leu Leu Ser Arg Gln
305                 310                 315                 320

Arg Asn Glu Thr Tyr Leu Phe Ala Ile Gly Ala Gly His Phe Val Gly
                325                 330                 335

Glu Arg Asn Val Val His Met Leu Lys Lys Gly Tyr Ser Val Asn
            340                 345                 350

Arg Leu Ser Val Thr Glu Thr Ile Pro Gly Pro Leu Pro Lys Asn
        355                 360                 365

Ile Ile Ser Leu Gly Asp Pro Ser Ser Gln Leu Thr Ile Leu Asn Ile
    370                 375                 380

Ser Ser Thr Ile Pro Thr Leu Pro Pro Asn Arg Pro Ser His Val Pro
385                 390                 395                 400

Pro Thr Leu Ser Pro Glu Thr Ile Ala Arg Ile Ile Gln Ser Val Phe
                405                 410                 415

Asn Asn Thr Gln Ser Ile Tyr Thr Val Asp Ser Val Glu Val Thr Pro
            420                 425                 430

Thr Thr Thr Ser Leu Asn Ser Ala Thr Ala Ser Thr Thr Val Ala Thr
        435                 440                 445

Pro Thr Ser Ser Val Thr Pro Pro Thr Ser Ser Ser Gln Thr Arg
450                 455                 460

Ser Leu Thr Ile Ser Asp Ser Gln Arg Thr Ser Asp Asp Ser Ala Phe
465                 470                 475                 480

Ile Pro Ser Ala Ser Ser Gly Leu Arg Tyr Asn Ile Gly Leu Val Cys
                485                 490                 495

Val Thr Leu Phe Phe Val Leu Leu Ile Ile Thr Ser Ala Leu
            500                 505                 510

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccaaatgatt accatcatag ctcag                                          25
```

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cctcttacct cagttacaat ttata                                          25

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccggctcgag gcaaaggtta tcgggagcaa                                     30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggcctctaga ggtccgttag gtccaattca                                     30

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaatagggaa gcgggtgaag                                                20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgttgttgc ccatgaaatg                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcttcaacca cgacacatcc                                                20

```
<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggcggaagta gctgtcaatc                                                  20

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acaagaggaa tgagcgcat                                                   19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gagctttact ggcgcttga                                                   19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gcacccgtgt ctactttga                                                   19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
taaactcgct catagagag                                                   19

<210> SEQ ID NO 45
<211> LENGTH: 1518
<212> TYPE: DNA
<213> ORGANISM: Homo sapiens

<400> SEQUENCE: 45
atgagtccct ggagctggtt cctgctgcag accctctgcc tcctgcccac gggcgcagct      60
tcgcggcgcg ggcgcccgg caccgccaac tgcgagctca gccccaaca aagcgagctg       120 aattccttct tgtggaccat taagcgagac ccaccatctt acttctttgg cacaatccat     180
gtcccgtaca cccgagtttg ggacttcatc cccgacaact ctaaggaggc tttcctgcag     240
```

```
agcagcattg tgtactttga gttggatctc acagacccct ataccatctc agctctcacc      300
agctgtcaga tgctgccaca gggcgagaac ctccaagatg tgctccccag ggacatctac      360
tgccgcctca agcgccacct ggagtatgtc aagctcatga tgcccttgtg gatgacccca      420
gaccagcgcg gcaaggggct ctacgcagac tacctcttca atgctattgc cggaaactgg      480
gagcgcaaga ggcctgtctg ggtgatgctc atggtcaact ccctgactga agtggacatt      540
aagtcccgtg gagtgcctgt cttagacctg ttccttgccc aggaggctga gcggctgagg      600
aaacagactg gggcagtgga aaaggtggaa gagcagtgcc atccattgaa tgggttgaac      660
ttttcacagg tcatctttgc tttgaaccag accctcctgc agcaggaaag cctgcgagca      720
ggcagtcttc agatccccta cacgacggag gatctcatca acactataa ctgcggggac       780 ctcagctccg tcatcctcag ccatgacagc tcccaggttc ccaattttat taatgccacg      840
ctaccacctc aggagcgcat cactgctcag gagattgaca gctacttacg ccgggagctg      900
atctacaagc ggaatgagag ataggggaag cgggtgaagg cccttttgga ggagttccct      960
gacaaaggct tcttctttgc ctttggagct ggtcatttca tgggcaacaa cacagtgctg     1020
gatgttttgc ggcgtgaagg ctatgaggta gaacacgccc ctgctggacg acccatccac     1080
aaagggaaga gtaaaaagac ctccacacgg cccactctgt ccaccatctt tgctccaaaa     1140
gtccctaccc tggaagtacc ggcaccagaa gccgtatcct cagggcactc aacgctgcct     1200 cccttgtgt cccggcctgg aagtgccgac acgcccagtg aggccgaaca gaggttccgg       1260
aagaagcgga ggcggtcaca gcggaggccg cgactccggc aattcagcga tctgtgggtc     1320
cgcctggagg agagtgacat agtcccgcaa ctccaggtcc ctgtcctgga caggcacatc     1380
tccactgaac tgcggctccc tcgccgtggg cattcccacc acagccagat ggtggccagc     1440
agtgcctgcc tgtctctctg gactcctgtg ttctgggtgc tggtgctggc tttccaaaca     1500
gagacacccc tcctgtaa                                                   1518
```

<210> SEQ ID NO 46
<211> LENGTH: 8
<212> TYPE: PRT
<213> ORGANISM: Homo sapiens

<400> SEQUENCE: 46

Ser Tyr Pro Ile Trp Trp Ser Leu
1               5

<210> SEQ ID NO 47
<211> LENGTH: 15
<212> TYPE: PRT
<213> ORGANISM: Homo sapiens

<400> SEQUENCE: 47

Ser Tyr Pro Ile Trp Trp Ser Leu Ala Val Gly Pro Gln Tyr Ser
1               5                   10                  15

<210> SEQ ID NO 48
<211> LENGTH: 16
<212> TYPE: PRT
<213> ORGANISM: Homo sapiens

<400> SEQUENCE: 48

Ser Tyr Pro Ile Trp Trp Ser Leu Ala Val Gly Pro Gln Tyr Ser Ser
1               5                   10                  15

```
<210> SEQ ID NO 49
<211> LENGTH: 17
<212> TYPE: PRT
<213> ORGANISM: Homo sapiens

<400> SEQUENCE: 49

Ala Trp Ser Val Asn Asn Phe Leu Met Thr Gly Pro Lys Ala Tyr Leu
1               5                   10                  15

Thr

<210> SEQ ID NO 50
<211> LENGTH: 20
<212> TYPE: PRT
<213> ORGANISM: Homo sapiens

<400> SEQUENCE: 50

Ala Trp Ser Val Asn Asn Phe Leu Met Thr Gly Pro Lys Ala Tyr Leu
1               5                   10                  15

Thr Tyr Ser Ala
            20

<210> SEQ ID NO 51
<211> LENGTH: 4
<212> TYPE: PRT
<213> ORGANISM: Unknown
<220> FEATURE:
<223> OTHER INFORMATION: Description of Unknown: 'KDEL'
      motif peptide

<400> SEQUENCE: 51

Lys Asp Glu Leu
1

<210> SEQ ID NO 52
<211> LENGTH: 10
<212> TYPE: PRT
<213> ORGANISM: Homo sapiens

<400> SEQUENCE: 52

Thr Glu Leu Arg Leu Pro Arg Arg Gly His
1               5                   10

<210> SEQ ID NO 53
<211> LENGTH: 10
<212> TYPE: PRT
<213> ORGANISM: Homo sapiens

<400> SEQUENCE: 53

Glu Glu Ser Asp Ile Val Pro Gln Leu Gln
1               5                   10

<210> SEQ ID NO 54
<211> LENGTH: 10
<212> TYPE: PRT
<213> ORGANISM: Homo sapiens

<400> SEQUENCE: 54

Ala Val Pro Glu Ala Pro Ser Val Thr Pro
1               5                   10

<210> SEQ ID NO 55
<211> LENGTH: 10
<212> TYPE: PRT
<213> ORGANISM: Homo sapiens
```

```
<400> SEQUENCE: 55

Thr Ala Pro Pro Glu Asp Glu Asp Pro Ala
1               5                   10

<210> SEQ ID NO 56
<211> LENGTH: 10
<212> TYPE: PRT
<213> ORGANISM: Homo sapiens

<400> SEQUENCE: 56

Gln Gln Asp Pro Pro Gly Pro Ala Ser Ser
1               5                   10

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 57

His His His His His His
1               5

<210> SEQ ID NO 58
<211> LENGTH: 35
<212> TYPE: PRT
<213> ORGANISM: Homo sapiens

<400> SEQUENCE: 58

Gly Ser Tyr Pro Ile Trp Trp Ser Leu Ala Val Gly Pro Gln Tyr Ser
1               5                   10                  15

Ser Leu Ser Thr Gln Pro Ile Leu Cys Ala Ser Ile Pro Gly Leu Val
            20                  25                  30

Pro Lys Gln
        35

<210> SEQ ID NO 59
<211> LENGTH: 27
<212> TYPE: PRT
<213> ORGANISM: Homo sapiens

<400> SEQUENCE: 59

Leu Ala Val Gly Pro Gln Tyr Ser Ser Leu Ser Thr Gln Pro Ile Leu
1               5                   10                  15

Cys Ala Ser Ile Pro Gly Leu Val Pro Lys Gln
            20                  25

<210> SEQ ID NO 60
<211> LENGTH: 20
<212> TYPE: PRT
<213> ORGANISM: Homo sapiens

<400> SEQUENCE: 60

Ser Ser Leu Ser Thr Gln Pro Ile Leu Cys Ala Ser Ile Pro Gly Leu
1               5                   10                  15

Val Pro Lys Gln
            20

<210> SEQ ID NO 61
<211> LENGTH: 19
<212> TYPE: PRT
```

<213> ORGANISM: Homo sapiens

<400> SEQUENCE: 61

Ser Leu Ser Thr Gln Pro Ile Leu Cys Ala Ser Ile Pro Gly Leu Val
1               5                   10                  15
Pro Lys Gln

<210> SEQ ID NO 62
<211> LENGTH: 18
<212> TYPE: PRT
<213> ORGANISM: Homo sapiens

<400> SEQUENCE: 62

Leu Ser Thr Gln Pro Ile Leu Cys Ala Ser Ile Pro Gly Leu Val Pro
1               5                   10                  15
Lys Gln

<210> SEQ ID NO 63
<211> LENGTH: 16
<212> TYPE: PRT
<213> ORGANISM: Homo sapiens

<400> SEQUENCE: 63

Arg Asn Tyr Val Glu Ile Met Pro Ser Val Ala Glu Gly Val Lys Ala
1               5                   10                  15

<210> SEQ ID NO 64
<211> LENGTH: 13
<212> TYPE: PRT
<213> ORGANISM: Homo sapiens

<400> SEQUENCE: 64

Lys Ala Gly Ile Gln Glu Cys Gln His Gln Phe Arg Gly
1               5                   10

<210> SEQ ID NO 65
<211> LENGTH: 21
<212> TYPE: PRT
<213> ORGANISM: Homo sapiens

<400> SEQUENCE: 65

Arg Glu Ser Ala Phe Val His Ala Ile Ala Ser Ala Gly Val Ala Phe
1               5                   10                  15
Ala Val Thr Arg Ser
            20

<210> SEQ ID NO 66
<211> LENGTH: 17
<212> TYPE: PRT
<213> ORGANISM: Homo sapiens

<400> SEQUENCE: 66

Arg Ser Cys Ala Glu Gly Ser Ala Ala Ile Cys Gly Cys Ser Ser Arg
1               5                   10                  15
Leu

<210> SEQ ID NO 67
<211> LENGTH: 18
<212> TYPE: PRT
<213> ORGANISM: Homo sapiens

<400> SEQUENCE: 67

-continued

```
Lys Trp Gly Gly Cys Ser Glu Asp Ile Glu Phe Gly Gly Met Val Ser
1               5                   10                  15
Arg Glu

<210> SEQ ID NO 68
<211> LENGTH: 12
<212> TYPE: PRT
<213> ORGANISM: Homo sapiens

<400> SEQUENCE: 68

Arg Gln Ala Ile Ala Ser His Met His Leu Lys Cys
1               5                   10

<210> SEQ ID NO 69
<211> LENGTH: 13
<212> TYPE: PRT
<213> ORGANISM: Homo sapiens

<400> SEQUENCE: 69

Lys Cys His Gly Leu Ser Gly Ser Cys Glu Val Lys Thr
1               5                   10

<210> SEQ ID NO 70
<211> LENGTH: 12
<212> TYPE: PRT
<213> ORGANISM: Homo sapiens

<400> SEQUENCE: 70

Lys Thr Cys Trp Trp Ser Gln Pro Asp Phe Arg Thr
1               5                   10

<210> SEQ ID NO 71
<211> LENGTH: 22
<212> TYPE: PRT
<213> ORGANISM: Homo sapiens

<400> SEQUENCE: 71

Arg Thr Ile Gly Asp Phe Leu Lys Asp Lys Tyr Asp Ser Ala Ser Glu
1               5                   10                  15

Met Val Val Glu Lys His
            20

<210> SEQ ID NO 72
<211> LENGTH: 15
<212> TYPE: PRT
<213> ORGANISM: Homo sapiens

<400> SEQUENCE: 72

Lys Asp Lys Tyr Asp Ser Ala Ser Glu Met Val Val Glu Lys His
1               5                   10                  15

<210> SEQ ID NO 73
<211> LENGTH: 13
<212> TYPE: PRT
<213> ORGANISM: Homo sapiens

<400> SEQUENCE: 73

Lys Tyr Asp Ser Ala Ser Glu Met Val Val Glu Lys His
1               5                   10

<210> SEQ ID NO 74
<211> LENGTH: 26
<212> TYPE: PRT
<213> ORGANISM: Homo sapiens
```

<400> SEQUENCE: 74

Arg Asp Leu Val Tyr Tyr Glu Ala Ser Pro Asn Phe Cys Glu Pro Asn
1               5                   10                  15

Pro Glu Thr Gly Ser Phe Gly Thr Arg Asp
            20                  25

<210> SEQ ID NO 75
<211> LENGTH: 21
<212> TYPE: PRT
<213> ORGANISM: Homo sapiens

<400> SEQUENCE: 75

Arg Thr Cys Asn Val Ser Ser His Gly Ile Asp Gly Cys Asp Leu Leu
1               5                   10                  15

Cys Cys Gly Arg Gly
            20

<210> SEQ ID NO 76
<211> LENGTH: 20
<212> TYPE: PRT
<213> ORGANISM: Homo sapiens

<400> SEQUENCE: 76

Lys Cys His Cys Val Phe His Trp Cys Tyr Val Ser Cys Gln Glu
1               5                   10                  15

Cys Thr Arg Val
            20

<210> SEQ ID NO 77
<211> LENGTH: 9
<212> TYPE: PRT
<213> ORGANISM: Homo sapiens

<400> SEQUENCE: 77

Arg Val Tyr Asp Val His Thr Cys Lys
1               5

<210> SEQ ID NO 78
<211> LENGTH: 33
<212> TYPE: PRT
<213> ORGANISM: Homo sapiens

<400> SEQUENCE: 78

Ser Tyr Pro Ile Trp Trp Ser Leu Ala Val Gly Pro Gln Tyr Ser Ser
1               5                   10                  15

Leu Ser Thr Gln Pro Ile Leu Cys Ala Ser Ile Pro Gly Leu Val Pro
            20                  25                  30

Lys

<210> SEQ ID NO 79
<211> LENGTH: 25
<212> TYPE: PRT
<213> ORGANISM: Homo sapiens

<400> SEQUENCE: 79

Ala Val Gly Pro Gln Tyr Ser Ser Leu Ser Thr Gln Pro Ile Leu Cys
1               5                   10                  15

Ala Ser Ile Pro Gly Leu Val Pro Lys
            20                  25

```
<210> SEQ ID NO 80
<211> LENGTH: 18
<212> TYPE: PRT
<213> ORGANISM: Homo sapiens

<400> SEQUENCE: 80

Ser Leu Ser Thr Gln Pro Ile Leu Cys Ala Ser Ile Pro Gly Leu Val
1               5                   10                  15

Pro Lys

<210> SEQ ID NO 81
<211> LENGTH: 17
<212> TYPE: PRT
<213> ORGANISM: Homo sapiens

<400> SEQUENCE: 81

Leu Ser Thr Gln Pro Ile Leu Cys Ala Ser Ile Pro Gly Leu Val Pro
1               5                   10                  15

Lys

<210> SEQ ID NO 82
<211> LENGTH: 16
<212> TYPE: PRT
<213> ORGANISM: Homo sapiens

<400> SEQUENCE: 82

Ser Thr Gln Pro Ile Leu Cys Ala Ser Ile Pro Gly Leu Val Pro Lys
1               5                   10                  15

<210> SEQ ID NO 83
<211> LENGTH: 15
<212> TYPE: PRT
<213> ORGANISM: Homo sapiens

<400> SEQUENCE: 83

Arg Asn Tyr Val Glu Ile Met Pro Ser Val Ala Glu Gly Val Lys
1               5                   10                  15

<210> SEQ ID NO 84
<211> LENGTH: 505
<212> TYPE: PRT
<213> ORGANISM: Homo sapiens

<400> SEQUENCE: 84

Met Ser Pro Trp Ser Trp Phe Leu Leu Gln Thr Cys Leu Leu Pro
1               5                   10                  15

Thr Gly Ala Ala Ser Arg Arg Gly Ala Pro Gly Thr Ala Asn Cys Glu
            20                  25                  30

Leu Lys Pro Gln Gln Ser Glu Leu Asn Ser Phe Leu Trp Thr Ile Lys
        35                  40                  45

Arg Asp Pro Pro Ser Tyr Phe Phe Gly Thr Ile His Val Pro Tyr Thr
    50                  55                  60

Arg Val Trp Asp Phe Ile Pro Asp Asn Ser Lys Glu Ala Phe Leu Gln
65                  70                  75                  80

Ser Ser Ile Val Tyr Phe Glu Leu Asp Leu Thr Asp Pro Tyr Thr Ile
                85                  90                  95

Ser Ala Leu Thr Ser Cys Gln Met Leu Pro Gln Gly Glu Asn Leu Gln
            100                 105                 110

Asp Val Leu Pro Arg Asp Ile Tyr Cys Arg Leu Lys Arg His Leu Glu
        115                 120                 125
```

Tyr Val Lys Leu Met Met Pro Leu Trp Met Thr Pro Asp Gln Arg Gly
130                 135                 140

Lys Gly Leu Tyr Ala Asp Tyr Leu Phe Asn Ala Ile Ala Gly Asn Trp
145                 150                 155                 160

Glu Arg Lys Arg Pro Val Trp Val Met Leu Met Val Asn Ser Leu Thr
                165                 170                 175

Glu Val Asp Ile Lys Ser Arg Gly Val Pro Val Leu Asp Leu Phe Leu
            180                 185                 190

Ala Gln Glu Ala Glu Arg Leu Arg Lys Gln Thr Gly Ala Val Glu Lys
        195                 200                 205

Val Glu Glu Gln Cys His Pro Leu Asn Gly Leu Asn Phe Ser Gln Val
210                 215                 220

Ile Phe Ala Leu Asn Gln Thr Leu Leu Gln Gln Glu Ser Leu Arg Ala
225                 230                 235                 240

Gly Ser Leu Gln Ile Pro Tyr Thr Thr Glu Asp Leu Ile Lys His Tyr
                245                 250                 255

Asn Cys Gly Asp Leu Ser Ser Val Ile Leu Ser His Asp Ser Ser Gln
            260                 265                 270

Val Pro Asn Phe Ile Asn Ala Thr Leu Pro Pro Gln Glu Arg Ile Thr
        275                 280                 285

Ala Gln Glu Ile Asp Ser Tyr Leu Arg Arg Glu Leu Ile Tyr Lys Arg
290                 295                 300

Asn Glu Arg Ile Gly Lys Arg Val Lys Ala Leu Leu Glu Glu Phe Pro
305                 310                 315                 320

Asp Lys Gly Phe Phe Phe Ala Phe Gly Ala Gly His Phe Met Gly Asn
                325                 330                 335

Asn Thr Val Leu Asp Val Leu Arg Arg Glu Gly Tyr Glu Val Glu His
            340                 345                 350

Ala Pro Ala Gly Arg Pro Ile His Lys Gly Lys Ser Lys Lys Thr Ser
        355                 360                 365

Thr Arg Pro Thr Leu Ser Thr Ile Phe Ala Pro Lys Val Pro Thr Leu
370                 375                 380

Glu Val Pro Ala Pro Glu Ala Val Ser Ser Gly His Ser Thr Leu Pro
385                 390                 395                 400

Pro Leu Val Ser Arg Pro Gly Ser Ala Asp Thr Pro Ser Glu Ala Glu
                405                 410                 415

Gln Arg Phe Arg Lys Lys Arg Arg Ser Gln Arg Arg Pro Arg Leu
            420                 425                 430

Arg Gln Phe Ser Asp Leu Trp Val Arg Leu Glu Glu Ser Asp Ile Val
        435                 440                 445

Pro Gln Leu Gln Val Pro Val Leu Asp Arg His Ile Ser Thr Glu Leu
450                 455                 460

Arg Leu Pro Arg Arg Gly His Ser His His Ser Gln Met Val Ala Ser
465                 470                 475                 480

Ser Ala Cys Leu Ser Leu Trp Thr Pro Val Phe Trp Val Leu Val Leu
                485                 490                 495

Ala Phe Gln Thr Glu Thr Pro Leu Leu
            500                 505

<210> SEQ ID NO 85
<211> LENGTH: 508
<212> TYPE: PRT
<213> ORGANISM: Xenopus tropicalis

<400> SEQUENCE: 85

-continued

```
Met Val Ile Ile Trp Asn Ile Phe Leu Pro Ala Phe Leu Val Leu
1               5                   10                  15

Ala Lys Ala Ser Leu Arg Ser Ser Arg Asp Ser Ala Asn Cys Lys Leu
                20                  25                  30

Asn Lys Lys Gln Ser Gln Leu Asn Ser Phe Leu Trp Thr Ile Lys Arg
            35                  40                  45

Asp Pro Pro Ser Tyr Phe Phe Gly Thr Ile His Val Pro Tyr Thr Arg
50                      55                  60

Val Trp Asp Phe Ile Pro Glu Asn Ser Lys Thr Ala Phe Gln Gln Ser
65                  70                  75                  80

Asn Ile Val Tyr Phe Glu Leu Asp Leu Thr Asp Pro Tyr Thr Ile Ser
                85                  90                  95

Ala Leu Thr Ser Cys Gln Met Leu Pro Gln Gly Glu Asn Leu Gln Asn
            100                 105                 110

Val Leu Pro Arg Asp Ile Tyr Arg Arg Leu Lys Arg His Leu Glu Tyr
        115                 120                 125

Val Lys Leu Met Met Pro Ser Trp Met Thr Pro Asp Gln Arg Gly Lys
130                 135                 140

Gly Leu Tyr Ala Asp Tyr Leu Phe Asn Ala Ile Ala Gly Asn Trp Glu
145                 150                 155                 160

Arg Lys Arg Pro Val Trp Val Met Leu Met Val Asn Ser Leu Thr Glu
                165                 170                 175

Val Asp Ile Lys Ser Arg Gly Val Pro Val Leu Asp Leu Tyr Leu Ala
            180                 185                 190

Gln Glu Ala Glu Arg Leu Lys Lys Arg Thr Gly Ala Val Glu Gln Val
        195                 200                 205

Glu Glu Gln Cys His Pro Leu Asn Gly Leu Asn Leu Ser Gln Val Ile
210                 215                 220

Phe Ala Leu Asn Gln Thr Leu Leu Gln Gln Glu Asn Leu Arg Ala Gly
225                 230                 235                 240

Ser Val Gln Val Pro Tyr Ser Thr Glu Asp Leu Ile Lys His Tyr Asn
                245                 250                 255

Cys Gly Asp Leu Asn Ser Ile Ile Phe Asn His Asp Ser Ser Gln Val
            260                 265                 270

Pro Asn Phe Ile Asn Ser Thr Leu Pro Pro Gln Glu Arg Ile Thr Ala
        275                 280                 285

Gln Glu Ile Asp Asn Tyr Phe Arg Gln Glu Leu Ile Tyr Lys Arg Asn
290                 295                 300

Glu Arg Met Gly Lys Arg Val Lys Asp Leu Leu Glu Gln Phe Pro Glu
305                 310                 315                 320

Lys Ser Phe Phe Phe Ala Phe Gly Ala Gly His Phe Leu Gly Asn Asn
                325                 330                 335

Thr Val Ile Asp Val Leu Lys Arg Tyr Gly Tyr Asp Val Leu His Thr
            340                 345                 350

Pro Ala Gly Arg Ser Ile Ile Asn Gly Lys Gly Lys Asn Leu
        355                 360                 365

Leu Pro Ser Lys Phe Ser Ser Ser Leu Pro Val Gly Leu Ser Ala
370                 375                 380

Pro Pro Cys Thr Val Thr Ser Arg Ile Lys Gln Ser Ile Asn Ser His
385                 390                 395                 400

Lys Asp Gln Glu Ser Leu Pro Asp Ile Leu Leu Asp Asp Ile Asp
                405                 410                 415
```

-continued

```
Gln Leu Asp Lys Asp Glu Arg Lys Tyr Lys Arg Lys Gln Arg Lys
                420                 425                 430

Glu Lys His Arg His Phe Ser Asp Leu Trp Val Arg Ile Gln Glu Ser
            435                 440                 445

Ser Thr Asp Thr Thr Pro Gln Ile Arg Ile Ile Asn Gly Tyr Ile Thr
450                 455                 460

Val Glu Pro His Pro Arg Glu His Gly Lys Asp Lys Tyr Ile Lys Ala
465                 470                 475                 480

Ala Gln Ser Val Ser Phe Ser Leu Ser Ile Pro Ser Ala Phe Leu Leu
                485                 490                 495

Leu Ala Trp Cys Phe Gln Gln Val Ala Val Leu Gln
            500                 505

<210> SEQ ID NO 86
<211> LENGTH: 517
<212> TYPE: PRT
<213> ORGANISM: Homo sapiens

<400> SEQUENCE: 86

Met His Ala Ala Leu Ala Gly Pro Leu Leu Ala Ala Leu Leu Ala Thr
1               5                   10                  15

Ala Arg Ala Arg Pro Gln Pro Pro Asp Gly Gly Gln Cys Arg Pro Pro
                20                  25                  30

Gly Ser Gln Arg Asp Leu Asn Ser Phe Leu Trp Thr Ile Arg Arg Asp
            35                  40                  45

Pro Pro Ala Tyr Leu Phe Gly Thr Ile His Val Pro Tyr Thr Arg Val
50                  55                  60

Trp Asp Phe Ile Pro Asp Asn Ser Lys Ala Ala Phe Gln Ala Ser Thr
65                  70                  75                  80

Arg Val Tyr Phe Glu Leu Asp Leu Thr Asp Pro Tyr Thr Ile Ser Ala
                85                  90                  95

Leu Ala Ser Cys Gln Leu Leu Pro His Gly Glu Asn Leu Gln Asp Val
            100                 105                 110

Leu Pro His Glu Leu Tyr Trp Arg Leu Lys Arg His Leu Asp Tyr Val
        115                 120                 125

Lys Leu Met Met Pro Ser Trp Met Thr Pro Ala Gln Arg Gly Lys Gly
    130                 135                 140

Leu Tyr Ala Asp Tyr Leu Phe Asn Ala Ile Ala Gly Asn Trp Glu Arg
145                 150                 155                 160

Lys Arg Pro Val Trp Val Met Leu Met Val Asn Ser Leu Thr Glu Arg
                165                 170                 175

Asp Val Arg Phe Arg Gly Val Pro Val Leu Asp Leu Tyr Leu Ala Gln
            180                 185                 190

Gln Ala Glu Lys Met Lys Lys Thr Thr Gly Ala Val Glu Gln Val Glu
        195                 200                 205

Glu Gln Cys His Pro Leu Asn Asn Gly Leu Asn Phe Ser Gln Val Leu
    210                 215                 220

Phe Ala Leu Asn Gln Thr Leu Leu Gln Gln Glu Ser Val Arg Ala Gly
225                 230                 235                 240

Ser Leu Gln Ala Ser Tyr Thr Thr Glu Asp Leu Ile Lys His Tyr Asn
                245                 250                 255

Cys Gly Asp Leu Ser Ala Val Ile Phe Asn His Asp Thr Ser Gln Leu
            260                 265                 270

Pro Asn Phe Ile Asn Thr Thr Leu Pro Pro His Glu Gln Val Thr Ala
        275                 280                 285
```

Gln Glu Ile Asp Ser Tyr Phe Arg Gln Glu Leu Ile Tyr Lys Arg Asn
    290                 295                 300

Glu Arg Met Gly Lys Arg Val Met Ala Leu Leu Arg Glu Asn Glu Asp
305                 310                 315                 320

Lys Ile Cys Phe Phe Ala Phe Gly Ala Gly His Phe Leu Gly Asn Asn
                325                 330                 335

Thr Val Ile Asp Ile Leu Arg Gln Ala Gly Leu Glu Val Asp His Thr
            340                 345                 350

Pro Ala Gly Gln Ala Ile His Ser Pro Ala Pro Gln Ser Pro Ala Pro
        355                 360                 365

Ser Pro Glu Gly Thr Ser Thr Ser Pro Ala Pro Val Thr Pro Ala Ala
370                 375                 380

Ala Val Pro Glu Ala Pro Ser Val Thr Pro Thr Ala Pro Pro Glu Asp
385                 390                 395                 400

Glu Asp Pro Ala Leu Ser Pro His Leu Leu Leu Pro Asp Ser Leu Ser
                405                 410                 415

Gln Leu Glu Glu Phe Gly Arg Gln Arg Lys Trp His Lys Arg Gln Ser
            420                 425                 430

Thr His Gln Arg Pro Arg Gln Phe Asn Asp Leu Trp Val Arg Ile Glu
        435                 440                 445

Asp Ser Thr Thr Ala Ser Pro Pro Leu Pro Leu Gln Pro Thr His
    450                 455                 460

Ser Ser Gly Thr Ala Lys Pro Pro Phe Gln Leu Ser Asp Gln Leu Gln
465                 470                 475                 480

Gln Gln Asp Pro Pro Gly Pro Ala Ser Ser Ala Pro Thr Leu Gly
                485                 490                 495

Leu Leu Pro Ala Ile Ala Thr Thr Ile Ala Val Cys Phe Leu Leu His
            500                 505                 510

Ser Leu Gly Pro Ser
        515

<210> SEQ ID NO 87
<211> LENGTH: 523
<212> TYPE: PRT
<213> ORGANISM: Xenopus tropicalis

<400> SEQUENCE: 87

Met Gly Lys Thr Met Trp Ala Arg Ala Val Phe Leu Cys Phe Ser Val
1               5                   10                  15

Gly Thr Leu Leu Trp Gln Glu Val Leu Thr Arg Arg Ile Pro Val Asp
            20                  25                  30

Thr Gly Gln Cys Gly Leu Pro Lys Ser Gln Glu Asp Leu Asn Ser Phe
        35                  40                  45

Leu Trp Thr Val Arg Arg His Pro Pro Ala Tyr Leu Phe Gly Thr Ile
    50                  55                  60

His Val Pro Tyr Thr Arg Val Trp Asp Phe Ile Pro Gln Asn Ser Lys
65                  70                  75                  80

Lys Ala Phe His Asp Ser Asn Ser Val Tyr Phe Glu Leu Asp Leu Thr
                85                  90                  95

Asp Pro Tyr Thr Ile Ser Ala Leu Ala Asn Cys Gln Met Leu Pro Gln
            100                 105                 110

Gly Glu Asn Leu Gln Asp Val Leu Pro Arg Asp Leu Tyr Arg Arg Leu
        115                 120                 125

Lys Arg His Leu Glu Tyr Val Lys His Met Met Pro His Trp Met Thr

```
              130                 135                 140
Pro Asp Gln Arg Gly Lys Gly Leu Tyr Ala Asp Tyr Leu Phe Asn Ala
145                 150                 155                 160

Ile Ala Gly Asn Trp Glu Arg Lys Arg Pro Val Trp Val Met Leu Met
                165                 170                 175

Val Asn Ser Leu Thr Glu Ala Asp Ile Arg Ser Arg Gly Val Pro Val
            180                 185                 190

Leu Asp Leu Tyr Leu Ala Gln Glu Ala Asp Arg Met Lys Lys Lys Thr
        195                 200                 205

Gly Ala Val Glu Arg Val Glu Glu Gln Cys His Pro Leu Asn Arg Leu
    210                 215                 220

Asn Leu Ser Gln Val Leu Phe Ala Leu Asn Gln Thr Leu Leu Gln His
225                 230                 235                 240

Glu Ser Leu Arg Ala Gly Ser Phe Gln Ala Pro Tyr Thr Thr Glu Asp
                245                 250                 255

Leu Ile Lys His Tyr Asn Cys Gly Asp Leu Asn Ala Val Ile Phe Ser
            260                 265                 270

His Asp Ser Ser Gln Leu Pro Asn Phe Ile Asn Val Thr Leu Pro Pro
        275                 280                 285

His Glu Gln Val Thr Ala Gln Glu Ile Asp Ile Tyr Phe Arg Gln Glu
    290                 295                 300

Leu Ile Tyr Lys Arg Asn Glu Arg Met Ala Arg Arg Val Ile Ala Leu
305                 310                 315                 320

Leu Lys Glu Asn Lys Asp Lys Ser Phe Phe Phe Ala Phe Gly Ala Gly
                325                 330                 335

His Phe Leu Gly Asn Asn Thr Val Ile Asp Val Leu Arg Gln Asn Gly
            340                 345                 350

Tyr Glu Val Glu His Thr Pro Ala Gly Gln Thr Phe Thr Ala Ala Lys
        355                 360                 365

Pro Lys Thr Asn Pro Thr Ser Asp Asp Ser Met Ala Thr Asp Ser Pro
    370                 375                 380

Ala Met Lys Tyr Phe Asp His Val Pro Ala Thr Ala Ser Tyr Phe Gly
385                 390                 395                 400

Glu Ser Asp Glu Glu Met Leu Pro Pro His Leu Leu Pro Asp Ser
                405                 410                 415

Ile Ser Gln Leu Glu Glu Phe Gly Lys Gln Asn Ser Trp His Arg Lys
            420                 425                 430

His Tyr Arg Asn Gln Arg Pro Arg Gln Phe Asn Asp Leu Trp Val Arg
        435                 440                 445

Leu Asp Asp Ser Thr Thr Thr Leu Pro Ser Asn Thr Arg Asn Thr Asn
    450                 455                 460

Gly Glu Gln Ser Ala Glu Ser Leu Val Trp Leu Pro Glu Gln Asp His
465                 470                 475                 480

His Asn Tyr Leu Asp Val Lys Leu Ser His Ser Gln Ser Asn Ser Ser
                485                 490                 495

Pro Lys Cys Leu Ser Ala Ser Pro Ala Phe Leu Tyr Thr Leu Val Thr
            500                 505                 510

Leu Cys Leu Ile Thr Thr Met Arg Thr Arg Ser
        515                 520

<210> SEQ ID NO 88
<211> LENGTH: 420
<212> TYPE: PRT
<213> ORGANISM: Caenorhabditis elegans
```

<400> SEQUENCE: 88

```
Met Thr Phe Tyr Ile Leu Val Val Ser Leu Tyr Leu Ser Leu Phe Leu
1               5                   10                  15

Val Thr Val Val Gln Ser Asp Cys Asp Thr Asp Val Glu Gln Arg Glu
            20                  25                  30

Arg Asn Ile Phe Leu Trp Ser Val Lys His Pro Gln Phe Ala Ser Ser
        35                  40                  45

Gln Gly Tyr Leu Phe Gly Thr Ile His Val Pro Phe Thr Glu Val Trp
    50                  55                  60

Lys Glu Val Ser Asp Arg Val Arg Asp Ala Phe Ala Val Ser Asp Thr
65                  70                  75                  80

Val Leu Leu Glu Ile Asp Leu His Asp Glu Ala Thr Ile His Glu Leu
                85                  90                  95

Ile Ala Cys Lys Asn Leu Ala Tyr Asp Glu Thr Val His Ser Tyr Leu
            100                 105                 110

Ser Ile Glu Leu Leu Glu Arg Ile Glu Lys Ile Met Glu Tyr Leu Arg
        115                 120                 125

Ser Ser Phe Leu Ala Trp Ala Gln Lys Gln Asn Pro Arg Asp Thr Lys
    130                 135                 140

Lys Ile Lys His Ala Glu Asp Ile Tyr Asn Asn Ile Ile Gly Asp Trp
145                 150                 155                 160

Trp Arg Lys Arg Pro Ile Trp Leu Leu Phe Leu Leu Tyr Gln Met Cys
                165                 170                 175

Glu Asn Val Phe Glu Lys Ser Ser Pro Leu Leu Asp Leu Tyr Ile
            180                 185                 190

Ala Gln Arg Ala Thr Asp Glu Lys Lys Thr Ile Ile Pro Ile Glu Thr
        195                 200                 205

Ala Glu Glu Gln Cys Asn Pro Val Ser Val Ser Thr Asn Glu Ile
    210                 215                 220

Ile Phe Ala Ile Glu His Thr Val His Tyr Phe Glu Asp Lys Ile Leu
225                 230                 235                 240

Asp Asn Pro Ser Lys Asp Asn Glu Ser Arg Ser Ser Leu Lys Glu Leu
                245                 250                 255

Val Glu His Tyr Lys Cys Gly Thr Leu Lys Glu Asp Met Phe Asp Lys
            260                 265                 270

Asp Gly Met Ser Ile Ile Asp Tyr Ala Thr Gly Thr Thr Glu Arg Phe
        275                 280                 285

Lys Ala Asp Glu Ile Asn Lys Lys Leu Lys Gln Asp Ile Phe Val Lys
    290                 295                 300

Arg Asn Leu Arg Met Ala Lys Arg Ile Glu Lys Ile Leu Lys Gly Arg
305                 310                 315                 320

Asn Ser Asn Thr Val Phe Ser Ala Ile Gly Ala Gly His Phe Phe Gly
                325                 330                 335

Ser Ser Ser Val Leu Thr Tyr Leu Glu Glu Ser Gly Phe Ile Val Gln
            340                 345                 350

Lys Leu Lys Asn Thr Asp Val Ile Gln Pro Leu Arg Ser Pro Tyr Arg
        355                 360                 365

Gln Thr Ala Lys Phe Lys Arg Val Trp Thr Lys Glu Thr Ala Val Arg
    370                 375                 380

Arg Lys Ser Ile Ile Ile Glu Glu Val Ala Pro Ser Ser Ser Arg Ile
385                 390                 395                 400

Ala Arg Leu Trp Leu Val Pro Cys Ile Phe Leu Leu His Ser Ile Phe
```

Ala Ile Phe Pro
420

<210> SEQ ID NO 89
<211> LENGTH: 363
<212> TYPE: PRT
<213> ORGANISM: Agrobacterium radiobacter

<400> SEQUENCE: 89

Met Ile Ser Ala Leu Gly Ile Lys Thr Ala Arg Leu Thr Ala Pro Arg
1               5                   10                  15

Pro Gly Asp Ile Phe Phe Trp Leu Ala Thr Ala Phe Pro Val Met Leu
            20                  25                  30

Val Ile Ala Leu Ile Ile Ala Val Leu Ser Ser Val Pro Ala His Ala
        35                  40                  45

Asp Glu Thr Ala Ser Asp Ser Cys Gly Gly Lys Asn Leu Met Thr Glu
    50                  55                  60

Leu Gln Lys Thr Asp Pro Ala Lys Tyr Ala Ser Ile Leu Ala Asp Gly
65                  70                  75                  80

Asp Lys Val Ala Asn Gly Lys Gly Ile Phe Trp Lys Ile Glu Lys Pro
                85                  90                  95

Gly Leu Lys Pro Ser Trp Leu Leu Gly Thr Met His Val Ser Asp Thr
            100                 105                 110

Arg Val Thr Thr Met Pro Lys Gly Ala Ala Glu Ala Ser Ala Thr Ala
        115                 120                 125

Asp Thr Ile Ile Val Glu Ser Asp Glu Ile Leu Asp Asp Lys Lys Ala
    130                 135                 140

Ala Ala Ala Leu Phe Ile Asn Pro Ser Leu Thr Met Leu Pro Asn Gly
145                 150                 155                 160

Gly Thr Ile Gly Gln His Leu Ser Pro Glu Asp Asn Ala Arg Leu Glu
                165                 170                 175

Ala Ala Leu Lys Gln Arg Gly Val Pro Leu Ala Ala Val Ser His Met
            180                 185                 190

Gln Pro Trp Leu Ile Ser Ser Ser Phe Gln Met Thr Gly Cys Glu Ile
        195                 200                 205

Arg Arg Lys Ala Ser Gly Ile Lys Phe Leu Asp Gln Lys Leu Ala Ala
    210                 215                 220

Asp Ala Ala Ala Gly Lys Gln Val Lys Gly Leu Glu Thr Leu Ala
225                 230                 235                 240

Glu Gln Ala Lys Ala Met Ser Asp Leu Pro Ile Glu Leu His Leu Lys
                245                 250                 255

Ser Leu Leu Gln Thr Leu Glu Leu Gly Asp Arg Ile Asn Asp Ile Asn
            260                 265                 270

Glu Thr Met Thr Asp Leu Tyr Leu Ala Gly Asn Val Gly Ala Ile Met
        275                 280                 285

Pro Met Leu Lys Asn Ile Asp Pro Gln Asn Leu Ser Asp Asp Asp
    290                 295                 300

Ala Gly Thr Phe Glu Gln Arg Ile Val Leu Asp Arg Asn Lys Val Met
305                 310                 315                 320

Gly Glu Arg Ala Ala Pro Ile Leu Thr Lys Gly Asn Val Phe Met Ala
                325                 330                 335

Val Gly Ala Leu His Leu Ala Gly Asp Glu Gly Leu Val Ala Leu Leu
            340                 345                 350

```
Arg Lys Gln Gly Phe Thr Val Thr Ala Val Asp
        355                 360

<210> SEQ ID NO 90
<211> LENGTH: 286
<212> TYPE: PRT
<213> ORGANISM: Brucella melitensis

<400> SEQUENCE: 90

Met Thr Ala Glu Ala Ala Ala Thr Pro Asn Ser Lys Gly Ile Phe Trp
1               5                   10                  15

Lys Ile Glu Lys Asp Gly Val Glu Pro Ser Tyr Leu Phe Gly Thr Leu
            20                  25                  30

His Leu Ser Asp Pro Arg Val Met Lys Met Pro Gln Ala Ala Ser Glu
        35                  40                  45

Ala Tyr Asp Ser Ala Gln Thr Val Val Ile Glu Ala Ala Asp Ile Thr
    50                  55                  60

His Arg Lys Thr Phe Pro Arg Ile Met Gln Glu Gln Pro Asp Leu Met
65                  70                  75                  80

Leu Phe Asn Asp Gly Thr Thr Leu Glu Ser His Leu Pro Lys Glu Arg
                85                  90                  95

Arg Ala Asp Ile Glu Gln Lys Leu Val Gln Arg Gly Ile Val Leu Ala
            100                 105                 110

Ala Met Asn Lys Ile Lys Pro Trp Val Leu Ser Asn Leu Leu Ala Thr
        115                 120                 125

Thr Lys Cys Glu Arg Ala Arg Lys Ala Arg Gly Glu Leu Phe Leu Asp
    130                 135                 140

Glu Gln Leu Ala Ile Glu Ala Gln Lys Gln Gly Arg Glu Val Lys Gly
145                 150                 155                 160

Leu Glu Ser Ile Ala Glu Gln Phe Ala Ala Met Asn Ser Leu Pro Leu
                165                 170                 175

Asp Phe His Ile Arg Asn Leu Ile Ala Thr Val Asp Phe Gly Asp Lys
            180                 185                 190

Ile Glu Asp Ser Met Glu Thr Ala Ile Thr Leu Tyr Leu Gln Gly Asp
        195                 200                 205

Val Gly Met Ile Ala Pro Ala Leu Arg Lys Ile Val Pro Glu Asp Leu
    210                 215                 220

Ser Asp Ala Asp Tyr Ala Leu Phe Gln Lys Val Ile Leu Thr Asp Arg
225                 230                 235                 240

Asn His Leu Met Val Asp Arg Ala Thr Pro Leu Leu Glu Lys Gly Gly
                245                 250                 255

Val Phe Leu Ala Ile Gly Ala Leu His Leu Pro Gly Lys Glu Gly Val
            260                 265                 270

Val Glu Leu Leu Arg Gln Lys Gly Tyr Arg Leu Thr Ala Leu
        275                 280                 285

<210> SEQ ID NO 91
<211> LENGTH: 346
<212> TYPE: PRT
<213> ORGANISM: Chelativorans sp.

<400> SEQUENCE: 91

Met Lys Lys His Leu Val Arg Phe Arg Arg Leu Trp Trp Leu Leu Pro
1               5                   10                  15

Ala Cys Leu Ser Gly Phe Leu Leu Ala Phe Ala Pro Ala Glu His Ala
            20                  25                  30
```

```
Arg Ala Glu Glu Ile Ala Cys Thr Gly Thr Asp Leu Val Gly Gln Leu
             35                  40                  45

Ala Glu Lys Asp Pro Ala Leu Leu Arg Lys Ile Lys Asp Glu Ala Ala
 50                  55                  60

Ala Ile Pro Asn Gly Lys Gly Leu Leu Trp Arg Val Glu Lys Asp Gly
 65                  70                  75                  80

Ile Ala Pro Ser Tyr Leu Phe Gly Thr Met His Leu Thr Asp Pro Arg
                 85                  90                  95

Val Thr Glu Leu Pro Ala Ala Lys Gly Ala Phe Ala Glu Ala Lys
            100                 105                 110

Thr Val Val Ile Glu Thr Lys Asp Ile Leu Asp Arg Asn Ala Met Met
            115                 120                 125

Ala Ala Met Ala Glu Lys Pro Glu Leu Met Met Phe Ser Gly Lys Glu
130                 135                 140

Asn Leu Ala Asp His Leu Thr Gln Glu Glu Arg Glu Ser Val Glu Lys
145                 150                 155                 160

Ala Leu Lys Glu Arg Gly Met Pro Leu Gly Ser Val Leu Lys Met Lys
                165                 170                 175

Pro Trp Ile Leu Ile Ser Leu Val Ser Leu Pro Glu Cys Glu Leu Gln
            180                 185                 190

Arg Gln Arg Gln Gly Leu Pro Val Leu Asp Ala Lys Ile Ala Gln Glu
            195                 200                 205

Ala Lys Ala Glu Gly Lys Glu Val Ala Gly Leu Glu Thr Val Ser Glu
210                 215                 220

Gln Leu Ala Ala Met Ala Ser Leu Pro Val Glu Leu His Ile Gln Gly
225                 230                 235                 240

Leu Val Gly Thr Leu Ala Leu Gly Asp Arg Met Asp Asp Leu Ile Glu
                245                 250                 255

Thr Met Val Ser Leu Tyr Leu Ala Gly Glu Thr Gly Met Phe Arg Pro
            260                 265                 270

Ala Leu Gly Gln Leu Leu Arg Ile Glu Gly Gln Glu Glu Ala Asp Tyr
            275                 280                 285

Ala Ala Phe Glu Lys Arg Met Val Glu Met Arg Asn Tyr Val Met Ala
290                 295                 300

Glu Arg Ala Glu Pro Leu Leu Glu Ser Gly Ser Ala Phe Ile Ala Val
305                 310                 315                 320

Gly Ala Met His Leu Pro Gly Glu Thr Gly Leu Val Thr Leu Leu Arg
                325                 330                 335

Gln Ala Gly Tyr Arg Leu Gln Pro Val Asp
            340                 345

<210> SEQ ID NO 92
<211> LENGTH: 328
<212> TYPE: PRT
<213> ORGANISM: Cytophaga hutchinsonii

<400> SEQUENCE: 92

Met Ile Ile Lys Thr Ser Phe Leu Ile Val Ile His Ala Gln Tyr Ala
1               5                   10                  15

Lys Lys Val Val Gly Lys Ile Ser Ile Tyr Phe Thr Ile His Ser
                20                  25                  30

Gly Ile Lys Ile Phe Val Lys Met Lys Thr Cys Ala Arg Ile Ser Cys
            35                  40                  45

Phe Leu Ile Leu Ala Val Cys Ser Phe Phe Asp Ala Ala Ala Gln Gly
 50                  55                  60
```

```
Asn Phe Leu Leu Trp Glu Ile Thr Gly Asn Gly Leu Ala Asp Thr Ser
 65                  70                  75                  80

Tyr Leu Phe Gly Thr Ile His Ile Arg Asp Lys Arg Val Phe Asn Leu
                 85                  90                  95

Gly Asp Ser Thr Tyr Tyr Ala Ile Thr His Thr Lys Ala Leu Tyr Gly
                100                 105                 110

Glu Leu Asn Leu Gln Asp Lys Ser Glu Met Lys Gln His Ala Pro Glu
            115                 120                 125

Leu Leu Met Pro Ser Gly Thr Ser Leu Gln Ala Met Leu Ser Ala Gln
130                 135                 140

Asp Tyr Lys Leu Val Lys Lys Tyr Cys Lys Lys His Ile Gly Val Tyr
145                 150                 155                 160

Ala Leu Leu Ile Asn Lys Ile Lys Pro Ile Tyr Ile Ser Ala Val Val
                165                 170                 175

Ser Glu Asp Leu Leu Lys Lys Glu Lys Lys Pro Leu Asp Leu Tyr
                180                 185                 190

Leu Gln Asp Tyr Ala Ala Arg Gln Gly Asn Glu Ile Gly Gly Ile Glu
            195                 200                 205

Thr Phe Gln Glu Gln Leu Ser Val Ile Asp Leu Leu Pro Leu Gln Glu
            210                 215                 220

Gln Ala Asp Met Leu Val Glu Gln Ile Lys Asn Ile Asp Gln Glu Lys
225                 230                 235                 240

Ile Leu Met Glu Gln Met Leu Gln Phe Tyr Leu Asn Glu Ser Leu Asp
                245                 250                 255

Ser Leu Glu Ile Leu Val Gln Glu Asp Thr Leu Ser Gln Glu Phe Asn
                260                 265                 270

Glu Ala Ile Leu Asp Ala Arg Asn Lys Val Met Leu Thr Arg Met Glu
            275                 280                 285

Thr Gln Met Asn Arg Glu Pro Thr Phe Phe Ala Val Gly Ala Ala His
            290                 295                 300

Leu Ala Gly Glu Lys Gly Leu Val Ile Leu Leu Arg Lys Ala Gly Tyr
305                 310                 315                 320

Thr Val Arg Pro Val Lys Arg Lys
                325

<210> SEQ ID NO 93
<211> LENGTH: 286
<212> TYPE: PRT
<213> ORGANISM: Dyadobacter fermentans

<400> SEQUENCE: 93

Met Lys Arg Val Leu Phe Leu Ile Phe Cys Ala Phe Thr Ile Ala
 1               5                  10                  15

Ser Arg Ala Gln Val Pro Val Glu Asn Ser Leu Leu Trp Glu Ile Ser
                 20                  25                  30

Gly Arg Gly Leu Ala Lys Pro Ser Tyr Leu Phe Gly Thr Ile His Leu
             35                  40                  45

Ile Cys Pro Thr Asp Phe Ser Ile Ser Asp Ser Leu Lys Ser Thr Leu
         50                  55                  60

Ala Arg Thr Gln Gln Val Ala Leu Glu Met Asp Met Asp Pro Gly
 65                  70                  75                  80

Met Met Thr Gly Met Met Lys Thr Met Asn Met Thr Asp Gly Asn Glu
                 85                  90                  95

Leu Lys Lys Leu Val Thr Ala Ser Glu Tyr Glu Arg Leu Asn Arg Phe
```

```
            100                 105                 110
Phe Thr Asp Ser Val His Val Gly Leu Ala Met Phe Glu Arg Ala Lys
        115                 120                 125
Pro Phe Ile Leu Met Gly Pro Leu Phe Asn Ala Leu Leu Asp Cys Gln
    130                 135                 140
Pro Gln Ser Tyr Glu Met Ala Leu Val Glu Leu Ala Gly Lys Gln Lys
145                 150                 155                 160
Ser Glu Val Ile Gly Ile Glu Thr Leu Glu Glu Gln Met Ala Ile Phe
                165                 170                 175
Asp Thr Ile Pro Tyr Lys Asp Gln Ala Lys Met Leu Leu Thr Leu Ile
            180                 185                 190
Asp Ser Leu Pro Ser Ala Lys Lys Glu Phe Arg Ser Leu Val Ala Leu
        195                 200                 205
Tyr Lys Met Gln Asp Ile Ser Lys Leu Tyr Asp Leu Thr Met Lys Ser
    210                 215                 220
Asp Phe Gly Met Asp Gly Asn Glu Glu Val Met Leu Phe Ala Arg Asn
225                 230                 235                 240
Gln Lys Trp Ile Pro Arg Ile Arg Arg Ile Ala Ser Ala Lys Pro Thr
                245                 250                 255
Phe Phe Ala Val Gly Ala Ala His Leu Gly Gly Glu Arg Gly Val Ile
            260                 265                 270
Ala Leu Leu Arg Lys Glu Gly Phe Gln Val Arg Ala Val Lys
        275                 280                 285

<210> SEQ ID NO 94
<211> LENGTH: 286
<212> TYPE: PRT
<213> ORGANISM: Flavobacterium johnsoniae

<400> SEQUENCE: 94

Met Lys Asn Leu Phe Lys Leu Phe Ile Thr Ala Leu Ile Leu Phe Gly
1               5                   10                  15
Leu Lys Thr Gln Ala Gln Pro Gln Ser Pro Lys Leu Glu Asn Ser Leu
            20                  25                  30
Leu Trp Glu Val Ser Gly Asn Gly Leu Ser Lys Pro Ser Tyr Leu Tyr
        35                  40                  45
Gly Thr Ile His Met Ile Cys Ser Ser Asp Tyr Phe Leu Thr Asp Lys
    50                  55                  60
Thr Lys Arg Ala Phe Glu Ser Ser Glu Lys Leu Met Leu Glu Ile Asn
65                  70                  75                  80
Phe Ser Asp Pro Lys Glu Met Ser Gln Met Gln Gln Leu Ala Met Gly
                85                  90                  95
Lys Glu Pro Leu Ser Lys Lys Leu Thr Pro Glu Gln Leu Ala Lys Leu
            100                 105                 110
Asp Asp Ile Leu Lys Lys Thr Thr Gly Met Thr Val Lys Gln Val Asp
        115                 120                 125
Ser Phe Ser Leu Leu Thr Val Met Ser Leu Ile Ser Met Lys Thr Phe
    130                 135                 140
Gly Cys Ala Asp Leu Lys Phe Tyr Glu Met Glu Phe Ile Glu Gln Ala
145                 150                 155                 160
Lys Lys Arg Asn Ile Glu Ile Gly Gly Leu Glu Ser Val Lys Asp Gln
                165                 170                 175
Phe Val Ile Leu Glu Asn Ala Tyr Thr Asn Asp Glu Ile Ile Ala Met
            180                 185                 190
```

-continued

```
Leu Asp Glu Ser Val Pro Glu Glu Thr Ala Lys Leu Val Ser Thr Tyr
        195             200             205

Lys Ala Glu Asn Ile Glu Ser Leu Tyr Asp Ile Thr Thr Asp Glu Arg
    210             215             220

Phe Thr Ser Lys Lys Thr Lys Lys Ile Ile Leu Asp Glu Arg Asn Leu
225             230             235                     240

Asn Trp Val Lys Ser Met Ala Glu Leu Ile Arg Lys Gln Ser Val Phe
                245             250             255

Phe Ala Val Gly Ser Ala His Leu Gly Gly Glu Phe Gly Val Ile Asn
            260             265             270

Leu Leu Arg Lys Ala Gly Tyr Lys Val Lys Pro Ile Leu Asn
        275             280             285
```